US012522827B2

(12) United States Patent
Glenn et al.

(10) Patent No.: US 12,522,827 B2
(45) Date of Patent: Jan. 13, 2026

(54) PAN-GENOTYPIC AGENTS AGAINST INFLUENZA VIRUS AND METHODS OF USING THE SAME

(71) Applicant: The Board of Trustees of the Leland Stanford Junior University, Stanford, CA (US)

(72) Inventors: Jeffrey S. Glenn, Palo Alto, CA (US); Rachel Hagey Saluti, Stanford, CA (US); Edward A. Pham, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 753 days.

(21) Appl. No.: 17/878,433

(22) Filed: Aug. 1, 2022

(65) Prior Publication Data

US 2023/0072073 A1 Mar. 9, 2023

Related U.S. Application Data

(63) Continuation of application No. PCT/US2021/018025, filed on Feb. 12, 2021.

(51) Int. Cl.

| | |
|---|---|
| ***C12N 15/113*** | (2010.01) |
| ***A61K 45/06*** | (2006.01) |
| ***A61P 31/16*** | (2006.01) |
| *C12Q 1/68* | (2018.01) |

(52) U.S. Cl.

CPC .......... *C12N 15/1131* (2013.01); *A61K 45/06* (2013.01); *A61P 31/16* (2018.01); *C12N 2310/11* (2013.01); *C12N 2310/113* (2013.01); *C12N 2310/3231* (2013.01)

(58) Field of Classification Search

None

See application file for complete search history.

(56) References Cited

U.S. PATENT DOCUMENTS

| | | | |
|---|---|---|---|
| 2004/0242518 | A1 | 12/2004 | Chen et al. |
| 2006/0148747 | A1 | 7/2006 | Stein et al. |
| 2009/0042823 | A1 | 2/2009 | Templin et al. |
| 2010/0254945 | A1 | 10/2010 | Ge et al. |
| 2012/0003156 | A1 | 1/2012 | Dang et al. |
| 2014/0303073 | A1 | 10/2014 | Iversen |
| 2015/0182005 | A1 | 7/2015 | Pires et al. |
| 2017/0161062 | A1 | 6/2017 | Banerjee et al. |

FOREIGN PATENT DOCUMENTS

| | | | |
|---|---|---|---|
| JP | 2009-532392 | A | 9/2009 |
| JP | 2012506698 | A | 3/2012 |
| JP | 2013049714 | A | 3/2013 |
| JP | 2013515504 | A | 5/2013 |
| JP | 2013532965 | A | 8/2013 |
| WO | WO1992003454 | A1 | 3/1992 |
| WO | WO2005013901 | A2 | 2/2005 |
| WO | WO2006110688 | A2 | 10/2006 |
| WO | WO2007084359 | A2 | 7/2007 |
| WO | WO2008049078 | A1 | 4/2008 |
| WO | WO2011060320 | A1 | 5/2011 |
| WO | WO2013166264 | A2 | 11/2013 |
| WO | WO2017151795 | A1 | 9/2017 |
| WO | WO2019159884 | A1 | 8/2019 |
| WO | WO2020021291 | A1 | 1/2020 |
| WO | WO2021188931 | A1 | 9/2021 |

OTHER PUBLICATIONS

Zhang et al., Downregulation of miR-146a inhibits influenza A virus replication by enhancing the type I interferon response in vitro and in vivo, Biomed Pharmacother, 111:740-750 (Mar. 2019).

Giannecchini et al., Packaging signals in the 5'-ends of influenza virus PA, PB1, and PB2 genes as potential targets to develop nucleic-acid based antiviral molecules, Antiviral Research, 92(1):64-72, Jun. 21, 2011.

Hagey et al., Programmable antivirals targeting critical conserved viral RNA secondary structures from influenza A virus and SARS-CoV-2, Nature Medicine, 28(9); 1944-1955, Aug. 18, 2022.

Abe et al. (2001) "Antisense therapy of influenza", European Journal of Pharmaceutical Sciences 13(1):61-69.

Akbari et al. (2008) "Improved DNA Fragment Length Estimation in Capillary Electrophoresis," *Electrophoresis Journal* 29:1273-1285.

Brown et al. (2006) "Inhibition of HIV-1 replication by oligonucleotide analogues directed to the packaging signal and trans-activating response region", Antivir Chem Chemother, 17(1):1-9.

Cordero et al. (2012) "An RNA Mapping DataBase for Curating RNA Structure Mapping Experiments," *Bioinformatics* 28(22):3006-3008.

Cordero (2013) "A Mutate-and-Map Protocol for Inferring Base Pairs in Structured RNA," 22 pages.

Darty et al. (2009) "VARNA: Interactive Drawing and Editing of the RNA Secondary Structure," *Bioinformatics* 25(15)1974-1975.

Deigan et al. (2009) "Accurate SHAPE-Directed RNA Structure Determination," PNAS 106(1):97-102.

De Rijk et al. (2003) "RNA Viz 2: An Improved Representation of RNA Secondary Structure," Bioinformatics 19(2):299-300.

Gao et al. (2012) "The Influenza A Virus PB2, PA, NP, and M Segments Play a Pivotal Role during Genome Packaging," *Journal of Virology* 86(13)7043-7051.

Giannecchini et al. (2009) "Oligonucleotides Derived from the Packaging Signal at the 5' End of the Viral PB2 Segment Specifically Inhibit Influenza Virus In Vitro," *Arch Virol.* 154(5):821-32.

(Continued)

*Primary Examiner* — Sean McGarry

(74) *Attorney, Agent, or Firm* — Kyle A. Gurley; Bret E. Field; Bozicevic, Field & Francis LLP

(57) ABSTRACT

Methods of inhibiting a respiratory virus, (i.e., a virus associated with a respiratory condition, e.g., influenza A, influenza B, RSV, etc.) in a sample are provided. Aspects of the methods include contacting a sample comprising viral RNA (vRNA) having a target motif with an effective amount of an agent that specifically binds the target motif to inhibit the respiratory virus. Also provided are methods of treating or preventing respiratory virus infection in a subject. Also provided are compounds and pharmaceutical compositions comprising an oligonucleotide sequence complementary to a target vRNA region that find use in the subject methods.

18 Claims, 36 Drawing Sheets

Specification includes a Sequence Listing.

(56) References Cited

OTHER PUBLICATIONS

Gog et al. (2007) "Codon Conservation in the Influenza A Virus Genome Defines RNA Packaging Signals," *Nucleic Acids Research* 35(6):1897-1907.
Hoffmann et al. (2000) "A DNA Transfection System for Generation of Influenza A Virus from Eight Plasmids," *PNAS* 97(11):6108-6113.
Integrated DNA Technologies, (2011) "Designing Antisense Oligonucleotides," 16 pages.
Jin et al. (2011) "Inhibition of highly pathogenic avian H5N1 influenza virus propagation by RNA oligonucleotides targeting the PB2 gene in combination with celecoxib", Gene Med; Apr.;13(4):243-9.
Kierzek et al. (2009) "Contributions of Stacking, Preorganization, and Hydrogen Bonding to the Thermodynamic Stability of Duplexes Between RNA and 2'-O-Methyl RNA with Locked Nucleic Acids," *Biochemistry* 48(20):4377-87.
Kim et al. (2009) "A Robust Peak Detection Method for RNA Structure Inference by High-Throughput Contact Mapping," *Bioinformatics* 25(9):1137-1144.
Kim et al. (2013) "HiTRACE-Web: An Online Tool for Robust Analysis of High-Throughput Capillary Electrophoresis," *Nucleic Acids Research* 41:W492-W498.
Kladwang et al. (2010) "A Mutate-and-Map Strategy for Inferring Base Pairs in Structured Nucleic Acids: Proof of Concept on a DNAA/RNA Helix," Biochemistry 49(35):7414-7416.
Kladwang et al. (2011) "A Mutate-and-Map Strategy Accurately Infers the Base Pairs of a 35-Nucleotide Model RNA," RNA 17(3):1-14.
Kladwang et al. (2013) "A Two-Dimensional Mutate-and-Map Strategy for Non-Coding RNA Structure," *Nat Chem.* 3(12):954-962.
Kladwang et al. (2014) "Standardization of RNA Chemical Mapping Experiments," *Biochemistry* 53:3063-3065.
Liang et al. (2008) "Mutational Analyses of Packaging Signals in Influenza Virus PA, PB1, and PB2 Genomic RNA Segments," *Journal of Virology* 82(1):229-236.
Marsh (2007) "Specific Residues of the Influenza A Virus Hemagglutinin Viral RNA Are Important for Efficient Packaging into Budding Virions," *Journal of Virology* 81(18):9727-9736.
Marsh (2008) "Highly Conserved Regions of Influenza A Virus Polymerase Gene Segments Are Critical for Efficient Viral RNA Packaging," *Journal of Virology* 82(5):2295-2304.
Mathews et al. (2004) "Incorporating Chemical Modification Constraints into a Dynamic Programming Algorithm for Prediction of RNA Secondary Structure," *PNAS* 101(19):7287-7292.
Mortimer et al. (2007) "A Fast Acting Reagent for Accurate Analysis of RNA Secondary and Tertiary Structure by SHAPE Chemistry," *J. Am. Chem. Soc.* 129(14):4144-4145.
Mortimer et al. (2009) "Time-Resolved RNA SHAPE Chemistry: Quantitative RNA Structure Analysis in One Second Snapshots and at Single Nucleotide Resolution," *Nat Protoc.* 4(10):1413-1421.
Moss et al. (2011) "Identification of Potential Conserved RNA Secondary Structure Throughout Influenza A Coding Regions," *RNA* 17:6(991-1011).
Muramoto et al. (2006) "Hierarchy Among Viral RNA (vRNA) Segments in Their Role in vRNA Incorporation into Influenza A Virions," *Journal of Virology* 80(5):2318-2325.
Pang (2011) "Simplified RNA Secondary Structure Mapping by Automation of SHAPE Data Analysis," Nucleic Acids Research 39(22):1-11.
Pang (2012) "Structural Map of a MicroRNA-122:Hepatitis C Virus Complex," *Journal of Virology* 86(2):1250-1254.
International Search Report and Written Opinion of corresponding PCT Application PCT/US2017/020241 dated Aug. 11, 2017, 18 pages.
IPRP of corresponding PCT Application PCT/US2017/020241 dated Sep. 13, 2018, 9 pages.
Priore (2012) "Influenza A Virus Coding Regions Exhibit Host-Specific Global Ordered RNA Structure," *PLoS ONE* 7(4)1-8.
Szretter et al. (2006) "Influenza: Propagation, Quantification, and Storage," *Current Protocols in Microbiology* 15G.1.1-15G.1.22.
Takahashi et al. "Inhibition of influenza virus infection by targeting genome conserved region with non-natural nucleic acid", Nucleic Acids Symp Ser (Oxf)., 2009;(53):285-6.
Tian et al. (2014) "High-Throughput Mutate-Map-Rescue Evaluates SHAPE-Directed RNA Structure and Uncovers Excited States," Cold Spring Harbor Laboratory Press 20:1815-1826.
Vester et al. (2004) "LNA (Locked Nucleic Acid): High-Affinity Targeting of Complementary RNA and DNA," *Biochemistry* 43(42):13233-13241.
Wilkinson et al., (2006) "Selective 2'-Hydroxyyl Acylation Analyzed by Primer Extension (SHAPE): Quantitative RNA Structure Analysis at Single Nucleotide Resolution," *Nature Protocols* 1(3):1610-1616.
Yoon et al. (2011) "HiTRACE: High-Throughput Robust Analysis for Capillary Electrophoresis," *Bioinformatics* 27(13):1798-1805.
Lebedeva et al., Phosphorothioate oligodeoxynucleotides as inhibitors of gene expression: antisense and non-antisense effects, Applications of antisense therapies to restenosis, p. 101, 1999: Abstract only.

| Mutant Name | Mutation Site(s) |
|---|---|
| m55c | CU35,36UC |
| m757 | G44C |
| m55a | CAU50,53,56 |
| m751 | G62C |
| m748 | C71U |
| m745 | A80U |
| m744b | AG83,85UA |
| m737 | U104A |
| m731 | C122G |

FIG. 2
A
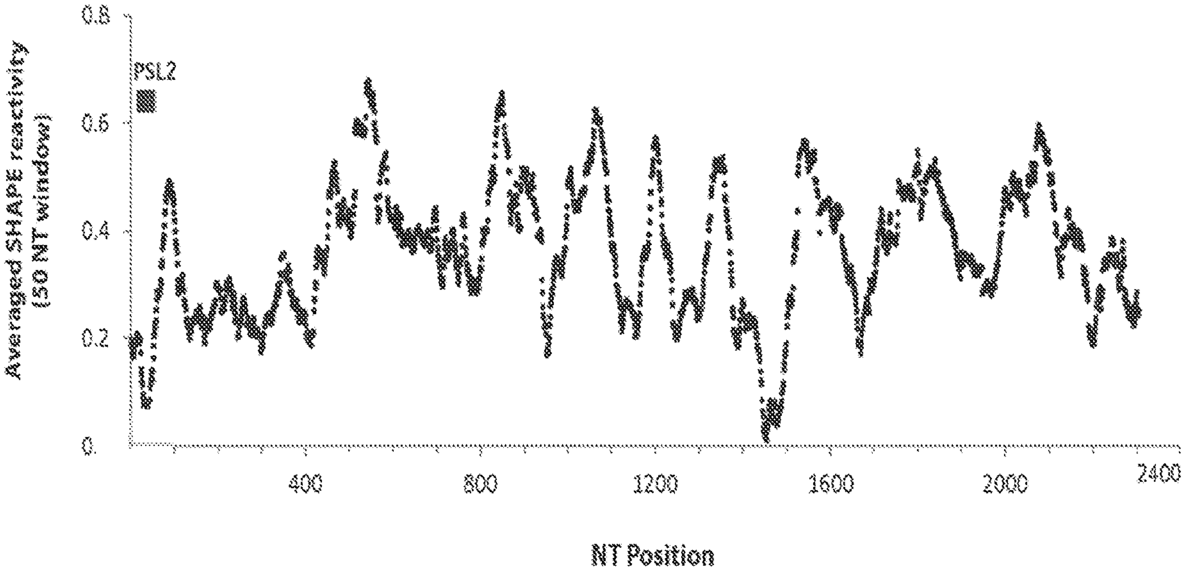
B
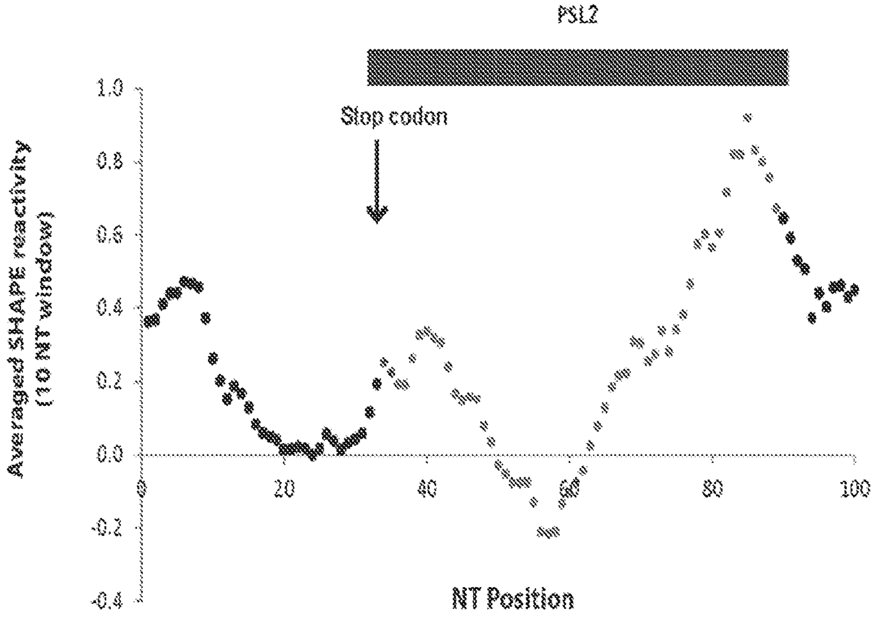

FIG. 7

A

2203 ATT GGG CAA 2215 GGA GAC GTG GTG 2227 TTG GTA ATG AAA CGG

ATT GGG CAA GGA GAC GTC GTG TTG GTA ATG AAA CGG m731

2239 AAA CGG AAC TCT 2251 AGC ATA CTT ACT 2263 GAC AGC CAG ACA

AAA CGG AAC TCT AGC ATA TTA ACA GAC AGC CAA ACA m744b m745 m748

2275 GCG ACC AAA AGA 2287 ATT CGG ATG GCC 2299 ATC AAT TAG TGT

GCG ACG AAA AGA ATT CGG ATG GCG ATC AAT TGA TGT m751 m757 m55c

B

Mutate-and-Map predicted PB2 mutations (Syn.) m74-1 (C2268T)-F: TAC TTA CTG ACA GTC AGA CAG CG
(Syn.) m74-1 (C2268T)-RC: CGC TGT CTG ACT GTC AGT AAG TA (Syn.) m74-2 (AGC2266-8UCG)-F: TAC TTA CTG ACT CGC AGA CAG CG
(Syn.) m74-2 (AGC2266-8UCG)-RC: CGC TGT CTG CGA GTC AGT AAG TA (Syn.) m68-1 (A2262T)-F: TGA CAG CCA GAC TGC GAC CAA AAG AAT TCG
(Syn.) m68-1 (A2262T)-RC: CGA ATT CTT TTG GTC GCA GTC TGG CTG TCA (Syn.) m56 (A2286C)-F: AGC GAC CAA AAG CAT TCG GAT GGC
(Syn.) m56 (A2286C)-RC: GCC ATC CGA ATG CTT TTG GTC GCT

C

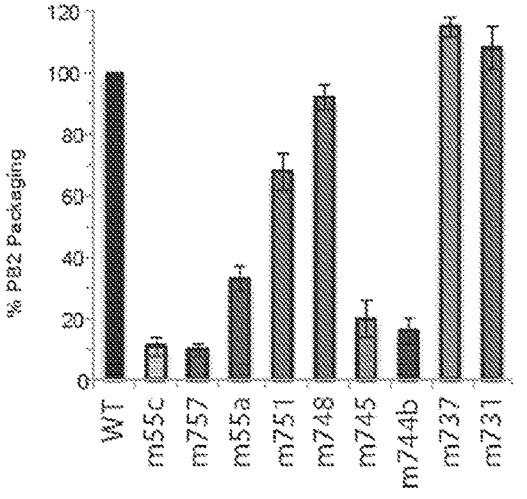

D

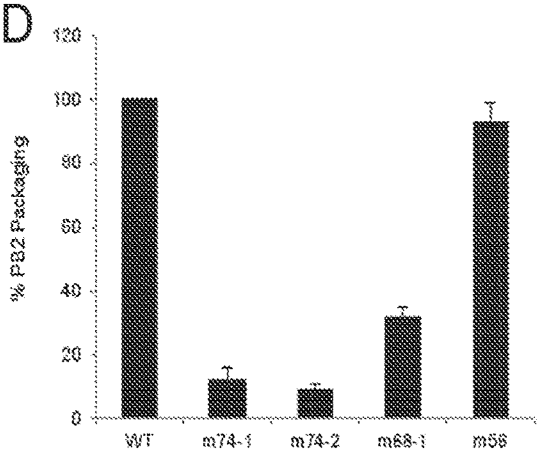

FIG. 8

Mutant Nomenclature and Mutation Sites

| Group | Mutant Name | Mutation Site(s) [(-)-sense orientation] | SYN or Non-SYN | Notes |
|---|---|---|---|---|
| Previously-described Mutants | m55c | CU35,36UC | SYN | |
| | m757 | G44C | SYN | |
| | m55a | CAU50,53,56 | SYN | |
| | m751 | G62C | SYN | |
| | m748 | C71U | SYN | |
| | m745 | A80U | SYN | |
| | m744b | AG83,85UA | SYN | |
| | m737 | U104 | SYN | |
| | m731 | C122G | SYN | |
| Novel PSL2-informed Mutants | m83,84 | AG83,84GA | Non-SYN | |
| | m55c-comp | CU35,36UC / AG83,84GA | Non-SYN | Dbl Mutant |
| | m76 | U76G | Non-SYN | |
| | m757-comp | G44C / U76G | Non-SYN | Dbl Mutant |
| | m40 | U40A | Non-SYN | |
| | m745-comp | A80U / U40A | Non-SYN | Dbl Mutant |
| | m74-1 | G74A | SYN | |
| | m74-2 | UCG74AGC | SYN | |
| | m68 | U68A | SYN | |
| | m56 | U56G | SYN | |
| | m41 | G41C | Non-SYN | |
| | m79 | C79G | Non-SYN | |
| | m41/79-comp | GC41,79CG | Non-SYN | Dbl Mutant |
| | m45 | G45C | Non-SYN | |
| | m75 | C75G | Non-SYN | |
| | m45/75-comp | GC45,75CG | Non-SYN | Dbl Mutant |
| | m46 | C46G | Non-SYN | |
| | m74 | G74C | Non-SYN | |
| | m46/74-comp | CG46,74GC | Non-SYN | Dbl Mutant |
| | m52 | G52U | SYN | |
| | m65 | C65A | SYN | |
| | m52/65-comp | GC52,65UA | SYN | Dbl Mutant |

SYN = Synonymous mutation, Non-SYN = non-synonymous mutation

FIG. 9A
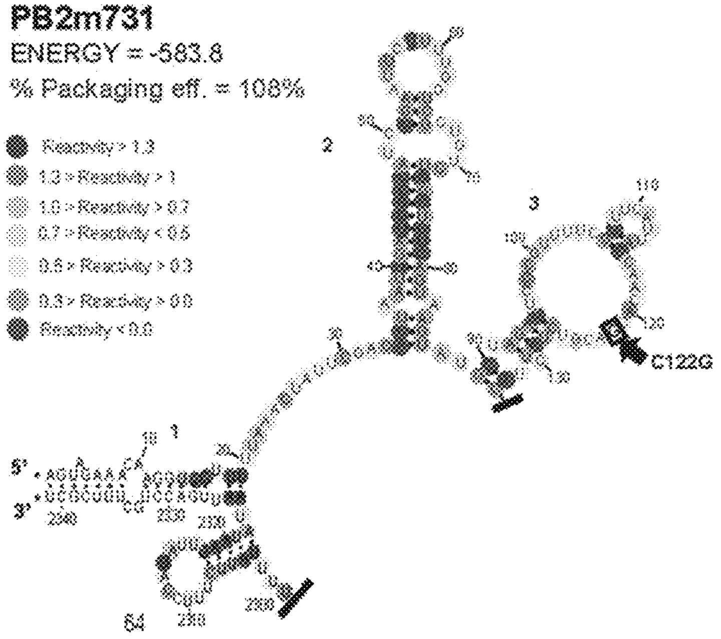
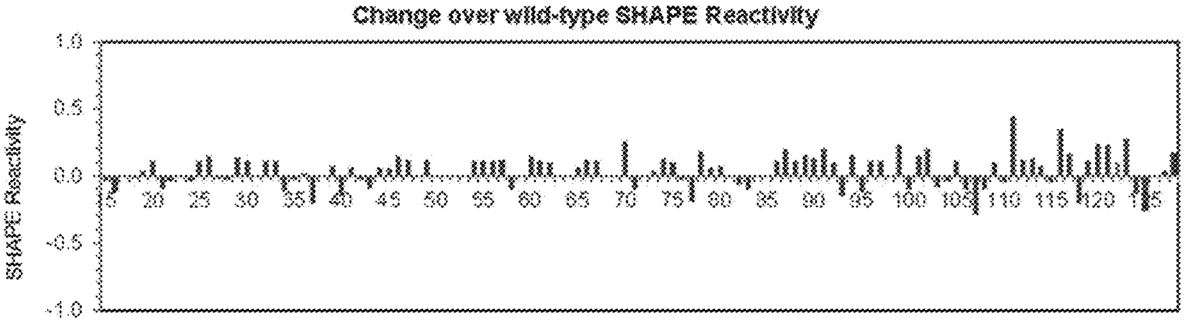

FIG. 9C
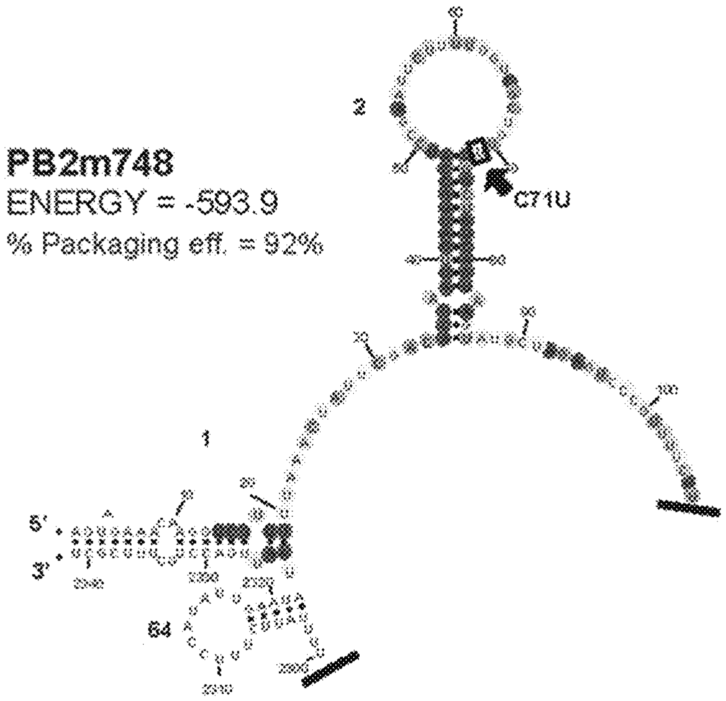
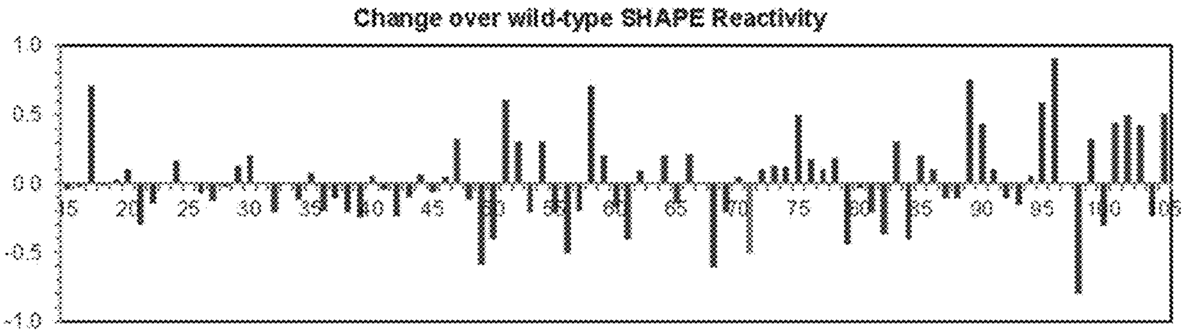

FIG. 13

| | |
|---|---|
| (Non-syn.) m46-F (G2296C): | AGA ATT CGG ATG CCC ATC AAT TAG TGT CG |
| (Non-syn.) m46-RC (G2296C): | CGA CAC TAA TTG ATG GGC ATC CGA ATT CT |
| (Syn.) m46/74-comp (C2268G)-F: | TAC TTA CTG ACA GGC AGA CAG CG |
| (Syn.) m46/74-comp (C2268G)-RC: | CGC TGT CTG CCT GTC AGT AAG TA |
| (Non-syn.) m45-F (G2297C): | TTC GGA TGG GCA TCA ATT AGT GTC G |
| (Non-syn.) m45-RC (G2297C): | CGA CAC TAA TTG ATG CCC ATC CGA A |
| (Non-syn) m45/75-comp (G2267C)-F: | ATA CTT ACT GAC ACC CAG ACA GCG |
| (Non-syn) m45/75-comp (G2267C)-RC: | CGC TGT CTG GGT GTC AGT AAG TAT |
| (Non-syn.) m41-F (C2301G): | TCG GAT GGC CAT GAA TTA GTG TCG |
| (Non-syn.) m41-RC (C2301G): | CGA CAC TAA TTC ATG GCC ATC CGA |
| (Syn.) m41/79-comp (G2263C)-F: | AGC ATA CTT ACT CAC AGC CAG ACA GC |
| (Syn.) m41/79-comp (G2263C)-RC: | GCT GTC TGG CTG TGA GTA AGT ATG CT |

| | | |
|---|---|---|
| (Syn.) m52-F (C2290A): | CCA AAA GAA TTA GGA TGG CCA TCA ATT AGT GTC G | Double synonymous mutant pair |
| (Syn.) m52-RC (C2290A): | CGA CAC TAA TTG ATG GCC ATC CTA ATT CTT TTG G | |
| (Syn.) m65-F (G2277T): | GAC AGC CAG ACA GCT ACC AAA AGA ATT CG | |
| (Syn.) m65-RC (G2277T): | CGA ATT CTT TTG GTA GCT GTC TGG CTG TC | |

Anti-miR-29 is LNA-191.12
Anti-miR-57 is LNA-6810.2

LNA-12.8 is Cov 12.8
LNA-8.5 is Cov 8.5
LNA-18.1 is Cov 18.1
Anti-miR-29 is LNA-191.12

Vehicle:
Glyceryltrioctanoate:octanoic
acid:NMP (80:10:10)

6.7 is Cov 6.7; 12.8 is Cov 12.8
10.1 is Cov 10.1; 13.9 is Cov 13.9
11.3 is Cov 11.3; 14.3 is Cov 14.3
18.1 is Cov 18.1;

PAN-GENOTYPIC AGENTS AGAINST INFLUENZA VIRUS AND METHODS OF USING THE SAME

CROSS-REFERENCE TO RELATED APPLICATIONS

This application is a continuation of prior International Application No. PCT/US2021/018025, filed Feb. 12, 2021, is incorporated herein by reference in its entirety.

GOVERNMENT RIGHTS

This invention was made with Government support under contract AI109662 awarded by the National Institutes of Health. The Government has certain rights in the invention.

INTRODUCTION

Influenza A virus (IAV) is a segmented RNA virus that causes significant morbidity and mortality worldwide. All currently approved IAV antiviral drugs are targeted against viral proteins, are subtype limited, and are challenged by rising antiviral resistance against all drug class members.

The IAV genome consists of eight single-stranded negative-sense viral RNA (vRNA) segments that encode a minimum of 14 known viral proteins. The vRNA, together with nucleoprotein (NP) and the heterotrimeric polymerase complex, comprised of PB2, PB1, and PA proteins, forms the complete viral ribonucleoprotein (vRNP). To be fully infectious, IAV virions must incorporate at least one of each segment's vRNP. Each vRNP interacts with at least one other partner to form a supramolecular complex likely maintained by intersegment RNA-RNA and/or protein-RNA interactions hypothesized to guide the packaging process.

Individuals can be infected with influenza A alone and/or with other respiratory viruses, including but not limited to influenza B viruses (IBV), coronavirus (Cov), respiratory syncytial viruses (RSV), and the like. IBV is a segmented RNA virus whose genome consists of eight segments of linear negative-sense, single-stranded RNA Respiratory syncytial virus (RSV), also called human respiratory syncytial virus (hRSV) is a negative-sense, single-stranded RNA virus. Patients infected with RSV are at higher risk of respiratory failure. It is a very common human respiratory viral pathogen.

Coronaviruses (CoV) are enveloped RNA viruses which typically cause self-limited respiratory tract infection in humans. However, in the past 2 decades, there have been life-threatening conditions caused by new strains of CoV, such as those found in the 2003 severe respiratory syndrome (SARS) outbreak, Middle East Respiratory Syndrome (MERS) in 2012, and most recently the 2019 CoV outbreak originated from Wuhan, China (SARS-CoV-2). New therapies are critically needed to contain the current outbreak and also future outbreaks.

SUMMARY

Aspects of the present disclosure provide pan-genotypic compositions designed to disrupt an RNA structural element of a respiratory disease associated virus, e.g., IAV, IBV, RSV, Coronavirus, etc. Aspects of the present disclosure provide pan-genotypic compositions designed to disrupt an RNA structural element of IAV, called Packaging Stem-Loop 2 (PSL2), within the 5' packaging signal region of genome segment PB2. Disruption of PSL2 structure dramatically inhibits IAV. PSL2 is conserved across all tested influenza A subtypes.

Methods of inhibiting influenza A virus in a sample are provided. Aspects of the methods include contacting a sample comprising viral RNA (vRNA) having a PSL2 motif with an effective amount of an agent that specifically binds the PSL2 motif to inhibit the influenza A virus. In some cases, the vRNA is isolated from a virion or a cell. In some cases, the vRNA is in a virion. In some cases, the vRNA is in an infected cell. Also provided are methods of treating or preventing influenza A virus infection in a subject. Also provided are methods for screening a candidate agent for the ability to inhibit influenza A virus in a cell, the method comprising: contacting a sample with a candidate agent; and determining whether the candidate agent specifically binds to the PSL2 motif of vRNA. Also provided are compounds and pharmaceutical compositions comprising an oligonucleotide sequence complementary to a PB2 vRNA (or its complimentary strand) region that find use in the subject methods.

Methods of inhibiting influenza B virus in a sample are provided. Aspects of the methods include contacting a sample comprising viral RNA (vRNA) having a motif with an effective amount of an agent that specifically binds the RNA motif to inhibit the influenza B virus. In some cases, the vRNA is isolated from a virion or a cell. In some cases, the vRNA is in a virion. In some cases, the vRNA is in an infected cell. Also provided are methods of treating or preventing influenza B virus infection in a subject. Also provided are methods for screening a candidate agent for the ability to inhibit influenza B virus in a cell, the method comprising: contacting a sample with a candidate agent; and determining whether the candidate agent specifically binds to the RNA motif of vRNA. Also provided are compounds and pharmaceutical compositions comprising an oligonucleotide sequence complementary to a IBV vRNA region that find use in the subject methods.

BRIEF DESCRIPTION OF THE FIGURES

The skilled artisan will understand that the drawings, described below, are for illustration purposes only. The drawings are not intended to limit the scope of the present teachings in any way.

FIG. 2, panels A and B, depicts the reactivity of full-length PB2 vRNA.

FIG. 7, panels A-D, depicts synonymous mutation of single highly conserved codons of the PR8 PB2 vRNA (panel A, SEQ ID NOs: 14-15; panel B, SEQ ID NOs: 16-23 top to bottom).

FIG. 8 depicts a table showing PB2 packaging mutant nomenclature and corresponding sites of mutation.

FIG. 9A-FIG. 9C depicts the effect of synonymous mutation on PSL2 structure, PB2m731 (SEQ ID NO: 24), PB2m751 (SEQ ID NO: 25) and PB2m748 (SEQ ID NO: 26).

FIG. 13 depicts the design of primer sequences for 2-dimensional Mutate-Map-Rescue mutants. Sequences correspond to SEQ ID NOs: 28-43, top to bottom.

DEFINITIONS

Figure 1A:
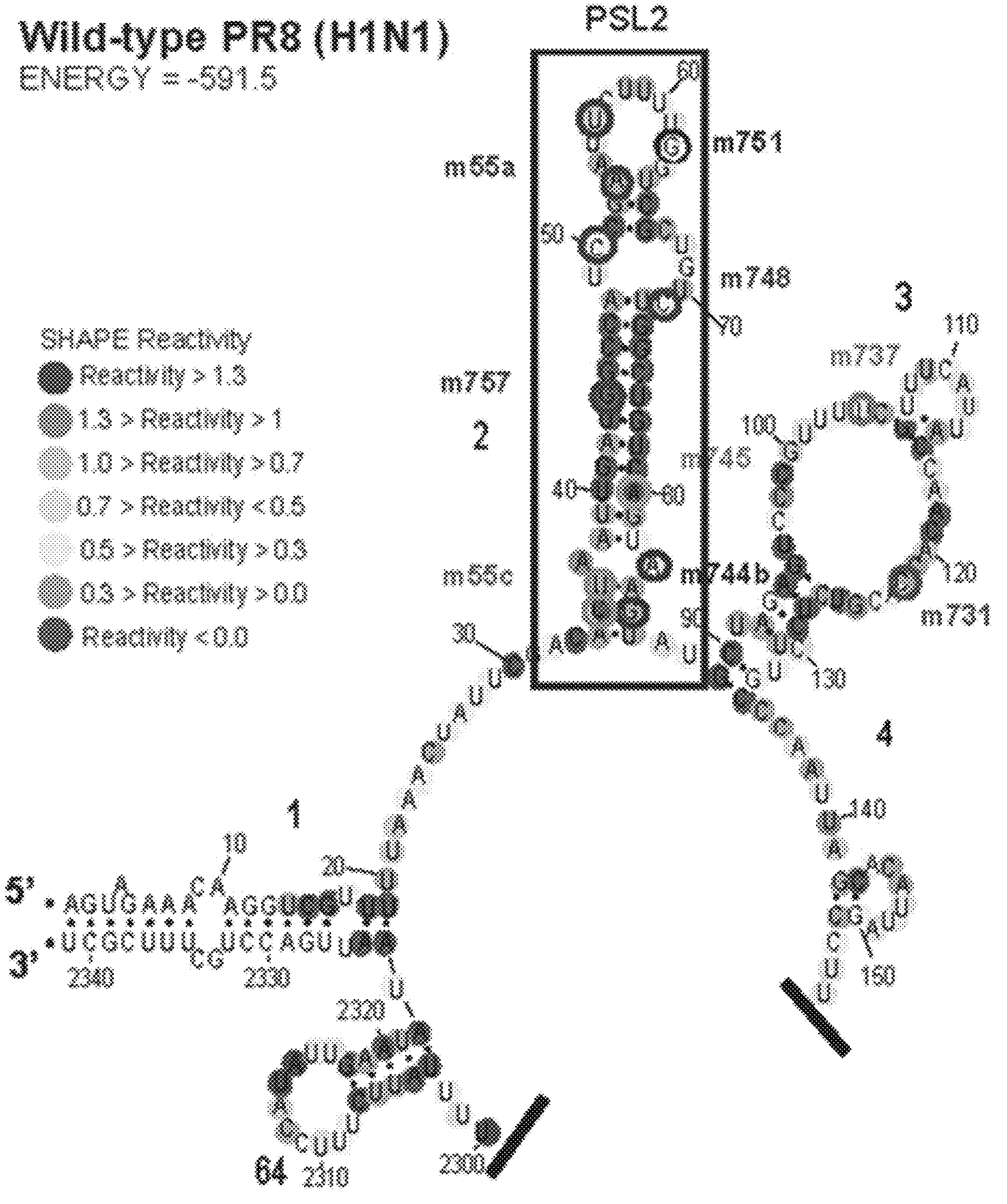
FIG. 1A-FIG. 1F depicts RNA secondary structures of wild-type PB2 (SEQ ID NO: 1) and packaging mutant vRNAs, PB2m757 (SEQ ID NO: 2), m745 (SEQ ID NO: 3), 1918 pandemic (H1N1) (SEQ ID NO: 4), High-path avian (H5M=N1) (SEQ ID NO: 5) and 2009 swine (H1N1) (SEQ ID NO: 6).
Figure 1B:
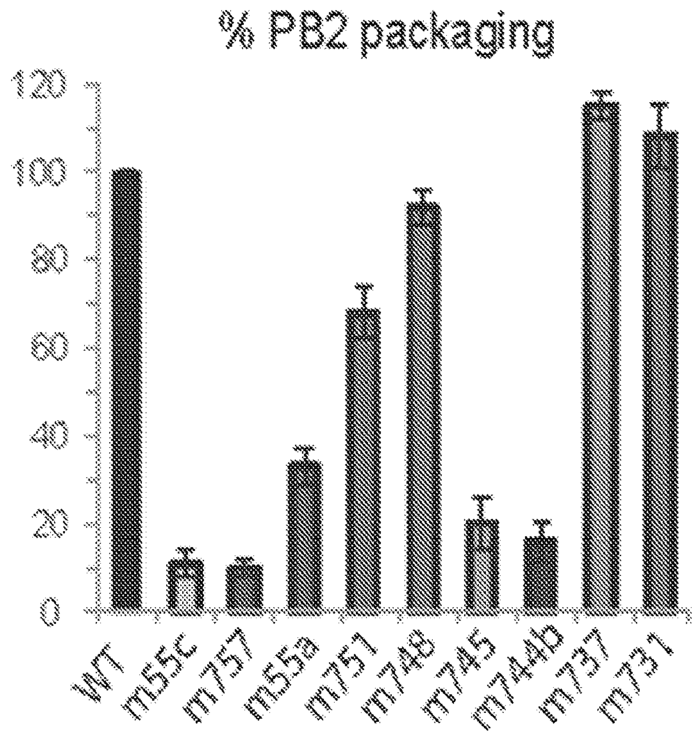

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, New York (1991) provide one of skill with the general meaning of many of the terms used herein. Still, certain terms are defined below for the sake of clarity and ease of reference.

It must be noted that as used herein and in the appended claims, the singular forms “a”, “an”, and “the” include plural referents unless the context clearly dictates otherwise. For example, the term “a primer” refers to one or more primers, i.e., a single primer and multiple primers. It is further noted that the claims can be drafted to exclude any optional element. As such, this statement is intended to serve as antecedent basis for use of such exclusive terminology as “solely,” “only” and the like in connection with the recitation of claim elements, or use of a “negative” limitation.

As used herein, the term “effective amount” refers to that amount of a substance (e.g., an agent of interest) that produces some desired local or systemic effect. Effective amounts of active agents of interest vary depending on a variety of factors including, but not limited to, the weight and age of the subject, the condition being treated, the severity of the condition, the manner of administration and the like, and can readily be determined, e.g., determined empirically using data such as that data provided in the experimental section below.

The term “sample” as used herein relates to a material or mixture of materials, typically, although not necessarily, in fluid, i.e., aqueous, form, containing one or more components of interest. Samples may be derived from a variety of sources such as from a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Components in a sample are termed “analytes” herein. In many embodiments, the sample is a complex sample containing at least about $10^2$, $5\times10^2$, 10, $5\times10^3$, $10^4$, $5\times10^4$, $10^5$, $5\times10^5$, $10^6$, $5\times10^6$, $10^7$, $5\times10^7$, $10^8$, $10^9$, $10^{10}$, $10^{11}$, $10^{12}$ or more species of analyte.

“Antibody fragments” comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; nanobodies, and multispecific and multifunctional antibodies formed from antibody fragments. Papain digestion of antibodies produces two identical antigen-binding fragments, called “Fab” fragments, each with a single antigen-binding site, and a residual “Fc” fragment, a designation reflecting the ability to crystallize readily. Pepsin treatment yields an F(ab')2 fragment that has two antigen combining sites and is still capable of cross-linking antigen.

The terms “polypeptide” and “protein”, used interchangeably herein, refer to a polymeric form of amino acids of any length, which can include coded and non-coded amino acids, chemically or biochemically modified or derivatized amino acids, and polypeptides having modified peptide backbones. The term “fusion protein” or grammatical equivalents thereof is meant a protein composed of a plurality of polypeptide components, that while typically unjoined in their native state, typically are joined by their respective amino and carboxyl termini through a linkage, e.g., a peptide linkage, to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. In addition, the term “protein” can further encompass the post-translational modification including but not limited to glycosylation, phosphorylation, methylation, and acetylation.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. “Peptides” are generally greater than 2 amino acids, greater than 4 amino acids, greater than about 10 amino acids, greater than about 20 amino acids, usually up to about 50 amino acids. In some embodiments, peptides are between 5 and 30 amino acids in length.

The term “specific binding” refers to the ability of an agent to preferentially bind to a particular target (e.g., PSL2) that is present in a homogeneous mixture of different analytes. In some cases, a specific binding interaction will discriminate between desirable and undesirable analytes in a sample, typically more than about 10 to 100-fold or more (e.g., more than about 1000-fold). Specific binding can include hybridization, polypeptide-nucleic acid interactions or small molecule-nucleic acid interactions.

“Oligonucleotide” refers to ribose and/or deoxyribose nucleoside subunit polymers having between about 2 and about 200 contiguous subunits. The nucleoside subunits can be joined by a variety of intersubunit linkages, including, but not limited to, phosphodiester, phosphotriester, an alkylphosphonate, e.g., methylphosphonate, P3'→N5' phosphoramidate, N3'→P5' phosphoramidate, N3'→P5' thiophosphoramidate, phosphorodiamidate, and phosphorothioate linkages. In certain cases, intersubunit linkage has a chiral atom. Representative chiral intersubunit linkages include, but are not limited to, alkylphosphonates, phosphorodiamidates and phosphorothioates. Further, “oligonucleotides” includes chemical and biochemical modifications, such as those known to one skilled in the art, e.g., to the sugar (e.g., 2' substitutions), the base (see the definition of “nucleoside” below), and/or the 3' and 5' termini. In embodiments where the oligonucleotide moiety includes a plurality of intersubunit linkages, each linkage may be formed using the same chemistry or a mixture of linkage chemistries may be used. In embodiments where the oligonucleotide moiety includes a plurality of intersubunit linkages, one or more of the linkages may be chiral. Linkages having a chiral atom can be prepared as racemic mixtures, or as separate enantiomers. The terms “oligonucleotide”, “nucleic acid,” “nucleic acid molecule,” “nucleic acid fragment,” “nucleic acid sequence or segment,” or “polynucleotide” are used interchangeably and may also be used interchangeably with gene, cDNA, DNA and RNA encoded by a gene.

A “bicyclic nucleic acid” or a “bridged nucleic acid” (BNA) refers to a modified RNA nucleotide where the ribose moiety is modified with an extra bridge connecting the 2' oxygen and 4' carbon, thereby forming a bicyclic ring system. BNA monomers can contain a five-membered, six-membered or a seven-membered bridge structure with a fixed 3'-endo conformation. Bridged nucleic acids include without limitation, locked nucleic acids (LNA), ethylene-bridged nucleic acids (ENA) and constrained ethyl (cEt). A “bridge” refers to a chain of atoms or a valence bond connecting two bridgeheads, where a "bridgehead" is any skeletal atom of a ring system (e.g., the ribose ring system) which is bonded to three or more skeletal atoms (excluding hydrogen). In some embodiments, the bridge in a BNA has 7-12 ring members and 1-4 heteroatoms independently selected from nitrogen, oxygen, or sulfur. Unless otherwise specified, a BNA is optionally substituted with one or more substituents, e.g., including, but not limited to alkyl, substituted alkyl, alkoxy, substituted alkoxy, hydroxy, amino and halogen.

A "Locked nucleic acid" (LNA) is a modified RNA nucleotide where the ribose moiety is modified with an extra bridge connecting the 2' oxygen and 4' carbon, thereby forming a bicyclic ring system. The bridge "locks" the ribose in the 3'-endo conformation, which is often found in the A-form duplexes. Locked nucleic acids are also encompassed by the term "bicyclic nucleic acids" or "bridged nucleic acids" (BNA). LNA nucleotides can be mixed with any convenient nucleotides or nucleotide analogs, such as DNA or RNA residues in an oligonucleotide whenever desired. LNA's hybridize with DNA or RNA according to Watson-Crick base-pairing rules. Such oligomers can be synthesized chemically. In general, the locked ribose conformation enhances base stacking and backbone pre-organization to increase the hybridization properties (melting temperature) of the oligonucleotide. A locked nucleic acid, in some cases can be Alpha-l-locked nucleic acid (α-l-LNA), a stereoisomeric analogue of locked nucleic acid (LNA) with the inverted stereochemistry at C2', C3' and C4' positions.

An "ethylene-bridged nucleic acid" (ENA) refers to an LNA modified RNA nucleotide where the ribose moiety is modified with an extra bridge containing two carbon atoms between the 2' oxygen and the 4' carbon (see, e.g., Morita et al., Bioorganic Medicinal Chemistry, 2003, 11(10), 2211-2226). Ethylene-bridged nucleic acids are also encompassed by the term "bicyclic nucleic acids" or "bridged nucleic acids" (BNA).

A "constrained ethyl (cEt)" refers to an LNA modified RNA nucleotide where the ribose moiety is modified with an extra bridge connecting the 2' oxygen and 4' carbon, wherein the carbon atom of the bridge includes a methyl group. In some cases, the cEt is (S)-constrained ethyl. In other cases, the cEt is (R)-constrained ethyl (see, e.g., Pallan et al., Chem. Commun. (Camb)., 2012, 48(66), 8195-8197). Constrained ethyl nucleic acids are also encompassed by the term "bicyclic nucleic acids" or "bridged nucleic acids" (BNA).

As used herein, the term "2-modified" or "2'-substituted" means a sugar comprising a substituent at the 2'-position other than H or OH. 2-modified nucleotides, include moieties with 2' substituents selected from alkyl, allyl, amino, azido, fluoro, thio, O-alkyl, e.g., O-methyl, O-allyl, $OCF_3$, O—$(CH_2)_2$O—$CH_3$ (e.g., 2'-O-methoxyethyl (MOE)), O—$(CH_2)_2SCH_3$, )—$(CH_2)_2$—$ONR_2$, and O—$CH_2C(O)$—$NR_2$, where each R is independently selected from H, alkyl, and substituted alkyl.

The disclosure encompasses isolated or substantially purified nucleic acid nucleic acid molecules and compositions containing those molecules. In the context of the present disclosure, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present disclosure. By "fragment" or "portion" is meant a full length or less than full length of the nucleotide sequence. The siRNAs of the present disclosure can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

A "small interfering" or "short interfering RNA" or siRNA is a RNA duplex of nucleotides that is targeted to a gene interest. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

The term "lipid" is used broadly herein to encompass substances that are soluble in organic solvents, but sparingly soluble, if at all, in water. The term lipid includes, but is not limited to, hydrocarbons, oils, fats (such as fatty acids, glycerides), sterols, steroids and derivative forms of these compounds. Preferred lipids are fatty acids and their derivatives, hydrocarbons and their derivatives, and sterols, such as cholesterol. As used herein, the term lipid also includes amphipathic compounds which contain both lipid and hydrophilic moieties. Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty amides produced by the conjugation reactions, e.g., with a modified terminal of an oligonucleotide.

Other definitions of terms may appear throughout the specification.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Methods for Modulating Host MicroRNA

Host microRNA can regulate a wide variety of physiological process. In some cases, the host microRNA can regulate fitness of influenza A, B, coronaviruses including SARS, SARS-Cov-2, MERS, and other respiratory viruses. In some cases, the miRNA is microRNA 191 (miR191). In some cases, the miRNA can be but not limited to one of the followings: miR-602; miR-6759; miR-6769; miR-4802; miR-942; miR-4462; miR-4696; miR-376c; miR-4433; miR-663; miR-10396; miR-4749; miR-6787; miR-4706; miR-3675; miR-6810; miR-6812; miR-663a, miR-381, miR-744, miR-4508, miR-4730, miR-6777, miR-10396, miR-4749, miR-6787, miR-4706, miR-3675, miR-6810, miR-3675, miR-6812, miR-6796. In some cases, the miRNA can directly bind to the influenza A viral RNA in virions or in the infected cells. In some cases, the miRNA can directly bind to the influenza B viral RNA in virions or in the infected cells. In some cases, the miRNA can directly bind to coronavirus viral RNA including SARS-Cov; SARS-Cov2; MERS in virions or in the infected cells. In some cases, the miRNA can directly bind to Respiratory syncytial virus (RSV) RNA in virions or in the infected cells. In some cases, the miRNA can regulate a host cell process that modulate the level of influenza A viral RNA in virions or in the infected cells in other ways. In some cases, the miRNA can regulate a host cell process that modulate the level of influenza A viral RNA in virions or in the infected cells in other ways. In some cases, the miRNA can regulate a host cell process that modulate the level of influenza B viral RNA in virions or in the infected cells in other ways. In some cases, the miRNA can regulate a host cell process that modulate the level of coronavirus viral RNA including SARS-Cov; SARS-Cov2; MERS viral RNA in virions or in the infected cells in other ways. In some cases, the miRNA can regulate a host cell process that modulate the level of respiratory syncytial virus (RSV) RNA in virions or in the infected cells in other ways. In some cases, the conserved RNA secondary structure includes the presence of miR191 binding sites. In some cases, the subject agent or composition is designed to sequester miR191 in cells transfected with a CoV.

Methods for Inhibiting Influenza A Virus

As summarized above, aspects of the present disclosure include pan-genotypic compositions designed to disrupt an RNA structural element of IAV, called Packaging Stem-Loop 2 (PSL2), within the 5' packaging signal region of genome segment PB2. By "pan-genotypic" is meant the compositions are effective across a variety of different types of IAV where the PSL2 structural element is conserved. In some cases, the subject compositions can be referred to as broad spectrum. As used herein, the term "broad spectrum" refers to the anti-viral activity of a single moiety that is active against two or more different viruses, such as three or more, four or more, five or more, six or more, eight or more, 10 or more different viruses. The two or more different viruses may be selected from different virus sub-groups (e.g., Influenza A group 1 or Influenza A group 2), or may be selected from within the same group (e.g., two or more of H1, H2, H5, H6, H8 and H9 group 1 influenza A viruses, or two or more of H3, H4, H7 and H10 Group 2 Influenza A viruses).

Figure 4:
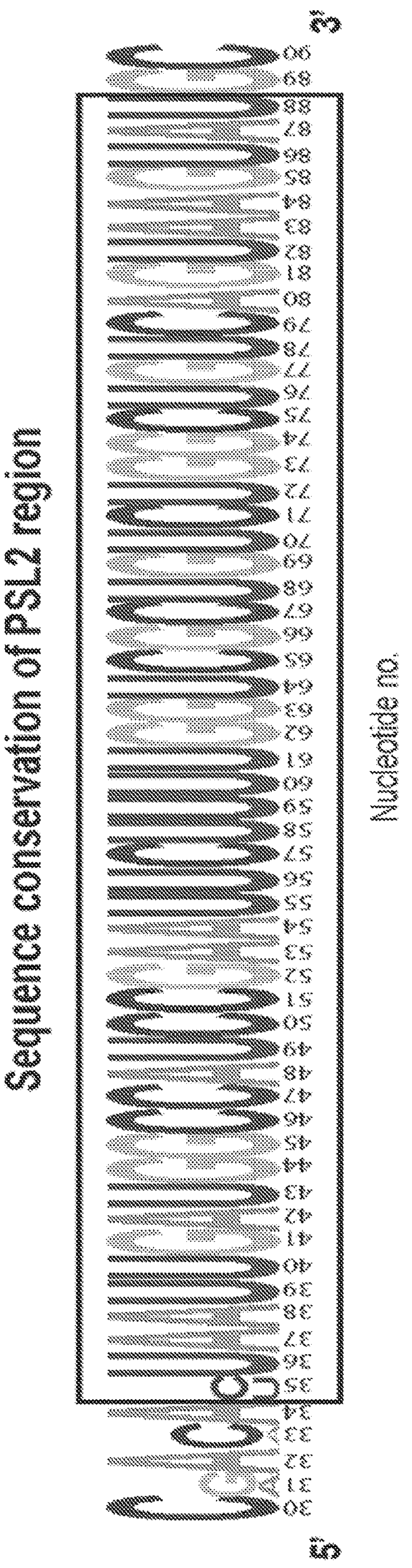
FIG. 4 depicts the conservancy of nucleotide sequence containing the PSL2 structure.

Disruption of PSL2 structure dramatically inhibits IAV. PSL2 is conserved across all tested influenza A subtypes. FIG. 1, panel a, shows an example of the PSL2 structure that can be targeted in the subject methods. FIG. 4 illustrates the conservancy of nucleotide sequences of interest containing the PSL2 structure. In some cases, the subject compositions have broad spectrum activity against IAVs, such as activity against 2 or more IAVs selected from H1N1, H3N2 and H5N.

Aspects of the present disclosure include methods for inhibiting influenza A virus (IAV) in a sample. In some embodiments, the method includes contacting a sample comprising viral RNA (vRNA) having a PSL2 motif with an effective amount of an agent that specifically binds the PSL2 motif to inhibit the influenza A virus. In some cases, the sample is in vitro. In certain cases, the sample is in vivo. The vRNA in the sample can be comprised in a virion. In some cases, the vRNA is comprised in a cell, such as a cell infected with the virus particle.

Aspects of the present disclosure include methods for inhibiting influenza A virus (IAV) in a cell. In some embodiments, the method includes contacting a cell comprising viral RNA (vRNA) having a PSL2 motif with an effective amount of an agent that specifically binds the PSL2 motif to inhibit the influenza A virus. In some cases, the cell is in vitro. In certain cases, the cell is in vivo.

In some embodiments, the vRNA in the sample (e.g., cell) comprises PB2 vRNA. As used here, by "PB2 vRNA" is meant viral RNA (e.g., IAV RNA) that includes the conserved RNA structural element called Packaging Stem-Loop 2 (PSL2). The agent can bind to particular sites of the PSL2 motif to disrupt the overall structure of the vRNA thereby inhibiting the virus (see e.g., FIG. 14). In some cases, the agent inhibits the packaging ability of the vRNA, thereby inhibiting the virus. For example, FIG. 1 illustrates RNA secondary structures of wild-type PB2 and packaging mutant vRNAs.

In some embodiments, contacting the sample (e.g., cell) with an agent results in 1 $\log_{10}$ or more titer deficits of the virus, such as 1.5 or more, 2 or more, 2.5 or more, 3 or more, 3.5 or more, 4 or more, 5 or more, 6 or more, 7 or more, 8 or more, 9 or more, 10 $\log_{10}$ or even more titer deficits of the virus.

In some embodiments, contacting the sample (e.g., cell) with an agent results in 2 $\log_{10}$ or more titer deficits of the virus, such as 2.5 or more, 3 or more, 3.5 or more, 4 or more, 5 or more, 6 or more, 7 or more, 8 or more, 9 or more, 10 $\log_{10}$ or even more titer deficits of the virus. In some embodiments, the agent is an oligonucleotide compound (e.g., as described herein) comprising a sequence complementary to a PSL2 motif of the vRNA, or a salt thereof.

In some instances of the methods, binding (e.g., via hybridization) of the oligonucleotide compound (e.g., one of the sequences described above) to the region of PB2 vRNA disrupts the overall secondary RNA structure of the PB2 vRNA. In some cases, binding of the oligonucleotide compound inhibits the packaging ability of the PB2 vRNA, thereby inhibiting the virus. In some cases, the subject compound targets at least part of the region defined by nucleotides 34-87 in the (−)-sense notation of the 5' terminal coding region of the PB2 vRNA. In some cases, the compound targets at least part of the region defined by nucleotides 1-14 in the (−)-sense notation of the 5' terminal coding region of the PB2 vRNA. In some instances of the methods, the method further includes recruiting an RNase to the PSL2 to degrade the vRNA.

Aspects of the present disclosure include a method of treating or preventing influenza A virus infection in a subject. In some embodiments, the method comprises administering to a subject in need thereof a pharmaceutical composition comprising an effective amount of an active agent that binds to a PSL2 motif of a viral RNA (vRNA) (e.g., as described herein). As such, in some cases, the subject is one who has been infected with the virus. In certain cases, the subject is one who is at risk of being infected, or is suspected of being infected with the virus. In some embodiments, the vRNA is a PB2 vRNA.

Any convenient protocol for administering the agent to a subject may be employed. The particular protocol that is employed may vary, e.g., depending on the site of administration and whether the agents are e.g., oligonucleotides, antibodies, proteins, peptides or small molecules. For in vivo protocols, any convenient administration protocol may be employed. Depending upon the identity and binding affinity of the agent, the response desired, the manner of administration, e.g. locally or systemic, intraocular, periocular, retrobalbar, intramuscular, intravenous, intraperitoneal, subcutaneous, subconjunctival, intranasal, topical, eye drops, i.v. s.c., i.p., oral, and the like, the half-life, the number of cells or size of the graft bed or transplanted tissue, various protocols may be employed. In some cases, the agent is administered nasally. In some cases, the agent is administered as an aerosol. In certain cases, the agent is administered by a nebulizer. In certain cases, the agent is administered via the assistance of breathing-assisting devices including but not limited to non-invasive positive pressure ventilation or mechanical ventilation. In certain cases, the agent is administered intravenously. In certain other cases, the agent is administered subcutaneously. In certain cases, the agent is administered by intramuscular injection.

Also provided are pharmaceutical compositions including the subject agents. Any convenient excipients, carriers, etc. can be utilized in the compositions. Pharmaceutically acceptable carriers that find use in the compositions may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. The agent composition may also be lyophilized, for subsequent reconstitution and use. The composition can also include a carrier as described here. Examples of carriers which may be used include, but are not limited to, alum, microparticles, liposomes, and nanoparticles. Any convenient additives can be included in the subject compositions to enhance the delivery of the subject active agent. Additives of interest include, cellular uptake enhancers, carrier proteins, lipids, dendrimer carriers, carbohydrates, and the like.

In some cases, the pharmaceutical composition further includes one or more additional active agents. Active agents of interest include an additional oligonucleotide compound of the present disclosure and any convenient antiviral compounds or drugs of interest. including but not limited to Amantadine, Rimantadine, Zanamivir, Oseltamivir, Peramivir and the like.

Methods for Inhibiting Influenza B Virus

Aspects of the present disclosure include pan-genotypic compositions designed to disrupt an RNA structural element of IBV, which can include a region of genome segment HA.

Aspects of the present disclosure include methods for inhibiting influenza B virus (IBV) in a sample. In some embodiments, the method includes contacting a sample comprising viral RNA (vRNA) having a IBV RNA motif with an effective amount of an agent that specifically binds the IBV HA motif to inhibit the influenza B virus. In some cases, the sample is in vitro. In certain cases, the sample is in vivo. The vRNA in the sample can be comprised in a virion. In some cases, the vRNA is comprised in a cell, such as a cell infected with the virus particle.

Aspects of the present disclosure include methods for inhibiting influenza B virus (IBV) in a cell. In some embodiments, the method includes contacting a cell comprising viral RNA (vRNA) having an IBV RNA motif with an effective amount of an agent that specifically binds IBV RNA motif to inhibit the influenza B virus. In some cases, the cell is in vitro. In certain cases, the cell is in vivo.

In some embodiments, contacting the sample (e.g., cell) with an agent results in 1 $\log_{10}$ or more titer deficits of the virus, such as 1.5 or more, 2 or more, 2.5 or more, 3 or more, 3.5 or more, 4 or more, 5 or more, 6 or more, 7 or more, 8 or more, 9 or more, 10 $\log_{10}$ or even more titer deficits of the virus.

In some embodiments, contacting the sample (e.g., cell) with an agent results in 2 $\log_{10}$ or more titer deficits of the virus, such as 2.5 or more, 3 or more, 3.5 or more, 4 or more, 5 or more, 6 or more, 7 or more, 8 or more, 9 or more, 10 $\log_{10}$ or even more titer deficits of the virus. In some embodiments, the agent is an oligonucleotide compound (e.g., as described herein) comprising a sequence complementary to a IBV RNA motif of the vRNA, or a salt thereof.

In some instances of the methods, binding (e.g., via hybridization) of the oligonucleotide compound (e.g., one of the sequences described above) to the region of IBV vRNA disrupts the overall secondary RNA structure of the IBV vRNA. In some cases, binding of the oligonucleotide compound inhibits the packaging ability of the HA vRNA, thereby inhibiting the virus. In some instances of the methods, the method further includes recruiting an RNase to the IBV vRNA to degrade the vRNA.

Aspects of the present disclosure include a method of treating or preventing influenza B virus infection in a subject. In some embodiments, the method comprises administering to a subject in need thereof a pharmaceutical composition comprising an effective amount of an active agent that binds to a IBV HA RNA motif of a viral RNA. As such, in some cases, the subject is one who has been infected with the virus. In certain cases, the subject is one who is at risk of being infected, or is suspected of being infected with the virus.

Any convenient protocol for administering the agent to a subject may be employed. The particular protocol that is employed may vary, e.g., depending on the site of administration and whether the agents are e.g., oligonucleotides, antibodies, proteins, peptides or small molecules. For in vivo protocols, any convenient administration protocol may be employed. Depending upon the identity and binding affinity of the agent, the response desired, the manner of administration, e.g. locally or systemic, intraocular, periocular, retrobulbar, intramuscular, intravenous, intraperitoneal, subcutaneous, subconjunctival, intranasal, topical, eye drops, i.v. s.c., i.p., oral, and the like, the half-life, the number of cells or size of the graft bed or transplanted tissue, various protocols may be employed. In some cases, the agent is administered nasally. In some cases, the agent is administered as an aerosol. In certain cases, the agent is administered by a nebulizer. In certain cases, the agent is administered via the assistance of breathing-assisting devices including but not limited to non-invasive positive pressure ventilation or mechanical ventilation. In certain cases, the agent is administered intravenously. In certain other cases, the agent is administered subcutaneously. In certain cases, the agent is administered by intramuscular injection.

Also provided are pharmaceutical compositions including the subject agents. Any convenient excipients, carriers, etc. can be utilized in the compositions. Pharmaceutically acceptable carriers that find use in the compositions may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. The agent composition may also be lyophilized, for subsequent reconstitution and use. The composition can also include a carrier as described here. Examples of carriers which may be used include, but are not limited to, alum, microparticles, liposomes, and nanoparticles. Any convenient additives can be included in the subject compositions to enhance the delivery of the subject active agent. Additives of interest include, cellular uptake enhancers, carrier proteins, lipids, dendrimer carriers, carbohydrates, and the like.

In some cases, the pharmaceutical composition further includes one or more additional active agents. Active agents of interest include an additional oligonucleotide compound of the present disclosure and any convenient antiviral compounds or drugs of interest. including but not limited to Amantadine, Rimantadine, Zanamivir, Oseltamivir, Peramivir and the like.

Methods for Inhibiting a Respiratory Synctial Virus (RSV)

As summarized above, aspects of the present disclosure include agents and compositions designed to disrupt an RNA secondary structure of an RSV. Disruption of an RNA secondary structure of a RSV can inhibit the RSV virus.

Methods for Inhibiting a Coronavirus (CoV)

As summarized above, aspects of the present disclosure include agents and compositions designed to disrupt an RNA secondary structure of a coronavirus (CoV). Disruption of an RNA secondary structure of a CoV can inhibit the CoV virus. The agents and compositions are effective across a variety of different types of coronaviruses (CoV) where RNA secondary structures are important in the viral life cycle. In some cases, the subject compositions can be referred to as broad spectrum. As used herein, the term "broad spectrum" refers to the anti-viral activity of a single moiety that is active against two or more different viruses, such as three or more, four or more, five or more, six or more, eight or more, 10 or more different viruses. The two or more different viruses may be selected from different virus sub-groups (e.g., human coronavirus 229E (HCoV-229E), human coronavirus OC43 (HCoV-OC43), SARS-CoV (the causative agent of severe acute respiratory syndrome (SARS)), human coronavirus NL63 (HCoV-NL63, New Haven coronavirus), human coronavirus HKU1, MERS-CoV ("Middle East Respiratory Syndrome Coronavirus" or MERS), and severe acute respiratory syndrome coronavirus 2 (SARS-CoV-2) or COVID-19 (the coronavirus disease 2019).

Figure 1C:
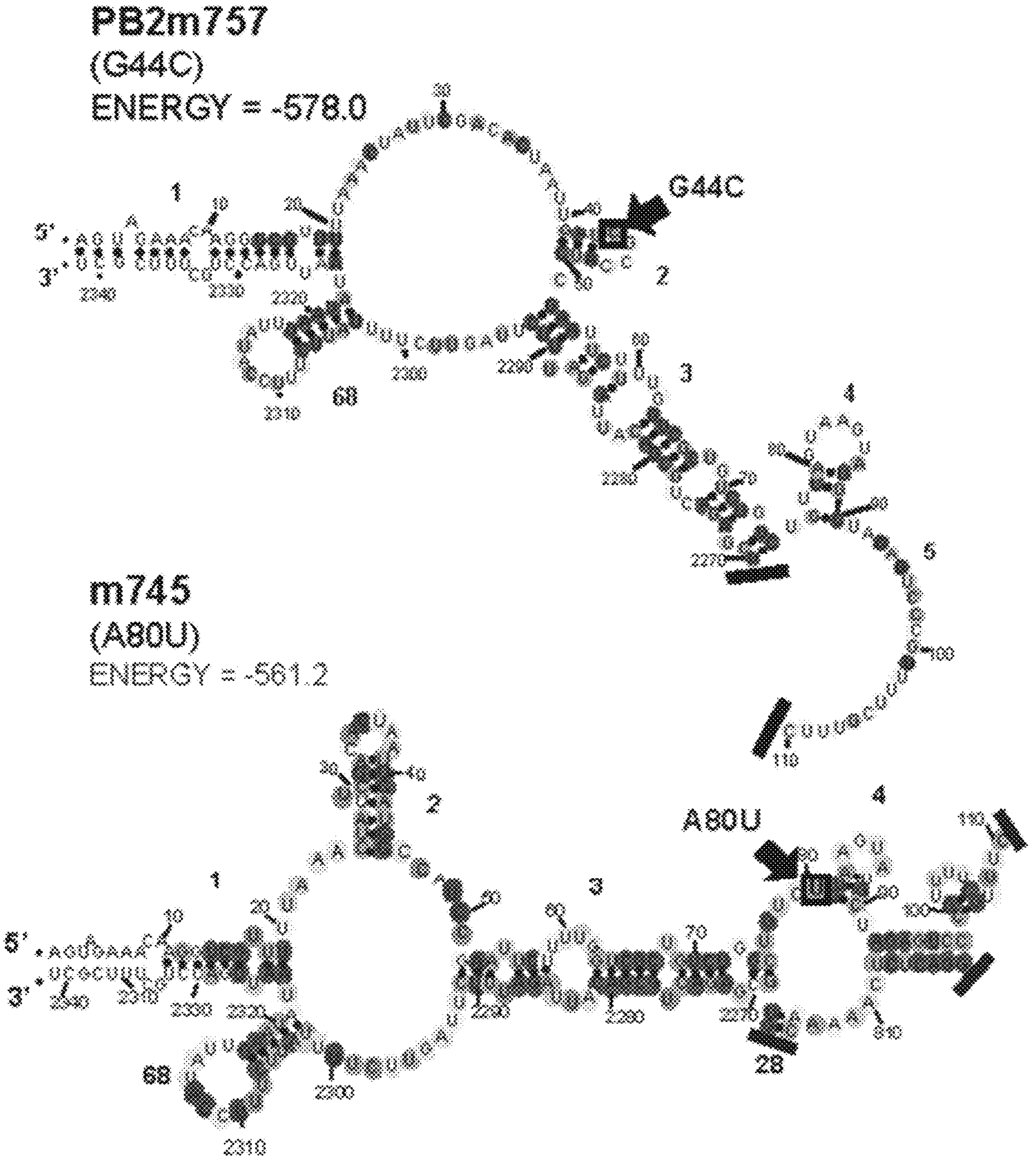
Figures 1D, 1E, 1F:
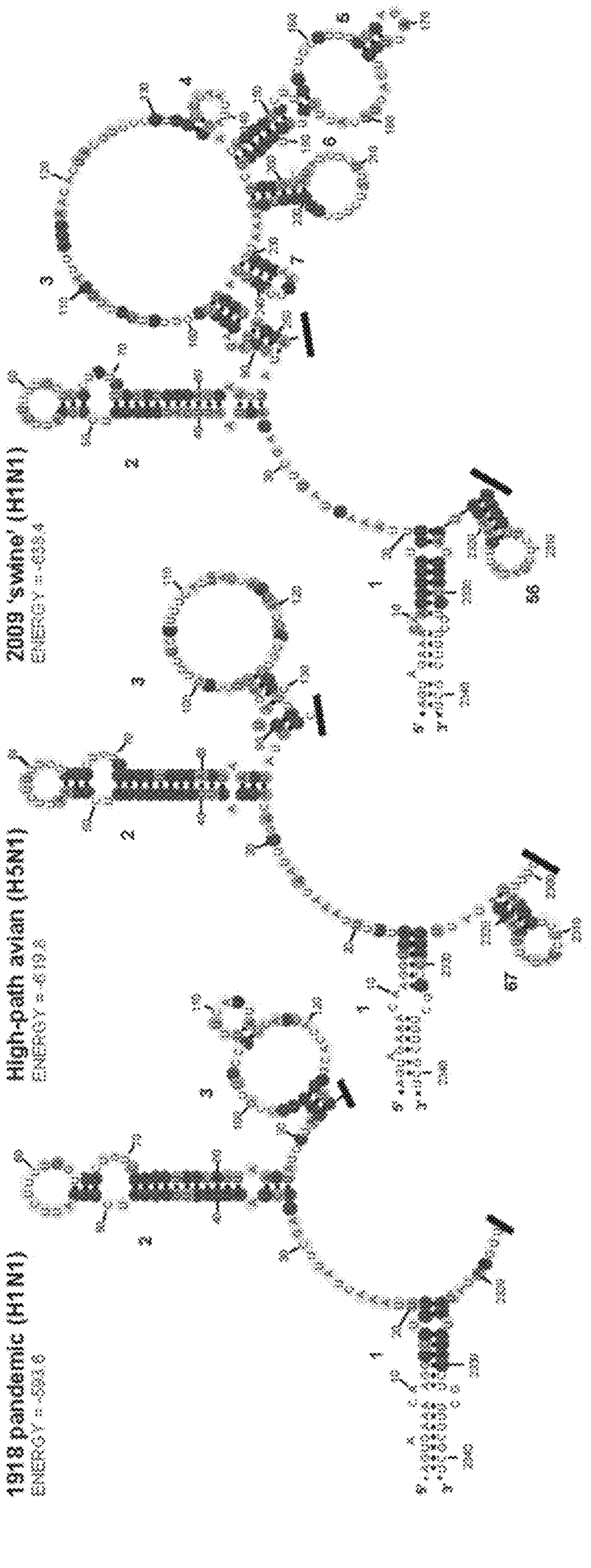
Figure 1G:
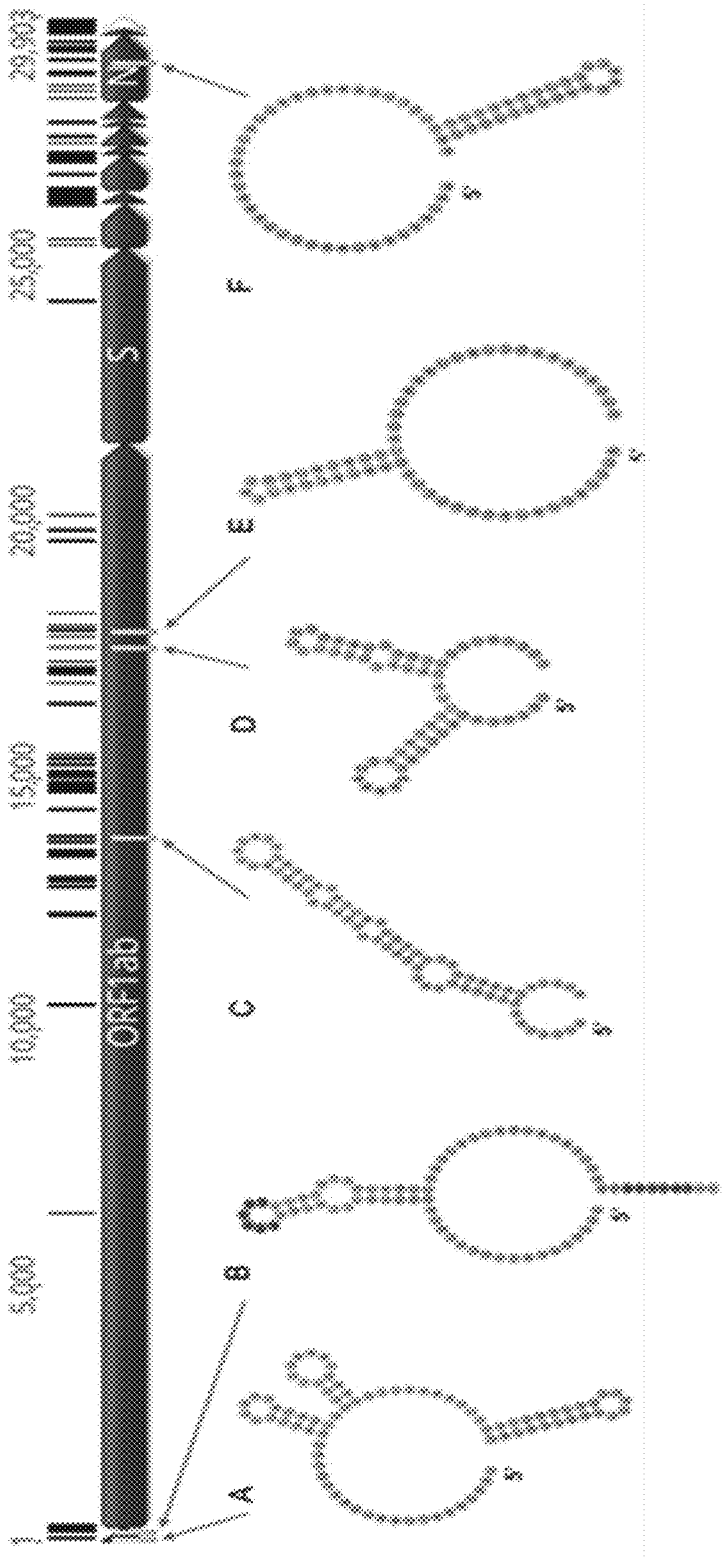
FIG. 1G illustrates predicted RNA secondary structures conserved across corona B viruses.
Figure 3A:
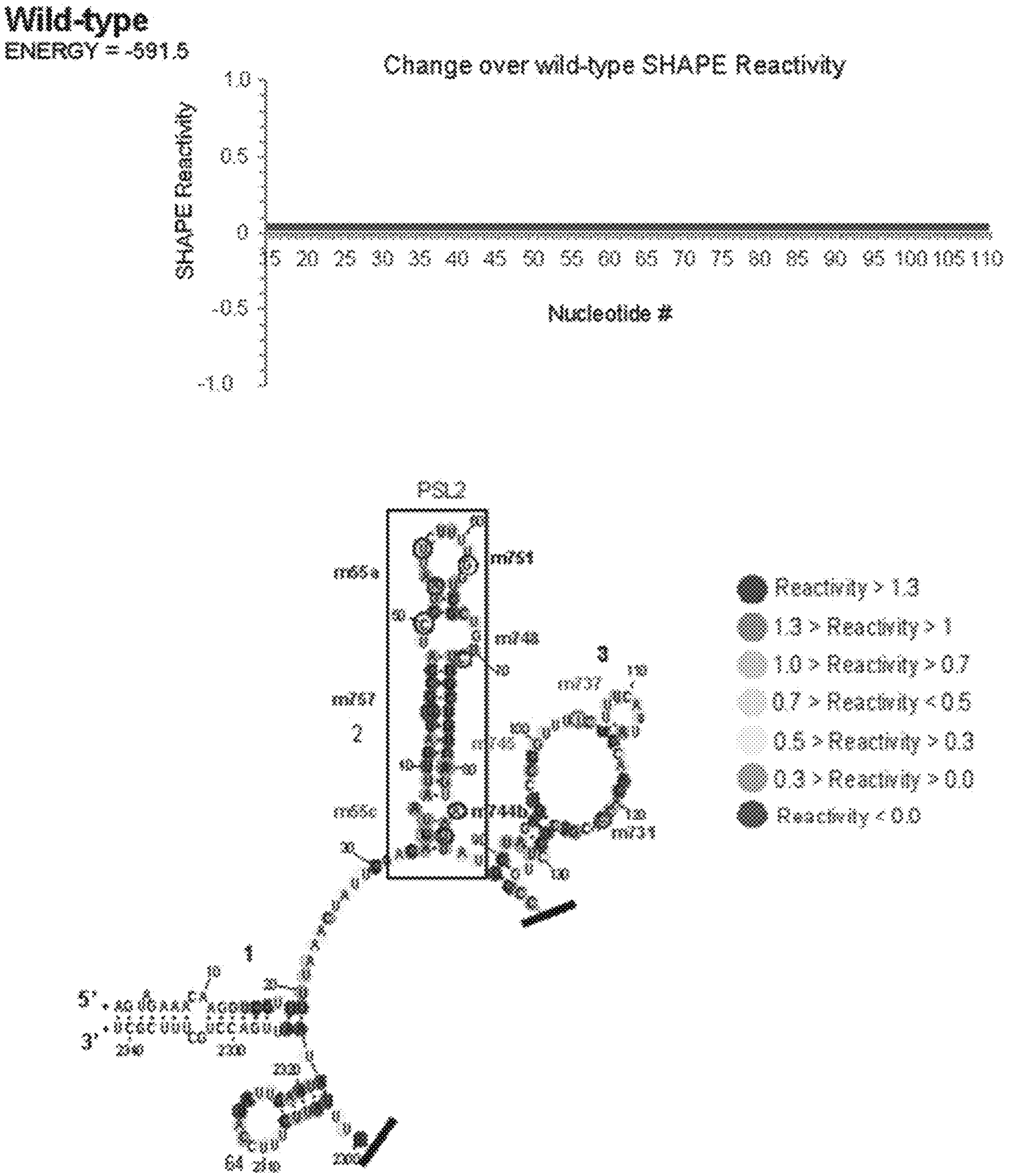
FIG. 3A-FIG. 3E depicts the disruption of wild-type reactivity (SEQ ID NO: 7) by packaging-defective mutations, PB2m744b (SEQ ID NO: 8), PB2m745 (SEQ ID NO: 9), PB2m55c (SEQ ID NO: 10) and PB2m757 (SEQ ID NO: 11).
Figure 3B:
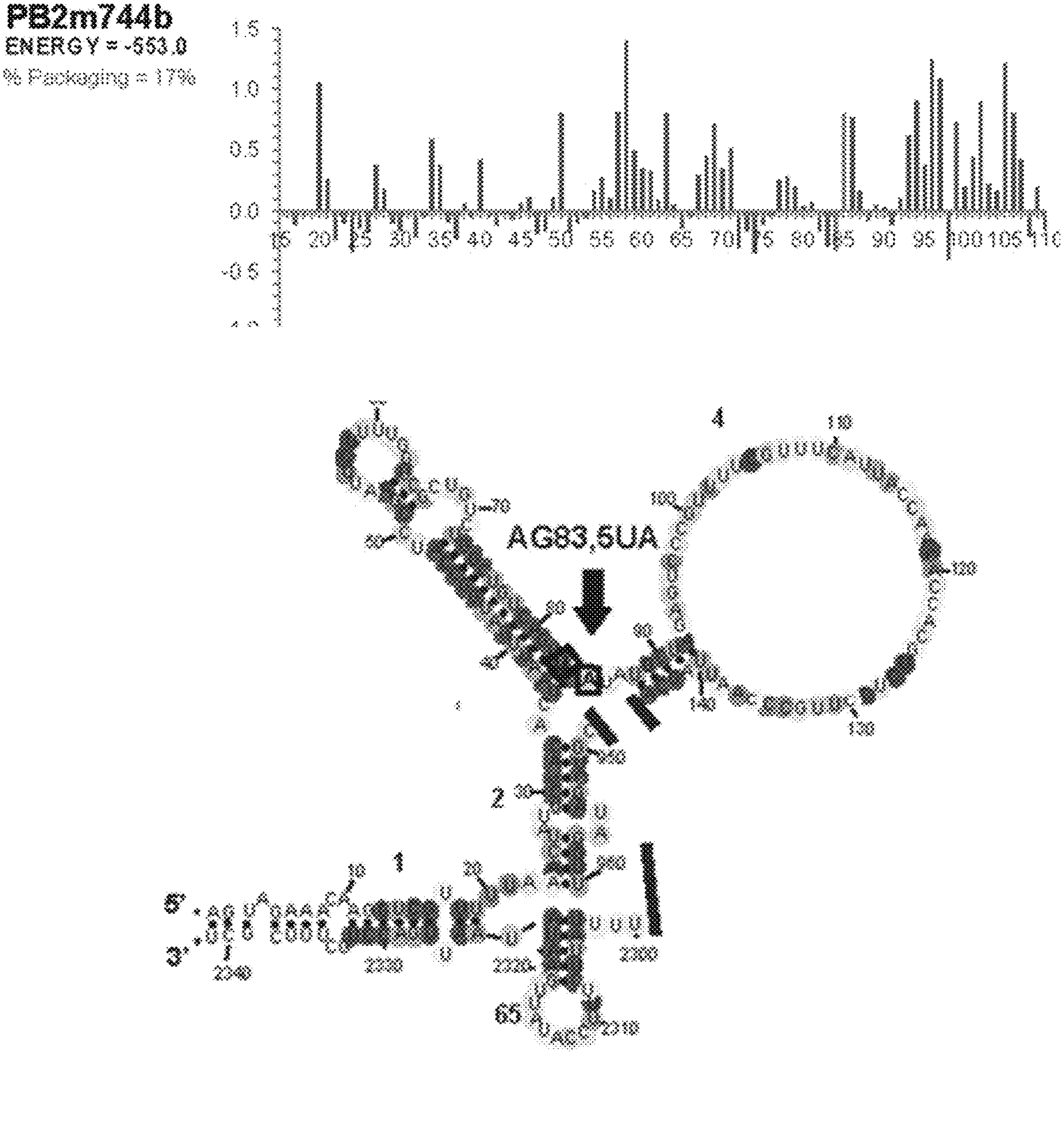
Figure 3C:
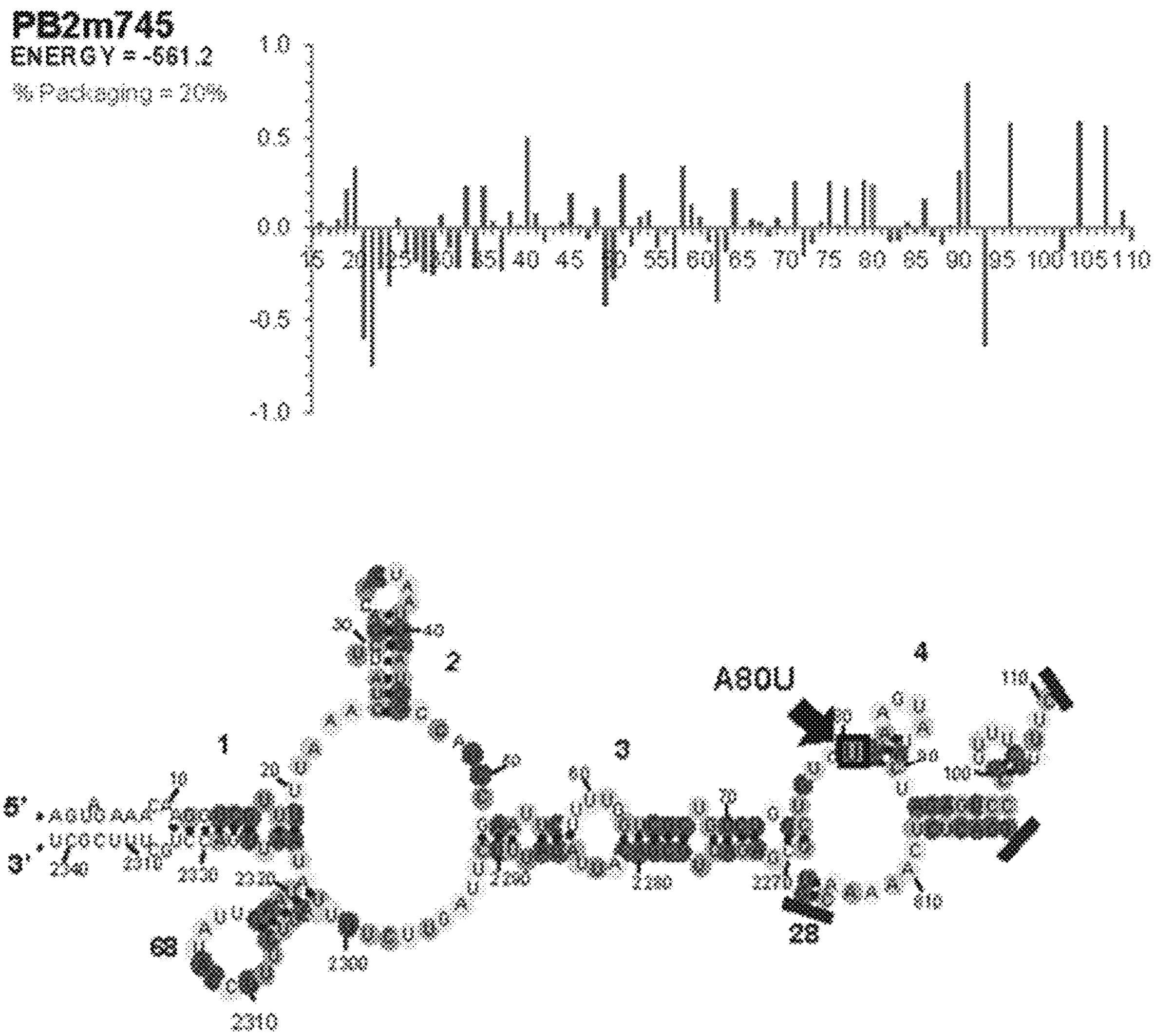
Figure 3D:
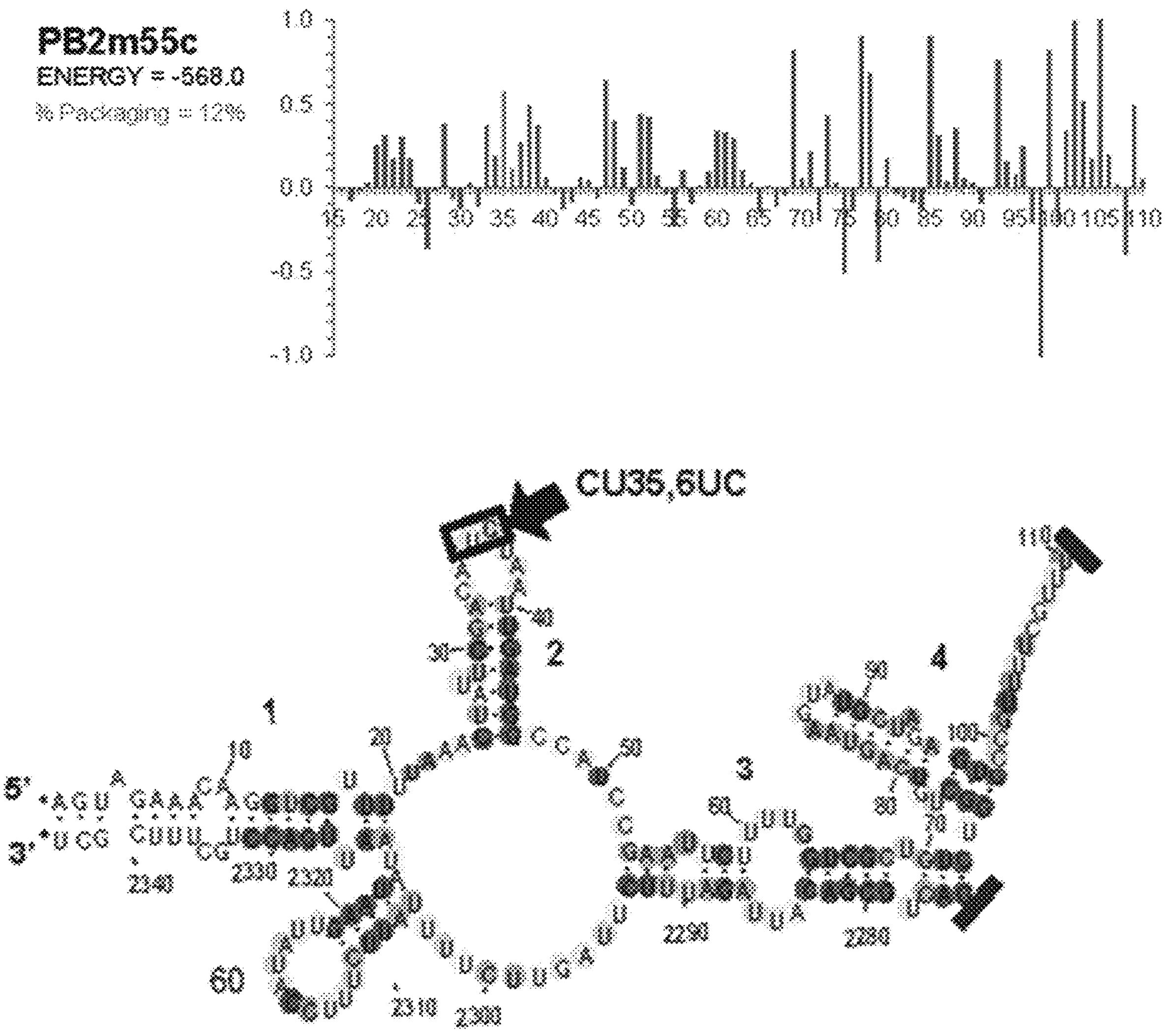
Figure 3E:
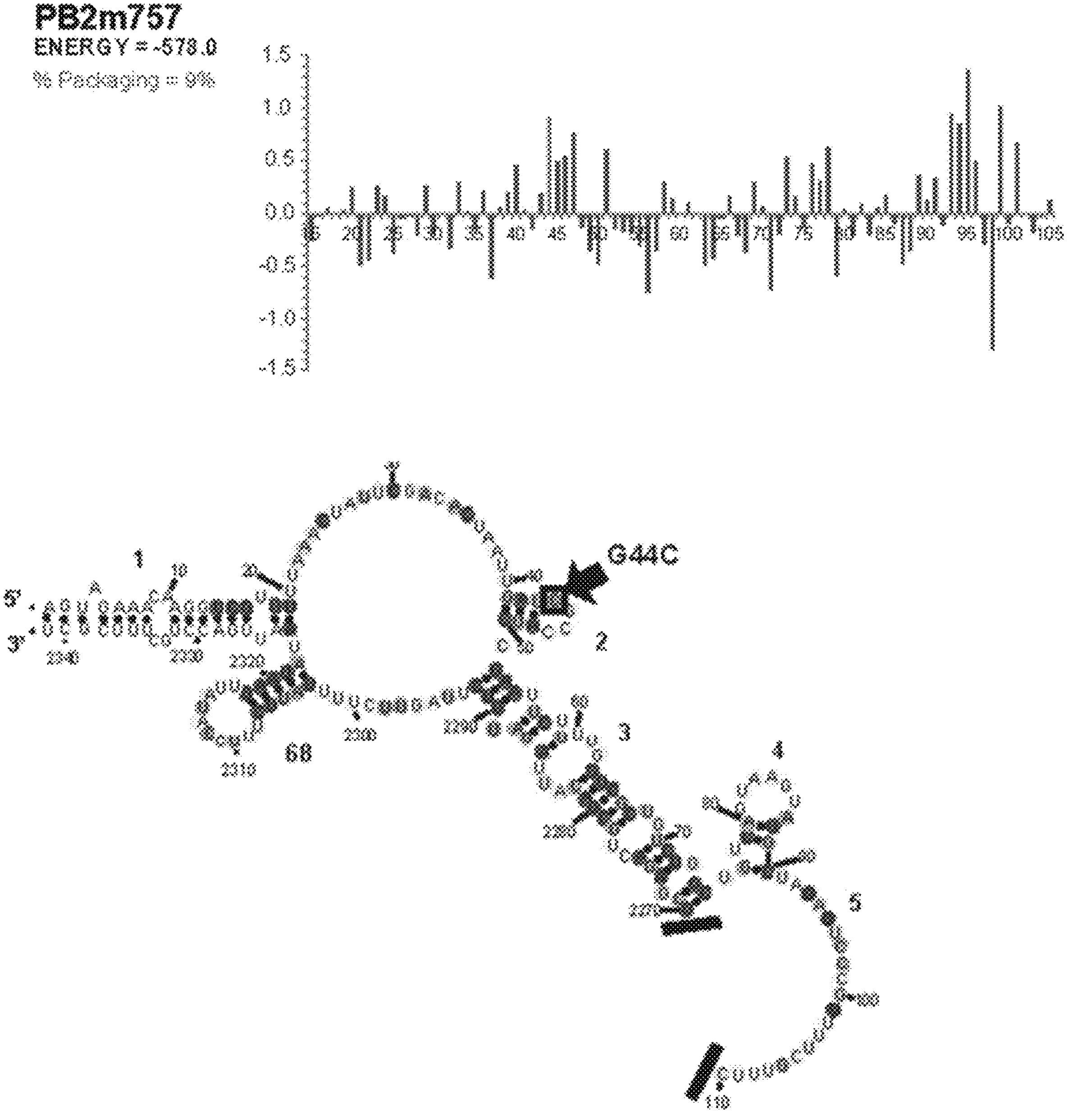

Disruption of an RNA secondary structure of a CoV can dramatically inhibit the CoV. FIG. 1G shows an example of the predicted RNA secondary structures conserved across corona B viruses that can be targeted in the subject methods. In some cases, the subject compositions have broad spectrum activity against CoVs, such as activity against 1 or more CoVs selected from HCoV-299E, HCoV-OC43, SARS-CoV, HCoV-NL63, HKU1, MERS-CoV, and SARS-CoV-2 or COVID-19. In some cases, the target CoV is SARS-CoV-2 or COVID-19. In some cases, the target CoV is SARS-CoV. In some cases, the target CoV is MERS-CoV. In some cases, the subject compositions disrupt a target CoV conserved RNA secondary structure, without induction of caspase or interferon.

Aspects of the present disclosure include methods for inhibiting a coronavirus (CoV) in a sample. In some embodiments, the method includes contacting a sample comprising viral RNA (vRNA) having a conserved RNA secondary structure of CoV with an effective amount of an agent that specifically binds the secondary structure to inhibit the CoV. In some embodiments, the method includes contacting a sample comprising viral RNA (vRNA), having a conserved RNA secondary structure of CoV, with an effective amount of an agent that inhibits a host microRNA (miRNA) interaction with the CoV. In some cases, the miRNA is microRNA 191 (miR191). In some cases, the miRNA can be one of the followings: miR663a, miR-381, miR-744, miR-4508, miR-4730, miR-6777, miR-10396, miR-4749, miR-6787, miR-4706, miR-3675, miR-6810, miR-3675, miR-6812, miR-6796. In some cases, the conserved RNA secondary structure includes the presence of microRNA binding sites. In some cases, the microRNA is miR-191. In some cases, the microRNA can be any of the microRNA listed above with a predicted binding sites in the viral RNA. In some cases, the subject agent or composition is designed to sequester miR191 in cells transfected with a CoV. In some cases, the cells are transfected with a CoV 5' terminal RNA segment linked to a luciferase report. In some cases, the CoV is SARS-CoV-2 or COVID-19.

In some cases, the sample is in vitro. In certain cases, the sample is in vivo. The vRNA in the sample can be comprised in a virion. In some cases, the vRNA is comprised in a cell, such as a cell infected with the virus.

Aspects of the present disclosure include methods for inhibiting a coronavirus (CoV) in a cell. Aspects of the present disclosure include methods for inhibiting a coronavirus (CoV) in a human. In some embodiments, the method includes contacting a cell comprising viral RNA (vRNA) having a conserved RNA secondary structure of CoV with an effective amount of an agent that specifically binds the secondary structure to inhibit the CoV. In some cases, the cell is in vitro. In certain cases, the cell is in vivo. In some embodiments, the agent (e.g., as described herein) can bind to particular sites of the conserved RNA secondary structure motif to disrupt the overall structure of the vRNA thereby inhibiting the virus. In some cases, the agent inhibits the packaging ability of the vRNA, thereby inhibiting the virus.

Agents

Any convenient agents may be utilized as an agent of a target of interest (e.g., PSL2) in the subject methods and compositions. Agents of interest include, but are not limited to, a ligand of PSL-2, a PSL2-binding antibody, a scaffolded protein binder of PSL2, an oligonucleotide, a small molecule, and a peptide; or a fragment, variant, or derivative thereof; or combinations of any of the foregoing.

Antibodies that may be used as agents in connection with the present disclosure can encompass, but are not limited to, monoclonal antibodies, polyclonal antibodies, bispecific antibodies, Fab antibody fragments, $F(ab)_2$ antibody fragments, Fv antibody fragments (e.g., $V_H$ or $V_L$), single chain Fv antibody fragments and dsFv antibody fragments. Furthermore, the antibody molecules may be fully human antibodies, humanized antibodies, or chimeric antibodies. The antibodies that may be used in connection with the present disclosure can include any antibody variable region, mature or unprocessed, linked to any immunoglobulin constant region. Minor variations in the amino acid sequences of antibodies or immunoglobulin molecules are encompassed by the present disclosure, providing that the variations in the amino acid sequence maintain 75% or more, e.g., 80% or more, 90% or more, 95% or more, or 99% or more of the sequence. In particular, conservative amino acid replacements are contemplated. Conservative replacements are those that take place within a family of amino acids that are related in their side chains. Whether an amino acid change results in a functional peptide can be determined by assaying the specific activity of the polypeptide derivative. In some embodiments, the agent is an antibody fragment (e.g., as described herein).

In some embodiments, the agent is a scaffolded polypeptide binder. A scaffold refers to an underlying peptidic framework (e.g., a consensus sequence or structural motif) from which a polypeptide agent arose. The underlying scaffold sequence includes those residues that are fixed and variant residues that may confer on the resulting polypeptide agents different functions, such as specific binding to a target receptor. Such structural motifs may be characterized and compared structurally as a combination of particular secondary and tertiary structural elements, or alternatively, as a comparable primary sequence of amino acid residues. Any convenient scaffolds and scaffolded polypeptides may be utilized as agents in the subject methods. In some embodiments, such agents may be identified utilizing a recombinant screening method such as phage display screening. Scaffolded polypeptide binders of interest include, but are not limited to, synthetic small proteins and recombinant small proteins such as Affibodies.

In some cases, the agent is a small molecule that binds PSL2. Small molecules of interest include, but are not limited to, small organic or inorganic compounds having a molecular weight (MW) of more than 50 and less than about 2,500 daltons (Da), such as more than 50 and less than about 1000 Da, or more than 50 and less than about 500 Da. "Small molecules" encompasses numerous biological and chemical classes, including synthetic, semi-synthetic, or naturally-occurring inorganic or organic molecules, including synthetic, recombinant or naturally-occurring polypeptides and nucleic acids. Small molecules of interest can comprise functional groups necessary for structural interaction with proteins, particularly hydrogen bonding, and can include at least an amine, carbonyl, hydroxyl or carboxyl group, and can contain at least two of the functional chemical groups. The small molecules can comprise cyclical carbon or heterocyclic structures and/or aromatic or polyaromatic structures substituted with one or more of the above functional groups. Small molecules are also found among biomolecules including peptides, saccharides, fatty acids, steroids, purines, pyrimidines, derivatives, structural analogs or combinations thereof.

Oligonucleotide Compounds

In some embodiments, the agent is an oligonucleotide or derivative thereof, or a salt thereof (e.g., a pharmaceutically acceptable salt). In some instances, the oligonucleotide in complementary to a particular segment of target motif (e.g., as described herein). Complementary oligonucleotides that find use in the subject methods will in some cases be at least 5, such at least 6, at least 7 at least 8, at least 9, at least 10, at least 11, about 12, at least 13, at least 14, at least 15, or even more. In some cases, the complementary oligonucleotide is 75 nucleotides or less in length, such as 50 nucleotides or less in length, 45 nucleotides or less in length, 40 nucleotides or less in length, or 35 nucleotides or less in length, where the length is governed by efficiency of inhibition, specificity, including absence of cross-reactivity, and the like. In some cases, the complementary oligonucleotide is 30 nucleotides or less in length, such as 25 nucleotides or less in length, 20 nucleotides or less in length, or 15 nucleotides or less in length, where the length is governed by efficiency of inhibition, specificity, including absence of cross-reactivity, and the like. The present disclosure provides for short oligonucleotides, e.g., of from 7, 8 to 15, or 15 to 16 nucleotides in length, can be strong and selective inhibitors of target function.

In some embodiments, the agent is an oligonucleotide compound comprising at least 5 nucleoside subunits (e.g., at least 6, at least 7, at least 8, at least 9, at least 10, at least 12, at least 14, at least 16, at least 18, or at least 20) complementary to a target motif of a vRNA, or a salt thereof. In certain cases, the linkages of the oligonucleotides are modified phosphate groups, e.g., where one or more oxygens of phosphate has been replaced with a different substituent. Without being bound to any particular theory, such modification can increase resistance of the oligonucleotide to nucleolytic breakdown. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. In some cases, the linkages of the oligonucleotides are modified phosphate groups where one or more of the non-bridging phosphonate oxygen atoms in the linkage has been replaced by a group selected from, S, Se, $BR^a_3$, alkyl, substituted alkyl, aryl, substituted aryl, H, $NR^a_2$, or $OR^b$, where $R^a$ is H, alkyl, substituted alkyl, aryl, substituted aryl, and $R^b$ is H, alkyl, substituted alkyl, aryl or substituted aryl. In certain cases, one or more of the linkages of the oligonucleotide the phosphorous atom is chiral, e.g., a stereogenic center. The stereogenic phosphorus atom can possess either the "R" configuration (referred to herein as Rp), or the "S" configuration (referred to herein as Sp). In certain embodiments, the linkages of the oligonucleotide include one or more stereogenic phosphorus atoms with at least 1%, 5%, 10%, 20%, 30%, 40%, 50%, 60%, 70%, 80%, 90%, 95%, or more enantiomeric excess of the Sp configuration. In certain other, the linkages of the oligonucleotide include one or more stereogenic phosphorus atoms with at least 1%, 5%, 10%, 20%, 30%, 40%, 50%, 60%, 70%, 80%, 90%, 95%, or more enantiomeric excess of the Rp configuration.

In certain embodiments, one or more of the linkages of the oligonucleotide are selected from methylphosphonate, P3'→N5' phosphoramidate, N3'→P5' phosphoramidate, N3'→P5' thiophosphoramidate, phosphorodithioate and phosphorothioate linkages. In certain cases, one or more linkages of the oligonucleotide is a phosphorothioate linkage. In certain cases, the phosphorus atom in one or more of the phosphorothioate linkages is chiral. In some cases, the chiral phosphorus atom in the one or more phosphorothioate linkages has Rp configuration. In some cases, the chiral phosphorus atom in the one or more phosphorothioate linkages has Sp configuration. In certain embodiments, the linkages of the oligonucleotide include one or more phosphorothioate linkages with at least 1%, 5%, 10%, 20%, 30%, 40%, 50%, 60%, 70%, 80%, 90%, 95%, or more enantiomeric excess of the Sp configuration. In certain other embodiments, the linkages of the oligonucleotide includes one or more phosphorothioates with at least 1%, 5%, 10%, 20%, 30%, 40%, 50%, 60%, 70%, 80%, 90%, 95%, or more enantiomeric excess of the Rp configuration.

In certain instances, the oligonucleotide sequence is a bridged nucleic acid (e.g., as described herein). In certain instances, the oligonucleotide sequence includes one or more bridged nucleic acid nucleotides, such as 2 or more, 3 or more, 4 or more, 5 or more, 6 or more, 7 or more, 8 or more, 9 or more, 10 or more, or even more.

In certain instances, the oligonucleotide sequence is a locked nucleic acid. In certain instances, the oligonucleotide sequence includes one or more locked nucleic acid nucleotides, such as 2 or more, 3 or more, 4 or more, 5 or more, 6 or more, 7 or more, 8 or more, 9 or more, 10 or more, or even more.

In certain instances, the oligonucleotide sequence is an ethylene-bridged nucleic acid (ENA). In certain instances, the oligonucleotide sequence includes one or more ENA nucleotides, such as 2 or more, 3 or more, 4 or more, 5 or more, 6 or more, 7 or more, 8 or more, 9 or more, 10 or more, or even more.

In certain instances, the oligonucleotide sequence is constrained ethyl (cEt) nucleic acid. In certain instances, the oligonucleotide sequence includes one or more cEt nucleotides, such as 2 or more, 3 or more, 4 or more, 5 or more, 6 or more, 7 or more, 8 or more, 9 or more, 10 or more, or even more. In certain instances, the oligonucleotide sequence includes one or more (S)-constrained ethyl nucleic acids, such as 2 or more, 3 or more, 4 or more, 5 or more, 6 or more, 7 or more, 8 or more, 9 or more, 10 or more, or even more. In certain instances, the oligonucleotide sequence includes one or more (R)-constrained ethyl nucleic acids, such as 2 or more, 3 or more, 4 or more, 5 or more, 6 or more, 7 or more, 8 or more, 9 or more, 10 or more, or even more. In certain instances, the oligonucleotide sequence includes one or more ribose modifications. In some cases, the oligonucleotide sequence includes one or more 2'-modified ribose sugars (also referred to herein as 2'-modified nucleotides). In certain instances, the oligonucleotide sequence includes one or more 2'-modified nucleotides, such as 2 or more, 3 or more, 4 or more, 5 or more, 6 or more, 7 or more, 8 or more, 9 or more, 10 or more, or even more. 2'-modified nucleotides, include, but are not limited to moieties with 2' substituents selected from alkyl, allyl, amino, azido, fluoro, thio, O-alkyl, e.g., O-methyl, O-allyl, $OCF_3$, O—$(CH_2)_2$O—$CH_3$ (e.g., 2'-O-methoxyethyl (MOE)), O—$(CH_2)_2SCH_3$, )—$(CH_2)_2$—$ONR_2$, and O—$CH_2$C(O)—$NR_2$, where each R is independently selected from H, alkyl, and substituted alkyl. In certain instances, the oligonucleotide sequence includes one or more 2'-O-methoxyethyl (MOE) modifications, such as 2 or more, 3 or more, 4 or more, 5 or more, 6 or more, 7 or more, 8 or more, 9 or more, 10 or more, or even more.

In some embodiments, the agent is an oligonucleotide that comprises at least 5 deoxyribonucleotide units (e.g., units complementary to a target motif, e.g., PSL2 motif) (e.g., least 6, at least 7, at least 8, at least 9, at least 10, at least 12, at least 14, at least 16, at least 18, at least 20) and is capable of recruiting an RNase. In some case, the oligonucleotide recruits an RNase to catalyze the degradation of the target vRNA into smaller components. Any convenient methods and moieties for recruiting an RNase can be incorporated into the subject agents (e.g., oligonucleotides). In some instances, the oligonucleotide agent further includes a sequence that recruits an RNase of interest. It is understood that unless indicated otherwise, an oligonucleotide sequence as depicted herein is meant to include DNA sequences, RNA sequences (e.g., where U can optionally replace T), mixed RNA/DNA sequences, and analogs thereof, including analogs where one or more nucleotides of the sequence are modified nucleotides, such as BNA analogs, LNA analogs, ENA analogs, cEt analogs, 2'-modified analogs, and/or analogs where one or more internucleoside linkages are replaced, e.g., with a non-naturally occurring linkage such as a phosphorothioate, phosphorodithioate, phosphoramidate or thiophosphoramidate linkage. It will be understood that in embodiments where one or more of the linkages of the oligonucleotide include a chiral phosphorous atom, e.g., a stereogenic center, the stereogenic phosphorus atom can possess either the "R" configuration (referred to herein as Rp), or the "S" configuration (referred to herein as Sp).

In some embodiments, the active agent is a compound comprising an oligonucleotide sequence comprising at least 8 nucleoside subunits complementary to the region of PB2 vRNA. In some embodiments, the active agent is a compound comprising an oligonucleotide sequence comprising at least 8 and 20 or less (e.g., 15 or less) nucleoside subunits complementary to the region of PB2 vRNA.

A specific region or regions of the endogenous strand PSL2 sequence is chosen to be complemented by the oligonucleotide agent. Selection of a specific sequence for the oligonucleotide may use an empirical method, where based on the structural analysis (e.g., as described herein) several candidate sequences are assayed for inhibition of the target IAV in an in vitro or animal model. A combination of oligonucleotides and sequences may also be used, where several regions of the target PSL2 are selected for antisense complementation.

In some embodiments, the oligonucleotide comprises a sequence selected from:

```
                                    (SEQ ID NO: 45)
5' ACCAAAAGAAT 3';

                                    (SEQ ID NO: 46)
5' TGGCCATCAAT 3';

                                    (SEQ ID NO: 47)
5' TAGCATACTTA 3';

                                    (SEQ ID NO: 48)
5' CCAAAAGA 3';

                                    (SEQ ID NO: 49)
5' CATACTTA 3';

                                    (SEQ ID NO: 50)
5' CAGACACGACCAAAA 3';

                                    (SEQ ID NO: 51)
5' TACTTACTGACAGCC 3';

                                    (SEQ ID NO: 52)
5' AGACACGACCAAAAG 3';

                                    (SEQ ID NO: 53)
5' ACCAAAAGAAT 3';

                                    (SEQ ID NO: 54)
5' TGGCCATCAAT 3';

                                    (SEQ ID NO: 55)
5' TAGCATACTTA 3';

                                    (SEQ ID NO: 56)
5' CGACCAAAAGAATTC 3';

                                    (SEQ ID NO: 57)
5' CGACCAAAAGAATTC 3';

                                    (SEQ ID NO: 58)
5' GATGGCCATCAATTA 3';

                                    (SEQ ID NO: 59)
5' GATGGCCATCAATTA 3';

                                    (SEQ ID NO: 60)
5' TCTAGCATACTTACT 3';

                                    (SEQ ID NO: 61)
5' TCTAGCATACTTACT 3';

                                    (SEQ ID NO: 62)
5' GAATTCGGATGGCCA 3';

                                    (SEQ ID NO: 63)
5' GGCCATCAATTAGTG 3';

                                    (SEQ ID NO: 64)
5' TTCGGATGGCCATCA 3';

                                    (SEQ ID NO: 65)
5' AGCCAGACAGCGA 3';
```

-continued

```
and

                                    (SEQ ID NO: 66)
5' GACAGCCAGACAGCA 3'.
```

In certain embodiments, the oligonucleotide comprises the sequence: 5' ACCAAAAGAAT 3' (SEQ ID NO:45). In certain embodiments, the oligonucleotide comprises the sequence: 5' TGGCCATCAAT 3' (SEQ ID NO:46). In certain embodiments, the oligonucleotide comprises the sequence: 5' TAGCATACTTA 3' (SEQ ID NO:47). In certain embodiments, the oligonucleotide comprises the sequence: 5' CCAAAAGA 3' (SEQ ID NO:48). In certain embodiments, the oligonucleotide comprises the sequence: 5' CATACTTA 3' (SEQ ID NO:49). In certain embodiments, the oligonucleotide comprises the sequence: 5' CAGACACGACCAAAA 3' (SEQ ID NO:50). In certain embodiments, the oligonucleotide comprises the sequence: 5' TACTTACTGACAGCC 3' (SEQ ID NO:51). In certain embodiments, the oligonucleotide comprises the sequence: 5' AGACACGACCAAAAG 3' (SEQ ID NO:52). In certain embodiments, the oligonucleotide comprises the sequence: 5' ACCAAAAGAAT 3' (SEQ ID NO:53). In certain embodiments, the oligonucleotide comprises the sequence: 5' TGGCCATCAAT 3' (SEQ ID NO:54). In certain embodiments, the oligonucleotide comprises the sequence: 5' TAGCATACTTA 3' (SEQ ID NO:55). In certain embodiments, the oligonucleotide comprises the sequence: 5' CGACCAAAAGAATTC 3' (SEQ ID NO:56). In certain embodiments, the oligonucleotide comprises the sequence: 5' CGACCAAAAGAATTC 3' (SEQ ID NO:57). In certain embodiments, the oligonucleotide comprises the sequence: 5' GATGGCCATCAATTA 3' (SEQ ID NO:58). In certain embodiments, the oligonucleotide comprises the sequence: 5' GATGGCCATCAATTA 3' (SEQ ID NO:59). In certain embodiments, the oligonucleotide comprises the sequence: 5' TCTAGCATACTTACT 3' (SEQ ID NO:60). In certain embodiments, the oligonucleotide comprises the sequence: 5' TCTAGCATACTTACT 3' (SEQ ID NO:61). In certain embodiments, the oligonucleotide comprises the sequence: 5' GAATTCGGATGGCCA 3' (SEQ ID NO:62). In certain embodiments, the oligonucleotide comprises the sequence: 5' GGCCATCAATTAGTG 3' (SEQ ID NO:63). In certain embodiments, the oligonucleotide comprises the sequence: 5' TTCGGATGGCCATCA 3' (SEQ ID NO:64). In certain embodiments, the oligonucleotide comprises the sequence: 5' AGCCAGACAGCGA 3' (SEQ ID NO:65). In certain embodiments, the oligonucleotide comprises the sequence: 5' GACAGCCAGACAGCA 3' (SEQ ID NO:66).

In some embodiments, the oligonucleotide comprises a sequence selected from:

```
                                    (SEQ ID NO: 98)
5'CGACCAAAAGAATT 3';
and

                                    (SEQ ID NO: 99)
5'GACCAAAAGAATTCGG 3'.
```

In certain embodiments, the oligonucleotide comprises the sequence: 5'CGACCAAAAGAATT 3' (SEQ ID NO:98). In certain embodiments, the oligonucleotide comprises the sequence: 5'GACCAAAAGAATTCGG 3' (SEQ ID NO:99).

In some embodiments, the oligonucleotide comprises a sequence selected from:

```
                         (SEQ ID NO: 100)
5' AGCATACTTACTGACA 3';

                         (SEQ ID NO: 101)
5' CATACTTACTGACA 3';

                         (SEQ ID NO: 102)
5' ATACTTACTGACAG 3';

                          (SEQ ID NO: 103
5' CATACTTACTGACAGC 3');

                         (SEQ ID NO: 104)
5' AGACAGCGACCAAAAG 3';
and

                         (SEQ ID NO: 105)
5' ACAGCGACCAAAAG.
```

In certain embodiments, the oligonucleotide comprises the sequence: 5' AGCATACTTACTGACA 3' (SEQ ID NO:100). In certain embodiments, the oligonucleotide comprises the sequence: 5' CATACTTACTGACA 3' (SEQ ID NO:101). In certain embodiments, the oligonucleotide comprises the sequence: 5' ATACTTACTGACAG 3' (SEQ ID NO: 102). In certain embodiments, the oligonucleotide comprises the sequence 5' CATACTTACTGACAGC 3' (SEQ ID NO: 103). In certain embodiments, the oligonucleotide comprises the sequence: 5' AGACAGCGACCAAAAG 3' (SEQ ID NO: 104). In certain embodiments, the oligonucleotide comprises the sequence: 5' ACAGCGACCAAAAG (SEQ ID NO: 105).

In some embodiments, the oligonucleotide comprises a sequence selected from:

```
                         (SEQ ID NO: 106)
5' CAGCCAGACAGCGAC 3';

                         (SEQ ID NO: 107)
5' CAGCCAGACAGCGA 3';

                         (SEQ ID NO: 108)
5' ACAGCCAGACAGCGA 3';
and

                         (SEQ ID NO: 109)
5' GACAGCCAGACAGCG 3'.
```

In certain embodiments, the oligonucleotide comprises the sequence: 5'CAGCCAGACAGCGAC 3' (SEQ ID NO:106). In certain embodiments, the oligonucleotide comprises the sequence: 5'CAGCCAGACAGCGA 3' (SEQ ID NO:107). In certain embodiments, the oligonucleotide comprises the sequence: 5'ACAGCCAGACAGCGA 3' (SEQ ID NO:108). In certain embodiments, the oligonucleotide comprises the sequence:

```
                         (SEQ ID NO: 109)
5' GACAGCCAGACAGCG 3'.
```

In some embodiments, the oligonucleotide comprises a sequence selected from:

```
                          (SEQ ID NO: 62)
5' GAATTCGGATGGCCA 3';
```

-continued

```
                          (SEQ ID NO: 65)
5' AGCCAGACAGCGA 3';

                         (SEQ ID NO: 110)
5' CATCAATTAGTGTCG 3';

                         (SEQ ID NO: 111)
5' CCATCAATTAGTGTCG 3';

                         (SEQ ID NO: 112)
5' GCCATCAATTAGTGTG 3';

                         (SEQ ID NO: 113)
5' AAGAATTCGGATGGC 3';

                         (SEQ ID NO: 114)
5' CAGACAGCGACCAA 3';
and

                         (SEQ ID NO: 115)
5' TGACAGCCAGACAGC 3'.
```

In certain embodiments, the oligonucleotide comprises the sequence: 5' GAATTCGGATGGCCA 3' (SEQ ID NO:62). In certain embodiments, the oligonucleotide comprises the sequence: 5' AGCCAGACAGCGA 3' (SEQ ID NO:65). In certain embodiments, the oligonucleotide comprises the sequence: 5' CATCAATTAGTGTCG 3' (SEQ ID NO:110). In certain embodiments, the oligonucleotide comprises the sequence: 5' CCATCAATTAGTGTCG 3' (SEQ ID NO:111). In certain embodiments, the oligonucleotide comprises the sequence: 5' GCCATCAATTAGTGTG 3' (SEQ ID NO:112). In certain embodiments, the oligonucleotide comprises the sequence: 5' AAGAATTCGGATGGC 3' (SEQ ID NO:113). In certain embodiments, the oligonucleotide comprises the sequence: 5' CAGACAGCGACCAA 3' (SEQ ID NO:114). In certain embodiments, the oligonucleotide comprises the sequence: 5' TGACAGCCAGACAGC 3' (SEQ ID NO:115). In some instances, binding (e.g., via hybridization) of the oligonucleotide compound (e.g., one of the sequences described above) to the region of PB2 vRNA disrupts the overall secondary RNA structure of the PB2 vRNA. In certain cases, binding of the oligonucleotide compound to the region of PB2 vRNA inhibits the packaging ability of the PB2 vRNA, thereby inhibiting the virus.

In some embodiments, the oligonucleotide comprises a sequence selected from (COV2):

```
                                        (SEQ ID NO: 192)
5' GGTGACATGGTACCACATATATCACGTC 3'

                                        (SEQ ID NO: 193)
5' GACGTGATATATGTGGTACCATGTCACC 3'

                                        (SEQ ID NO: 194)
5' GACGTGATATATGTGG 3'

                                        (SEQ ID NO: 195)
5' CGTGATATATGTGGTA 3'

                                        (SEQ ID NO: 196)
5' GATATGTGGTACCAT 3'

                                        (SEQ ID NO: 197)
5' TGGTACCATGTCAC 3'

                                        (SEQ ID NO: 198)
5' GTCACTAAGAAATCTGCTGCTGAGG 3'

                                        (SEQ ID NO: 199)
5' CCTCAGCAGCAGATTTCTTAGTGAC 3'

                                        (SEQ ID NO: 200)
5' CCTCAGCAGCAGATTT 3'
```

-continued (SEQ ID NO: 201)
5' TCAGCAGCAGATTTC 3'

(SEQ ID NO: 202)
5' CAGCAGCAGATTTC 3'

(SEQ ID NO: 203)
5' CAGATTTCTTAGTGAC 3'

(SEQ ID NO: 204)
5' TGCTTACGGTTTCGTCCGTGTTGCA 3'

(SEQ ID NO: 205)
5' TGCAACACGGACGAAACCGTAAGCA 3'

(SEQ ID NO: 206)
5' TGCAACACGGACGAAA 3'

(SEQ ID NO: 207)
5' GCAACACGGACGAAAC 3'

(SEQ ID NO: 208)
5' ACACGGACGAAACCG 3'

(SEQ ID NO: 209)
5' GGACGAAACCCGTAA 3'

(SEQ ID NO: 210)
5' ACGAAACCGTAAGCA 3'

(SEQ ID NO: 211)
5' ACGAAACCGTAAGCA 3'

(SEQ ID NO: 212)
5' GCAACACGGACGAAAC 3'

(SEQ ID NO: 213)
5' GCAACACGGACGAAA 3'

(SEQ ID NO: 214)
5' GCAACACGGACGAAAC 3'

(SEQ ID NO: 215)
5' GCAACACGGACGAAAC 3'

(SEQ ID NO: 216)
5' GCAACACGGACGAAAC 3'

(SEQ ID NO: 217)
5' GCAACACGGACGAA 3'

(SEQ ID NO: 218)
5' ACACGGACGAAACCG 3'

(SEQ ID NO: 219)
5' ACACGGACGAAACCG 3'

(SEQ ID NO: 220)
5' AACACGGACGAAACCG 3'

(SEQ ID NO: 221)
5' AACACGGACGAAACCG 3'

(SEQ ID NO: 222)
5' ACGAAACCGTAAGCA 3'

(SEQ ID NO: 223)
5' ACGAAACCGTAAGCA 3'

(SEQ ID NO: 224)
5' ATAGGTCCAGACATGTTCC 3'

(SEQ ID NO: 225)
5' GGAACATGTCTGGACCTAT 3'

(SEQ ID NO: 226)
5' AACATGTCTGGACCTA 3'

(SEQ ID NO: 227)
5' ACATGTCTGGACCTAT 3'

-continued (SEQ ID NO: 228)
5' TATGACTATGTCATATTCA 3'

(SEQ ID NO: 229)
5' AGTGAATATGACATAGTCATATT 3'

(SEQ ID NO: 230)
5' TGAATATGACATAGT 3'

(SEQ ID NO: 231)
5' AATATGACATAGTC 3'

(SEQ ID NO: 232)
5' GATCTCTTGTAGATCTGTTCTCTAAACGAACTTTAAAATCTGTG 3'

(SEQ ID NO: 233)
5' CACAGATTTTAAAGTTCGTTTAGAGAACAGATCTACAAGAGATC 3'

(SEQ ID NO: 234)
5' CACAGATTTTAAAGTT 3'

(SEQ ID NO: 235)
5' CACAGATTTTAAAGTT 3'

(SEQ ID NO: 236)
5' CAGATTTTAAAGTTCG 3'

(SEQ ID NO: 237)
5' GATTTTAAAGTTCGT 3'

(SEQ ID NO: 238)
5' TAAAGTTCGTTTAGA 3'

(SEQ ID NO: 239)
5' AAAGTTCGTTTAGA 3'

(SEQ ID NO: 240)
5' TCGTTTAGAGAACAGAT 3'

(SEQ ID NO: 241)
5' AGAGAACAGATCTACA 3'

(SEQ ID NO: 242)
5' AGATCTACAAGAGA 3'

(SEQ ID NO: 243)
5' ATCTACAAGAGATC 3'

(SEQ ID NO: 244)
5' AGATTTTAAAGTTCGT 3'

(SEQ ID NO: 245)
5' GATTTTAAAGTTCGT 3'

(SEQ ID NO: 246)
5' GATTTTAAAGTTCGT 3'

(SEQ ID NO: 247)
5' AGATTTTAAAGTTCG 3'

(SEQ ID NO: 248)
5' TCGTTTAGAGAACAGAT 3'

(SEQ ID NO: 249)
5' TTCGTTTAGAGAACAG 3'

(SEQ ID NO: 250)
5' TTCGTTTAGAGAACAG 3'

(SEQ ID NO: 251)
5' GAGAAAACACACGTCCAACTCAGTTTGCCTG 3'

(SEQ ID NO: 252)
5' CAGGCAAACTGAGTTGGACGTGTGTTTTCTC 3'

(SEQ ID NO: 253)
5' CAGGCAAACTGAGTTG 3'

(SEQ ID NO: 254)
5' CAGGCAAACTGAGTTG 3'

-continued (SEQ ID NO: 255)
5' CAGGCAAACTGAGT 3'

(SEQ ID NO: 256)
5' CAAACTGAGTTGGACG 3'

(SEQ ID NO: 257)
5' AAACTGAGTTGGAC 3'

(SEQ ID NO: 258)
5' AAACTGAGTTGGACGT 3'

(SEQ ID NO: 259)
5' GAGTTGGACGTGTGT 3'

(SEQ ID NO: 260)
5' TTGGACGTGTGTTTTC 3'

(SEQ ID NO: 261)
5' GGACGTGTGTTTTCTC 3'

(SEQ ID NO: 262)
5' GGTTTCGTCCGGGTGTGACCG 3'

(SEQ ID NO: 263)
5' TTTCGGTCACACCCGGACGAAACCTAGAT 3'

(SEQ ID NO: 264)
5' TTTCGGTCACACCCGG 3'

(SEQ ID NO: 265)
5' CGGTCACACCCGGACG 3'

(SEQ ID NO: 266)
5' TCACACCCGGACGAAA 3'

(SEQ ID NO: 267)
5' CACCCGGACGAAAC 3'

(SEQ ID NO: 268)
5' CACCCGGACGAAACC 3'

(SEQ ID NO: 269)
5' CACCCGGACGAAACCT 3'

(SEQ ID NO: 270)
5' CCGGACGAAACCTA 3'

(SEQ ID NO: 21)
5' CGGTCACACCCGGACGA 3'

(SEQ ID NO: 272)
5' CGGTCACACCCGGACG 3'

(SEQ ID NO: 273)
5' CGGTCACACCCGGACG 3'

(SEQ ID NO: 274)
5' CGGTCACACCCGGACG 3'

(SEQ ID NO: 275)
5' GTCACACCCGGACG 3'

(SEQ ID NO: 276)
5' GTCACACCCGGACG 3'

(SEQ ID NO: 277)
5' CACCCGGACGAAACC 3'

(SEQ ID NO: 278)
5' CACCCGGACGAAACC 3'

(SEQ ID NO: 279)
5' CACCCGGACGAAAC 3'

(SEQ ID NO: 280)
5' CACACCCGGACGAAAC 3'

(SEQ ID NO: 281)
5' CACACCCGGACGAAA 3'

-continued (SEQ ID NO: 282)
5' CACACCCGGACGAA 3'

(SEQ ID NO: 283)
5' CGAGGCCACGCGGAGTACGATCGA 3'

(SEQ ID NO: 284)
5' ACTCGATCGTACTCCGCGTGGCCTCGGTGAA 3'

(SEQ ID NO: 285)
5' TCGATCGTACTCCGC 3'

(SEQ ID NO: 286)
5' TCGATCGTACTCCG 3'

(SEQ ID NO: 287)
5' ATCGTACTCCGCGTG 3'

(SEQ ID NO: 288)
5' ACTCGATCGTACTC 3'

(SEQ ID NO: 289)
5' CGTGGCCTCGGTGAA 3'

(SEQ ID NO: 290)
5' GTGGCCTCGGTGAA 3'

(SEQ ID NO: 291)
5' TAGTTAACTTTAATCTCACATAGCAATCTTTAATC 3'

(SEQ ID NO: 292)
5' GATTAAAGATTGCTATGTGAGATTAAAGTTAACTA 3'

(SEQ ID NO: 293)
5' GATTAAAGATTGCTAT 3'

(SEQ ID NO: 294)
5' TAAAGATTGCTATGTG 3'

(SEQ ID NO: 295)
5' AAGATTGCTATGTGAG 3'

(SEQ ID NO: 296)
5' GCTATGTGAGTTAAAG 3'

(SEQ ID NO: 297)
5' TATGTGAGTTAAAGTT 3'

(SEQ ID NO: 298)
5' TGTGAGTTAAAGTTAA 3'

(SEQ ID NO: 299)
5' CGTGCTACAACTTCCTCAAGGAACAACATTGCCAAAAGGCTTCTACG
CAG 3'

(SEQ ID NO: 300)
5' CTGCGTAGAAGCCTTTTGGCAATGTTGTTCCTTGAGGAAGTTGTAGC
ACG 3'

(SEQ ID NO: 301)
5' TCGTAGAAGCCTTTTG 3'

(SEQ ID NO: 302)
5' CGTAGAAGCCTTTTGGC 3'

(SEQ ID NO: 303)
5' TAGAAGCCTTTTGGCA 3'

(SEQ ID NO: 304)
5' AAGCCTTTTGGCAATG 3'

(SEQ ID NO: 305)
5' TTGGCAATGTTGTTCC 3'

(SEQ ID NO: 306)
5' GCAATGTTGTTCCT 3'

(SEQ ID NO: 307)
5' CTTGAGGAAGTTGT 3'

-continued (SEQ ID NO: 308)
5' AGGAAGTTGTAGCACG 3'

(SEQ ID NO: 309)
5' GCCTATATGGAAGAGCCCTAATGTGTAAAATTAATTTTAGTAG 3'

(SEQ ID NO: 310)
5' CTACTAAAATTAATTTTACACATTAGGGCTCTTCCATATAGGC 3'

(SEQ ID NO: 311)
5' CTACTAAAATTAATT 3'

(SEQ ID NO: 312)
5' TACTAAAATTAATTT 3'

(SEQ ID NO: 313)
5' ACTAAAATTAATTT 3'

(SEQ ID NO: 314)
5' AATTAATTTTACACAT 3'

(SEQ ID NO: 315)
5' ATTTTACACATTAGGG 3'

(SEQ ID NO: 316)
5' TACACATTAGGGCTC 3'

(SEQ ID NO: 317)
5' ACATTAGGGCTCTTC 3'

(SEQ ID NO: 318)
5' TAGGGCTCTTCCATA 3'

(SEQ ID NO: 319)
5' GCTCTTCCATATAGG 3'

(SEQ ID NO: 320)
5' AGGTAAGATGGAGAGCCTT 3'

(SEQ ID NO: 321)
5' AAGGCTCTCCATCTTACCTTTCGG 3'

(SEQ ID NO: 322)
5' AAGGCTCTCCATCTTA 3'

(SEQ ID NO: 323)
5' AAGGCTCTCCATCT 3'

(SEQ ID NO: 324)
5' GCTCTCCATCTTACCT 3'

(SEQ ID NO: 325)
5' TCCATCTTACCTTTCG 3'

(SEQ ID NO: 326)
5' TGTGTAACATTAGGGAGG 3'

(SEQ ID NO: 327)
5' CCTCCCTAATGTTACACA 3'

(SEQ ID NO: 328)
5' CCTCCCTAATGTTACA 3'

(SEQ ID NO: 329)
5' CTCCCTAATGTTACAG 3'

(SEQ ID NO: 330)
5' CTCCCTAATGTTACAG 3'

(SEQ ID NO: 331)
5' TCATGTGGTAGTGTTGGTTTTA 3'

(SEQ ID NO: 332)
5' TAAAACCAACACTACCACATGA 3'

(SEQ ID NO: 333)
5' TAAAACCAACACTACC 3'

(SEQ ID NO: 334)
5' AAACCAACACTACCAC 3'

-continued (SEQ ID NO: 335)
5' AAACCAACACTACCAC 3'

(SEQ ID NO: 336)
5' ACCAACACTACCACAT 3'

(SEQ ID NO: 336)
5' CAACACTACCACATGA 3'

In some embodiments, the oligonucleotide comprises a sequence selected from: (IAV PSL2 (+)

(SEQ ID NO: 337)
5' TGTCAGTAAGTATG 3'

(SEQ ID NO: 338)
5' CTGGCTGTCAGTAAGT 3'

(SEQ ID NO: 339)
5' TCGCTGTCTGGCTGT 3'

(SEQ ID NO: 340)
5' CTTTTGGTCGCTGTCT 3'

(SEQ ID NO: 341)
5' CTTTTGGTCGCTGT 3'

(SEQ ID NO: 342)
5' TTGGTCGCTGTCTGGC 3'

(SEQ ID NO: 343)
5' TTGGTCGCTGTCTG 3'

(SEQ ID NO: 344)
5' GAATTCTTTTGGTCGC 3'

(SEQ ID NO: 345)
5' GAATTCTTTTGGTCG 3'

(SEQ ID NO: 346)
5' AATTCTTTTGGTCGC 3'

(SEQ ID NO: 347)
5' CGAATTCTTTTGGTCG 3'

(SEQ ID NO: 348)
5' ACACTAATTGATGGC 3'

(SEQ ID NO: 349)
5' AATTGATGGCCAT 3'

In some embodiments, the oligonucleotide comprises a sequence selected from: (IBV (−)

(SEQ ID NO: 350)
5' CCACAAAATGAAGGCA 3'

(SEQ ID NO: 351)
5' CACAAAATGAAGGCA 3'

(SEQ ID NO: 352)
5' CACAAAATGAAGGC 3'

(SEQ ID NO: 353)
5' CAATAATTGTACTA 3'

(SEQ ID NO: 354)
5' CAATAATTGTACTA 3'

(SEQ ID NO: 355)
5' CAATAATTGTACTA 3'

(SEQ ID NO: 356)
5' CAATAATTGTACTAC 3'

(SEQ ID NO: 357)
5' CAATAATTGTACTAC 3'

-continued (SEQ ID NO: 358)
5' TGTACTACTCATGGTA 3'

(SEQ ID NO: 359)
5' TGTACTACTCATGGTA 3'

(SEQ ID NO: 360)
5' TGTACTACTCATGGTA 3'

(SEQ ID NO: 361)
5' GTACTACTCATGGT 3'

(SEQ ID NO: 362)
5' TTGTACTACTCATGG 3'

(SEQ ID NO: 363)
5' CATGGTAGTAACATC 3'

(SEQ ID NO: 364)
5' CTCATGGTAGTAACATC 3'

(SEQ ID NO: 365)
5' CTCATGGTAGTAACAT 3'

(SEQ ID NO: 366)
5' CTCATGGTAGTAACAT 3'

(SEQ ID NO: 367)
5' ACTCATGGTAGTAACA 3'

(SEQ ID NO: 368)
5' ACTCATGGTAGTAACA 3'

(SEQ ID NO: 369)
5' ACTCATGGTAGTAAC 3'

(SEQ ID NO: 370)
5' ACTCATGGTAGTAA 3'

(SEQ ID NO: 371)
5' CAATGCAGATCGAAT 3'

(SEQ ID NO: 372)
5' CAATGCAGATCGAAT 3'

(SEQ ID NO: 373)
5' GATTGCCTTCACGAAA 3'

(SEQ ID NO: 374)
5 GATTGCCTTCACGAAA 3'

In some embodiments, the oligonucleotide comprises a sequence selected from: (IBV (+)

(SEQ ID NO: 375)
5' GCCTTCATTTTGTG 3'

(SEQ ID NO: 376)
5' ATTGCCTTCATTTTGT 3'

(SEQ ID NO: 377)
5' ATTGCCTTCATTTTGT 3'

(SEQ ID NO: 378)
5' TAGTACAATTATTGCC 3'

(SEQ ID NO: 379)
5' AGTACAATTATTGCC 3'

(SEQ ID NO: 380)
5' GTACAATTATTGCCTT 3'

(SEQ ID NO: 381)
5' ACCATGAGTAGTACA 3'

(SEQ ID NO: 382)
5' CATGAGTAGTACAAT 3'

-continued (SEQ ID NO: 383)
5' GATGTTACTACCATGAG 3'

(SEQ ID NO: 384)
5' ATGTTACTACCATGAG 3'

(SEQ ID NO: 385)
5' CATTGGATGTTACTAC 3'

(SEQ ID NO: 386)
5' ATTGGATGTTACTACC 3'

(SEQ ID NO: 387)
5' ATTGGATGTTACTAC 3'

(SEQ ID NO: 388)
5' TTTCGTGAAGGCAATC 3'

(SEQ ID NO: 389)
5' TCGTGAAGGCAATC 3'

In some embodiments, the oligonucleotide comprises a sequence selected from: (miRNA targeting sequences)

(SEQ ID NO: 390)
5' GGTTTCGTCCGTGTT 3'

(SEQ ID NO: 391)
5' GTTTCGTCCGTGTT 3'

(SEQ ID NO: 392)
5' GCTGTCGCCCGTGTC 3'

(SEQ ID NO: 393)
5' GCTGTCGCCCGTGTC 3'

(SEQ ID NO: 394)
5' GCTGTCGCCCGTGTC 3'

(SEQ ID NO: 395)
5' GCTGTCGCCCGTGT 3'

(SEQ ID NO: 396)
5' TTCGTCCGTG 3'

(SEQ ID NO: 397)
5' TTCGTCCGTG 3'

(SEQ ID NO: 398)
5' TTCGTCCGTG 3'

(SEQ ID NO: 399)
5' CCCACCCAC 3'

(SEQ ID NO: 400)
5' CCCACCCAC 3'

(SEQ ID NO: 401)
5' CCCACCCAC 3'

(SEQ ID NO: 402)
5' TTTCGTCCGT 3'

(SEQ ID NO: 403)
5' TTTCGTCCGT 3'

(SEQ ID NO: 404)
5' TTTCGTCCGT 3'

(SEQ ID NO: 405)
5' CCCCACCCAC 3'

(SEQ ID NO: 406)
5' CCCCACCCAC 3'

(SEQ ID NO: 407)
5' CCCCACCCAC 3'

-continued (SEQ ID NO: 408)
5' TTTCGTCCGTGT 3'

(SEQ ID NO: 409)
5' TTTCGTCCGTGT 3'

(SEQ ID NO: 410)
5' TTTCGTCCGTGT 3'

(SEQ ID NO: 411)
5' TTCCATCCATGT 3'

(SEQ ID NO: 412)
5' TTCCATCCATGT 3'

(SEQ ID NO: 413)
5' TTCCATCCATGT 3'

(SEQ ID NO: 414)
5' TTCCATCCATGT 3'

(SEQ ID NO: 415)
5' GTTTCGTCCGTGTT 3'

(SEQ ID NO: 416)
5' GTTTCGTCCGTGTT 3'

(SEQ ID NO: 417)
5' GTTTCGTCCGTGTT 3'

(SEQ ID NO: 418)
5' GTTTCGGCCATGTG 3'

(SEQ ID NO: 419)
5' CGTCCGTGTT 3'

(SEQ ID NO: 420)
5' CGTCCGTGTT 3'

(SEQ ID NO: 421)
5' CGTCCGTGTT 3'

(SEQ ID NO: 422)
5' CGTCCGTGTT 3'

(SEQ ID NO: 423)
5' CCTCCGTGTC 3'

(SEQ ID NO: 424)
5' CCTCCGTGTC 3'

(SEQ ID NO: 425)
5' CCTCCGTGTC 3'

(SEQ ID NO: 426)
5' TCCGTGTTGC 3'

(SEQ ID NO: 427)
5' TCCGTGTTGC 3'

(SEQ ID NO: 428)
5' TCCGTGTTGC 3'

(SEQ ID NO: 429)
5' TCCGTCTTGC 3'

(SEQ ID NO: 430)
5' TCCGTCTTGC 3

(SEQ ID NO: 431)
5' TCCGTTTGC 3'

(SEQ ID NO: 432)
5' TTTCGTCCGTGTT 3'

(SEQ ID NO: 433)
5' TTTCGTCCGTGTT 3'

(SEQ ID NO: 434)
5' TTTCCTCTATGTT 3'

-continued (SEQ ID NO: 435)
5' TTTCCTCTATGTT 3'

(SEQ ID NO: 436)
5' GTTTCGTCCGTGT 3'

(SEQ ID NO: 437)
5' GGTTTCGTCCGTGTT 3'

(SEQ ID NO: 438)
5' GGTTTCGTCCGTGTT 3'

(SEQ ID NO: 439)
5' AAGTACGTCCTACTT 3'

(SEQ ID NO: 440)
5' GGTTTCGTCC 3'

(SEQ ID NO: 441)
5' GGTTTCGTCC 3'

(SEQ ID NO: 442)
5' TGGGTTTCGTCCGTT 3'

(SEQ ID NO: 443)
5' TTTTGGGATTCCGT 3'

(SEQ ID NO: 444)
5' GCTTTTGGGATTCCGT 3'

(SEQ ID NO: 445)
5' GCTTTTGGGATTCCGT 3'

(SEQ ID NO: 446)
5' AGCTGCTTTTGGGATT 3'

(SEQ ID NO: 447)
5' GAGCTGCTTTTGGGAT 3'

(SEQ ID NO: 448)
5' CTGCTTTTGGGATTCC 3'

(SEQ ID NO: 449)
5' TGCTTTTGGGATTC 3'

(SEQ ID NO: 450)
5' AGCTGCTTTTGGGATT 3'

(SEQ ID NO: 451)
5' AGCTGCTTTTGGGA 3'

(SEQ ID NO: 452)
5' CAGCTGCTTTTGGGAT 3'

(SEQ ID NO: 453)
5' AGCTGCTTTTGGGATT 3'

(SEQ ID NO: 454)
5' AGCTGCTTTTGGGA 3'

(SEQ ID NO: 455)
5' AGCTGCTTTTGGGA 3'

(SEQ ID NO: 456)
5' AGCTGCTTTTGGGATT 3'

(SEQ ID NO: 457)
5' TGCTTTTGGGATTC 3'

(SEQ ID NO: 458)
5' GCGGCGCCCCGCCT 3'

(SEQ ID NO: 459)
5' GCGGCGCCCCGCCT 3'

(SEQ ID NO: 460)
5' CGGTCCCGCGGCGCCCCGCCT 3'

(SEQ ID NO: 461)
5' TTTGGGCTTCCTCGCT 3'

-continued (SEQ ID NO: 462)
5' TTTGGGCTTCCTCG 3'

(SEQ ID NO: 463)
5' TTTGGGCTTCCTCG 3'

(SEQ ID NO: 464)
5' TGGGCTTCCTCGCT 3'

(SEQ ID NO: 465)
5' ATATACTTTGGGCTTC 3'

(SEQ ID NO: 466)
5' ATATACTTTGGGCTTC 3'

(SEQ ID NO: 467)
5' ATATACTTTGGGCT 3'

(SEQ ID NO: 468)
5' ATATACTTTGGGCTT 3'

(SEQ ID NO: 469)
5' TAGCCCTAGCCCCGCA 3'

(SEQ ID NO: 470)
5' TAGCCCTAGCCCCGCA 3'

(SEQ ID NO: 471)
5' TAGCCCTAGCCCCG 3'

(SEQ ID NO: 472)
5' TGCTGTTAGCCCTA 3'

(SEQ ID NO: 473)
5' TGCTGTTAGCCCTA 3'

(SEQ ID NO: 474)
5' GTGTTAGCCCTAGCC 3'

(SEQ ID NO: 475)
5' GCGCCCAGCCCCGC 3'

(SEQ ID NO: 476)
5' GCGCCCAGCCCCGC 3'

(SEQ ID NO: 477)
5' CGCGCGCCCAGCCC 3'

(SEQ ID NO: 478)
5' CGCGCGCCCAGCCCCGC 3'

(SEQ ID NO: 479)
5' TGGCATGGAATGGG 3'

(SEQ ID NO: 480)
5' ATGGAATGGGCTCCGC 3'

(SEQ ID NO: 481)
5' ATGGAATGGGCTCC 3'

(SEQ ID NO: 482)
5' AATGGGCTCCGCCAG 3'

(SEQ ID NO: 483)
5' AATGGGCTCCGCCAG 3'

(SEQ ID NO: 484)
5' AATGGGCTCCGCCA 3'

(SEQ ID NO: 485)
5' AATGGGCTCCGCCA 3'

(SEQ ID NO: 486)
5' CTTACCCGAGGCGGTC 3'

(SEQ ID NO: 487)
5' TTACCCGAGGCGGT 3'

(SEQ ID NO: 488)
5' ACCGTACCTTACCCGA 3'

-continued (SEQ ID NO: 489)
5' CGTACCTTACCCGA 3'

(SEQ ID NO: 490)
5' CTCCGAGCCCCGCC 3'

(SEQ ID NO: 491)
5' CCCGGCTCCGAGCCCCGCC 3'

(SEQ ID NO: 492)
5' TGGCCTGTCCCCGCA 3'

(SEQ ID NO: 493)
5' TGGCCTGTCCCCGCA 3'

(SEQ ID NO: 494)
5' GATGCCCTGGCCTG 3'

(SEQ ID NO: 495)
5' GATGCCCTGGCCTG 3'

(SEQ ID NO: 496)
5' GCAGCCAGCTCTAC 3'

(SEQ ID NO: 497)
5' GCAGCCAGCTCTAC 3'

(SEQ ID NO: 498)
5' AGCCAGCTCTACCC 3'

(SEQ ID NO: 499)
5' AGCTCTACCCCCGCCA 3'

(SEQ ID NO: 500)
5' AGCTCTACCCCCGCCA 3'

(SEQ ID NO: 501)
5' AAAGCAGCGCCCACTT 3'

(SEQ ID NO: 502)
5' ACTTCCTCCCCGCT 3'

(SEQ ID NO: 503)
5' CTACAGAAGCCCCATA 3'

(SEQ ID NO: 504)
5' CTACAGAAGCCCCATA 3'

(SEQ ID NO: 505)
5' GAAATCTCTACAGAAG 3'

(SEQ ID NO: 506)
5' GAAATCTCTACAGAAG 3'

(SEQ ID NO: 507)
5' TGATCCCTGTCCCCAT 3'

(SEQ ID NO: 508)
5' ATGCTGATCCCTGTC 3'

(SEQ ID NO: 509)
5' GCCATGCTGATCCCTGTCCCCAT 3'

(SEQ ID NO: 510)
5' CCATCTCACCCCAT 3'

(SEQ ID NO: 511)
5' GCTGCTCCTCCCCAT 3'

(SEQ ID NO: 512)
5' TCTCCAACCCCACAA 3'

(SEQ ID NO: 513)
5' CTCCAACCCCACAA 3'

(SEQ ID NO: 514)
5' CAGCCAGCTCTCCAA 3'

(SEQ ID NO: 515)
5' AGCCAGCTCTCCAA 3'

In some embodiments, the oligonucleotide comprises a sequence selected from: (Negative-strand targeted LNA)

```
                                    (SEQ ID NO: 516)
5' ATCTGTTCTCTAAACGA 3'

                                    (SEQ ID NO: 517)
5' ATCTGTTCTCTAAACG 3'

                                    (SEQ ID NO: 518)
5' AGATCTGTTCTCTAAA 3'

                                    (SEQ ID NO: 519)
5' TCTCTAAACGAACTTT 3'

                                    (SEQ ID NO: 520)
5' TCTCTAAACGAACTTT 3'

                                    (SEQ ID NO: 521)
5' CTCTAAACGAACTTTA 3'

                                    (SEQ ID NO: 522)
5' ACTTTAAAATCTGT 3'

                                    (SEQ ID NO: 523)
5' GGTTTCGTCCGTGTT 3'

                                    (SEQ ID NO: 524)
5' GGTTTCGTCCGTGTT 3'

                                    (SEQ ID NO: 525)
5' GGTTTCGTCCGTGTT 3'

                                    (SEQ ID NO: 526)
5' TGCTTACGGTTTCGTCC 3'

                                    (SEQ ID NO: 527)
5' GTTTCGTCCGTGTTGC 3'

                                    (SEQ ID NO: 528)
5' TAGGTTTCGTCCGG 3'

                                    (SEQ ID NO: 529)
5' TCGTCCGGGTGTGA 3'

                                    (SEQ ID NO: 530)
5' TTCGTCCGGGTGTGA 3'

                                    (SEQ ID NO: 531)
5' TTTCGTCCGGGTGTGA 3'

                                    (SEQ ID NO: 532)
5' AGGTTTCGTCCGGGT 3'

                                    (SEQ ID NO: 533)
5' AGGTTTCGTCCGGG 3'

                                    (SEQ ID NO: 534)
5' AGGTTTCGTCCGGGT 3'

                                    (SEQ ID NO: 535)
5' TTTCGTCCGGGTGTG 3'

                                    (SEQ ID NO: 536)
5' AGGCCACGCGGAGTA 3'

                                    (SEQ ID NO: 537)
5' CACGCGGAGTACGATC 3'
```

The oligonucleotide sequences can include any convenient number of DNA, RNA BNA, LNA, ENA, cEt, 2'-modified nucleotides, or other chemically modified nucleotides. In some instances of the oligonucleotide sequences described herein, the sequence is a mixed RNA/DNA sequence. In some instances of the oligonucleotide sequences described herein, the sequence is a mixed BNA/DNA sequence. In some instances of the oligonucleotide sequences described herein, the sequence is a mixed BNA/RNA sequence. In some instances of the oligonucleotide sequences described herein, the sequence includes only BNA nucleotides. In some instances of the oligonucleotide sequences described herein, the sequence is a mixed LNA/DNA sequence. In some instances of the oligonucleotide sequences described herein, the sequence is a mixed LNA/RNA sequence. In some instances of the oligonucleotide sequences described herein, the sequence includes only LNA nucleotides. In some instances of the oligonucleotide sequences described herein, the sequence is a mixed ENA/DNA sequence. In some instances of the oligonucleotide sequences described herein, the sequence is a mixed ENA/RNA sequence. In some instances of the oligonucleotide sequences described herein, the sequence includes only ENA nucleotides. In some instances of the oligonucleotide sequences described herein, the sequence is a mixed cEt/DNA sequence. In some instances of the oligonucleotide sequences described herein, the sequence is a mixed cEt/RNA sequence. In some instances of the oligonucleotide sequences described herein, the sequence includes only cEt nucleotides. In some instances of the oligonucleotide sequences described herein, the sequence is a mixed 2'-modified nucleotide/DNA sequence. In some instances of the oligonucleotide sequences described herein, the sequence is a mixed 2'-modified nucleotide/RNA sequence. In some instances of the oligonucleotide sequences described herein, the sequence includes only 2'-modified nucleotides. In some instances of the oligonucleotide sequences described herein, the sequence includes only DNA nucleotides. In some instances of the oligonucleotide sequences described herein, the sequence includes only RNA nucleotides.

In certain instances, the subject oligonucleotide has one of the following arrangements of types of nucleotide in the sequence (e.g., one of SEQ ID NOs:45-66, or SEQ ID Nos: 98-115):

A;
A-B-A;
A-B-A-B-A;
A-B-A-B-A-B-A;
A-B-A-B-A-B-A-B-A;
B;
B-A-B;
B-A-B-A-B;
B-A-B-A-B-A-B; or
B-A-B-A-B-A-B-A-A;

where each A is independently a sequence of modified nucleotides, and each B is a sequence of DNA nucleotides. In certain instances, A is a sequence of modified nucleotides where the ribose moiety is modified to include a modification selected from BNA, LNA, ENA, cEt, and 2'-modified nucleotides. In certain instances, each A is a sequence from 1 to 50 nucleotides, such as 1 to 40, 1 to 30, 1 to 20, 1 to 10, or 1 to 5. In certain instances, each B is a sequence from 1 to 50 nucleotides, such as 1 to 40, 1 to 30, 1 to 20, 1 to 10, or 1 to 5.

In certain instances, the subject oligonucleotide has one of the following arrangements of types of nucleotide in the sequence (e.g., one of SEQ ID NOs:45-66, or SEQ ID Nos: 98-115):

$(A)_{n1}$;
$(A)_{n2}$-$(B)_{n3}$-$(A)_{n2}$;
$(A)_{n4}$-$(B)_{n5}$-$(A)_{n4}$-$(B)_{n5}$-$(A)_{n4}$-$(B)_{n5}$-$(A)_{n4}$; or
$(A)_{n4}$-$(B)_{n5}$-$(A)_{n4}$-$(B)_{n5}$-$(A)_{n4}$-$(B)_{n5}$-$(A)_{n4}$-$(B)_{n5}$-$(A)_{n4}$;

where A is a modified nucleotide, B is a DNA nucleotide, n1 is 8 or more, n2 is 3-4, n3 is 6-8, n4 is 1-2, and n5 is 1-3. In certain instances, A is a modified nucleotide where the ribose moiety is modified to include a modification selected from BNA, LNA, ENA, cEt, and 2'-modified nucleotides.

In certain instances, the subject oligonucleotide has one of the following arrangements of types of nucleotide in the sequence (e.g., one of SEQ ID NOs:45-66, or SEQ ID Nos: 98-115):

A, where A is a sequence of 8 or more LNA nucleotides;

A-B-A, where B is a sequence of 6-8 DNA nucleotides, and each A is a sequence of 3-4 LNA nucleotides;

A-B-A, where B is a sequence of 7-8 DNA nucleotides, and each A is a sequence of 4 LNA nucleotides;

L-D-L-D-L-D-L, where each L is a sequence of 1-2 LNA nucleotides, and each D is a sequence of 2 DNA nucleotides;

L-D-L-D-L-D-L, where each L is a sequence of 1-2 LNA nucleotides, and each D is a sequence of 1-2 DNA nucleotides;

L-D-L-D-L-D-L, where each L is a sequence of 1-2 LNA nucleotides, and each D is a sequence of 1-3 DNA nucleotides;

L-D-L-D-L-D-L-D-L, where each L is a sequence of 1-2 LNA nucleotides, and each D is a sequence of 1-3 DNA nucleotides; and L-D-L-D-L-D-L-D-L, where each L is a sequence of 1-2 LNA nucleotides, and each D is a sequence of 1-2 DNA nucleotides.

The subject oligonucleotide sequences may further include one or more modified internucleoside linkages, such as phosphorothioate, phosphorodithioate, phosphoramidate and/or thiophosphoramidate linkages. A non-naturally occurring internucleoside linkage may be included at any convenient position(s) of the sequence of the subject oligonucleotide. In embodiments where the internucleoside linkage includes a chiral phosphorous atom, e.g., a stereogenic center, the stereogenic phosphorus atom can possess either the "R" configuration (referred to herein as Rp), or the "S" configuration (referred to herein as Sp). The subject oligonucleotide sequences including a chiral phosphorous atom may be prepared as racemic mixtures, or as separate enantiomers.

In certain embodiments, the oligonucleotide has one of the following sequences where capitalized letters denote LNA nucleotides and lowercase letters denote DNA nucleotides (i.e., deoxyribonucleotide units):

```
LNA1:
                              (SEQ ID NO: 67)
5' AccAaaAGaaT 3';

LNA2:
                              (SEQ ID NO: 68)
5' TggCcATcaaT 3';

LNA3:
                              (SEQ ID NO: 69)
5' TagCAtActtA 3';

LNA4:
                              (SEQ ID NO: 70)
5' CCAAAAGA 3';

LNA5:
                              (SEQ ID NO: 71)
5' CATACTTA 3';

LNA6:
                              (SEQ ID NO: 72)
5' CagaCaCGaCCaaAA 3';
```

-continued

```
LNA7:
                              (SEQ ID NO: 73)
5' TAcTtaCTgaCagCC 3';

LNA8:
                              (SEQ ID NO: 74)
5' AGACacgaccaAAAG 3';

LNA9:
                              (SEQ ID NO: 75)
5' TACTtactgacaGCC 3';

LNA9.2:
                              (SEQ ID NO: 76)
5' TACttactgacAGCC 3';

LNA10:
                              (SEQ ID NO: 77)
5'ACCaaaagAAT 3';

LNA11:
                              (SEQ ID NO: 78)
5' TGGccatcAAT 3';

LNA12:
                              (SEQ ID NO: 79)
5'TAGcatacTTA 3';

LNA13:
                              (SEQ ID NO: 80)
5'CgacCAaaAGaattC 3';

LNA14:
                              (SEQ ID NO: 81)
5'CGACcaaaagaATTC 3';

LNA15:
                              (SEQ ID NO: 82)
5'GaTGgCcATcaAttA 3';

LNA16:
                              (SEQ ID NO: 83)
5'GATGgccatcaATTA 3';

LNA17:
                              (SEQ ID NO: 84)
5'TcTAgCaTActTacT 3';

LNA18:
                              (SEQ ID NO: 85)
5'TCTAgcatactTACT 3';

LNA19:
                              (SEQ ID NO: 86)
5'GAAttcggatgGCCA 3';

LNA20:
                              (SEQ ID NO: 87)
5'GGCCatcaattaGTG 3';

LNA21:
                              (SEQ ID NO: 88)
5'TTCGgatggccaTCA 3';

LNA22:
                              (SEQ ID NO: 89)
5'AGCCagacagCGA 3';
and

LNA23:
                              (SEQ ID NO: 90)
5'GACAgccagacaGCA 3'.
```

It will be understood that for any of the sequences LNA1-LNA23 (SEQ ID NO: 67)-(SEQ ID NO: 90), one or more of the LNA nucleotides can be replaced with a modified nucleotide selected from BNA nucleotides, ENA nucleotides, cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain embodiments, the oligonucleotide has one of the following sequences where capitalized letters denote LNA nucleotides and lowercase letters denote DNA nucleotides (i.e., deoxyribonucleotide units):

```
LNA19:
                              (SEQ ID NO: 86)
5'GAAttcggatgGCCA 3';

LNA22:
                              (SEQ ID NO: 89)
5'AGCCagacagCGA 3';

LNA22.2:
                             (SEQ ID NO: 116)
5'CAGCcagacagCGAC 3';

LNA22.3:
                             (SEQ ID NO: 117)
5'CAGccagacagCGAC 3';

LNA22.5:
                             (SEQ ID NO: 118)
5'CAGccagacaGCGA 3';

LNA22.6:
                             (SEQ ID NO: 119)
5'CAGccagacagCGA 3';

LNA22.7:
                             (SEQ ID NO: 120)
5'CAGCcagacagCGA 3';

LNA22.8:
                             (SEQ ID NO: 121)
5'ACAgccagacagCGA 3';

LNA22.9:
                             (SEQ ID NO: 122)
5'ACAGccagacaGCGA 3';

LNA22.10:
                             (SEQ ID NO: 123)
5'ACAgccagacaGCGA 3';

LNA22.11:
                             (SEQ ID NO: 124)
5'GACAgccagacaGCG 3';

LNA22.13:
                             (SEQ ID NO: 125)
5'GACagccagacaGCG 3';
and

LNA22.14:
                             (SEQ ID NO: 126)
5'GACAgccagacAGCG.
```

It will be understood that for any of the sequences LNA19, or LNA22-LNA22.14 ((SEQ ID NO: 86); (SEQ ID NO: 89); and (SEQ ID NO:116)-(SEQ ID NO:126)), one or more of the LNA nucleotides can be replaced with a modified nucleotide selected from BNA nucleotides, ENA nucleotides, cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain embodiments, the oligonucleotide has one of the following sequences where capitalized letters denote LNA nucleotides and lowercase letters denote DNA nucleotides (i.e., deoxyribonucleotide units):

```
LNA24:
                             (SEQ ID NO: 127)
5'CATcaattagtgTCG 3';

LNA25:
                             (SEQ ID NO: 128)
5'CCAtcaattagtgTCG 3';

LNA26:
                             (SEQ ID NO: 129)
5'GCCatcaattagtGTG 3';

LNA27:
                             (SEQ ID NO: 130)
5'AAGAattcggaTGGC 3';

LNA28:
                             (SEQ ID NO: 131)
5' CAGacagcgacCAA 3';
and

LNA29:
                             (SEQ ID NO: 132)
5' TGAcagccagacAGC 3'.
```

It will be understood that for any of the sequences LNA24, or LNA29 (SEQ ID NO: 127)-(SEQ ID NO: 132), one or more of the LNA nucleotides can be replaced with a modified nucleotide selected from BNA nucleotides, ENA nucleotides, cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain embodiments, the oligonucleotide has the sequence LNA14, or a derivative thereof, as shown in Table 1, where a "+" before the letter denotes LNA nucleotides, or other chemically modified nucleotides (e.g., as described herein), and other letters denote DNA nucleotides (i.e., deoxyribonucleotide units):

TABLE 1

LNA14 derivatives

| NAME | SEQUENCE | SEQ ID NO: |
|---|---|---|
| LNA14.1 | +G+C+G+ACCAAAAGA+A+T+T | 133 |
| LNA14.2 | +G+C+G+ACCAAAAG+A+A+T+T | 134 |
| LNA14.5 | +C+G+A+CCAAAAGA+A+T+T | 135 |
| **LNA14** | **+C+G+A+CCAAAAGA+A+T+T+C** | **81** |
| LNA14.7 | +C+G+ACCAAAAGA+A+T+T+C | 136 |
| LNA14.8 | +C+G+A+CCAAAAGAA+T+T+C | 137 |
| LNA14_9 | +C+G+ACCAAAAGAA+T+T+C | 138 |
| LNA14.10 | +G+A+CCAAAAGAA+T+T+C | 139 |

TABLE 1-continued

| LNA14 derivatives | | |
|---|---|---|
| NAME | SEQUENCE | SEQ ID NO: |
| LNA14.14 | +G+C+G+ACCAAAAGA+A+T+T+C | 140 |
| LNA14.15 | +G+C+GACCAAAAGA+A+T+T+C | 141 |
| LNA14.16 | +G+C+GACCAAAAGAA+T+T+C | 142 |
| LNA14.17 | +C+G+ACCAAAAGAA+T+T+C+G | 143 |
| LNA14.19 | +C+G+A+CCAAAAGAA+T+T+C+G | 144 |
| LNA14.22 | +G+A+CCAAAAGAA+T+T+C | 145 |
| LNA14.24 | +A+C+C+AAAAGAA+T+T+C | 146 |
| LNA14.27 | +C+G+ACCAAAAGAAT+T+C+G+G | 147 |
| LNA14.28 | +G+A+CCAAAAGAAT+T+C+G+G | 148 |
| LNA14.30 | +G+A+C+CAAAAGAATT+C+G+G | 149 |
| LNA14.31 | +G+A+CCAAAAGAATT+C+G+G | 150 |
| LNA14.32 | +A+C+C+AAAAGAATT+C+G+G+A | 151 |
| LNA14.36 | +C+C+A+AAAGAATT+C+G+G+A | 152 |
| LNA14.37 | +C+A+A+AAGAATTC+G+G+A | 153 |
| LNA14.39 | +C+A+AAAGAATTC+G+G+A | 154 |
| LNA14.40 | +C+C+AAAAGAATTCG+G+A+T | 155 |
| LNA14.42 | +C+C+A+AAAGAATTCG+G+A+T | 156 |
| LNA14.45 | +C+A+A+AAGAATTC+G+G+A+T | 157 |
| LNA14.47 | +C+A+AAAGAATTC+G+G+A+T | 158 |

In certain embodiments, the oligonucleotide has the sequence LNA9, or a derivative thereof, as shown in Table 2, where a "+" before the letter denotes LNA nucleotides, or other chemically modified nucleotides (e.g., as described herein), and other letters denote DNA nucleotides (i.e., deoxyribonucleotide units):

TABLE 2

| LNA9 derivatives | | |
|---|---|---|
| NAME | SEQUENCE | SEQ ID NO: |
| LNA9.1 | +A+G+C+ATACTTACT+G+A+C+A | 159 |
| LNA9.2a | +C+A+TACTTACTG+A+C+A | 160 |
| LNA9.3 | +C+A+T+ACTTACTG+A+C+A+G | 161 |
| LNA9.5 | +A+T+ACTTACTGA+C+A+G | 162 |
| LNA9.6 | +A+T+A+CTTACTG+A+C+A+G | 163 |
| LNA9.8 | +A+T+ACTTACTG+A+C+A+G | 164 |
| LNA9.9 | +C+A+T+ACTTACTGA+C+A+G+C | 165 |
| LNA9.11 | +C+A+TACTTACTGA+C+A+G+C | 166 |
| LNA9.12 | +C+A+T+ACTTACTGAC+A+G+C | 167 |
| LNA9.13 | +A+T+ACTTACTGAC+A+G+C | 168 |
| LNA9.14 | +A+T+A+CTTACTGA+C+A+G+C | 169 |

TABLE 2-continued

| LNA9 derivatives | | |
|---|---|---|
| NAME | SEQUENCE | SEQ ID NO: |
| LNA9.15 | +A+T+A+CTTACTGAC+A+G+C | 170 |
| LNA9.16 | +A+T+ACTTACTGA+C+A+G+C | 171 |
| LNA9.18 | +T+A+CTTACTGAC+A+G+C | 172 |
| LNA9.19 | +T+A+CTTACTGA+C+A+G+C | 173 |
| LNA9.20 | +T+A+C+TTACTGA+C+A+G+C | 174 |
| LNA9.22 | +A+T+ACTTACTGACA+G+C+C | 175 |
| LNA9.23 | +A+T+ACTTACTGAC+A+G+C+C | 176 |
| **LNA9** | **+T+A+C+TTACTGACA+G+C+C** | **75** |
| LNA9.25 | +T+A+C+TTACTGAC+A+G+C+C | 177 |
| LNA9.26 | +T+A+CTTACTGACA+G+C+C | 178 |
| LNA9.28 | +T+A+C+TTACTGACA+G+C+C+A | 179 |
| LNA9.29 | +T+A+CTTACTGACA+G+C+C+A | 180 |
| LNA9.30 | +T+A+C+TTACTGACAG+C+C+A | 181 |
| LNA9.31 | +T+A+CTTACTGACAG+C+C+A | 182 |
| LNA9.32 | +A+C+TTACTGACA+G+C+C+A | 183 |
| LNA9.33 | +A+C+TTACTGACAG+C+C+A | 184 |
| LNA9.35 | +A+C+T+TACTGACA+G+C+C+A | 185 |
| LNA9.41 | +C+T+T+ACTGACAG+C+C+A+G | 186 |
| LNA9.45 | +T+T+ACTGACAGCC+A+G+A | 187 |

In certain embodiments, the oligonucleotide has the sequence LNA8a, or a derivative thereof, as shown in Table 3, where a "+" before the letter denotes LNA nucleotides, or other chemically modified nucleotides (e.g., as described herein), and other letters denote DNA nucleotides (i.e., deoxyribonucleotide units):

TABLE 3

| LNA8a derivatives | | |
|---|---|---|
| NAME | SEQUENCE | SEQ ID NO: |
| **LNA8a** | **+A+G+ACAGCGACCAA+A+A+G** | **188** |
| LNA8a_1 | +A+G+A+CAGCGACCA+A+A+A+G | 189 |
| LNA8a_2 | +A+C+A+GCGACCA+A+A+A+G | 190 |
| LNA8a_3 | +A+C+AGCGACCAA+A+A+G | 191 |

In certain embodiments, the oligonucleotide has the sequence IAV-Pos, or a derivative thereof, as shown in Table 4, where a "+" before the letter denotes LNA nucleotides, or other chemically modified nucleotides (e.g., as described herein), and other letters denote DNA nucleotides (i.e., deoxyribonucleotide units):

TABLE 4

| IAV-Pos Targeting LNAs | |
|---|---|
| Name | Composition |
| IAV-Pos9.1 | +T+G+T+CAGTAAG+T+A+T+G (SEQ ID NO: 538) |
| IAV-Pos9.2 | +C+T+GGCTGTCAGTA+A+G+T (SEQ ID NO: 539) |
| IAV-Pos9.3 | +T+C+GCTGTCTGGC+T+G+T (SEQ ID NO: 540) |
| IAV-Pos8.1 | +C+T+TTTGGTCGCTG+T+C+T (SEQ ID NO: 541) |
| IAV-Pos8.2 | +C+T+T+TTGGTCGC+T+G+T (SEQ ID NO: 542) |
| IAV-Pos8.3 | +T+T+GGTCGCTGTC+T+G+G+C (SEQ ID NO: 543) |
| IAV-Pos8.4 | +T+T+GGTCGCTGT+C+T+G (SEQ ID NO: 544) |
| IAV-POS14.1 | +G+A+A+TTCTTTTGG+T+C+G+C (SEQ ID NO: 545) |

TABLE 4-continued

| IAV-Pos Targeting LNAs | |
|---|---|
| Name | Composition |
| IAV-POS14.2 | +G+A+ATTCTTTTGG+T+C+G (SEQ ID NO: 546) |
| IAV-POS14.3 | +A+A+T+TCTTTTGG+T+C+G+C (SEQ ID NO: 547) |
| IAV-POS14.4 | +C+G+A+ATTCTTTTG+G+T+C+G (SEQ ID NO: 548) |
| IAV-Pos1.1 | +A+C+A+CTAATTGAT+G+G+C (SEQ ID NO: 549) |
| IAV-Pos1.2 | +A+A+TTGATGGC+C+A+T (SEQ ID NO: 550) |

In certain embodiments, the oligonucleotide has the sequence IBV, or a derivative thereof, as shown in Table 5, where a "+" before the letter denotes LNA nucleotides, or other chemically modified nucleotides (e.g., as described herein), and other letters denote DNA nucleotides (i.e., deoxyribonucleotide units):

TABLE 5

| IBV Targeting LNAs | |
|---|---|
| Name | Composition |
| IBV-LNA4.1 | +C+C+A+CAAAATGAA+G+G+C+A (SEQ ID NO: 551) |
| IBV-LNA4.2 | +C+A+C+AAAATGAAG+G+C+A (SEQ ID NO: 552) |
| IBV-LNA4.3 | +C+A+CAAAATGAA+G+G+C+A (SEQ ID NO: 553) |
| IBV-LNA4.4 | +C+A+C+AAAATGAA+G+G+C (SEQ ID NO: 554) |
| IBV-LNA3.1 | +C+A+A+TAATTGT+A+C+T+A (SEQ ID NO: 556) |
| IBV-LNA3.2 | +C+A+A+TAATTGTA+C+T+A (SEQ ID NO: 556) |
| IBV-LNA3.3 | +C+A+ATAATTGTA+C+T+A (SEQ ID NO: 557) |
| IBV-LNA3.4 | +C+A+ATAATTGTA+C+T+A+C (SEQ ID NO: 558) |
| IBV-LNA3.5 | +C+A+A+TAATTGTAC+T+A+C (SEQ ID NO: 559) |
| IBV-LNA2.1 | +T+G+T+ACTACTCAT+G+G+T+A (SEQ ID NO: 560) |
| IBV-LNA2.2 | +T+G+T+ACTACTCATG+G+T+A (SEQ ID NO: 561) |
| IBV-LNA2.3 | +T+G+TACTACTCATG+G+T+A (SEQ ID NO: 562) |
| IBV-LNA2.4 | +G+T+A+CTACTCAT+G+G+T (SEQ ID NO: 563) |
| IBV-LNA2.5 | +G+T+ACTACTCAT+G+G+T (SEQ ID NO: 564) |
| IBV-LNA2.6 | +T+T+GTACTACTCA+T+G+G(SEQ ID NO: 565) |
| IBV-LNA1.1 | +C+A+TGGTAGTAAC+A+T+C (SEQ ID NO: 566) |
| IBV-LNA1.2 | +C+T+C+ATGGTAGTAAC+A+T+C (SEQ ID NO: 567) |
| IBV-LNA1.3 | +C+T+C+ATGGTAGTAA+C+A+T (SEQ ID NO: 568) |
| IBV-LNA1.4 | +C+T+CATGGTAGTAA+C+A+T (SEQ ID NO: 569) |
| IBV-LNA1.5 | +A+C+TCATGGTAGTA+A+C+A (SEQ ID NQ:570) |
| IBV-LNA1.6 | +A+C+T+CATGGTAGTA+A+C+A (SEQ ID NO: 571) |
| IBV-LNA1.7 | +A+C+TCATGGTAGT+A+A+C (SEQ ID NO: 572) |
| IBV-LNA1.8 | +A+C+TCATGGTAG+T+A+A (SEQ ID NO: 573) |

TABLE 5-continued

| IBV Targeting LNAs | |
|---|---|
| Name | Composition |
| IBV-LNA0.1 | +C+A+A+TGCAGATC+G+A+A+T (SEQ ID NO: 574) |
| IBV-LNA0.2 | +C+A+ATGCAGATCG+A+A+T (SEQ ID NO: 575) |
| IBV-LNA_opp.1 | +G+A+T+TGCCTTCAC+G+A+A+A (SEQ ID NO: 576) |
| IBV-LNA_opp.2 | +G+A+TTGCCTTCACG+A+A+A (SEQ ID NO: 577) |

In certain embodiments, the oligonucleotide has the sequence IBV-Pos, or a derivative thereof, as shown in Table 6, where a "+" before the letter denotes LNA nucleotides, or other chemically modified nucleotides (e.g., as described herein), and other letters denote DNA nucleotides (i.e., deoxyribonucleotide units):

TABLE 6

| IBV-Pos Targeting LNAs | |
|---|---|
| Name | Composition |
| IBV-Pos4.1 | +G+C+CTTCATTTT+G+T+G (SEQ ID NO: 578) |
| IBV-Pos4.2 | +A+T+TGCCTTCATTT+T+G+T (SEQ ID NO: 579) |
| IBV-Pos4.3 | +A+T+T+GCCTTCATT+T+T+G+T (SEQ ID NO: 580) |
| IBV-Pos3.1 | +T+A+G+TACAATTAT+T+G+C+C (SEQ ID NO: 581) |
| IBV-Pos3.2 | +A+G+TACAATTATT+G+C+C (SEQ ID NO: 582) |
| IBV-Pos3.3 | +G+T+ACAATTATTGC+C+T+T (SEQ ID NO: 583) |
| IBV-Pos2.1 | +A+C+C+ATGAGTAG+T+A+C+A (SEQ ID NO: 584) |
| IBV-Pos2.2 | +C+A+TGAGTAGTAC+A+A+T (SEQ ID NO: 585) |
| IBV-Pos 1.1 | +G+A+TGTTACTACCAT+G+A+G (SEQ ID NO: 586) |
| IBV-Pos 1.2 | +A+T+G+TTACTACCAT+G+A+G (SEQ ID NO: 587) |
| IBV-Pos 1.3 | +C+A+T+TGGATGTTA+C+T+A+C (SEQ ID NO: 588) |
| IBV-Pos 1.4 | +A+T+TGGATGTTAC+T+A+C+C (SEQ ID NO: 589) |
| IBV-Pos 1.5 | +A+T+TGGATGTTA+C+T+A+C (SEQ ID NO: 590) |
| IBV-Pos-Opp.1 | +T+T+TCGTGAAGGCA+A+T+C (SEQ ID NO: 591) |
| IBV-Pos-Opp.2 | +T+C+GTGAAGGCA+A+T+C (SEQ ID NO: 592) |

In certain embodiments, the oligonucleotide has the sequence Neg, or a derivative thereof, as shown in Table 7, where a "+" before the letter denotes LNA nucleotides, or other chemically modified nucleotides (e.g., as described herein), and other letters denote DNA nucleotides (i.e., deoxyribonucleotide units):

TABLE 7

| Neg Targeting LNAs | |
|---|---|
| Name | Composition |
| Neg6.1 | +A+T+CTGTTCTCTAAA+C+G+A (SEQ ID NO: 593) |
| Neg6.2 | +A+T+C+TGTTCTCTAA+A+C+G (SEQ ID NO: 594) |
| Neg6.3 | +A+G+A+TCTGTTCTC+T+A+A+A (SEQ ID NO: 595) |
| Neg6.4 | +T+C+T+CTAAACGAA+C+T+T+T (SEQ ID NO: 596) |
| Neg6.5 | +T+C+TCTAAACGAA+C+T+T+T (SEQ ID NO: 597) |
| Neg6.6 | +C+T+C+TAAACGAAC+T+T+T+A (SEQ ID NO: 598) |
| Neg6.7 | +A+C+T+TTAAAATC+T+G+T (SEQ ID NO: 599) |
| **Neg3.1 (original Neg18)** | **+G+G+TTTCGTCCGT+G+T+T** (SEQ ID NO: 600) |

TABLE 7-continued

| Neg Targeting LNAs | |
|---|---|
| Name | Composition |
| Neg3.2 (original Neg18) | +G+G+T+TTCGTCCG+T+G+T+T (SEQ ID NO: 601) |
| Neg3.3 (original Neg18) | +G+G+TTTCGTCCG+T+G+T+T (SEQ ID NO: 602) |
| Neg3.4 (original Neg18) | +T+G+CTTACGGTTTCG+T+C+C (SEQ ID NO: 603) |
| Neg3.5 (original Neg18) | +G+T+T+TCGTCCGTGT+T+G+C (SEQ ID NO: 604) |
| Neg8.1 | +T+A+GGTTTCGTCC+G+G (SEQ ID NO: 605) |
| **Neg8.2** | **+T+C+GTCCGGGTG+T+G+A** (SEQ ID NO: 606) |
| Neg8.3 | +T+T+CGTCCGGGTG+T+G+A (SEQ ID NO: 607) |
| **Neg8.4** | **+T+T+TCGTCCGGGTG+T+G+A** (SEQ ID NO: 608) |
| Neg8.5 | +A+G+G+TTTCGTCCG+G+G+T (SEQ ID NO: 609) |
| Neg8.6 | +A+G+G+TTTCGTCC+G+G+G (SEQ ID NO: 610) |
| Neg8.7 | +A+G+GTTTCGTCCG+G+G+T (SEQ ID NO: 611) |
| Neg8.8 | +T+T+TCGTCCGGGT+G+T+G (SEQ ID NO: 612) |
| **Neg10.1** | **+A+G+GCCACGCGGA+G+T+A** (SEQ ID NO: 613) |
| Neg10.2 | +C+A+CGCGGAGTACG+A+T+C (SEQ ID NO: 614) |
| Neg10.3 | +G+C+GGAGTACGAT+C+G+A (SEQ ID NO: 615) |
| Neg10.4 | +G+C+GGAGTACGATC+G+A+G (SEQ ID NO: 616) |
| Neg10.5 | +G+C+G+GAGTACGATC+G+A+G (SEQ ID NO: 617) |
| Neg10.6 | +A+G+GCCACGCGG+A+G+T (SEQ ID NO: 618) |
| Neg11.1 | +T+A+A+CTTTAATCT+C+A+C+A (SEQ ID NO: 619) |
| Neg11.2 | +A+T+C+TCACATAGC+A+A+T+C (SEQ ID NO: 620) |
| Neg11.3 | +C+A+C+ATAGCAATC+T+T+T+A (SEQ ID NO: 621) |
| Neg11.4 | +A+T+A+GCAATCTTTA+A+T+C (SEQ ID NO: 622) |
| Neg11.5 | +G+T+AGTTAACTTTAA+T+C+T (SEQ ID NO: 623) |
| Neg11.6 | +T+A+A+CTTTAATCTC+A+C+A (SEQ ID NO: 624) |
| Neg11.7 | +T+A+A+CTTTAATCT+C+A+C+A (SEQ ID NO: 625) |
| Neg11.8 | +C+T+T+TAATCTCACA+T+A+G+C (SEQ ID NO: 626) |
| Neg11.9 | +C+A+CATAGCAAT+C+T+T (SEQ ID NO: 627) |
| Neg11.10 | +C+T+CACATAGCAA+T+C+T+T (SEQ ID NO: 628) |
| Neg12.1 | +C+G+TGCTACAACTT+C+C+T (SEQ ID NO: 629) |
| **Neg12.2** | **+T+G+C+TACAACTTC+C+T+C** (SEQ ID NO: 630) |
| Neg12.3 | +C+T+CAAGGAACAAC+A+T+T (SEQ ID NO: 631) |
| Neg12.4 | +A+A+GGCTTCTACG+C+A+G (SEQ ID NO: 632) |
| Neg12.5 | +T+G+C+TACAACTT+C+C+T+C (SEQ ID NO: 633) |
| Neg12.6 | +T+G+C+TACAACTT+C+C+T (SEQ ID NO: 634) |

TABLE 7-continued

| Neg Targeting LNAs | |
|---|---|
| Name | Composition |
| Neg12.7 | +T+C+GTGCTACAAC+T+T+C (SEQ ID NO: 635) |
| Neg12.8 | +C+G+TGCTACAAC+T+T+C (SEQ ID NO: 636) |
| Neg13.1 | +C+C+TATATGGAA+G+A+G+C (SEQ ID NO: 637) |
| Neg13.2 | +T+G+CCTATATGGAA+G+A+G (SEQ ID NO: 638) |
| Neg13.3 | +G+C+CTATATGGAA+G+A+G (SEQ ID NO: 639) |
| Neg13.4 | +T+A+TATGGAAG+A+G+C+C (SEQ ID NO: 640) |
| Neg13.5 | +A+G+AGCCCTAATGT+G+T+A (SEQ ID NO: 641) |
| Neg13.6 | +G+A+AGAGCCCTAAT+G+T+G (SEQ ID NO: 642) |
| Neg16.1 | +T+G+T+GTAACATTAG+G+G+A (SEQ ID NO: 643) |
| Neg16.2 | +G+T+AACATTAGGG+A+G+G+A (SEQ ID NO: 644) |
| Neg18.1 (M) | +G+T+AGTGTTGGTT+T+T+A (SEQ ID NO: 645) |
| **Neg18.2 (M)** | **+G+T+A+GTGTTGGT+T+T+T** (SEQ ID NO: 646) |
| **Neg18.3 (M)** | **+T+C+A+TGTGGTAGT+G+T+T+G** (SEQ ID NO: 647) |
| **Neg18.4 (M)** | **+T+C+A+TGTGGTAGT+G+T+T** (SEQ ID NO: 648) |
| Neg18.5 (M) | +A+T+G+TGGTAGTGT+T+G+G+T (SEQ ID NO: 649) |
| Neg18.6 (M) | +A+T+G+TGGTAGTGT+T+G+G (SEQ ID NO: 650) |
| Neg18.7 (M) | +T+G+TGGTAGTGT+T+G+G+T (SEQ ID NO: 651) |
| Neg18.8 (M) | +G+T+GGTAGTGT+T+G+G+T (SEQ ID NO: 652) |
| Neg18.9 (M) | +G+T+G+GTAGTGTTGG+T+T+T (SEQ ID NO: 653) |
| Neg18.10 (M) | +T+G+GTAGTGTTGG+T+T+T (SEQ ID NO: 654) |

In certain embodiments, the oligonucleotide has the sequence miR, or a derivative thereof, as shown in Table 8, where a "+" before the letter denotes LNA nucleotides, or other chemically modified nucleotides (e.g., as described herein), and other letters denote DNA nucleotides (i.e., deoxyribonucleotide units):

TABLE 8

| miR-Targeting LNAs | | |
|---|---|---|
| miR targeted | Name | Composition |
| miR-602 | LNA-602.1 | +G+G+TTTCGTCCGT+G+T+T (SEQ ID NO: 655) |
| | LNA-602.2 | +G+T+TTCGTCCGT+G+T+T (SEQ ID NO: 656) |
| | LNA-602.3 | +G+C+T+GTCGCCCG+T+G+T+C (SEQ ID NO: 657) |
| | LNA-602.4 | +G+C+TGTCGCCCGT+G+T+C (SEQ ID NO: 658) |
| | LNA-602.5 | +G+C+TGTCGCCCG+T+G+T+C (SEQ ID NO: 659) |
| | LNA-602.6 | +G+C+TGTCGCCCG+T+G+T (SEQ ID NO: 660) |
| miR-6759 | LNA-6759-5P.1 | +T+T+CGTCCG+T+G (SEQ ID NO: 661) |
| | LNA-6759-5P.2 | +T+T+CGTCC+G+T+G (SEQ ID NO: 662) |
| | LNA-6759-5P.3 | +T+TC+GT+CC+GT+G (SEQ ID NO: 663) |
| | LNA-6759-5P.4 | +C+CCACCC+A+C (SEQ ID NO: 664) |
| | LNA-6759-5P.5 | +C+CCACC+C+A+C (SEQ ID NO: 665) |
| | LNA-6759-5P.6 | +CC+CA+CCC+A+C (SEQ ID NO: 666) |
| miR-6769 | LNA-6769-5P.1 | +T+T+TCGTCC+G+T (SEQ ID NO: 667) |
| | LNA-6769-5P.2 | +T+T+TCGTC+C+G+T (SEQ ID NO: 668) |
| | LNA-6769-5P.3 | +T+TTCGTC+C+G+T (SEQ ID NO: 669) |
| | LNA-6769-5P.4 | +C+CCCACC+C+A+C (SEQ ID NO: 670) |
| | LNA-6769-5P.5 | +C+CCCACCC+A+C (SEQ ID NO: 671) |
| | LNA-6769-5P.6 | +CC+CC+ACC+CA+C (SEQ ID NO: 672) |

TABLE 8-continued miR-Targeting LNAs

| miR targeted | Name | Composition |
|---|---|---|
| miR-4802 | LNA-4802-3P.1 | +T+T+TCGTCCG+T+G+T (SEQ ID NO: 673) |
| | LNA-4802-3P.2 | +T+T+T+CGTCCG+T+G+T (SEQ ID NO: 674) |
| | LNA-4802-3P.3 | +TT+TC+GTC+CG+TG+T (SEQ ID NO: 675) |
| | LNA-4802-3P.4 | +T+T+CCATCCA+T+G+T (SEQ ID NO: 676) |
| | LNA-4802-3P.5 | +T+T+CCATCCA+T+G+T (SEQ ID NO: 677) |
| | LNA-4802-3P.6 | +TTC+C+AT+CC+ATG+T (SEQ ID NO: 678) |
| | LNA-4802-3P.7 | +TTC+C+AT+CC+ATG+T (SEQ ID NO: 679) |
| miR-942 | LNA-942-3P.1 | +G+T+TTCGTCCGT+G+T+T (SEQ ID NO: 680) |
| | LNA-942-3P.2 | +G+T+TTCGTCCG+T+G+T+T (SEQ ID NO: 681) |
| | LNA-942-3P.3 | +GT+TTC+GTC+CG+TGT+T (SEQ ID NO: 682) |
| | LNA-942-3P.4 | +G+T+TTCGGCCAT+G+T+G (SEQ ID NO: 683) |
| | LNA-942-3P.5 | +G+T+T+TCGGCCA+T+G+T+G (SEQ ID NO: 684) |
| | LNA-942-3P.6 | +G+T+TTCGGCCA+T+G+T+G (SEQ ID NO: 685) |
| | LNA-942-3P.7 | +G+TTT+CGG+CCA+TG+T+G (SEQ ID NO: 686) |
| miR-4462 | LNA-4462.1 | +C+G+TCCGT+G+T+T (SEQ ID NO: 687) |
| | LNA-4462.2 | +C+GTCCGT+G+T+T (SEQ ID NO: 688) |
| | LNA-4462.3 | +C+GTCCGT+G+T+T (SEQ ID NO: 689) |
| | LNA-4462.4 | +CG+TC+CG+TGT+T (SEQ ID NO: 690) |
| | LNA-4462.5 | +C+CTCCGT+G+T+C (SEQ ID NO: 691) |
| | LNA-4462.6 | +C+CTCCGTG+T+C (SEQ ID NO: 692) |
| | LNA-4462.7 | +CC+TCC+GTG+T+C (SEQ ID NO: 693) |
| miR-4696 | LNA-4696.1 | +T+C+CGTGT+T+G+C (SEQ ID NO: 694) |
| | LNA-4696.2 | +T+C+C+GTGT+T+G+C (SEQ ID NO: 695) |
| | LNA-4696.3 | +T+CCG+TGT+T+G+C (SEQ ID NO: 696) |
| | LNA-4696.4 | +T+C+CGTCT+T+G+C (SEQ ID NO: 697) |
| | LNA-4696.5 | +T+C+C+GTCT+T+G+C (SEQ ID NO: 698) |
| | LNA-4696.6 | +TCC+GT+TTG+C (SEQ ID NO: 699) |
| miR-376c | LNA-376c.1 | +T+T+TCGTCCGT+G+T+T (SEQ ID NO: 700) |
| | LNA-376c.2 | +T+T+TCGTCCG+T+G+T+T (SEQ ID NO: 701) |
| | LNA-376c.3 | +T+T+TCCTCTAT+G+T+T (SEQ ID NO: 702) |
| | LNA-376c.4 | +T+T+TCCTCTA+T+G+T+T (SEQ ID NO: 703) |
| miR-4433 | LNA-4433b.1 | +G+T+TTCGTCCG+T+G+T (SEQ ID NO: 704) |
| miR-4426 = Neg18 | LNA-4426.1 | +G+G+TTTCGTCCGT+G+T+T (SEQ ID NO: 705) |
| | LNA-4426.2 | +G+G+T+TTCGTCCG+T+G+T+T (SEQ ID NO: 706) |
| | LNA-4426.3 | +G+G+TTTCGTCCG+T+G+T+T (SEQ ID NO: 707) |
| | LNA-4426.4 | +A+A+GTACGTCCTA+C+T+T (SEQ ID NO: 708) |
| miR-191 | LNA-191.1 | +GG+TT+TC+GTC+C (SEQ ID NO: 709) |
| | LNA-191.2 | +G+GTTTCG+T+C+C (SEQ ID NO: 710) |
| | LNA-191.3 | +T+G+G+GTTTCGTCC+G+T+T (SEQ ID NO: 711) |
| | LNA-191.4 | +T+T+TTGGGATTC+C+G+T (SEQ ID NO: 712) |
| | LNA-191.5 | +G+C+TTTTGGGATTC+C+G+T (SEQ ID NO: 713) |
| | LNA-191.6 | +G+C+T+TTTGGGATTC+C+G+T (SEQ ID NO: 714) |
| | LNA-191.7 | +A+G+CTGCTTTTGGG+A+T+T (SEQ ID NO: 715) |
| | LNA-191.8 | +G+A+GCTGCTTTTGG+G+A+T (SEQ ID NO: 716) |
| | LNA-191.10 | +C+T+GCTTTTGGGAT+T+C+C (SEQ ID NO: 717) |
| | LNA-191.11 | +T+G+C+TTTTGGGA+T+T+C (SEQ ID NO: 718) |
| | LNA-191.12 | +T+G+C+TTTTGGG+A+T+T+C (SEQ ID NO: 719) |
| | LNA 191.7-1 | +A+G+C+TGCTTTTGGG+A+T+T (SEQ ID NO: 720) |
| | LNA 191.7-2 | +AGC+TGC+TT+TTG+GG+A (SEQ ID NO: 721) |
| | LNA 191.8-1 | +C+A+GCTGCTTTTGG+G+A+T (SEQ ID NO: 722) |
| | LNA 191.8-2 | +A+G+C+TGCTTTTGGG+A+T+T (SEQ ID NO: 723) |
| | LNA 191.8-3 | +A+G+CTGCTTTTG+G+G+A (SEQ ID NO: 724) |
| | LNA 191.8-4 | A+GC+TGC+TTT+TGG+GA (SEQ ID NO: 725) |
| | LNA 191.8-5 | A+GCT+GCT+TT+TGG+GATT (SEQ ID NO: 726) |
| | LNA-191.13 | +T+G+CTTTTGGGA+T+T+C (SEQ ID NO: 727) |
| miR-663 | LNA-663.1 | +G+C+G+GCGCCCCG+C+C+T (SEQ ID NO: 728) |
| | LNA-663.2 | +GCG+GCG+CCC+CGCC+T (SEQ ID NO: 729) |
| | LNA-663.3 | CGGTCCCGCGGCGCCCCGCCT (SEQ ID NO: 730) |
| miR-381 | LNA-381.1 | +T+T+T+GGGCTTCCTC+G+C+T (SEQ ID NO: 731) |
| | LNA-381.2 | +T+T+T+GGGCTTCCT+C+G+C+T (SEQ ID NO: 732) |
| | LNA-381.3 | +T+T+TGGGCTTCC+T+C+G (SEQ ID NO: 733) |
| | LNA-381.4 | +T+T+TGGGCTTC+C+T+C+G (SEQ ID NO: 734) |

TABLE 8-continued

| miR-Targeting LNAs | | |
|---|---|---|
| miR targeted | Name | Composition |
| | LNA-381.5 | +T+G+GGCTTCCTC+G+C+T (SEQ ID NO: 735) |
| | LNA-381.6 | +A+T+A+TACTTTGGG+C+T+T+C (SEQ ID NO: 736) |
| | LNA-381.7 | +A+T+ATACTTTGGGC+T+T+C (SEQ ID NO: 737) |
| | LNA-381.8 | +A+T+ATACTTTGG+G+C+T (SEQ ID NO: 738) |
| | LNA-381.9 | +A+T+A+TACTTTGGG+C+T+T (SEQ ID NO: 739) |
| miR-744 | LNA-744.1 | +T+A+G+CCCTAGCCCC+G+C+A (SEQ ID NO: 740) |
| | LNA-744.2 | +T+A+GCCCTAGCCCC+G+C+A (SEQ ID NO: 741) |
| | LNA-744.3 | +T+A+GCCCTAGCC+C+C+G (SEQ ID NO: 742) |
| | LNA-744.4 | +T+G+CTGTTAGCC+C+T+A (SEQ ID NO: 743) |
| | LNA-744.5 | +T+G+C+TGTTAGC+C+C+T+A (SEQ ID NO: 744) |
| | LNA-744.6 | +T+G+C+TGTTAGC+C+C+T+A (SEQ ID NO: 745) |
| | LNA-744.7 | +G+T+GTTAGCCCTA+G+C+C (SEQ ID NO: 746) |
| miR-4508 | LNA-4508.1 | +GCG+CCC+AGCC+CCG+C (SEQ ID NO: 747) |
| | LNA-4508.2 | +G+C+GCCCAGCCC+C+G+C (SEQ ID NO: 748) |
| | LNA-4508.3 | C+G+CGCGCCCA+G+C+C+C (SEQ ID NO: 749) |
| | LNA-4508.4 | CGCGCGCCCAGCCCCGC (SEQ ID NO: 750) |
| miR-4730 | LNA-4730.1 | +T+G+GCATGGAATG+G+G+C+T (SEQ ID NO: 751) |
| | LNA-4730.2 | +T+G+GCATGGAAT+G+G+G (SEQ ID NO: 752) |
| | LNA-4730.3 | +A+T+GGAATGGGCTC+C+G+C (SEQ ID NO: 753) |
| | LNA-4730.4 | +A+T+GGAATGGGC+T+C+C (SEQ ID NO: 754) |
| | LNA-4730.5 | +A+A+T+GGGCTCCG+C+C+A+G (SEQ ID NO: 755) |
| | LNA-4730.6 | +A+A+TGGGCTCCGC+C+A+G (SEQ ID NO: 756) |
| | LNA-4730.7 | +A+A+TGGGCTCCG+C+C+A (SEQ ID NO: 757) |
| | LNA-4730.8 | +A+A+T+GGGCTCC+G+C+C+A (SEQ ID NO: 758) |
| miR-6777 | LNA-6777.1 | +C+T+TACCCGAGGCG+G+T+C (SEQ ID NO: 759) |
| | LNA-6777.2 | +T+T+ACCCGAGGC+G+G+T (SEQ ID NO: 760) |
| | LNA-6777.3 | +A+C+CGTACCTTACC+C+G+A (SEQ ID NO: 761) |
| | LNA-6777.4 | +C+G+TACCTTACC+C+G+A (SEQ ID NO: 762) |
| | LNA-6777.5 | +C+G+T+ACCTTAC+C+C+G+A (SEQ ID NO: 763) |
| miR-10396 | LNA-10396.1 | +C+T+CCGAGCCC+C+G+C+C (SEQ ID NO: 764) |
| | LNA-10396.2 | CCCGGCTCCGAGCCCCGCC (SEQ ID NO: 765) |
| miR-4749 | LNA-4749.1 | +T+G+GCCTGTCCCC+G+C+A (SEQ ID NO: 766) |
| | LNA-4749.2 | +T+G+GCCTGTCCC+C+G+C+A (SEQ ID NO: 767) |
| | LNA-4749.3 | +G+A+T+GCCCTGGC+C+T+G (SEQ ID NO: 768) |
| | LNA-4749.4 | +G+A+TGCCCTGGC+C+T+G (SEQ ID NO: 769) |
| miR-6787 | LNA-6787.1 | +G+C+AGCCAGCTC+T+A+C (SEQ ID NO: 770) |
| | LNA-6787.2 | +G+C+A+GCCAGCTC+T+A+C (SEQ ID NO: 771) |
| | LNA-6787.3 | +A+G+CCAGCTCTA+C+C+C (SEQ ID NO: 772) |
| | LNA-6787.4 | +A+G+CTCTACCCCG+C+C+A (SEQ ID NO: 773) |
| | LNA-6787.5 | +A+G+C+TCTACCCC+G+C+C+A (SEQ ID NO: 774) |
| miR-4706 | LNA-4706.1 | +A+A+AGCAGCGCCC+A+C+T+T (SEQ ID NO: 775) |
| | LNA-4706.2 | +A+A+AGCAGCGCCC+A+C+T (SEQ ID NO: 776) |
| | LNA-4706.3 | +A+A+AGCAGCGCC+C+A+C (SEQ ID NO: 777) |
| | LNA-4706.4 | +A+C+TTCCTCCCC+G+C+T (SEQ ID NO: 778) |
| miR-3675 | LNA-3675.1 | +C+T+A+CAGAAGCCC+C+A+T+A (SEQ ID NO: 779) |
| | LNA-3675.2 | +C+T+ACAGAAGCCCC+A+T+A (SEQ ID NO: 780) |
| | LNA-3675.3 | +G+A+A+ATCTCTACA+G+A+A+G (SEQ ID NO: 781) |
| | LNA-3675.4 | +G+A+AATCTCTACAG+A+A+G (SEQ ID NO: 782) |
| miR-6810 | LNA-6810.1 | +T+G+ATCCCTGTCCC+C+A+T (SEQ ID NO: 783) |
| | LNA-6810.2 | +A+T+G+CTGATCCCT+G+T+C (SEQ ID NO: 784) |
| | LNA-6810.3 | +GCC+ATGC+TGATCCC+TGTCCCC+AT (SEQ ID NO: 785) |
| miR-6812 | LNA-6812.1 | +C+C+ATCTCACCC+C+A+T (SEQ ID NO: 786) |
| | LNA-6812.2 | +G+C+TGCTCCTCCC+C+A+T (SEQ ID NO: 787) |
| miR-6796 | LNA-6796.1 | +T+C+TCCAACCCCA+C+A+A (SEQ ID NO: 788) |
| | LNA-6796.2 | +C+T+CCAACCCCA+C+A+A (SEQ ID NO: 789) |
| | LNA-6796.3 | +C+A+G+CCAGCTCTC+C+A+A (SEQ ID NO: 790) |
| | LNA-6796.4 | +A+G+C+CAGCTCT+C+C+A+A (SEQ ID NO: 791) |

In certain embodiments, the oligonucleotide has the sequence Coy, or a derivative thereof, as shown in Table 8, where a "+" before the letter denotes LNA nucleotides, or other chemically modified nucleotides (e.g., as described herein), and other letters denote DNA nucleotides (i.e., deoxyribonucleotide units):

TABLE 9

| Cov Targeting LNAs | |
|---|---|
| Name | Composition |
| Cov 1.1 | +G+A+CGTGATATATG+T+G+G (SEQ ID NO: 792) |
| Cov 1.2 | +C+G+TGATATATGTG+G+T+A (SEQ ID NO: 793) |
| Cov 1.3 | +G+A+TATGTGGTAC+C+A+T (SEQ ID NO: 794) |
| Cov 1.4 | +T+G+GTACCATGT+C+A+C (SEQ ID NO: 795) |
| Cov 2.1 | +C+C+TCAGCAGCAG+A+T+T+T (SEQ ID NO: 796) |
| Cov 2.2 | +T+C+AGCAGCAGAT+T+T+C (SEQ ID NO: 797) |
| Cov 2.3 | +C+A+G+CAGCAGAT+T+T+C (SEQ ID NO: 798) |
| Cov 2.4 | +C+A+GATTTCTTAGT+G+A+C (SEQ ID NO: 799) |
| Cov 3.1 | +T+G+CAACACGGAC+G+A+A+A (SEQ ID NO: 800) |
| Cov 3.2 | +G+C+AACACGGACG+A+A+A+C (SEQ ID NO: 801) |
| Cov 3.3 | +A+C+ACGGACGAAA+C+C+G (SEQ ID NO: 802) |
| Cov 3.4 | +G+G+ACGAAACCC+G+T+A+A (SEQ ID NO: 803) |
| Cov 3.5 | +A+C+GAAACCGTA+A+G+C+A (SEQ ID NO: 804) |
| Cov 3.6 | +A+C+G+AAACCGTA+A+G+C+A (SEQ ID NO: 805) |
| Cov 3.2-1 | +G+C+A+ACACGGACG+A+A+A+C (SEQ ID NO: 806) |
| Cov 3.2-2 | +G+C+AACACGGAC+G+A+A+A (SEQ ID NO: 807) |
| Cov 3.2-3 | +GC+AA+CAC+GG+ACG+AAA+C (SEQ ID NO: 808) |
| Cov 3.2-4 | +G+CA+AC+ACG+GAC+GAA+A+C (SEQ ID NO: 809) |
| Cov 3.2-5 | +G+CAA+CAC+GGA+CGA+AA+C (SEQ ID NO: 810) |
| Cov 3.2-6 | +G+CAA+CAC+GGA+CGA+A (SEQ ID NO: 811) |
| Cov 3.2-7 | +A+C+ACGGACGAAA+C+C+G (SEQ ID NO: 812) |
| Cov 3.2-8 | +A+CAC+GG+ACG+AAAC+C+G (SEQ ID NO: 813) |
| Cov 3.2-9 | +AA+CAC+GG+ACG+AA+AC+C+G (SEQ ID NO: 814) |
| Cov 3.2-10 | +AA+CAC+GG+AC+GAA+AC+C+G (SEQ ID NO: 815) |
| Cov 3.5n | +A+C+GAAACCGTA+A+G+C+A (SEQ ID NO: 816) |
| Cov 3.6n | +A+C+G+AAACCGTA+A+G+C+A (SEQ ID NO: 817) |
| Cov 4.1 | +A+A+CATGTCTGGAC+C+T+A (SEQ ID NO: 818) |
| Cov 4.2 | +A+C+ATGTCTGGAC+C+T+A+T (SEQ ID NO: 819) |
| Cov 5.1 | +T+G+AATATGACAT+A+G+T (SEQ ID NO: 820) |
| Cov 5.2 | +A+A+TATGACATA+G+T+C (SEQ ID NO: 821) |
| Cov 6.1 | +C+A+CAGATTTTAAA+G+T+T (SEQ ID NO: 822) |
| Cov 6.2 | +C+A+C+AGATTTTAA+A+G+T+T (SEQ ID NO: 823) |
| Cov 6.3 | +C+A+G+ATTTTAAAG+T+T+C+G (SEQ ID NO: 824) |
| Cov 6.4 | +G+A+TTTTAAAGT+T+C+G+T (SEQ ID NO: 825) |
| Cov 6.5 | +T+A+A+AGTTCGTT+T+A+G+A (SEQ ID NO: 826) |
| Cov 6.6 | +A+A+A+GTTCGTTT+A+G+A (SEQ ID NO: 827) |
| Cov 6.7 | +T+C+GTTTAGAGAAC+A+G+A+T (SEQ ID NO: 828) |
| Cov 6.8 | +A+G+AGAACAGATCT+A+C+A (SEQ ID NO: 829) |

TABLE 9-continued

| Cov Targeting LNAs | |
|---|---|
| Name | Composition |
| Cov 6.9 | +A+G+ATCTACAAG+A+G+A (SEQ ID NO: 830) |
| Cov 6.10 | +A+T+CTACAAGAG+A+T+C (SEQ ID NO: 831) |
| Cov 6.4-1 | +A+G+A+TTTTAAAGTT+C+G+T (SEQ ID NO: 832) |
| Cov 6.4-2 | +G+A+TTTTAAAGTT+C+G+T (SEQ ID NO: 833) |
| Cov 6.4-3 | +GAT+TTT+AAA+GTT+CG+T (SEQ ID NO: 834) |
| Cov 6.4-4 | +A+G+A+TTTTAAAG+T+T+C+G (SEQ ID NO: 835) |
| Cov 6.7-1 | +T+C+GTTTAGAGAACA+G+A+T (SEQ ID NO: 836) |
| Cov 6.7-2 | +T+T+C+GTTTAGAGAA+C+A+G (SEQ ID NO: 837) |
| Cov 6.7-3 | +TTC+GTT+TAG+AGA+ACA+G (SEQ ID NO: 838) |
| Cov 7.1 | +C+A+GGCAAACTGAG+T+T+G (SEQ ID NO: 839) |
| Cov 7.2 | +C+A+G+GCAAACTGAG+T+T+G (SEQ ID NO: 840) |
| Cov 7.3 | +C+A+G+GCAAACTG+A+G+T (SEQ ID NO: 841) |
| Cov 7.4 | +C+A+AACTGAGTTGG+A+C+G (SEQ ID NO: 842) |
| Cov 7.5 | +A+A+ACTGAGTTG+G+A+C (SEQ ID NO: 843) |
| Cov 7.6 | +A+A+ACTGAGTTGGA+C+G+T (SEQ ID NO: 844) |
| Cov 7.7 | +G+A+GTTGGACGTG+T+G+T (SEQ ID NO: 845) |
| Cov 7.8 | +T+T+GGACGTGTGTT+T+T+C (SEQ ID NO: 846) |
| Cov 7.9 | +G+G+ACGTGTGTTTT+C+T+C (SEQ ID NO: 847) |
| Cov8.1 | +T+T+TCGGTCACACC+C+G+G (SEQ ID NO: 848) |
| Cov 8.2 | +C+G+GTCACACCCGG+A+C+G (SEQ ID NO: 849) |
| Cov 8.3 | +T+C+ACACCCGGACG+A+A+A (SEQ ID NO: 850) |
| Cov 8.4 | +C+A+CCCGGACGA+A+A+C (SEQ ID NO: 851) |
| Cov 8.5 | +C+A+CCCGGACGAA+A+C+C (SEQ ID NO: 852) |
| Cov 8.6 | +C+A+CCCGGACGAAA+C+C+T (SEQ ID NO: 853) |
| Cov 8.7 | +C+C+GGACGAAAC+C+T+A (SEQ ID NO: 854) |
| Cov 8.2-1 | +C+G+GTCACACCCGGA+C+G+A (SEQ ID NO: 855) |
| Cov 8.2-2 | +C+G+G+TCACACCCGG+A+C+G (SEQ ID NO: 856) |
| Cov 8.2-3 | +C+GGT+CAC+ACC+CGG+AC+G (SEQ ID NO: 857) |
| Cov 8.2-4 | +C+GG+TC+AC+ACC+CGGA+C+G (SEQ ID NO: 858) |
| Cov 8.2-5 | +GT+CAC+ACC+CGGA+C+G (SEQ ID NO: 859) |
| Cov 8.2-6 | +GTC+ACA+CCC+GGA+C+G (SEQ ID NO: 860) |
| Cov 8.5-1 | +CAC+CC+GGA+CGA+AAC+C (SEQ ID NO: 861) |
| Cov 8.5-2 | +CA+CCC+GG+AC+GA+AAC+C (SEQ ID NO: 862) |
| Cov 8.5-3 | +CA+CCC+GG+AC+GA+AA+C (SEQ ID NO: 863) |
| Cov 8.4-1 | +C+A+C+ACCCGGACGA+A+A+C (SEQ ID NO: 864) |
| Cov 8.4-2 | +C+A+C+ACCCGGACG+A+A+A (SEQ ID NO: 865) |
| Cov 8.4-3 | +C+A+C+ACCCGGA+C+G+A+A (SEQ ID NO: 866) |
| Cov 10.1 | +T+C+GATCGTACTC+C+G+C (SEQ ID NO: 867) |

TABLE 9-continued

Cov Targeting LNAs

| Name | Composition |
|---|---|
| Cov 10.2 | +T+C+GATCGTACT+C+C+G (SEQ ID NO: 868) |
| Cov 10.3 | +A+T+C+GTACTCCGC+G+T+G (SEQ ID NO: 869) |
| Cov 10.4 | +A+C+TCGATCGT+A+C+T+C (SEQ ID NO: 870) |
| Cov 10.5 | +C+G+TGGCCTCGG+T+G+A+A (SEQ ID NO: 871) |
| Cov 10.6 | +G+T+GGCCTCGG+T+G+A+A (SEQ ID NO: 872) |
| Cov 11.1 | +G+A+T+TAAAGATTG+C+T+A+T (SEQ ID NO: 873) |
| Cov 11.2 | +T+A+A+AGATTGCT+A+T+G+T+G (SEQ ID NO: 874) |
| Cov 11.3 | +A+A+G+ATTGCTATG+T+G+A+G (SEQ ID NO: 875) |
| Cov 11.4 | +G+C+T+ATGTGAGTT+A+A+A+G (SEQ ID NO: 876) |
| Cov 11.5 | +T+A+T+GTGAGTTAA+A+G+T+T (SEQ ID NO: 877) |
| Cov 11.6 | +T+G+T+GAGTTAAAGT+T+A+A (SEQ ID NO: 878) |
| Cov 12.1 | +T+C+GTAGAAGCCTT+T+T+G (SEQ ID NO: 879) |
| Cov 12.2 | +C+G+T+AGAAGCCTTT+T+G+G+C (SEQ ID NO: 880) |
| Cov 12.3 | +T+A+G+AAGCCTTTTG+G+C+A (SEQ ID NO: 881) |
| Cov 12.4 | +A+A+G+CCTTTTGGC+A+A+T+G (SEQ ID NO: 882) |
| Cov 12.5 | +T+T+G+GCAATGTTG+T+T+C+C (SEQ ID NO: 883) |
| Cov 12.6 | +G+C+A+ATGTTGTT+C+C+T (SEQ ID NO: 884) |
| Cov 12.7 | +C+T+TGAGGAAG+T+T+G+T (SEQ ID NO: 885) |
| Cov 12.8 | +A+G+G+AAGTTGTAG+C+A+C+G (SEQ ID NO: 886) |
| Cov 13.1 | +C+T+A+CTAAAATTA+A+T+T (SEQ ID NO: 887) |
| Cov 13.2 | +T+A+C+TAAAATTAA+T+T+T (SEQ ID NO: 888) |
| Cov 13.3 | +A+C+T+AAAATTAA+T+T+T (SEQ ID NO: 889) |
| Cov 13.4 | +A+A+T+TAATTTTAC+A+C+A+T (SEQ ID NO: 890) |
| Cov 13.5 | +A+T+T+TTACACATT+A+G+G+G (SEQ ID NO: 891) |
| Cov 13.6 | +T+A+CACATTAGGG+C+T+C (SEQ ID NO: 892) |
| Cov 13.7 | +A+C+ATTAGGGCTC+T+T+C (SEQ ID NO: 893) |
| Cov 13.8 | +T+A+GGGCTCTTCC+A+T+A (SEQ ID NO: 894) |
| Cov 13.9 | +G+C+T+CTTCCATAT+A+G+G (SEQ ID NO: 895) |
| Cov 14.1 | +A+A+GGCTCTCCATC+T+T+A (SEQ ID NO: 896) |
| Cov 14.2 | +A+A+G+GCTCTCC+A+T+C+T (SEQ ID NO: 897) |
| Cov 14.3 | +G+C+TCTCCATCTTA+C+C+T (SEQ ID NO: 898) |
| Cov 14.4 | +T+C+CATCTTACCTT+T+C+G (SEQ ID NO: 899) |
| Cov 16.1 | +C+C+T+CCCTAATGT+T+A+C+A (SEQ ID NO: 900) |
| Cov 16.2 | +C+T+C+CCTAATGTT+A+C+A+G (SEQ ID NO: 901) |
| Cov 16.3 | +C+T+CCCTAATGTTA+C+A+G (SEQ ID NO: 902) |
| Cov 18.1 | +T+A+A+AACCAACAC+T+A+C+C (SEQ ID NO: 903) |
| Cov 18.2 | +A+A+A+CCAACACTA+C+C+A+C (SEQ ID NO: 904) |
| Cov 18.3 | +A+A+ACCAACACTAC+C+A+C (SEQ ID NO: 905) |

TABLE 9-continued

Cov Targeting LNAs

| Name | Composition |
|---|---|
| Cov 18.4 | +A+C+C+AACACTACCA+C+A+T (SEQ ID NO: 906) |
| Cov 18.5 | +C+A+A+CACTACCAC+A+T+G+A (SEQ ID NO: 907) |

In certain embodiments, the oligonucleotide has one of the following sequences where capitalized letters denote LNA nucleotides and lowercase letters denote DNA nucleotides (i.e., deoxyribonucleotide units):

a) LNA14: (SEQ ID NO: 81)
5'CGACcaaaagaATTC 3';

b) LNA14.5: (SEQ ID NO: 135)
5'CGACcaaaagaATT 3';

c) LNA14.8: (SEQ ID NO: 137)
5'CGACcaaaagaaTTC 3';

d) LNA14.28: (SEQ ID NO: 148)
5'GACcaaaagaatTCGG 3';

e) LNA14.30: (SEQ ID NO: 149)
5'GACCaaaagaattCGG 3';

f) LNA 9: (SEQ ID NO: 75)
5' TACTtactgacaGCC 3';

g) LNA9.1: (SEQ ID NO: 159)
5' AGCAtacttactGACA 3';

h) LNA9.2a: (SEQ ID NO: 160)
5' CATacttactgACA 3';

i) LNA9.8: (SEQ ID NO: 164)
5' ATActtactgACAG;

j) LNA9.12: (SEQ ID NO: 167)
5' CATActtactgacAGC;

k) LNA8a: (SEQ ID NO: 188)
5' AGAcagcgaccaaAAG;

l) LNA8a.1: (SEQ ID NO: 189)
5' AGACagcgaccaAAAG;
and m) LNA8a.2: (SEQ ID NO: 190)
5' ACAGcgaccaAAAG.

In certain embodiments, the oligonucleotide has a sequence selected from (a)-(e). In certain cases, the oligonucleotide has a sequence selected from (f)-(j). In certain other cases, the oligonucleotide has a sequence selected from (k)-(m).

It will be understood that for any of the sequences (a)-(m), or a sequence selected from any one of Tables 1-9, one or more of the LNA nucleotides can be replaced with a modified nucleotide selected from BNA nucleotides, ENA nucleotides, cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

It will also be understood that for any of the oligonucleotide sequences described above, one or more of the DNA nucleotides can be modified to provide a corresponding BNA, LNA, ENA, cEt, or 2'-modified nucleotide. In certain cases, 1, 2, 3, 4, or more of the DNA nucleotides can be replaced with a BNA nucleotide. In certain cases, 1, 2, 3, 4, or more of the DNA nucleotides can be modified to provide the corresponding LNA nucleotides. In certain cases, 1, 2, 3, 4, or more of the DNA nucleotides can be modified to provide the corresponding ENA nucleotides. In certain cases, 1, 2, 3, 4, or more of the DNA nucleotides can be modified to provide the corresponding cEt nucleotides. In certain cases, 1, 2, 3, 4, or more of the DNA nucleotides can be modified to provide a corresponding 2'-modified nucleotides (e.g., as described herein).

Sequence mutants of the oligonucleotide sequences described above are also encompassed by the present disclosure. It is understood that in any of the sequences described herein that 1, 2, 3, 4 or more of the nucleotide may be mutated to provide for a desirable property, such as enhanced inhibition activity, conjugation to a modifying agent, etc.

In some cases, any one of the sequences described herein (e.g., one of SEQ ID NO: 45-907) is comprised in a longer sequence, e.g., includes additional 5' and/or 3' nucleotides. In certain instances, the subject oligonucleotide is 75 nucleotides or less in length, such as 50 or less, 40 or less, or 35 nucleotides or less in length. In certain instances, the subject oligonucleotide is 30 nucleotides or less in length, such as 25 or less, 20 or less, 19 or less, 18 or less, 17 or less, 16 or less, 15 or less, 14 or less, 13 or less, 12 or less, 11 or less, or 10 nucleotides or less in length.

In some cases, the subject oligonucleotide compound comprises a sequence having a deletion relative to one of the sequences described herein (e.g., one of SEQ ID NO: 45-907). For example, a sequence where 1, 2 or 3 nucleotides are deleted from the 5' and/or 3' terminal of the sequence, e.g., one of SEQ ID NOs: 45-96. In some cases, the deletion sequence has one nucleotide missing from the 5' terminal of one of SEQ ID NOs: 45-907. In some cases, the deletion sequence has one nucleotide missing from the 3' terminal of one of SEQ ID NOs: 45-191. In some cases, the deletion sequence has two nucleotides missing from the 5' terminal of one of SEQ ID NOs: 45-907. In some cases, the deletion sequence has two nucleotides missing from the 3' terminal of one of SEQ ID NOs: 45-907.

In certain instances, the oligonucleotide comprises a sequence with at least 70% homology to any one of sequences (SEQ ID NO: 45)-(SEQ ID NO: 907) (e.g., as defined herein). In certain instances, the oligonucleotide comprises a sequence with 70% or more homology to any one of sequences (SEQ ID NO: 45)-(SEQ ID NO: 907), such as 75% or more, 80% or more, 85% or more, 90% or more or even more. In certain cases, the oligonucleotide comprises a sequence with from 70 to 80% homology to any one of the sequences (SEQ ID NO: 45)-(SEQ ID NO: 907). In certain cases, the oligonucleotide comprises a sequence with from 80% to 90% homology to any one of sequences (SEQ ID NO: 45)-(SEQ ID NO: 907). In certain cases, the oligonucleotide comprises a sequence with from 90% to 99% homology to any one of sequences (SEQ ID NO: 45)-(SEQ ID NO: 907).

In certain cases, the oligonucleotide sequence can include a mutation designed to cover single-nucleotide polymorphisms (SNPs) in a target PSL2 sequence. In some cases, the oligonucleotide is a modified version of LNA9 with single mutation sites that protect against PLS2 target sequences containing a nucleotide change with the LNA9 target sequence. It is understood that SNP mutations of interest can be applied to any of the sequences described herein. Mutated sequences of interest include, but are not limited to the following:

```
                                    (SEQ ID NO: 91)
5' TACTTACTGACAGTC 3';
                                    (SEQ ID NO: 92)
5' TACTTACCGACAGCC 3';
and
                                    (SEQ ID NO: 93)
5' GGATTTCGGATGGCCA 3'.
```

In certain embodiments, the oligonucleotide has one of the following sequences where capitalized letters denote LNA nucleotides and lowercase letters denote DNA nucleotides:

```
LNA9.G74C:
                                    (SEQ ID NO: 94)
5' TACTtactgacaGTC 3';
LNA9.T80C:
                                    (SEQ ID NO: 95)
5' TACTtaccgacaGCC 3';
and
LNA19.U56C:
                                    (SEQ ID NO: 96)
5' GGATttcggatggCCA 3'.
```

It will be understood that for any of the sequences (SEQ ID NO:94)-(SEQ ID NO:96), or one or more of the LNA nucleotides can be replaced with a modified nucleotide selected from ENA nucleotides, cEt nucleotides, and 2'-modified nucleotides. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain instances, the oligonucleotide has a maximum length that corresponds to the particular region of the PSL2 structure (e.g., a sub-region corresponding to nucleotides 34-87). In certain instances, the oligonucleotide length is 20 nucleotides or less, such as 15 nucleotides or less, 14 nucleotides or less, 13 nucleotides or less, 12 nucleotides or less, 11 nucleotides or less, 10 nucleotides or less, 9 nucleotides or less, 8 nucleotides or less, 7 nucleotides or less, or even less.

Oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate, 3'-NH-5'-O-phosphoroamidate, and thiophosphoramidates. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. In certain cases, the 2'-OH of the ribose sugar may be altered, e.g., as described herein. The 2'-OH of the ribose sugar may be altered to form 2'-O-methyl or 2'-O-allyl sugars, which provides resistance to degradation without comprising affinity. In certain cases, modification of the 2'-OH of the ribose sugar can improve toxicity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The oligonucleotide agents may be derivatized with any convenient modifying agent, e.g., by conjugation of the modifying agent to the 5'- and/or 3'terminal of the oligonucleotide sequence. In some cases, the modifying agent is a moiety that enhances cellular uptake (e.g., a lipid). Any convenient lipids may be conjugated to the subject oligonucleotides. In some instances, the modifying agent is a fatty acid, connected to the 5' or 3' terminal via an optional linker. The lipid group can be an aliphatic hydrocarbon or fatty acid, including but not limited to, derivatives of hydrocarbons and fatty acids, with examples being saturated straight chain compounds having 14-20 carbons, such as myristic (tetradecanoic) acid, palmitic (hexadecanoic) acid, and stearic (octadeacanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group includes derivatives such as amine, amide, ester and carbamate derivatives.

In some cases, the modifying agent is a further nucleic acid sequence having a desirable activity (e.g., recruitment of an RNase, as described herein). In certain instances, the modifying agent has a specific binding activity that provides for delivery of the oligonucleotide to a particular target, such as a cell-specific protein. In some cases, the modifying agent is an antibody of interest that specifically binds a cell-specific target of interest. In certain instances, the antibody modifying agent is specifically binds a hemagglutinin (HA) target.

The oligonucleotide active agent can be utilized in any convenient form. In some instances, the oligonucleotide active agent is single stranded. In some instances, the oligonucleotide active agent is double stranded. In some instances, the oligonucleotide active agent is an siRNA. In some instances, the oligonucleotide active agent is an shRNA. In some instances, the oligonucleotide active agent is a ssRNA. In some instances, one or more nucleotides of the ssRNA can be replaced with LNA nucleotides. In some instances, the oligonucleotide active agent is a ssDNA. In some instances, one or more nucleotides of the ssDNA can be replaced with LNA nucleotides.

Methods of Treatment

Individuals can be infected with influenza A alone and/or other respiratory viruses including but not limited to influenza B viruses (IBV), coronavirus (Cov), respiratory syncytial viruses (RSV).

The present invention is particularly well suited to prevent and/or treat respiratory infection as well as to function as a just-in-time vaccine. In addition, the present invention can be co-administered with other vaccines so as to provide immediate protection during the period of time required for the other vaccines to become effective. In addition, the present invention can be administered to vaccinated individuals who are at risk of being exposed to a vaccine resistant variant. In addition, the present invention can be administered to vaccinated individuals who are asymptomatic but can still transmit the virus.

The oligonucleotides described in this present invention can be used alone or in combination with other oligonucleotides to prevent and/or treat the respiratory viruses described herein.

Aspects of the present disclosure include methods of treating or preventing influenza A virus infection, influenza B, coronaviruses, respiratory syncytial viruses (RSV) in a subject. The subject oligonucleotide compounds find use as a new class of antiviral therapeutics that can efficiently disrupt packaging and completely prevent otherwise lethal disease in vivo. As demonstrated in the examples section, in vivo, intranasal dosing of exemplary oligonucleotide compounds resulted in potent antiviral efficacy and prevented lethal IAV infection in mice.

Aspects of the method include administering to a subject in need thereof a therapeutically effective amount of a subject compound to treat the subject for an infection or prevent infection in the subject. By "a therapeutically effective amount" is meant the concentration of a compound that is sufficient to elicit the desired biological effect (e.g., treatment or prevent of the condition or disease, influenza A virus infection). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease (e.g., infection); and/or (iii) relief, that is, causing the regression of clinical symptoms. In the context of influenza A virus infection, the term "treating" includes any or all of: reducing the number of viral cells in patient samples, inhibiting replication of viral cells, and ameliorating one or more symptoms associated with an infection.

The subject to be treated can be one that is in need of therapy, where the host to be treated is one amenable to treatment using the subject compound. In some embodiments, the subject is one that is suspected of having an influenza A virus infection. In certain embodiments, the subject is diagnosed as having an influenza A virus infection. As such, in some cases, the subject is one who has been infected with the virus.

In certain cases, the subject is one who is at risk of being infected, or is suspected of being infected with the virus. In some embodiments, the vRNA is a PB2 vRNA. The subject methods can be used to prevent infection of the subject with an influenza A virus. By "prevention" is meant that the subject at risk of influenza A virus infection is not infected despite exposure to the virus under conditions that would normally lead to infection. In some cases, the administering of the subject active agent (e.g., oligonucleotide compound) protects the subject against infection for 1 week or more, such as 2 weeks or more, 3 weeks or more, 1 month or more, 2 months or more, 3 months or more, etc. Multiple doses of the subject compound can be administered according to the subject methods to provide for protection of the subject form infection for an extended period of time. The timing and dosage amounts can be readily determined using conventional methods.

In some cases, the subject methods of treatment include a step of determining or diagnosing whether the subject has an influenza A virus infection. The determining step can be performed using any convenient methods. In some cases, the determining step includes obtaining a biological sample from the subject and assaying the sample for the presence of viral cells. The sample can be a cellular sample. The determining step can include identification of viral cells including a particular mutation.

Accordingly, a variety of subjects may be amenable to treatment using the subject compounds and pharmaceutical compositions disclosed herein. As used herein, the terms "subject" and "host" are used interchangeably. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of the subject compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

Aspects of the present disclosure include methods of treating or preventing a coronavirus (CoV) infection. The subject oligonucleotide compounds find use as a new class of antiviral therapeutics that can efficiently disrupt the RNA secondary structures of CoV, and thus treat or prevent the CoV infection in a subject. In some cases, the subject oligonucleotide compounds can inhibit a host miRNA interaction with CoV. In some instances the subject oligonucleotide compounds find use as a new antiviral therapeutic that can efficiently disrupt the RNA secondary structures of CoV, and disrupt packaging and completely prevent otherwise lethal disease in vivo. In certain cases, the CoV is selected from HCoV-229E, HCoV-OC43, SARS-CoV, HCoV-NL63, HKU1, MERS-CoV, and SARS-CoV-2. In certain cases, the CoV is SARS-CoV-2.

Aspects of the method include administering to a subject in need thereof a therapeutically effective amount of a subject compound to treat the subject for an infection or prevent infection in the subject. By "a therapeutically effective amount" is meant the concentration of a compound that is sufficient to elicit the desired biological effect (e.g., treatment or prevent of the condition or disease, influenza A, influenza B, coronavirus infection, RSV infection). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are partially or completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease (e.g., infection); (iii) relief, that is, causing the regression of clinical symptoms; (iv) prevents hospitalization or the need to be in a critically ill conditions that require intensive care unit (ICU); (v) shortens the length of hospitalization or ICU stay; (vi) prevents or shortens the need to have assisted ventilation including but not limited to supplemental oxygen, non-invasive positive pressure ventilation (CPAP and or BPAP), mechanical ventilation; (vi) prevents or shortens the need to have assisted cardiopulmonary bypass such as extracorporeal membrane oxygenation (ECMO) devices; (vii) prevent the development of super-imposed bacterial infections; and (viii) prevent death. In the context of influenza A, influenza B, and coronavirus (CoV) infection, the term "treating" includes any or all of: reducing the number of viruses in the body, reducing the number of virally infected cells in a patient, inhibiting replication of intra and/or extracellular viruses and virus-infected cells, and ameliorating one or more symptoms associated with an infection.

The subject to be treated can be one that is in need of therapy, where the host to be treated is one amenable to treatment using the subject compound. In some embodiments, the subject is one that is suspected of having a coronavirus infection. In certain embodiments, the subject is diagnosed as having a coronavirus infection. As such, in some cases, the subject is one who has been infected with the virus.

In certain cases, the subject is one who is at risk of being infected, or is suspected of being infected with the virus. The subject methods can be used to prevent infection of the subject with a coronavirus. By "prevention" is meant that the subject at risk of coronavirus infection is not infected despite exposure to the virus under conditions that would normally lead to infection or the subject's infection severity is attenuated upon infection. In some cases, the administering of the subject active agent (e.g., oligonucleotide compound) protects the subject against infection instantaneously, for 1 week or more, such as 2 weeks or more, 3 weeks or more, 1 month or more, 2 months or more, 3 months or more, etc. Multiple doses of the subject compound can be administered according to the subject methods to provide for protection of the subject form infection for an extended period of time. The timing and dosage amounts can be readily determined using conventional methods.

In some cases, the subject methods of treatment include a step of determining or diagnosing whether the subject has a coronavirus infection. The determining step can be performed using any convenient methods. In some cases, the determining step includes obtaining a biological sample from the subject and assaying the sample for the presence of intra and/or extracellular viruses and virus-infected cells. The sample can be a cellular sample. The determining step can include identification of intra and/or extracellular viruses and virus-infected cells including a particular mutation.

In some embodiments, an effective dosage of the subject compound is an effective volume in a mass concentration that ranges from about 50 ng/ml to about 50 μg/ml (e.g., from about 50 ng/ml to about 40 μg/ml, from about 30 ng/ml to about 20 μg/ml, from about 50 ng/ml to about 10 μg/ml, from about 50 ng/ml to about 1 μg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 μg, from about 1 μg to about 10 μg, from about 10 μg to about 50 μg, from about 50 g to about 150 μg, from about 150 μg to about 250 μg, from about 250 μg to about 500 μg, from about 500 μg to about 750 μg, from about 750 μg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the subject compound can be administered twice daily (qid), daily (qd), every other day (qod), every third day, three times per week (tiw), or twice per week (biw) over a period of time. For example, a compound can be administered qid, qd, qod, tiw, or biw over a period of from one day to about 2 years or more. For example, a compound can be administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of viral cells. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of viral cells or components thereof that are associated with the disease or condition of interest (e.g., as described herein). The sample can be a cellular sample. The assessment step(s) of the subject method can be performed at one or more times before, during and/or after administration of the subject compounds, using any convenient methods. In certain cases, the assessment step includes identification and/or quantitation of viral cells. In certain instances, assessing the subject include diagnosing whether the subject has a viral infection or symptoms thereof.

Screening Methods

Aspects of the present disclosure also include screening assays configured to identify agents that find use in methods of the invention, e.g., as reviewed above. Aspects of the present disclosure include methods for screening a candidate agent for the ability to inhibit influenza A virus in a cell. In some instances, the method comprises: contacting a sample comprising viral RNA (vRNA) comprising a PSL2 motif with a candidate agent; and determining whether the candidate agent specifically binds to the PSL2 motif. In some cases, an agent that specifically binds to the PSL2 motif will treat the subject having the influenza A virus infection. In some instances, the method comprises: contacting a sample comprising viral RNA (vRNA) comprising a segment of the influenza B genomic RNA with a candidate agent; and determining whether the candidate agent specifically binds to the vRNA. In some cases, an agent that specifically binds to the HA motif will treat the subject having the influenza B virus infection. By assessing or determining is meant at least predicting that a given test compound will have a desirable activity, such that further testing of the compound in additional assays, such as animal model and/or clinical assays, is desired.

The candidate agent is selected from: a small molecule, an oligonucleotide, an antibody and a polypeptide. In some instances, the determining step comprises detecting a cellular parameter, wherein a change in the parameter in the cell as compared to in a cell not contacted with candidate agent indicates that the candidate agent specifically binds the PSL2 motif. In some cases, the subject screening method is a method of RNA structure mapping, such as SHAPE analysis (Selective 2'-hydroxyl acylation analyzed by primer extension). In certain instances, the candidate agent is an oligonucleotide.

Drug screening may be performed using an in vitro model, a genetically altered cell or animal, or purified PSL2 protein. One can identify ligands that compete with, modulate or mimic the action of a lead agent. Drug screening identifies agents that bind to particular sites of PSL2 motif. A wide variety of assays may be used for this purpose, including labeled in vitro binding assays, electrophoretic mobility shift assays, immunoassays for protein binding, and the like. Knowledge of the 3-dimensional structure of PSL2, derived from the structural studies described herein, can also lead to the rational design of small drugs that specifically inhibit IAV activity.

The term "agent" as used herein describes any molecule, e.g., oligonucleotide, protein or pharmaceutical, with the capability of binding PSL2 to inhibit IAV. Generally, a plurality of assay mixtures are run in parallel with different agent concentrations to obtain a differential response to the various concentrations. Typically one of these concentrations serves as a negative control, i.e., at zero concentration or below the level of detection.

Aspects of the present disclosure also include screening assays configured to identify agents that find use in methods of the invention, e.g., as reviewed above. Aspects of the present disclosure include methods for screening a candidate agent for the ability to inhibit a coronavirus in a cell. In some instances, the method comprises: contacting a sample comprising viral RNA (vRNA) comprising a conserved RNA secondary structure of CoV with a candidate agent; and determining whether the candidate agent specifically binds to the conserved RNA secondary structure motif. In some cases, an agent that specifically binds to the conserved RNA secondary structure motif will treat the subject having the coronavirus infection. By assessing or determining is meant at least predicting that a given test compound will have a desirable activity, such that further testing of the compound in additional assays, such as animal model and/or clinical assays, is desired.

Candidate agents encompass numerous chemical classes, such as oligonucleotides, antibodies, polypeptides, and organic molecules, e.g., small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Of interest in certain embodiments are compounds that pass the blood-brain barrier.

Where the screening assay is a binding assay, one or more of the molecules may be joined to a member of a signal producing system, e.g., a label, where the label can directly or indirectly provide a detectable signal. Various labels include, but are not limited to: radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

Cells and viruses: HEK 293T and MDCK cells were obtained from American Type Culture Collection (Manassas, VA) and were maintained in Dulbecco's modified Eagle's medium with 10% fetal bovine serum and penicillin-streptomycin (Gibco). Influenza A/PR/8/34 (PR8) H1N1 virus was generated using an eight-plasmid reverse genetic system. Tissue-cultured adapted influenza A/Hong Kong/8/68 (HK68) H3N2 virus was obtained from ATCC (ATCC-VR-1679). Viruses were grown and amplified in 10-day-old specific-pathogen-free chicken embryos at 35° C. (Charles River Laboratories; SPAEAS).

Plasmid constructs and cloning: Plasmids were used containing the wild-type PB2 segments from influenza viruses A/PuertoRico/8/34 (H1N1) [PR8], A/New York/470/2004 (H3N2) [NY470], A/New York/312/2001 (H1N1) [NY312], A/Brevig Mission/1/1918 (H1N1) [1918], A/California/04/2009 (H1N1) [CA09], A/Vietnam/03/2004 (H5N1) [VN1203], and A/Anhui/1/2013 (H7N9). For the generation of PR8 packaging mutant vRNA, we utilized a Stratagene QuickChange XL site-directed mutagenesis kit (Stratagene) for mutagenesis of a pDZ plasmid containing the PB2 gene of PR8. Sequences of each mutated construct were confirmed by automated sequencing.

Reverse genetics and virus titrations: Influenza A/Puerto Rico/8/34 (PR8) virus was generated using an eight-plasmid reverse genetic system (Hoffman et al., 2000). Briefly, to produce recombinant PR8 viruses, $10^6$ cells of a 293T/MDCK co-culture were Lipofectamine 3000 (Invitrogen) transfected with 1 ug of one of each of the eight segments contained within plasmids that utilize a bidirectional dual Pol I/II promoter system for the simultaneous synthesis of genomic vRNA and mRNA. Cells were collected 24 hours post-transfection and inoculated into the allantoic cavities of 10-day-old chicken embryos (Charles River, research grade specific-pathogen-free eggs). Rescue of recombinant viruses was assessed by hemagglutination activity. Each newly rescued virus was further plaque titered and mutations were confirmed by sequencing of mutated genes. Plaque assays were carried out on confluent MDCK cells as described previously (Szretter et al., 2006). Hemagglutination (HA) assays were carried out in 96-well round-bottomed plates at room-temperature, using 50 ul of virus dilution and 50 ul of a 0.5% suspensions of turkey red blood cells in phosphate-buffered saline (PBS).

Viral growth kinetics: Growth kinetics for PR8 viruses was determined by inoculation of 10-day-old chicken eggs with 100 plaque-forming units (PFU) of virus. At 72 h post-inoculation, the virus titer in the allantoic fluid was determined by titration of plaques on MDCK cells.

Isolation of packaged vRNAs: To analyze packaged vRNA for PR8 mutated viruses, 10-day-old eggs were inoculated with approximately 1000 PFU of recombinant virus and incubated for 72 h. Allantoic fluid was harvested, and supernatant was clarified by low-speed centrifugation. Clarified supernatant was then layered on a 30% sucrose cushion and ultra-centrifuged at 30,000 RPM for 2.5 h (Beckman Rotor SW41). Pelleted virus was resuspended in PBS and TRIzol (Invitrogen) extracted. Precipitated vRNA was resuspended in a final volume of 20 ul of 10 mM Tris-HCl (pH 8.0) and stored at −80° C.

qPCR analysis of packaged vRNAs: Approximately 200 ng of extracted vRNAs were reverse transcribed using a universal 3' primer (5'-AGGGCTCTTCGGCCAGCRAAAGCAGG) (SEQ ID NO:97) and Superscript III reverse transcriptase (RT) (Invitrogen). The RT product was diluted 10,000-fold and used as a template for quantitative PCR (qPCR). Separate PCRs were then carried out as previously described (Marsh et al., 2007) with segment-specific primers. The 10 ul reaction mixture contained 1 ul of diluted RT product, a 0.5 uM primer concentration, and SYBR Select Master Mix (Applied Biosystems) that included SYBR GreenER dye, 200 uM deoxynucleoside triphosphates, heat-labile UDG, optimized SYBR Green Select Buffer, and AmpliTaq DNA polymerase UP enzyme. Relative vRNA concentrations were determined by analysis of cycle threshold values, total vRNA amount was normalized by equalization of the level of HA vRNA, and then percentages of incorporation were calculated relative to the levels of wt vRNA packaging. Viral packaging results represent the averaged levels of vRNA incorporation±standard deviations derived from two independent virus purifications, with vRNA levels quantified in triplicate, n=6.

Mouse infections: Groups of 6-8 week old female BALB/C mice (Jackson Laboratory) were lightly anesthetized with isoflurane and intranasally infected with 50 ul of 1000 PFU of wild type mouse-adapted PR8 (H1N1) virus (ATCC), PB2 mutated PR8 recombinant viruses, or sterile PBS. Weights were measured daily, and animals were humanely sacrificed by day 10 or when weight loss exceeded 20%. All animal care and experimental procedures are in accordance with the National Institutes of Health Guidelines for the Care and Use of Laboratory Animals and approved by the Stanford University Administrative Panel on Laboratory Animal Care.

Locked nucleic acid (LNA) design and preparation: Oligonucleotides containing locked nucleic acids (LNA) were custom synthesized from Exiqon. Capitalized letters denote LNA. Lowercase letters denote typical (non-locked) DNA nucleotides. All oligonucleotides contained phosphorothioate internucleoside linkages. The LNAs were designed to be complementary to different sequences contained in the PSL2 structure of segment PB2. LNA 8a and 9 are designed to contain a stretch of 6-8 DNA nucleotides for RNAse-H recruitment. Sequences of all LNAs are shown below.

```
LNA 1:
                                    (SEQ ID NO: 67)
5' AccAaaAGaaT 3'

LNA 2:
                                    (SEQ ID NO: 68)
5' TggCcATcaaT 3'

LNA 3:
                                    (SEQ ID NO: 69)
5' TagCAtActtA 3'

LNA 4:
                                    (SEQ ID NO: 70)
5' CCAAAAGA 3'

LNA 5:
                                    (SEQ ID NO: 71)
5' CATACTTA 3'

LNA 6:
                                    (SEQ ID NO: 72)
5' CagaCaCGaCCaaAA 3'

LNA 7:
                                    (SEQ ID NO: 73)
5' TAcTtaCTgaCagCC 3'

LNA 8a:
                                   (SEQ ID NO: 188)
5' AGAcagcgaccaaAAG 3'-with RNase-H activity

LNA 9:
                                    (SEQ ID NO: 75)
5' TACTtactgacaGCC 3'-with RNase-H activity

LNA9.2:
                                    (SEQ ID NO: 76)
5' TACttactgacAGCC 3'

LNA10:
                                    (SEQ ID NO: 77)
5'ACCaaaagAAT 3'

LNA11:
                                    (SEQ ID NO: 78)
5' TGGccatcAAT 3'

LNA12:
                                    (SEQ ID NO: 79)
5'TAGcatacTTA 3'

LNA13:
                                    (SEQ ID NO: 80)
5'CgacCAaaAGaattC 3'
```

-continued

```
LNA14:
                                    (SEQ ID NO: 81)
5'CGACcaaaagaATTC 3'

LNA15:
                                    (SEQ ID NO: 82)
5'GaTGgCcATcaAttA 3'

LNA16:
                                    (SEQ ID NO: 83)
5'GATGgccatcaATTA 3'

LNA17:
                                    (SEQ ID NO: 84)
5'TcTAgCaTAcTTacT 3'

LNA18:
                                    (SEQ ID NO: 85)
5'TCTAgcatactTACT 3'

LNA19:
                                    (SEQ ID NO: 86)
5'GAAttcggatgGCCA 3'

LNA20:
                                    (SEQ ID NO: 87)
5'GGCCatcaattaGTG 3'

LNA21:
                                    (SEQ ID NO: 88)
5'TTCGgatggccaTCA 3'

LNA22:
                                    (SEQ ID NO: 89)
5'AGCCagacagCGA 3'

LNA23:
                                    (SEQ ID NO: 90)
5'GACAgccagacaGCA 3'
```

The following oligonucleotides were designed to cover single-nucleotide polymorphisms (SNPs) in PSL2 sequence. The following exemplary sequences are modified versions of LNA9 with single mutation sites that would protect against a few avian and bat strains whose PLS2 sequence contains a nucleotide change with the LNA9 target sequence. It is understood that similar design can be applied to any of the sequences described herein.

```
LNA9.G74C:
                                    (SEQ ID NO: 94)
5' TACTtactgacaGTC 3';

LNA9.T80C:
                                    (SEQ ID NO: 95)
5' TACTtaccgacaGCC 3';
and

LNA19.U56C:
                                    (SEQ ID NO: 96)
5' GGATttcggatggCCA 3'.
```

Antiviral assays: LNAs were reconstituted in RNAse free water at 100 μM, aliquoted and stored at −20° C. prior to single use. Lipofectamine 3000 (Life Technology) was used to transfect LNA into cells at a final concentrations of 1 μM, 100 nM, 10 nM, and 1 nM per manufacturer's protocol. For prophylactic antiviral assays, $10^6$ MDCK cells were plated in 6-well plates 24 h prior to being transfected with the indicated LNA. Cells were then infected at 4 h, 2 h, or 1 h post-transfection with 0.01 MOI of PR8 (H1N1) or HK68 (H3N2) virus. For post-infection, therapeutic antiviral assessment, MDCK cells were infected with PR8 or HK68 as described. LNAs were then transfected at 4 h, 2 h, or 1 h post-infection. After 48 h post-infection, supernatant was collected, and viral titer was determined by plaque assay.

Cellular SARS-CoV-2 replication assays: For cellular replication assays, LNA ASOs were reconstituted in RNase-free water at 100 μM stock solutions, aliquoted and stored at −20° C. prior to single-use. One day prior to transfection, Huh-7, Vero E6, or ACE-A549 cells were plated in 96-well clear bottom plates to be 60-70% confluency at the time of treatment with LNA ASOs or Scrambled LNA. Lipofectamine 3000@ (Life Technologies) was used to transfect LNA ASO's into cells at 25 nM or 100 nM final concentration per manufacturer's protocol. Cells were then infected with SARS-CoV-2 reporter virus expressing nanoluciferase (SARS-CoV-2 nLUC) at an MOI of 0.3 for 1 h after which the virus was removed and fresh medium was added. Recombinant SARS-CoV-2 nLUC is an authentic fully replicating virus where ORF7 has been deleted and replaced with nLUC. Thus the measurement of nLUC expression is a surrogate marker of virus replication enabling the screening of antiviral compounds.

In vitro transcription of vRNA: For each wild-type isolate (PR8, 1918, VN1203, NY470, NY312, CA09, and A/Anhui/1/2013 H7N9) and PR8 packaging mutant clones, PB2 cDNA was amplified from plasmid using segment-specific primers under a T7 promoter. Amplified cDNA was gel-purified using an Invitrogen DNA gel kit. vRNAs were then produced by in vitro transcription, using T7-MEGAscript. vRNAs for SHAPE were purified by MEGAclear (Thermofisher, cat. no. AM1908) with purity and length verified by capillary electrophoresis.

sf-SHAPE analysis of vRNA: PB2 vRNA was folded (100 mM NaCl; 2.5 mM MgCl; 65° C. for 1 min, 5 min cooling at room temperature, 37° C. for 20-30 min) in 100 mM HEPES, pH=8.2 min acylation with NMIA (Wilkinson et al., 2006) and reverse transcription (RT) primer extension were performed at 45° C. for 1 min, 52° C. for 25 min, 65° C. for 5 min, as previously described (Mortimer and Weeks, 2009). 6FAM was used for all labeled primers. Exceptions to these protocols were as follows: (i) RNA purification after acylation was performed using RNA C&C columns (Zymo Research), rather than ethanol precipitation; (ii) before and after SHAPE primer buffer was added, the mixture was placed at room temperature for 2-5 min, which enhanced RT transcription yields significantly; (iii) DNA purification was performed using Sephadex G-50 size exclusion resin in 96-well format then concentrated by vacuum centrifugation, resulting in a more significant removal of primer; and (iv) 2 pmol RNA was used in ddGTP RNA sequencing reactions.

The ABI 3100 Genetic Analyzer (50 cm capillaries filled with POP6 matrix) was set to the following parameters: voltage 15 kV, T=60° C., injection time=15 s. The GeneScan program was used to acquire the data for each sample, which consisted of purified DNA resuspended in 9.75 ul of Hi-Di formamide, to which 0.25 ul of ROX 500 internal size standard (ABI Cat. 602912) was added. PeakScanner parameters were set to the following parameters: smoothing=none; window size=25; size calling=local southern; baseline window=51; peak threshold=15. Fragments 250 and 340 were computationally excluded from the ROX500 standard (Akbari et al., 2008). The data from PeakScanner were then processed into SHAPE data by using FAST (fast analysis of SHAPE traces), a custom program (Pang et al., 2011). FAST automatically corrects for signal differences due to handling errors, adjusts for signal decay, and converts fragment length to nucleotide position, using a ddGTP ladder as an external sizing standard and the local Southern method (Pang et al., 2011 and Pang et al., 2012).

RNAstructure parameters: slope and intercept parameters of 2.6 and −0.8 kcal/mol, were initially tried, as suggested (Deigan et al., 2009); smaller intercepts closer to 0.0 kcal/mol (e.g. ~−0.3) were found to produce fewer less optimal structures (within a maximum energy difference of 10%). This minor parameter difference may be due to the precise fitting achieved between experimental and control data sets by the automated FAST algorithm. In its current implementation, FAST is integrated into RNAstructure, which requires MFC (Microsoft Foundation Classes). RNA structures were drawn and colored using RNAViz 2 (De Rijk et al., 2003) and finalized in Adobe Illustrator.

Construct design, RNA synthesis and chemical modification for mutate-and-map experiments: Double-stranded DNA templates were prepared by PCR assembly of DNA oligomers designed by an automated MATLAB script as previously described (NA_Thermo, available at "https:" followed by "//github." Followed by "com/DasLab/NA_thermo") (Kladwang and Cordero et al., 2011). Constructs for mutate-and-map ($M^2$) includes all single mutants to Watson-Crick counterpart. Compensatory mutants for mutation/rescue were designed based on base-pairing in the proposed secondary structure (Tian et al., 2014). In vitro transcription reactions, RNA purification and quantification steps were as described previously (Kladwang and Cordero et al., 2011). One-dimensional chemical mapping, mutate-and-map ($M^2$), and mutation/rescue were carried out in 96-well format as described previously (Kladwang and VanLang et al., 2011; Kladwang and Cordero et al., 2011; Cordero et al., 2013). Briefly, RNA was heated up and cooled to remove secondary structure heterogeneity; then folded properly and incubated with SHAPE reagent (5 mg/mL 1-methyl-7-nitroisatoic anhydride (1M7)) (Mortimer and Weeks, 2007); modification reaction was quenched and RNA are recovered by poly(dT) magnetic beads (Ambion) and FAM-labeled Tail2-A20 primer; RNA was washed by 70% ethanol (EtOH) twice and resuspended in $ddH_2O$; followed by reverse transcription to cDNA and heated NaOH treatment to remove RNA. Final cDNA library was recovered by magnetic bead separation, rinsed, eluted in Hi-Di formamide (Applied Biosystems) with ROX-350 ladder, loaded to capillary electrophoresis sequencer (ABI3100). Data processing, structural modeling, and data deposition: The HiTRACE software package version 2.0 was used to analyze CE data (both MATLAB toolbox and web server available (Yoon et al., 2011; Kim et al., 2013)). Trace alignment, baseline subtraction, sequence assignment, profile fitting, attenuation correction and normalization were accomplished as previously described (Kim et al., 2009; Kladwang et al., 2014). Sequence assignment was accomplished manually with verification from sequencing ladders. Data-driven secondary structure models were obtained using the Fold program of the RNAstructure package version 5.4 (Mathews et al., 2004) with pseudo-energy slope and intercept parameters of 2.6 kcal/mol and −0.8 kcal/mol. 2-dimensional Z score matrices for $M^2$ datasets, and helix-wise bootstrapping confidence values were calculated as described previously (Tian et al., 2014; Kladwang and VanLang et al., 2011). Z score matrices were used as base-pair-wise pseudofree energies with a slope and intercept of 1.0 kcal/mol and 0 kcal/mol. Secondary structure images were generated by VARNA (Darty et al., 2009). All chemical mapping datasets, including one-dimensional mapping, mutate-and-map, and mutation/rescue, have been deposited at the RNA Mapping Database ("http:" followed by "//rmdb.stanford." followed by "edu") (Cordero et al., 2012).

SHAPE analysis of LNA-targeted vRNA: DNA template of PR8 segment PB2 was prepared by PCR assembly of DNA oligomers, and in vitro transcription reactions, RNA purification and quantification steps were as described previously (Kladwang and VanLang et al., 2011). One-dimensional SHAPE chemical mapping was performed in 96-well plate format as described above with the following exception: once RNA was denatured and refolded as described, 100 nM of each prepared LNA was added to the folded RNA and incubated with 5 mg/mL of SHAPE reagent 1M7 (1-methyl-7-nitroisatoic anhydride). Modification quenching, RNA recovery, re-suspension, reverse transcription, cDNA sequencing and data processing was performed as described, see, Kladwang and VanLang et al., 2011.

Example 1

SHAPE-Characterization of IAV Segment PB2 Packaging Signal Identifies Conserved Structure Selective 2'-hydroxyl acylation analyzed by primer extension (SHAPE) and computational modeling was applied to IAV segment PB2 genomic vRNA to search for structured RNA domains. In vitro transcribed full-length (−)-sense PB2 vRNA from strain A/Puerto Rico/8/1934 (H1N1) “PR8” was folded in solution (Pang et al., 2011) and interrogated using an electrophilic SHAPE reagent that preferentially reacts with nucleotides existing in flexible, single-stranded states (Wilkinson et al., 2006) (FIG. 1). This analysis revealed that much of the 2341-nt vRNA is largely unstructured (FIG. 2), consistent with recent bioinformatics studies that found higher potential for RNA secondary structure conservation in the (+)-sense over the (−)-sense RNA for all segments, including PB2 (Priore et al., 2012; Moss et al., 2011). These previous studies did not analyze the terminal coding regions (TCR), and instead stopped 80 nucleotides short of the PB2 5' TCR’s end. SHAPE-guided modeling suggested several areas in this region which contain stable RNA secondary structures, most notably a stem-loop motif, named herein as the Packaging Stem-Loop 2 (PSL2) (FIG. 1A), comprising nucleotides 34-87 ((−)-sense notation). This segment included a set of nucleotides that were previously implicated in PB2 packaging through mutational analysis via an unidentified mechanism (FIG. 1A-1B, see circled nucleotides) (Gao et al., 2012; Marsh et al., 2008; Liang et al., 2008; Gog et al., 2007). Supporting the hypothesis that these prior mutations act through disruption of PSL2 structure, SHAPE analysis of the mutants yielded different conformations that all abrogated the wild-type PSL2 structure (FIG. 1C, FIG. 3). The 60-nucleotide region encompassing PSL2 displays near 100% sequence conservation at the single nucleotide level between seasonal as well as pandemic strains of different subtypes and species origins (FIG. 4), suggesting the existence of a strict biologic requirement to maintain an intact PSL2 structure. Because differing downstream sequences within PB2 vRNA could alter the secondary structure of PSL2, PSL2’s structural conservancy was explored by performing SHAPE analysis on full-length wild-type PB2 vRNAs isolated from a variety of IAV strains and subtypes, including the highly pathogenic avian H5N1 and pandemic 1918 H1N1 strains. Despite the presence of two diverging nucleotides within the stem-loop and significant divergence in flanking sequences, the PSL2 stem-loop structure was recovered in SHAPE-guided modeling of PB2 RNA across these diverse species and subtypes (FIG. 1D-1F).

FIG. 1A-FIG. 1F shows SHAPE-chemical mapping performed on full-length (−)-sense wild-type PB2 vRNAs. Colors denote SHAPE reactivity, which is proportional to the probability that a nucleotide is single-stranded. All structures are truncated to highlight the 5' termini sequence structure. Energy=ΔG free energy value of determined structures generated by the RNAstructure modeling algorithm using SHAPE pseudofree energy parameters. (FIG. 1A) Wild-type PB2 RNA secondary structure from strain A/Puerto Rico/8/1934 “PR8” (H1N1). Color-coded circles correspond to nucleotides sites where synonymous mutations were reported to affect PB2 packaging (Gao et al., 2012; Marsh et al., 2011). (FIG. 1B) Packaging efficiency of synonymous mutants in (FIG. 1*a*), determined by qPCR. Results performed in triplicate. Error bars=±SD. Box below indicates mutant name and corresponding mutational change. Nucleotide numbering shown in the genomic (−)-sense orientation. (FIG. 1C) SHAPE-determined structures of PB2 packaging-defective mutant vRNAs, m757 (G44C) and m745 (A80U). Black boxes=site(s) of synonymous mutation, (FIG. 1D-FIG. 1F) SHAPE-determined structures of wild-type PB2 from pandemic and highly pathogenic strains, including different subtypes: (FIG. 1D) 1918 pandemic (A/Brevig Mission/1/1918 (H1N1)), (FIG. 1E) Highly-pathogenic avian (A/Vietnam/1203/2004 (H5N1)), (FIG. 1F) 2009 pandemic ‘swine’ (A/California/04/2009 (H1N1)).

FIG. 2, panels A-B, shows SHAPE reactivity of full-length PB2 vRNA. (FIG. 2, panel A) Average SHAPE reactivity (window bin size=100 nt) as a function of nucleotide position for the full-length (−)-sense PB2 vRNA from IAV strain A/Puerto Rico/8/1934 (H1N1). The PSL2 region (highlighted in blue, nts 34-86) encompasses the 5' packaging signal domain, which possesses a high density of codons whose third position is conserved, and has one of the lowest SHAPE reactivities within the vRNA. The region after PSL2 is relatively unstructured yet contains another potential site for the presence of RNA structure between nucleotides 1400 and 1500. Interestingly, this second internal region was also predicted to contain structural elements by a 2011 bioinformatics study (ref. 19). (FIG. 2, panel B) Zoomed in view of PSL2 region from (FIG. 2*a*). Window bin size=10 nt.

FIG. 3A-FIG. 3E shows packaging-defective mutations disrupt wild-type SHAPE reactivity. Left: Mutant SHAPE reactivity plotted as change over WT. Nucleotide numbering starts from 5' end of (−)-sense vRNA. Orange bars indicate site of mutation. Energy values represent ΔG free energy of the predicted structure generated by the RNAstructure modeling algorithm using SHAPE pseudofree energy parameters. Right: SHAPE-determined structures of full-length (−)-sense mutant PB2 vRNA from PR8 strain (H1N1). Images are truncated to highlight 5' terminal region. (FIG. 3A) Wild-type. Packaging-defective mutants: (FIG. 3B) m744b (AG83, 85UA). (FIG. 3C) m745 (A80U). (FIG. 3D) m55c (CU35, 36UC). (FIG. 3E) m757 (G44C).

FIG. 4 shows conservancy of nucleotide sequence containing the PSL2 structure. Graphical representation of nucleic acid sequence alignments across diverse influenza A viral subtypes and strains (“weblogo.” followed by “berkeley” followed by “.edu”). The overall height represents sequence conservation at that nucleotide position, while the height of symbols within each position indicates the relative frequency of each nucleotide at that site. Black box=PSL2 region. Sequences included in the alignment: highly pathogenic A/Brevig Mission/1/1918 (H1N1), pandemic “swine flu” A/California/04/2009 (H1N1), modern human A/New York/470/2004 (H3N2), human A/Puerto Rico/8/1934 (H1N1), high pathogenic avian A/Vietnam/03/2004 (H5N1), human A/Hong Kong/8/1968 (H3N2), and human A/New York/312/2001 (H1N1). RNA nucleotides numbered in (−)-sense orientation. Sequence alignment of the terminal 5' region of PB2 corresponding to the above sequences. Shaded blue box encompasses the PSL2 RNA secondary structural element. Black dots designate divergent nucleotide sites.

Figure 5A:
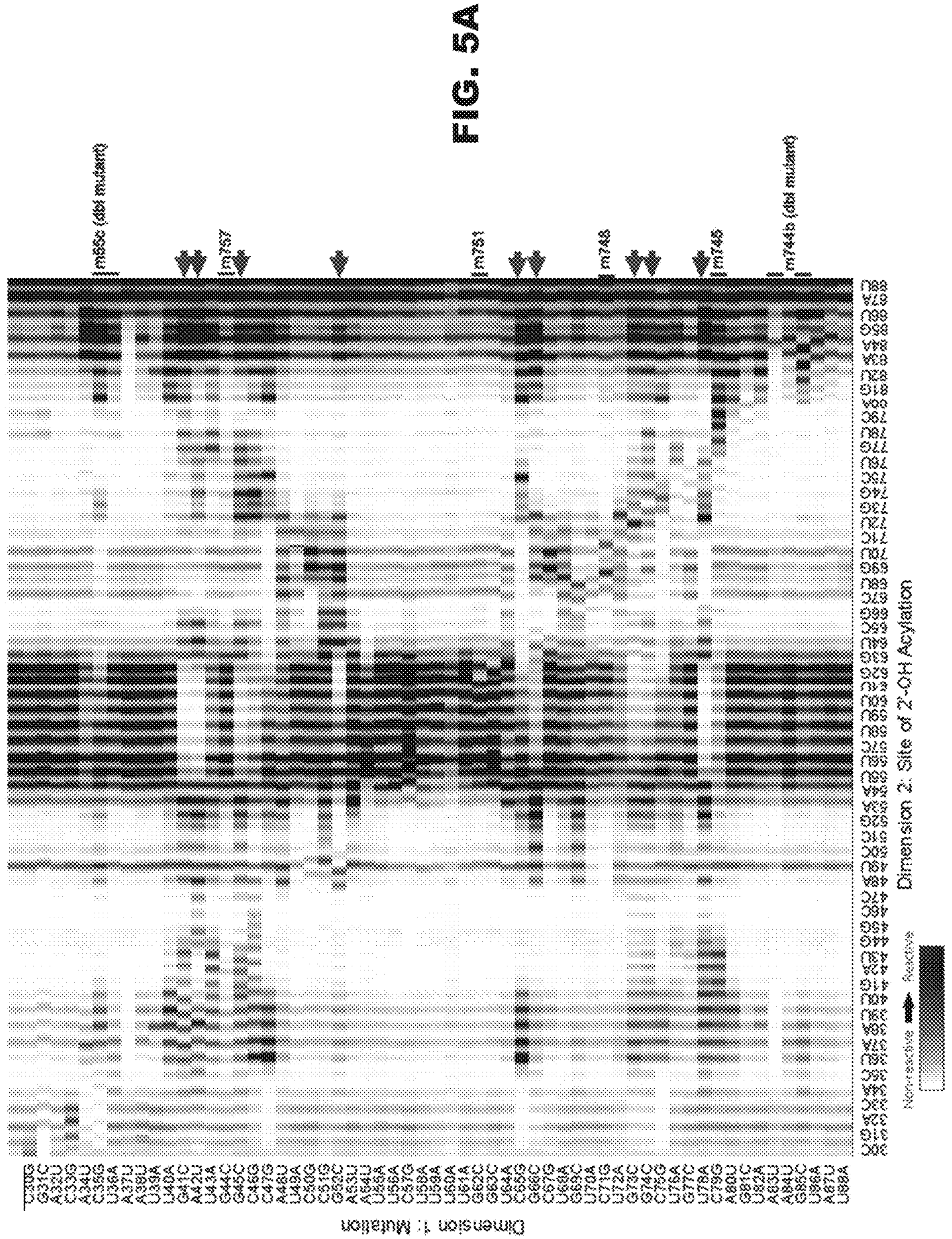
FIG. 5A-FIG. 5D depicts the 2-dimensional Mutate-and-Map analysis of PSL2 RNA secondary structure (FIG. 5C, SEQ ID NO: 12).
Figure 5B:
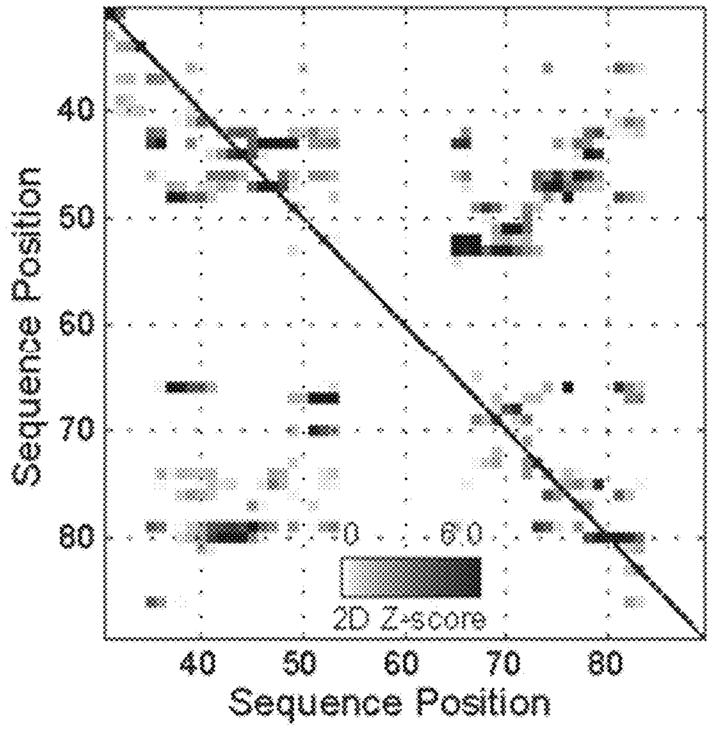
Figure 5C:
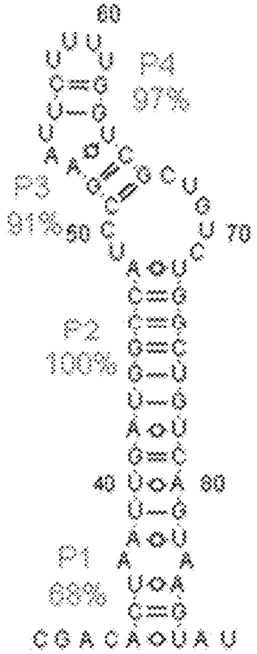
Figure 5D:
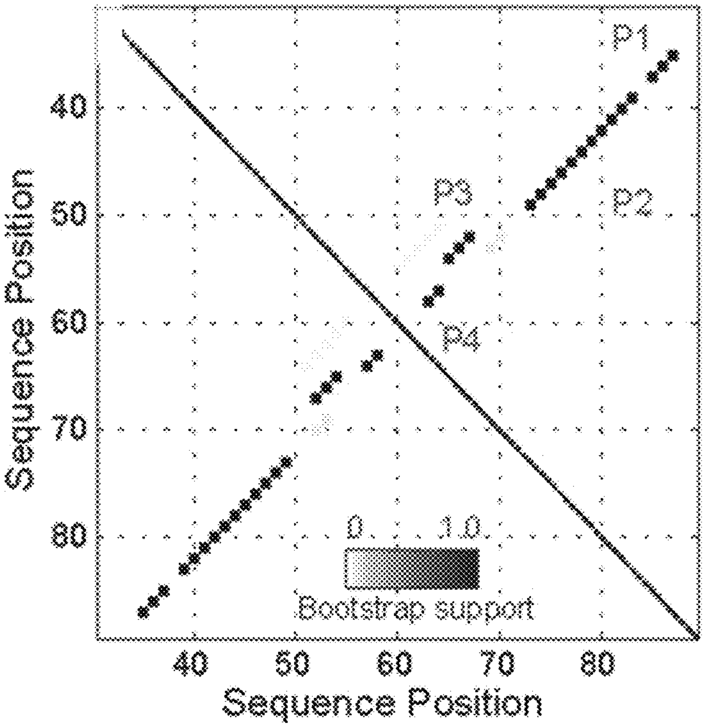
Figure 6:
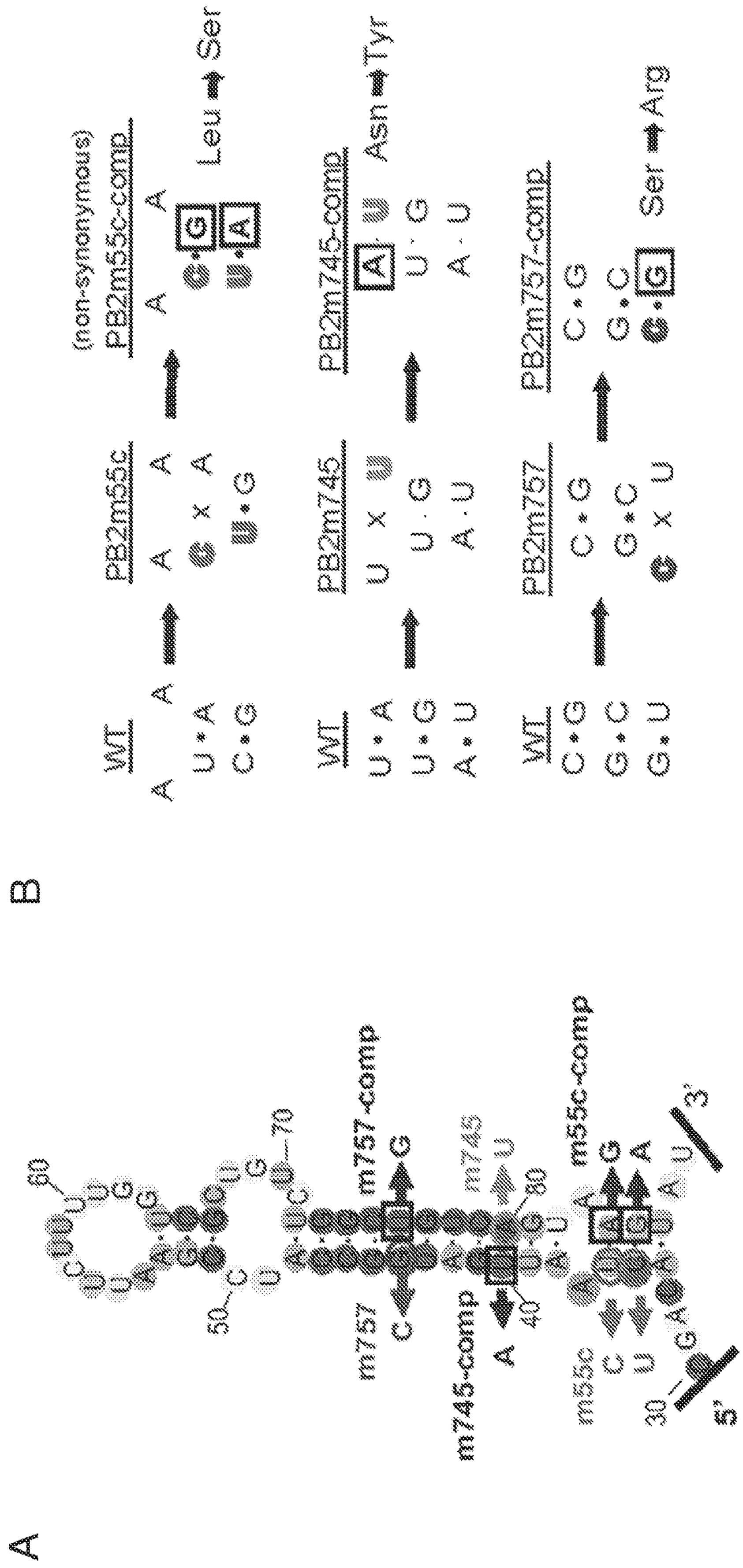
FIG. 6, panels A-B, depicts the design of compensatory mutations to previously described PR8 PB2 mutants (panel A, SEQ ID NO: 13).

Mutate-and-Map Strategy Validates PSL2 Structure and Predicts Novel Packaging Mutants To further test the SHAPE analysis of the PSL2 RNA structure and to uncover additional informative mutations needed for in vivo tests, multidimensional chemical mapping (Kladwang and Das, 2010) methods were applied to the PSL2 segment. First, mutate-and-map ($M^2$) measurements confirmed disruption of the chemical reactivity pattern upon systematic mutation of each stem residue, including changes at nucleotides previously found to be critical for PB2 packaging (FIG. 5A, see noted fields) (Marsh et al., 2008; Gog et al., 2007). Automated computational analysis based on these $M^2$ data recovered the SHAPE-guided PSL2 structure with high confidence (FIG. 1C, FIG. 3, FIG. 5B-FIG. 5D), further validating the structural model. Second, as predictive tests, compensatory mutations were designed to restore the base pairs in the wild-type stem-loop structure that were disrupted by the initial packaging-defective mutations (FIG. 6, panels A-B). These mutation-rescue variants indeed restored the PSL2 SHAPE pattern, providing base-pair resolution in vitro validation of the modeled structure and suggesting sequence variants to test the role of PSL2 structure in vivo.

FIG. 5A-FIG. 5D shows 2-Dimensional Mutate-and-Map (M2) analysis of PSL2 RNA secondary structure. (FIG. 5A) Systematic single nucleotide mutation and mapping of resulting chemical accessibility reveals interactions in the three-dimensional structure of the RNA. Chemical accessibilities, plotted in grey scale (black=highest SHAPE reactivity), across 88 single mutations at single-nucleotide resolutions of PSL2 element from PR8 strain PB2. Reactivity peaks (left to right) correspond to nucleotides from the 5' to 3' end of the PB2 RNA. Nucleotide sites corresponding to known packaging mutations (as reported by Marsh et al., 2008) are indicated on right in blue. Red arrows denote prominent packaging-defective mutant sites predicted by M2 analysis. (FIG. 5B) Strong features of mutate-and-map data isolated by Z-score analysis (number of standard deviations from mean at each residue). Z-scores were calculated for each nucleotide reactivity by subtracting the average reactivity of this nucleotide across all mutants and dividing by standard deviation (output_Zscore_from_rdat in HiTRACE). Squares show secondary structure model guided by mutate-and-map data. Dark signals highlight evidence of structured nucleotide pairing. (FIG. 5C) RNA secondary structure for 5' packaging signal region (nts 30-93) derived from incorporating Z-scores into the RNA-structure modelling algorithm: bootstrap confidence estimates given as green percentage values. Bootstrap values provide numerically accurate indicators of structural confidence. Low bootstrap confidence values suggest existence of alternative structural models. (FIG. 5D) Bootstrap support values for each base-pair shown as grayscale shading.

FIG. 6 shows Design of compensatory mutations to previously described PR8 PB2 mutants. (FIG. 6, panel A) Previously described synonymous mutants (m757, m745, m55c) are mapped onto PSL2 structure. (FIG. 6, panel B) Compensatory mutations (m55c-comp, m745-comp, and m757-comp) were designed at sites predicted to restore wild-type PSL2 structure based on SHAPE and mutate-and-map chemical analyses. Black boxed nucleotides denote site of compensatory mutation. (−)-sense vRNA orientation is shown. For mutations where a non-synonymous change was required to restore the structure, the alteration in encoded protein sequence is indicated.

To test whether the PSL2 stem-loop structure observed in solution was relevant to virus packaging in the cellular milieu, the same nine synonymous mutations reported by Gog et al., 2007 and Marsh et al., 2008 (FIG. 1A-FIG. 1B, FIG. 7 panel A) as well as four new synonymous mutations characterized by $M^2$ analysis (FIG. 7, panel B) were cloned into pDZ plasmids containing the PR8 PB2 gene (Marsh et al., 2008; Liang et al., 2008; Gog et al., 2007) (FIG. 8). The packaging efficiencies of the 9 previously known mutants now in the PR8 background were comparable to those originally described in the WSN33 virus[15] (FIG. 7, panel C). Of these, mutants m55c, m757, m745, and m744b, were predicted to show the most significant impairment based on their location within PSL2's stem regions (FIG. 1C, FIG. 3A-FIG. 3F, FIG. 7). In contrast, published mutations that have no effect on PB2 packaging (e.g. m731) mapped to the unstructured apical loop or fell outside of PSL2 and did not alter its structural integrity (FIG. 9A) (Marsh et al., 2008). The three novel synonymous mutants (m74-1, m74-2, and m68) identified by $M^2$-analysis as having a significant effect on in vitro PSL2 structure (FIG. 5A) showed significant loss in PB2 packaging, whereas mutation sites that resulted in negligible change in SHAPE reactivity compared to the wild-type PSL2 structure, gave wild-type-like packaging efficiency levels (e.g., m56) (FIG. 7, panel D).

FIG. 7 shows synonymous mutation of single highly conserved codons of the PR8 PB2 vRNA. (FIG. 7, panel A) Previously published synonymous mutations implicated in PB2 packaging. Upper line is the parental PR8 vRNA sequence ((+)-sense orientation), and the mutated single nucleotides are bolded in red on the line below. Numbering and nomenclature of introduced mutations are based on the reports by Marsh et al., 2008 and Gog et al., 2007. Yellow highlighted region indicates sequence containing PSL2 structure. (FIG. 7, panel B) Design of primer sequences for cloning of synonymous mutations identified from M2-analysis (see Supplemental FIG. 4*a*) into pDZ plasmids. Sequences are in (+)-sense orientation. Highlighted nucleotides=mutation site. (FIG. 7, panels C-D) Packaging efficiencies representing the percentage of mutant PB2 packaging relative to parental wild-type PB2 for (FIG. 7, panel C) Previously published synonymous mutants, and (FIG. 7, panel D) M2-analysis identified synonymous mutants. Results from two independent experiments, assays performed in triplicate (n=6). Error bars represent ±SD.

FIG. 8 shows PB2 Packaging mutant nomenclature and corresponding sites of mutation. Mutation nomenclature chart indicating names and site(s) of mutation from: 1) Previously published synonymous mutations implicated in PB2 packaging (shown in blue), based on the reports by Marsh et al., 2008 and Gog et al., 2007; and 2) PSL2 structure designed single mutants (shown in black) and double-compensatory mutants (shown in red). Numbering and nomenclature of introduced mutations are based on the genomic, (−)-sense vRNA. Instances where mutation results in change in protein coding are indicated by synonymous (SYN) or non-synonymous (Non-SYN) fields.

Figure 9B:
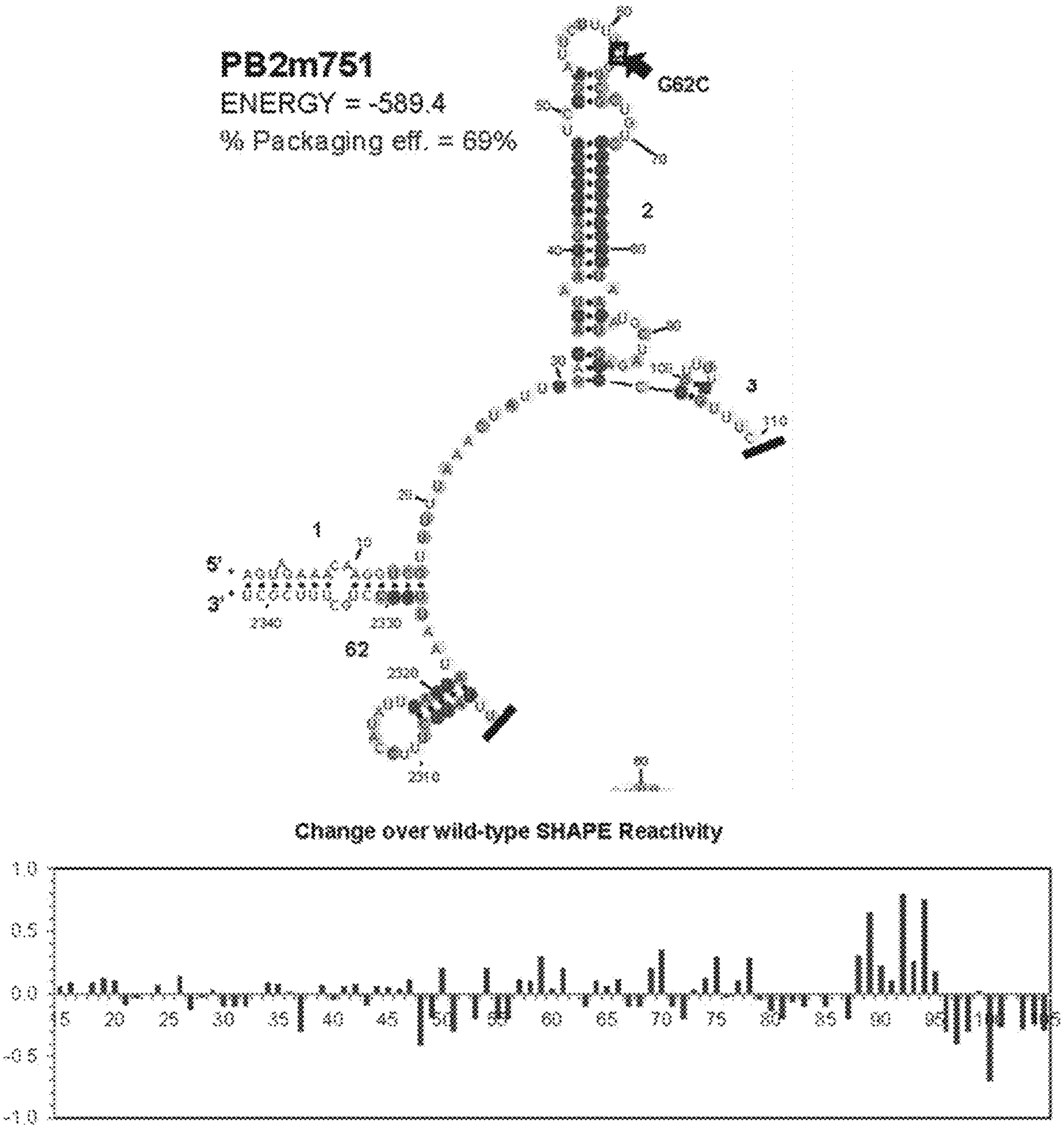

FIG. 9A-FIG. 9C shows effect of synonymous mutation on PSL2 structure. Left: Predicted RNA secondary structure of PB2 packaging mutants determined by sf-SHAPE analysis on full-length (−)-sense PB2 vRNA from PR8 strain. For clarity only, the wild-type structure is shown in upper righthand corner box. Right: SHAPE reactivity graph shown as change of mutant reactivity over wild-type. Energy values and percent packaging efficiencies indicated below figure headings. Mutants: (FIG. 9A) m731. (FIG. 9B) m751. (FIG. 9C) m748. Percent packaging efficiencies of PB2 incorporation for each of the previously described mutants are highlighted in blue.

Figure 10:
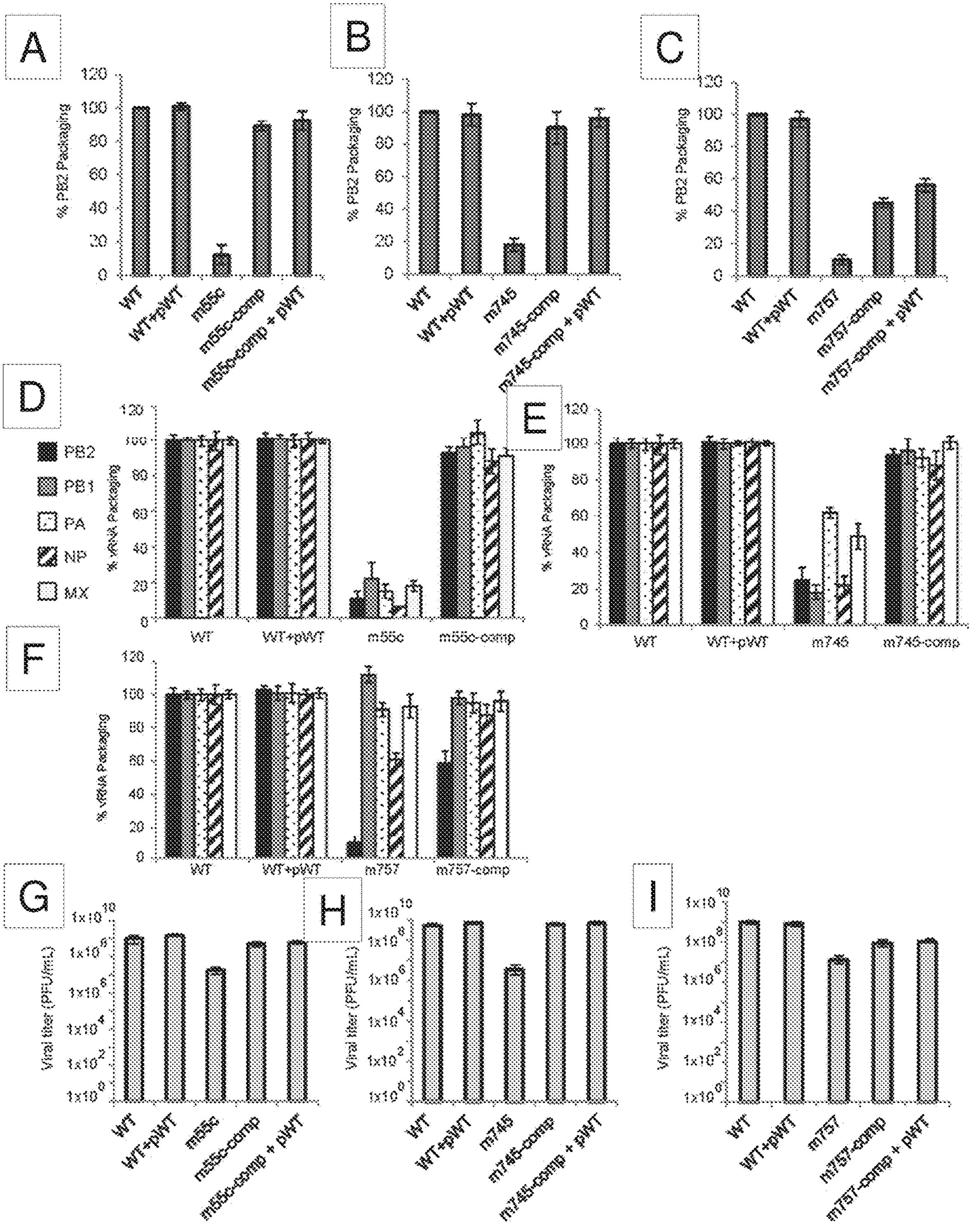
FIG. 10, panels A-I, depicts the effect of compensatory mutations in PR8 PB2 packaging-defective mutants on viral packaging and titer.
Figure 11:
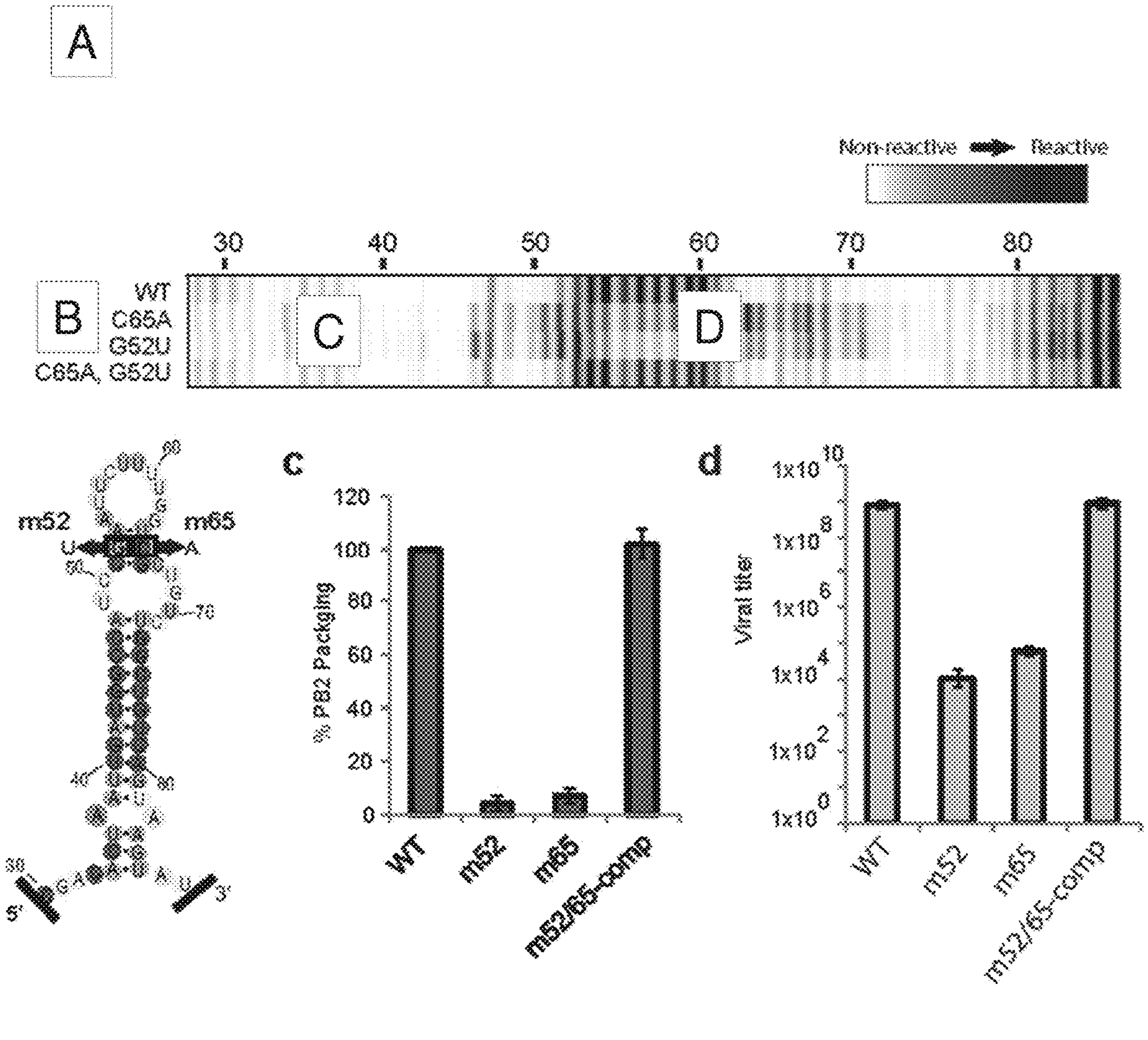
FIG. 11, panels A-D, depicts multidimensional chemical mapping of PB2 packaging-defective and compensatory mutant partners (panel B, SEQ ID NO: 27).

The compensatory mutations rescued not only the viral packaging for segment PB2 (FIG. 10, panels A-C, FIG. 6, panels A-B), but also other segments previously reported to be affected by the deleterious mutations, consistent with the proposed hierarchal role of PB2 in IAV packaging (Muramoto et al., 2006; Gao et al., 2012; Marsh et al., 2008) (FIG. 10, panels D-F). In addition to recovering PB2 packaging, the compensatory mutations gave complete or near-complete rescue of the viral titer loss caused by the defective mutations (FIG. 10, panels G-I). Some non-synonymous compensatory mutations were able to restore PB2 packaging better than others (m745-comp and m55c-comp, compared to m757-comp) (FIG. 10, panels A-C), possibly reflecting incomplete restoration of PB2 protein function through exogenous addition. Such exogenous addition was necessitated because some non-synonymous mutations affected both PSL2 structure and protein sequence. The most incisive test of PSL2 structure came from packaging experiments that did not require supplemental wild-type PB2 protein addition. Based on computational enumeration and multidimensional mutation-rescue experiments (Tian et al., 2014), a single mutation-rescue pair of substitutions was discovered that were both synonymous, obviating wild-type PB2 protein addition (m52/m65, FIG. 11, panels A-B, FIG. 12, panel s, FIG. 13). Making each mutation alone (m52 and m65) resulted in packaging efficiencies below 4% PB2 incorporation and titer loss exceeding 4 $\log_{10}$—an extreme impairment beyond what has been previously reported (i.e. 2 $\log_{10}$) for packaging-defective viruses (FIG. 11, panel C-D, FIG. 7, panel c, FIG. 10). When introduced together into a doubly mutated m52/65-comp strain that restored PSL2 structure, albeit with an altered sequence, the compensatory mutations restored both packaging efficiency and viral titer to wild-type levels.

FIG. 10, panels A-I, shows effect of compensatory mutations in PR8 PB2 packaging-defective mutants on viral packaging and titer. (FIG. 10, panels A-C) Packaging efficiencies of packaging-defective and compensatory mutant PB2 vRNAs. For compensatory mutations where a non-synonymous change was required, a wild-type PB2 protein expression plasmid was co-transfected during virus rescue. pWT=expression plasmid encoding for wild-type PR8 PB2 protein. Values given as percentage of PB2 vRNA packaging in comparison to wt parental PR8 virus. Results from two independent experiments, assays performed in triplicate (n=6). (FIG. panels D-F) Packaging efficiencies of packaging-defective and compensatory mutant viruses and their effect on the packaging of other interacting segments, PB1, PA, NP, and MX. Assays performed in triplicate (n=6). (FIG. 10, panels G-I) Viral titer by plaque assay. Results in PFU/mL, assays performed in triplicate.

FIG. 11 shows multidimensional chemical mapping reveals novel PB2 packaging-defective and compensatory mutant partners. (FIG. 11, panel A) Electropherogram result from systematic single nucleotide mutation mapping with rescue (Mutate-Map-Rescue) analysis of individual and compensatory double mutations to test base-pairings from 1-D-data-guided models and to identify predicted successful synonymous PSL2-defective and compensatory mutant pairs. Chemical accessibilities, plotted in grey scale (black=highest SHAPE reactivity), across 88 single mutations at single-nucleotide resolutions of PSL2 element from PR8 strain PB2. Reactivity peaks (left to right) correspond to nucleotides from the 5' to 3' end of the PB2 RNA. See FIG. 12 for complete list of Mutate-Rescue pairs. (FIG. 11, panel B) Mutational design of single mutants m52 (G52U) and m65 (C65A), and the double m52/65 rescue pair on the PSL2 structure. (FIG. 11, panel C) Packaging efficiency of the synonymous single and double mutant mutate-and-rescue pair. Values given as percentage of PB2 vRNA packaging in comparison to wt parental PR8 virus. Results from two independent experiments, assays performed in triplicate (n=6). (FIG. 11, panel D) Viral titer in PFU/mL, results in triplicate. Error bars represent ±SD.

Figure 12:
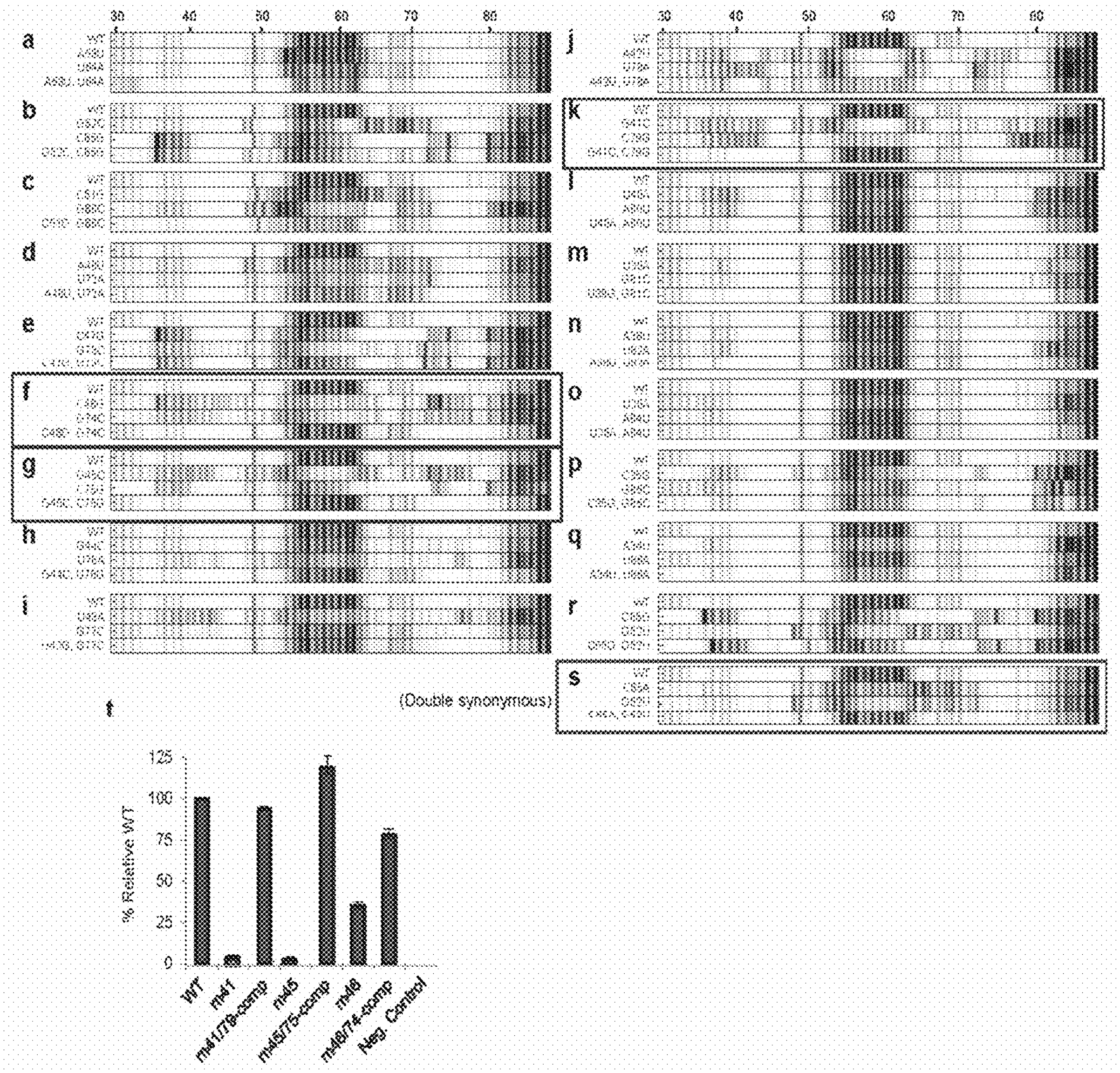
FIG. 12, panels a-t, depicts 2-dimensional Mutate-Map-Rescue analysis.

FIG. 12 panels a-t, shows 2-Dimensional Mutate-Map-Rescue (M2R) analysis. Mutation/Rescue results validate PSL2 RNA secondary structure. Electropherograms of SHAPE analysis with compensatory double mutations to test base-pairings from 1-D-data-guided models and to identify successful PSL2-defective and compensatory mutant pairs. Chemical accessibilities, plotted in grey scale (black=highest SHAPE reactivity), across 88 single mutations at single-nucleotide resolutions of PSL2 element from PR8 strain PB2. For each tested pairing, a "quartet" of wild-type, single mutant 1, single mutant 2, and compensatory double mutant are grouped for comparison. (FIG. 12, panels a-r) Non-synonymous mutate-and-rescue pairs. All non-boxed electropherograms are pairings for which disruption and/or rescue were not observed. Blue boxes indicate successful defective and rescue mutations. (FIG. 12, panel s) Double synonymous mutate-and-rescue pair. Green box=successful synonymous defective and rescue pair. (FIG. 12, panel t) Packaging efficiency for non-synonymous mutate-and-rescue pairs. Values given as percentage of PB2 vRNA packaging in comparison to wt parental PR8 virus. Results from two independent experiments, assays performed in triplicate (n=6). Error bars represent ±S.D.

FIG. 13 shows design of primer sequences for 2-Dimensional Mutate-Map-Rescue (M2R) mutants. SEQ ID NOs: (28-43) top to bottom. Primer sequences used for QuickChange mutational cloning of M2R mutants into pDZ plasmids. Sequences are in (+)-sense orientation. Left field denotes synonymous (Syn.) or non-synonymous (Non-syn.) change. Highlighted nucleotides=mutation site. Boxed mutant primer set indicates double synonymous mutant partners, m52 and m65.

Figure 14:
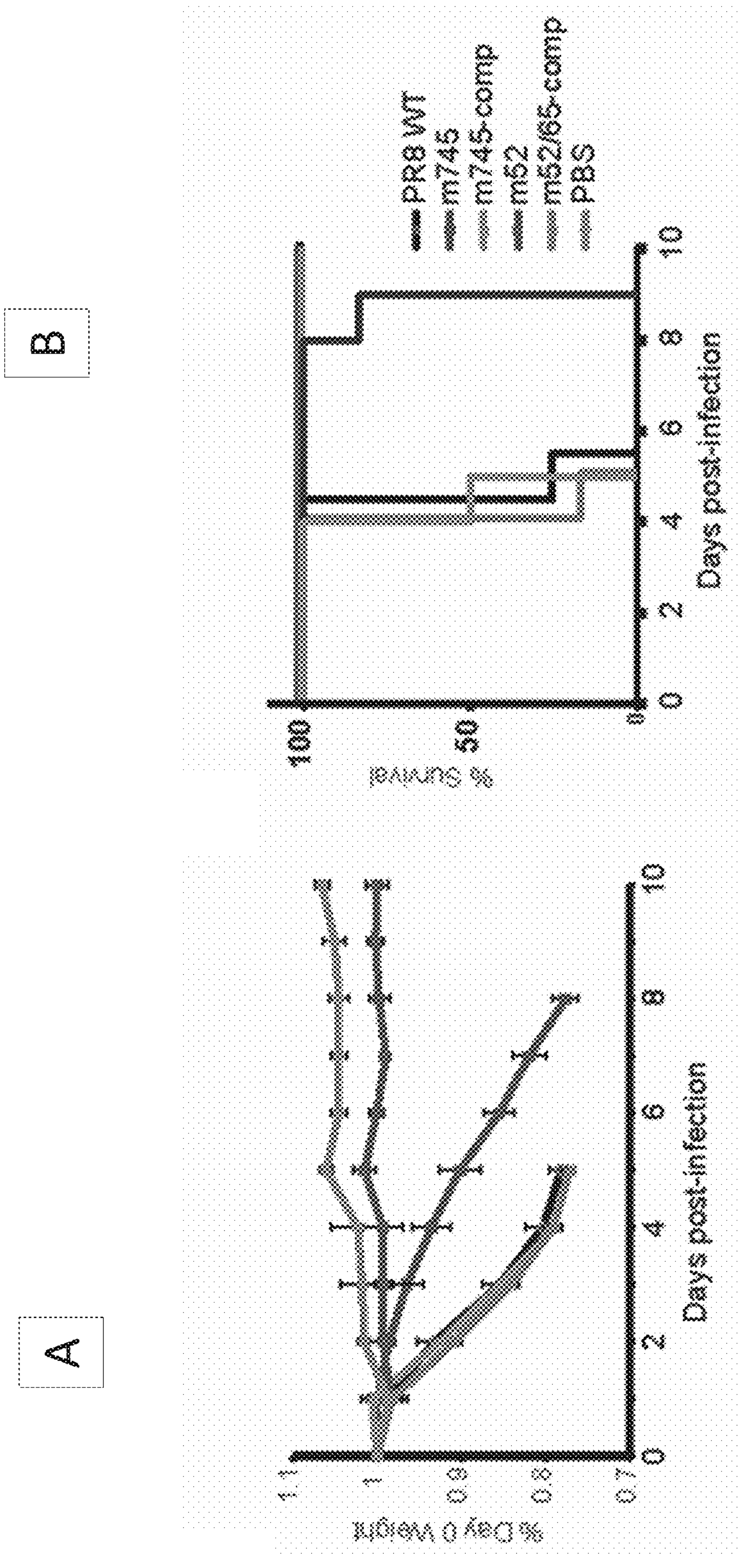
FIG. 14, panels A-B, depicts that packaging-defective viruses are attenuated in vivo.

To test the relevance of the PSL2 structure in an in vivo model, 6-8 week old BALB/C mice were intranasally inoculated with 1000 PFU of wild-type PR8 viruses or of strains harboring mutations predicted to disrupt or restore PSL2 structure. Mice infected with the PSL2-disrupting mutations-m745 mutant strain (20% packaging efficiency) or the severely packaging-defective single mutant virus, m52 (<4% packaging efficiency)—showed reduced or no clinical signs of illness, respectively, either in weight loss or survival as compared to the PBS control (FIG. 14, panels A-B). Remarkably, inclusion of compensatory mutations that restore PSL2 structure rescued viral pathogenicity: animals infected with m52/65-comp and m745-comp, displayed comparable mortality profiles and survival curves as mice infected with wild-type PR8 (FIG. 14, panels A-B). Consistent with APLAC guidelines, all mice were humanely sacrificed upon reaching greater than 20% weight loss.

FIG. 14 panels A-B shows packaging-defective viruses are attenuated in vivo. Percent weight loss and survival of mice infected with single PSL2-disrupting and compensatory, PSL2-restoring double-mutant viruses. 6-8 week old BALB/C female mice were intranasally infected with 1000 PFU of PR8 wild-type (wt) virus, packaging defective single mutant viruses, m52 and m745, compensatory double mutant viruses, m52/65 and m745-comp, or PBS control. Mice were monitored daily for percent day 0 weight loss and percent survival. Results as an average of two independent experiments, 6 mice per condition. (FIG. 14, panel A) Percent weight loss. (FIG. 14, panel B) Kaplan-Meir survival plot of the individual cohorts depicted in (FIG. 14, panel A).

Example 2

Figure 15:
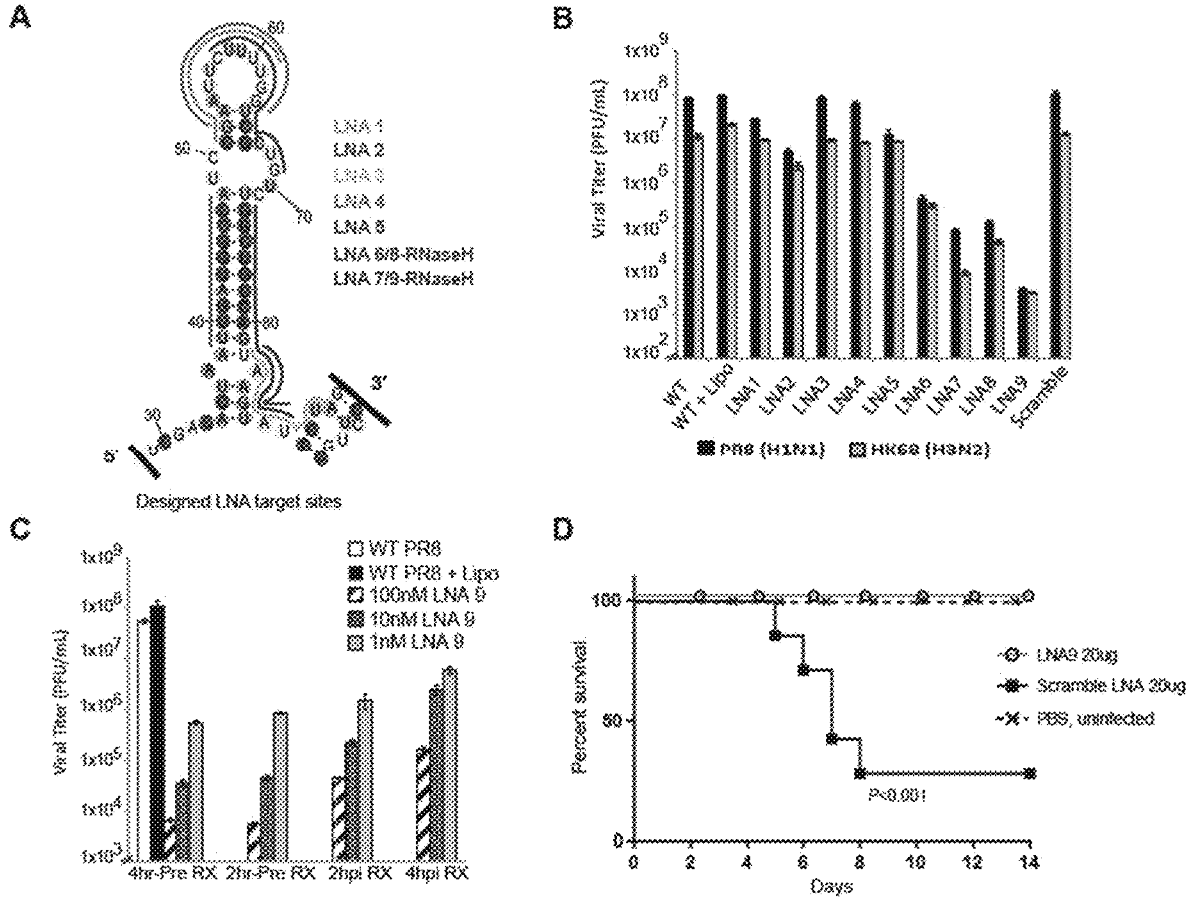
FIG. 15, panels A-D, depicts antiviral activity of Locked Nucleic Acids targeting PSL2 RNA structure (panel A, SEQ ID NO: 44).

Therapeutic Design and Targeting of PSL2 Structure Inhibits IAV Infection In Vitro and In Vivo To explore the therapeutic potential of targeting PSL2-mediated viral packaging, nine locked nucleic acids (LNAs) containing phosphorothioate internucleoside linkages (Vester and Wengel, 2004) were designed against key residues predicted to disrupt the overall RNA secondary structure of the element and thereby inhibit viral production (FIG. 15, panel A). Two of the designed LNAs, LNA8a and LNA9, are identical in sequence to LNA6 and LNA7, respectively, but possess 6-7 unmodified (non-locked) DNA nucleotides optimized for RNase-H activation (see, e.g., LNA 6/8-RNaseH; and LNA 7/9-RNaseH respectively). First, to assess the impact that LNA binding has on PSL2 RNA secondary structure, toeprinting and SHAPE chemical mapping were performed on PB2 vRNA in the presence of the LNAs. In corroboration with the antiviral assay results, sequences encoded in LNAs 6-9 exhibited the greatest ability to bind and disrupt the wild-type PSL2 structure (FIG. 16).

FIG. 15, panels A-D shows Locked Nucleic Acids targeting PSL2 RNA structure display potent antiviral activity in vitro and in vivo. (FIG. 15, panel A) Location of complementary Locked Nucleic Acids (LNAs) designed against different regions of the PSL2 structure. (FIG. 15, panel B) To screen the LNAs for antiviral activity, MDCK cells were pretreated with 100 nM of each designated LNA by Lipofectamine transfection for 1 hr prior to infection with 0.01 MOI of either PR8 (H1N1) virus or A/Hong Kong/8/68 (H3N2) virus. 48 hours post-infection, supernatant was collected and viral titers determined by plaque assay. Results from 2 independent experiments, assays performed in triplicate (n=6). (FIG. 15, panel C) Time course of pre-treatment (RX) versus post-infection treatment with LNA9 at titrating concentrations (100 nM, 10 nM, 1 nM). WT+Lipo=infection with Lipofectamine control. Pretreatment: confluent MDCK cells in 6-well plates were treated with LNA9 either 2 hours or 4 hours prior to infection. Treated supernatant was removed at the indicated time point and cells were infected with 0.01 MOI of wt PR8 virus for one hour. For post-infection treatment: MDCK cells were infected with 0.01 MOI of PR8 virus for one hour, after which the supernatant was replaced and the cells were treated with LNA9 at either 2 or 4 hours post-infection. Supernatant was collected 48 hrs later, and viral titers determined by plaque assay in triplicate. FIG. 15, panel d shows the effects of intranasal LNA treatment on survival of virus-infected mice. Mice were intranasally administered 20 ug of LNA9, scrambled LNA, or PBS (uninfected control) at 12 hours prior to infection with PR8 virus. All mice received two additional treatments at 8 hpi and 36 hpi (n=7 mice per condition).

As depicted herein in FIG. 15, panels A-D, sequence label "LNA8" refers to sequence LNA8a (SEQ ID NO:188), e.g., as described herein. Further, in FIG. 15, panels A-D, FIG. 16A, and FIG. 16B, LNA 6/8 refers to sequences LNA6 (SEQ ID NO:72) and LNA8a (SEQ ID NO:155), e.g., as described herein.

Figure 16A:
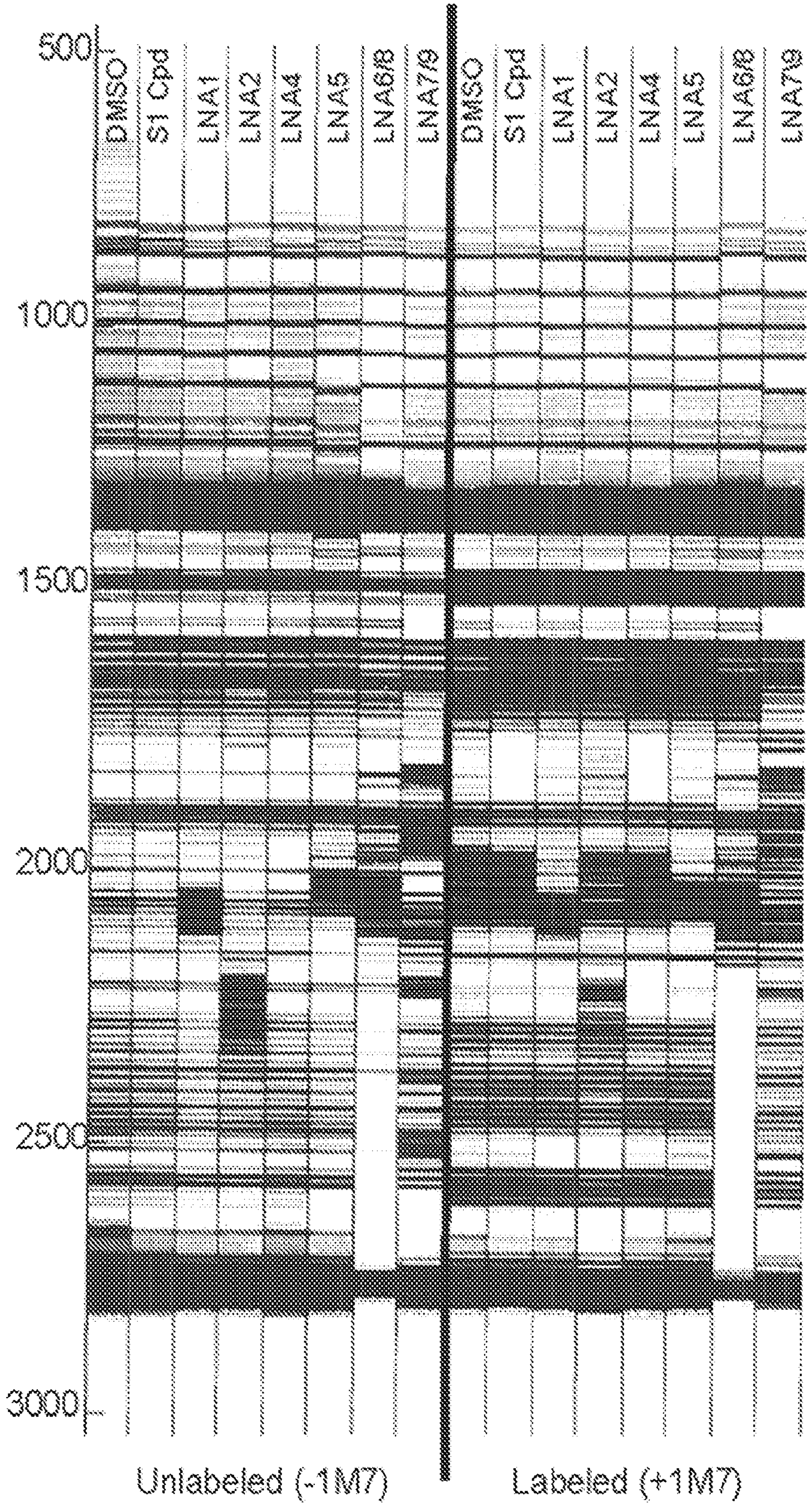
FIG. 16A-FIG. 16B depicts analysis on LNA-RNA binding.
Figure 16B:
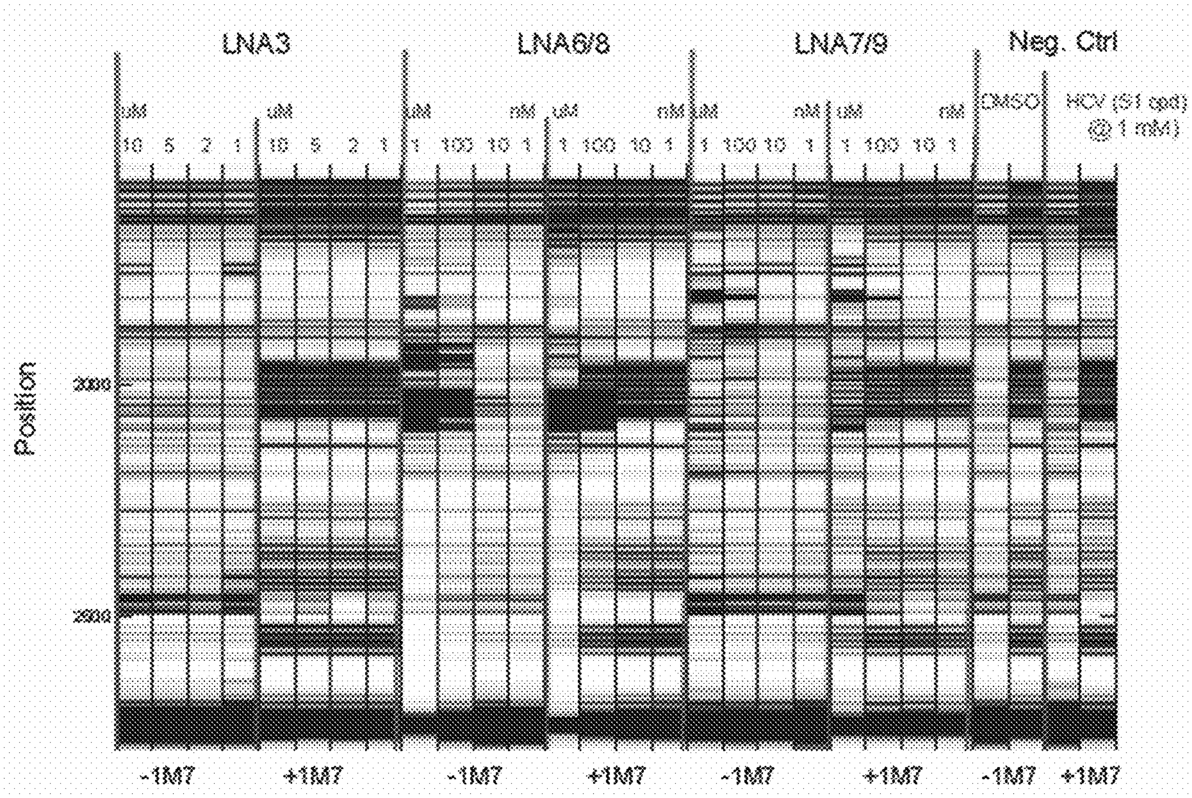

FIG. 16A-FIG. 16B shows SHAPE analysis on LNA-RNA binding. (FIG. 16A) Electrophoretic profile of SHAPE analysis performed on LNAs 1, 2, 4, 5, 6/8a, and 7/9 (100 nM) in the presence of PR8 PB2 vRNA. S1, a small molecule that interacts with the Hepatitis C virus IRES RNA was added as a control for RNA binding. Columns on the left, unlabeled reaction without SHAPE reagent, 1M7. Right: with labeling reagent. (FIG. 16B) Electrophoretic profile of SHAPE performed on LNA-vRNA combination in titrating concentrations of LNA. For each LNA, the left set of columns is without labeling reagent.

Then, in a first pilot experiment to determine the antiviral potential of LNA-mediated targeting of PSL2 across two different IAV subtypes, MDCK cells were pre-treated with 100 nM of each LNA and delivered by Lipofectamine™ transfection for 1 hour prior to infection with 0.01 MOI of either the wild-type PR8 (H1N1) virus or tissue-culture adapted A/Hong Kong/8/68 (HK68) (H3N2) virus. Forty-eight hours post-infection, the supernatants were collected and viral production was measured by plaque assay (FIG. 15, panel B). LNAs directed against only the top loop of PSL2 (LNA1, LNA4) had little to no effect on viral titer. Similarly, LNAs 3 and 5, which target the 3' base of PSL2, also failed to inhibit viral production. In contrast, nucleotide coverage of both the top loop and middle bulge by LNA6 resulted in greater than 2 $\log_{10}$ titer deficits for PR8 (FIG. 15, panels A-B). LNA8a, the RNase-H activated copy of LNA6, produced even greater antiviral activity against both viruses of up to 3 logs. Most strikingly, LNA9, the RNase-H activated copy of LNA7, possessed the strongest antiviral capacity, dropping viral production by nearly 5 logs and 4 logs against PR8 and HK68, respectively.

Having identified the optimal candidate LNAs, the treatment time-course and concentration parameters of LNA9's antiviral activity were further investigated. MDCK cells were treated with one dose of 10-fold dilutions of LNA9 at either 2 or 4 hours pre-infection or, alternatively, 2 or 4 hours post-infection with 0.01 MOI of wild-type PR8 virus. Cells pre-treated with the LNA had the most potent antiviral response (greater than 4 logs), and displayed strong viral inhibition (greater than 2 logs) even at the lowest dilution (1 nM) (FIG. 15, panel C). There was a trend towards decreasing antiviral activity as the time post-infection treatment increased, but even at the latest tested time point of addition, greater than 3 logs suppression of viral titer was achieved.

Example 3

In Vivo Efficacy Experiment: Extended Single-Dose Prophylaxis

Figure 17:
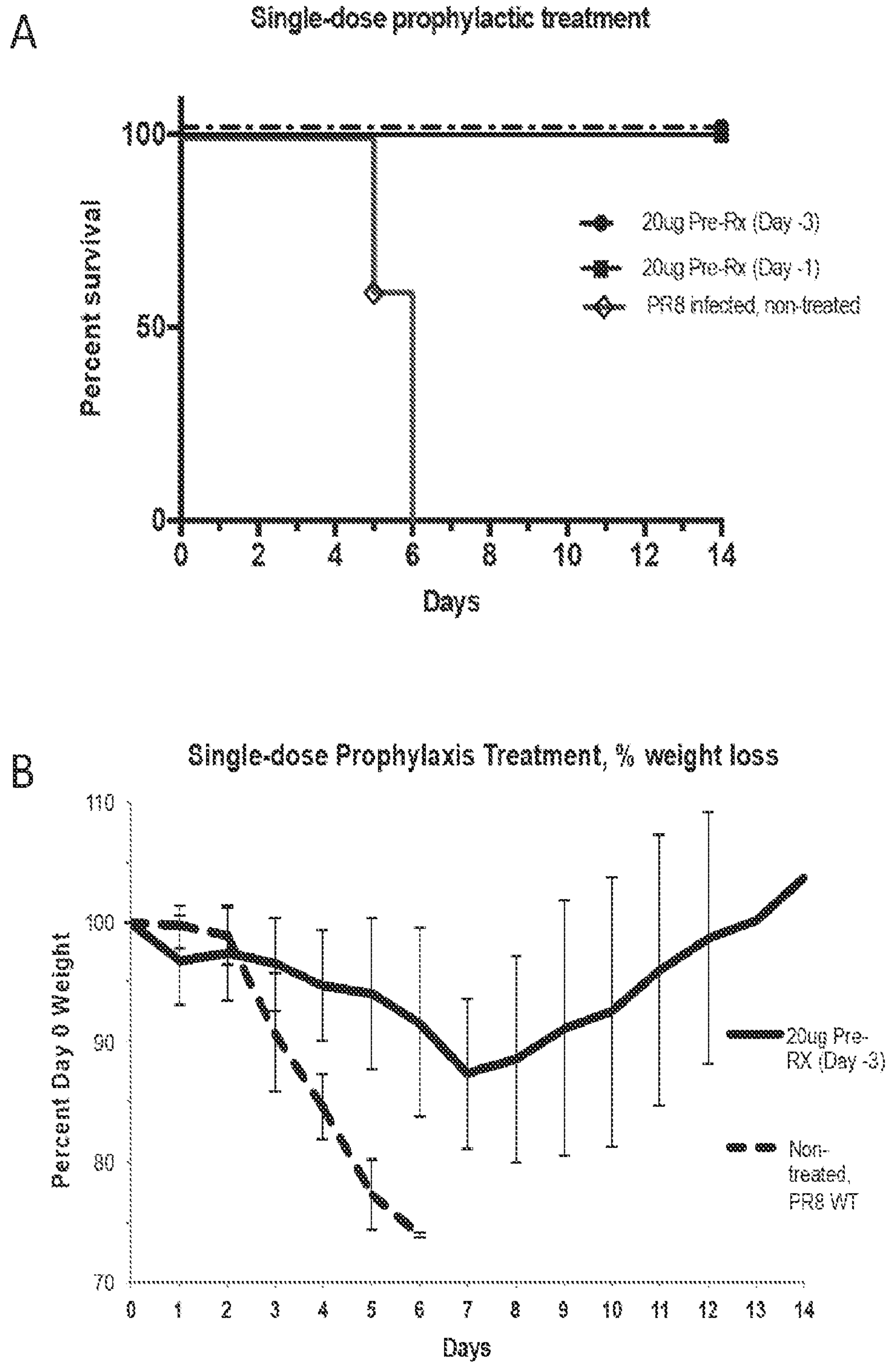
FIG. 17, panels A-B shows the percent survival and weight loss of mice over time after intranasal administration of a single dose of exemplary compound LNA9.

Balb/C female mice (5 mice/group) were pre-treated intranasally with a single dose of 20 ug LNA9 either 3 days before infection (Day −3) or 1 day before infection (Day −1) with a lethal dose of wild-type PR8 virus. Mice were monitored daily for weight loss, clinical score, and survival. FIG. 17, panel A shows the percent survival of mice over time. FIG. 17, panel B shoes the percent weight loss over time after administration.

A single administration of 20 ug LNA9 three days prior to infection completely protected mice from fatal influenza disease. Non-treated control mice were humanely sacrificed when they lost greater than 25% weight loss, at an average of 5.5 days. In contrast, the pretreatment group showed minimal weight loss, little-to-no clinical signs of disease, and fully recovered to pre-infection weight.

This result demonstrates that a single, inhalable dose of LNA9 administered days before infection can provide lasting protection against fatal disease, and suggests the subject compounds can find use in prophylaxis treatment during influenza outbreaks and pandemics.

Example 4

Susceptibility of Influenza Viruses to Oseltamivir and LNA9, after Serial Passaging in the Presence of Drug: Drug Selection Experiment Oseltamivir (Tamiflu) is the most widely used and stockpiled neuraminidase inhibitor (NAI) on the market. Like all NAIs, oseltamivir requires a conformational rearrangement in the viral neuraminidase (NA) protein to accommodate the drug. Any mutations in the NA protein that affect this rearrangement reduce the binding affinity of oseltamivir, thus reducing drug efficacy. Notably, the H274Y mutant (also known as the H275Y mutation depending on nomenclature) is most commonly associated with oseltamivir resistance. The rapid selection of the H274Y mutation in an immunocompromised patient can lead to clinical failure of the last-resort NAI drug, peramivir, suggesting that the selection for multi-drug resistant viruses in immunocompromised hosts may be more common than previously believed. This, together with the recent spread of oseltamivir-resistant and NAI-resistant viruses in circulation, indicates the need to reevaluate usage of NAIs in general. The development of new classes of antivirals is imperative in order to reduce the adverse impact current and future influenza pandemics can have on human health.

The sequence region in segment PB2 that contains the PSL2 stemloop is highly conserved across IAV subtypes, strains and isolates from a wide range of host-species, and likely reflects a strict biologic requirement for its preservation. SHAPE analysis of this region confirmed maintenance of the PSL2 structure between seasonal as well as pandemic viruses of different subtypes and host origins, strongly suggesting that this structural element could be a novel pan-genotypic therapeutic target (and hence LNA9 has broad spectrum potential against IAV isolates). Additionally, since the subject LNAs are directed against a highly conserved viral genomic RNA target that clearly has strong constraints on its ability to mutate, the subject LNAs targeting PSL2 are expected to have a higher barrier to the development of resistance compared to NAIs.

Figure 18:
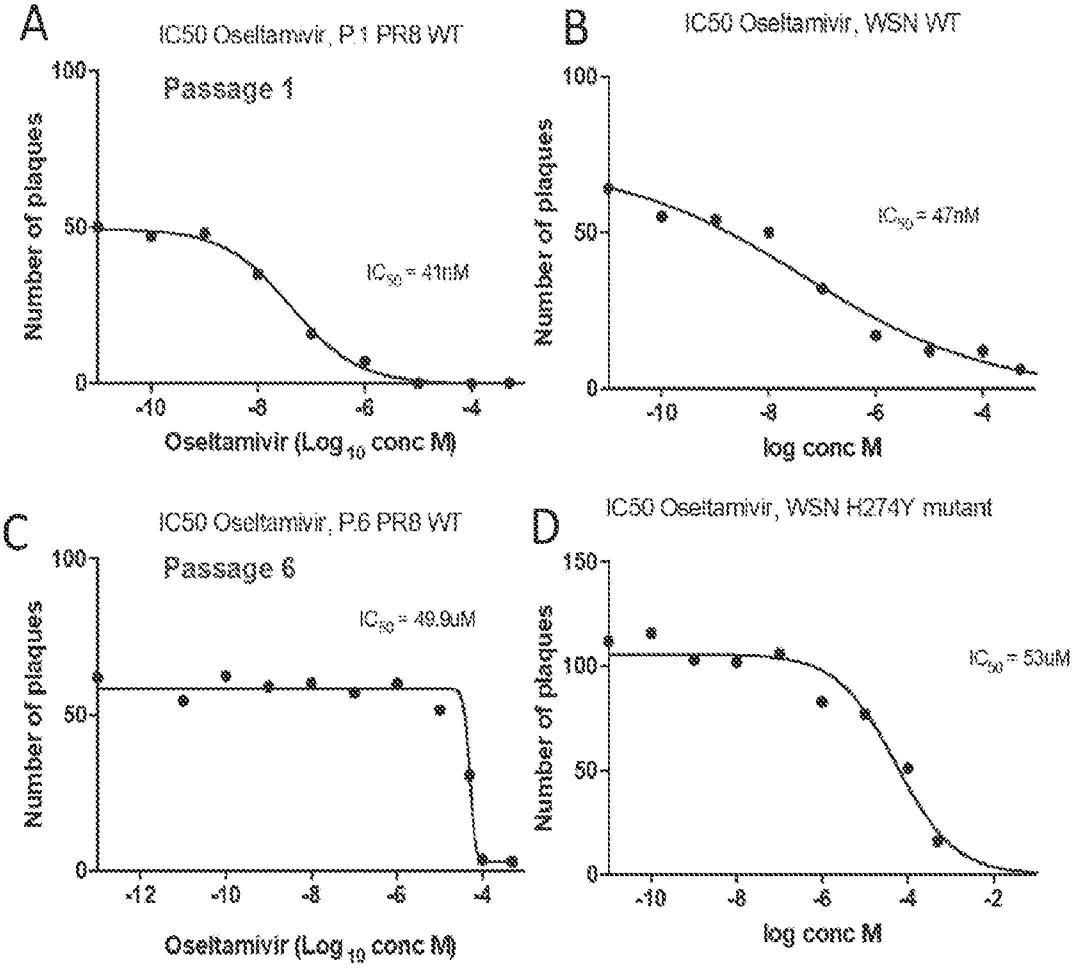
FIG. 18, panels A-D, show the susceptibility of influenza virus to oseltamivir after serial passages under drug pressure.
Figure 19:
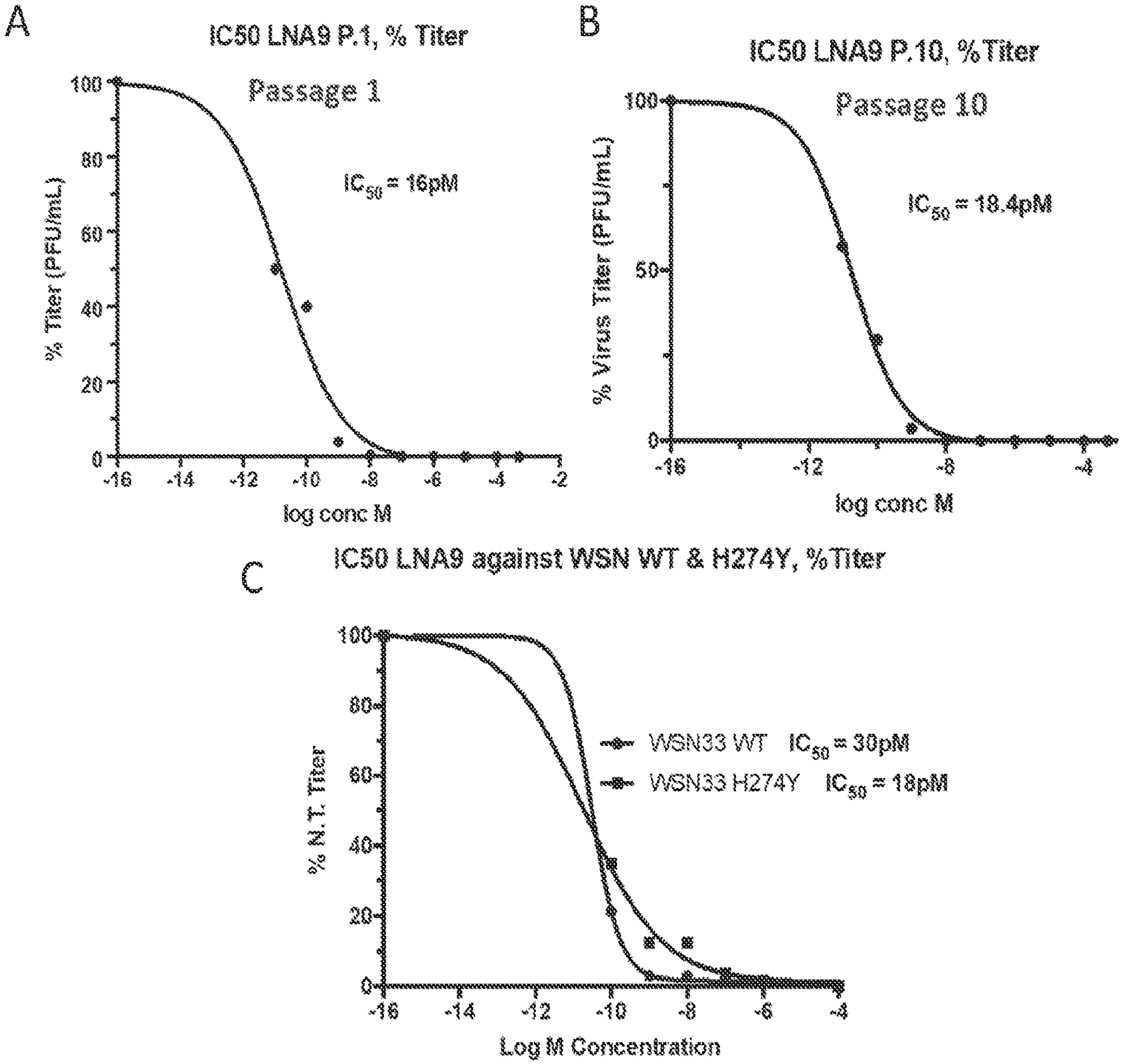
FIG. 19, panels A-C, show the susceptibility of influenza virus to exemplary compound LNA9, including viruses after serial passages under drug pressure and drug resistant virus.

The susceptibility of influenza viruses to LNA9 versus oseltamivir after serial passages under drug pressure was investigated. Oseltamivir had a starting $IC_{50}$ of 41 nM against PR8 at passage 1 of drug treatment, as determined by a plaque reduction assay. After only six virus passages with increasing amounts of drug, the $IC_{50}$ of oseltamivir leapt to 50 uM—a 1000× increase fold. See FIG. 18, panels A-D. In comparison, after 10 passages of virus in the presence of LNA9, the $IC_{50}$ held stable from 18 to 16 pM. FIG. 19, panels A and B.

LNA9 can also be used to treat drug resistant viruses. A drug-resistant mutant of A/WSN/33 (H1N1) virus was generated using a reverse genetic virus rescue system that mutated the NA gene to contain the H274Y resistance mutation. Against this virus, oseltamivir has an $IC_{50}$ of 53 uM. Importantly, LNA9 maintained its potency and efficacy against the WSN H274Y virus with picomolar activity. FIG. 19, panel C. This result is strong evidence for the therapeutic treatment of NAI-resistant viruses with PSL2-targeting LNAs. This result also highlights the activity of LNA9 against different IAV isolates.

Example 5

Figure 20:
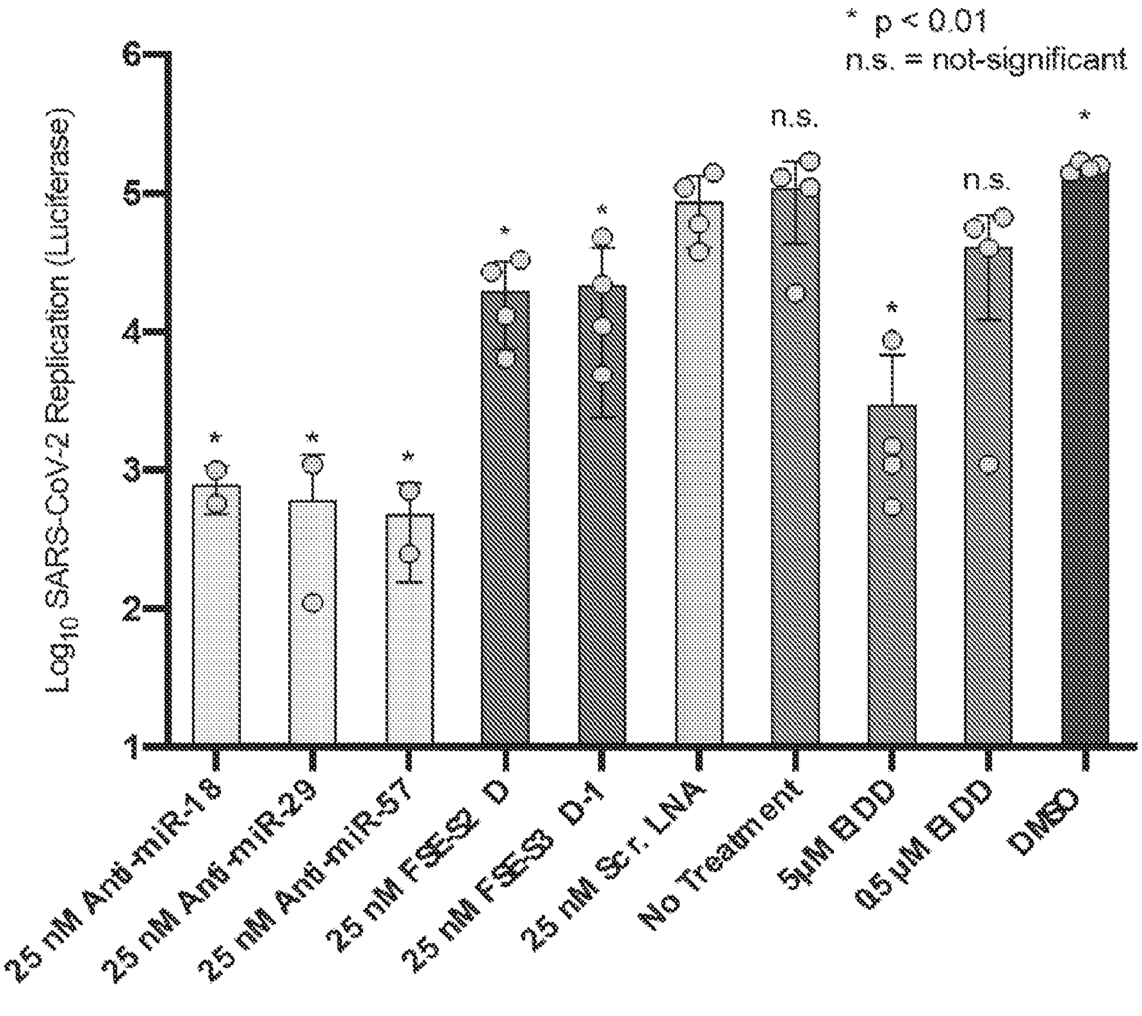
FIG. 20, antiviral efficacy of miRNA-directed LNAs designed to disrupt respiratory viral infection. Huh7 cells were pre-treated with 25 nM of miRNA-directed LNAs 12-24 hours prior to infection with 0.3 MOI of a fully-replicating, BSL3 SARS-CoV-2-nLuc reporter virus. 48 hr post-infection, luciferase signal was read. Results shown as $\log_{10}$ luciferase signal. Samples performed in duplicate, N=2; controls in quadruplicate, N=4. Statistical analysis performed by GraphPad Prism software and calculated using an ordinary one-way ANOVA with Dunnett's multiple comparisons test between samples and the Scrambled LNA (Scr. LNA) control mean. A positive control nucleoside analog, EIDD-2801 (EIDD), was included as positive control.

Anti-viral activity of miR-targeting LNA: Determining the in vitro antiviral efficacy of LNAs designed against microRNAs hypothesized to mediate respiratory virus replication. Individual LNAs designed to target microRNAs were transfected into Huh7 cells, followed by infection with a fully replicating SARS-CoV-2-nLuc virus, which harbors a nanoluciferase reporter in ORF7. 48 hours post-infection, the effect on replication was measured by luciferase activity, as compared to control cells treated with negative control Scrambled LNA (Scr. LNA), or positive control nucleoside analog EIDD (FIG. 20). While LNAs targeting the frame shift element (FSE) region of the SARS-CoV-2 RNA genome had minimal effect on viral replication, multiple $\log_{10}$ reductions were observed with our anti-miR LNAs designed to sequester miR-191. The extent of inhibition with the anti-miR LNAs was greater than the EIDD positive control! Moreover, this degree of inhibition was observed with LNAs at 25 nanomolar concentration, whereas the EIDD positive control was used at 5 micromolar concentration. Other microRNA-targeting LNAs with anti-respiratory virus activity have been similarly identified and include: LNA-602.1; LNA-602.6; LNA-6769-5P.3; LNA-6769-5P.6; LNA-942.3P.4; LNA-376c.3; LNA-4433b.1; LNA-191.1; LNA-191.2; LNA-191.3; LNA-191.4; LNA-191.8; LNA-191.8; LNA-19110; LNA-191.11; LNA-191.12; LNA-191.13; LNA-663.1; LNA-663.3; LNA-381.2; LNA-744.2; LNA-744.4; LNA-744.7; LNA-4508.1; LNA-4508.4; LNA-4730.2; LNA-4730.6; LNA-6777.4; LNA-10396.1; LNA-10396.2; LNA-4749.2; LNA-4749.4; LNA-4706.3; LNA-4706.4; LNA-3675.2; LNA-3675.3; LNA6810.1; LNA-6810.2; LNA-6810.3; LNA-6812.1; LNA-6796.1; LNA-6796.3 to have potent antiviral activity against SARS-Cov-2, all having inhibition of viral replication of about 1 log 10 or more. These LNAs are listed in Table 8 above.

Example 6

Figure 21:
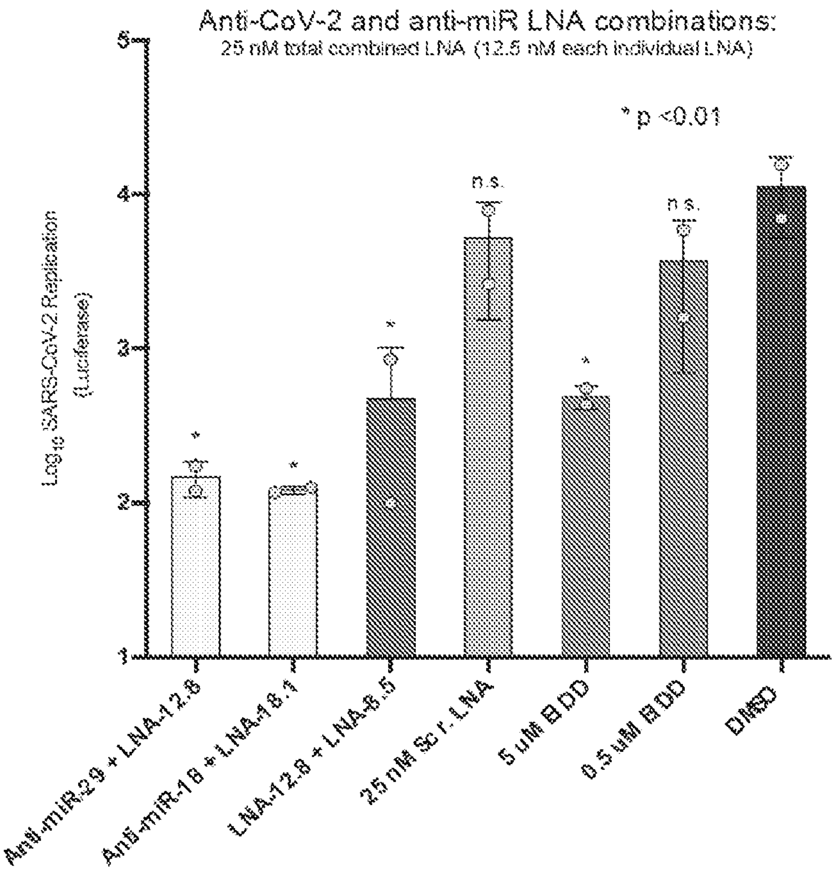
FIG. 21, Huh7 cells were pretreated with 25 nM of a combination of LNAs (12.5 nM each LNA=25 nM total) 12-24 hours prior to infection with 0.3 MOI of a fully-replicating, BSL3 SARS-CoV-2-nLuc reporter virus. 48 hr post-infection, luciferase signal was read. Results shown as log 10 luciferase signal. Samples performed in duplicate, N=2; controls in quadruplicate, N=4. Statistical analysis performed by GraphPad Prism software and calculated using an ordinary one-way ANOVA with Dunnet's multiple comparisons test between samples and the DMSO control mean. A positive control nucleoside analog, EIDD-2801 (EIDD), was included as positive control.

Determining the in vitro antiviral efficacy of LNA combinations against respiratory viruses: Combining an LNA targeting a conserved SARS-CoV-2 RNA secondary structure with an LNA designed to sequester miR-191 leads to profound inhibition of viral replication. Using the assay described in Example 5 above, individual LNAs were combined to show anti-respiratory virus activity (FIG. 21).

Example 7

In vivo efficacy of LNA combination against respiratory viruses. Mice transgenic for human ACE2 were treated with vehicle, small molecule A, or a combination of LNAs administered intranasally once 5 days prior to infection with a lethal inoculum of SARS-Cov-2. Following infection, animals were monitored by clinical score daily where 1=asymptomatic and higher score indicates worsening clinical status (FIG. 21). Combination of LNAs inhibit respiratory virus infection in vivo Example 8

Figure 22:
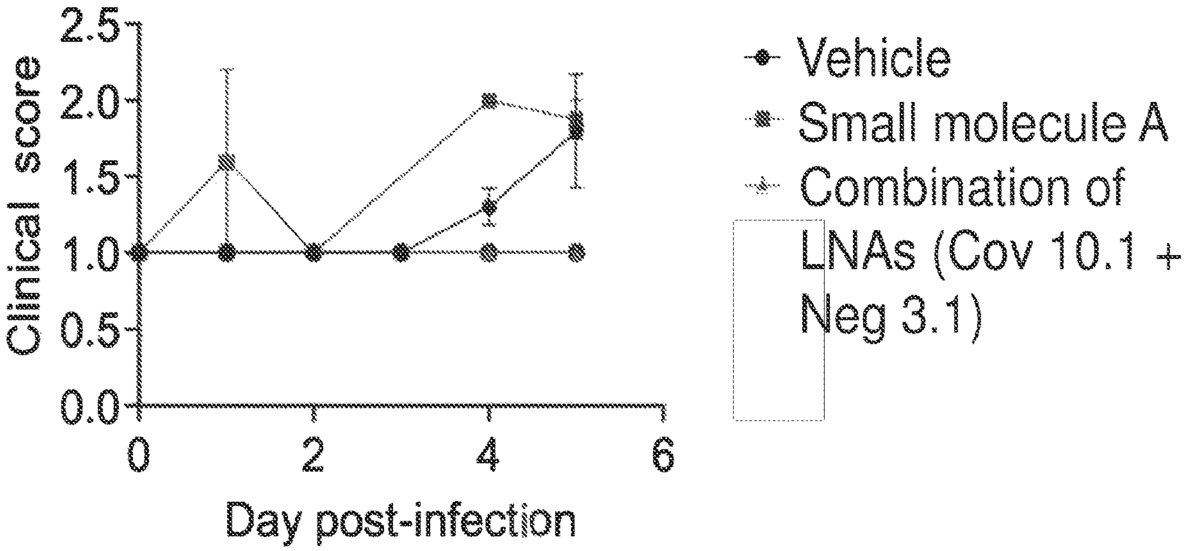
FIG. 22, in vivo efficacy of combination of LNAs against a respiratory virus. Mice transgenic for human ACE2 were treated with vehicle, small molecule A, or a combination of LNAs administered intranasally once 5 days prior to infection with a lethal inoculum of SARS-Cov-2. Following infection, animals were monitored by clinical score daily where 1=asymptomatic and higher score indicates worsening clinical status.

Anti-viral activity of single microRNA-targeting LNAs, or LNAs targeting either negative or positive strand of respiratory viruses. Using assay described in example 5 individual LNAs were shown to have anti respiratory virus activity (FIG. 22). Other LNAs with anti respiratory virus activity have been similarly identified and include but not limit to: Neg 3.1; Neg 8.2; Neg 8.4; Neg 10.1; Neg 10.1; Neg 12.2; Neg 18.2; Neg 18.3; Neg 18.4; Cov 8.5; Cov 10.1; Cov 11.3; Cov 12.8; Cov 13.9; Cov 14.3; Cov 16.3; Cov 18.1; Cov1.1; Cov 1.2; Cov 1.4; Cov 2.1; Cov 2.2; Cov 3.2; Cov 3.2-2; Cov 3.2-3; Cov 3.2-4; Cov 3.2-5; Cov 3.2-6; Cov 3.2-7; Cov 4.1; Cov 4.2; Cov 6.4; Cov 6.5; Cov 6.6; Cov 6.7; Cov 6.8; Cov 6.9; Cov 6.7-1; Cov 6.7-2; Cov 6.8; Cov 6.9; Cov 6.7-1; Cov 6.7-2; Cov 7.2; Cov 7.7; Cov 7.9; Cov 8.1; Cov 8.2; Cov 8.3; Cov 8.4; Cov 8.5; Cov 8.6; Cov 8.2-1; Cov 10.1; Cov 10.4; Cov 11.1; Cov 11.2; Cov 11.3; Cov 12.4; Cov 12.5; Cov 12.7; Cov 12.8; Cov 13.1; Cov 13.4; Cov 13.5; Cov 13.6; Cov 13.8; Cov 13.9; Cov 14.1; Cov 14.2; Cov 14.3; Cov 14.4; Cov 16.1; Cov 16.2; Cov 16.3; Cov 18.1; Cov 18.5; IBV-LNA0.2; IBV-LNA4.4; IBV-LNA3.4; IBV-LNA2.5; IBV-LNA 1.5 to have potent antiviral activity, all having inhibition of viral replication about 1 log 10 or more. These LNAs are listed in Table 7 and Table 9, above.

Example 9

Figure 23:
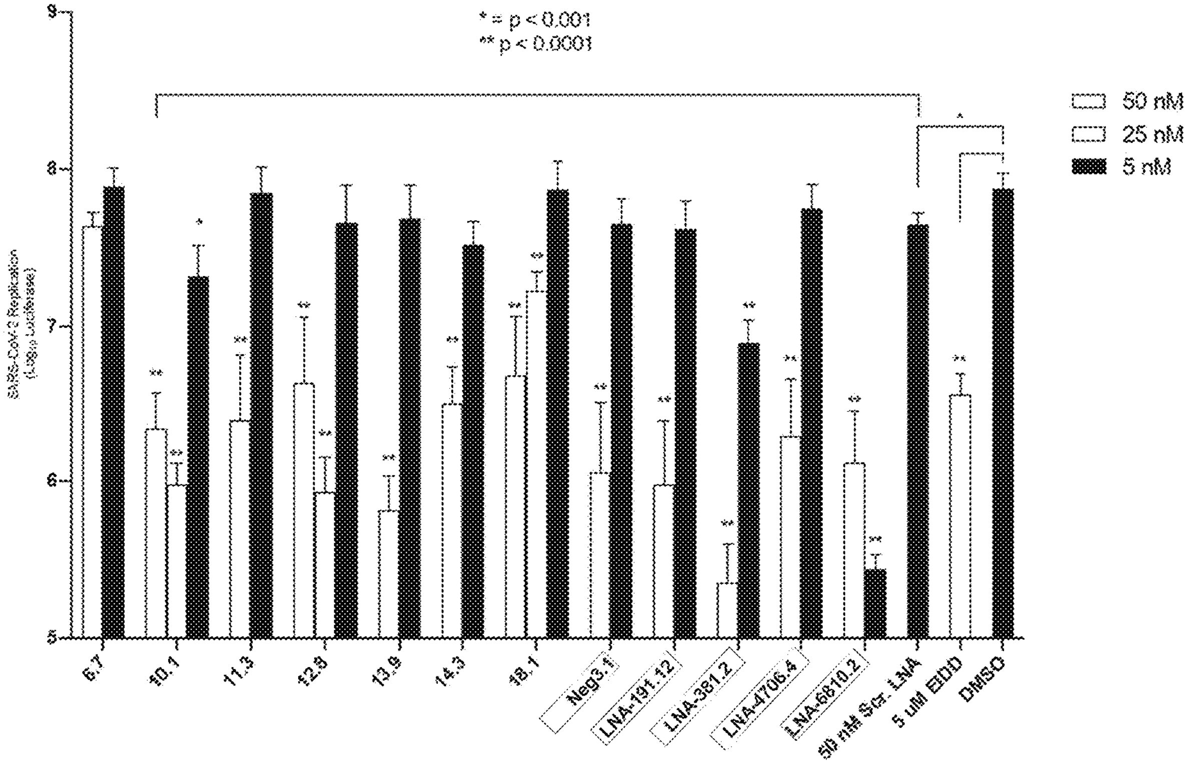
FIG. 23, ACE2-A549 cells were pre-treated with either 50 nM, 25 nM, or 5 nM of CoV-2 positive-strand targeted, CoV-2 negative-strand targeted, or miRNA-directed LNAs 12-24 hours prior to infection with 0.3 MOI of a fully-replicating, BSL3 SARS-CoV-2-nLuc reporter virus. 48 hr post-infection, luciferase signal was read. Results shown as log 10 luciferase signal. Samples performed in replicates of 6, N=6. Statistical analysis performed by GraphPad Prism software and calculated using an ordinary one-way ANOVA with Dunnett's multiple comparisons test between samples and the Scrambled LNA (Scr. LNA) control mean. A positive control nucleoside analog, EIDD-2801 (EIDD), was included as positive control.
Figure 24:
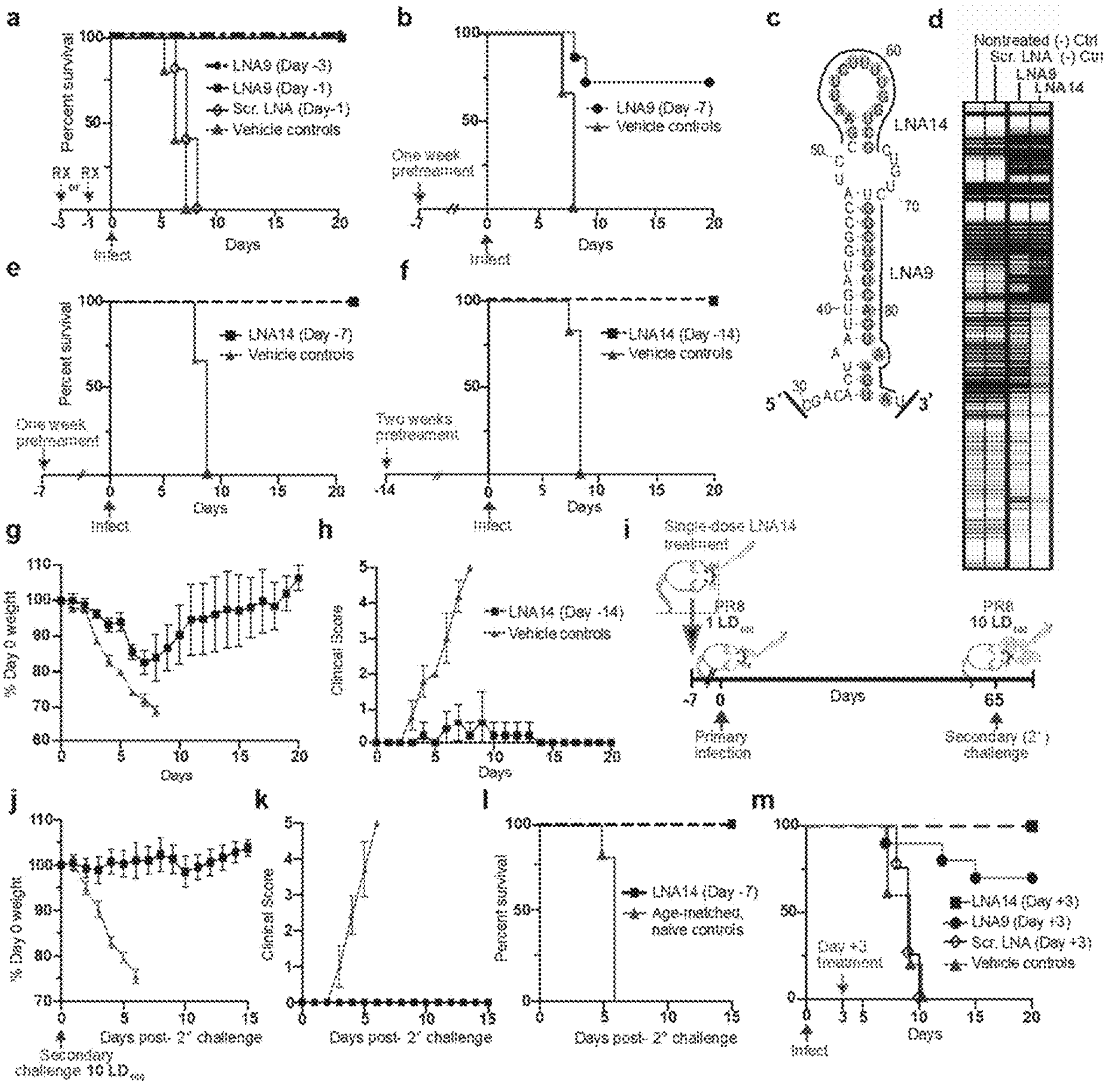
FIG. 24, (a-b) Effect of intranasal LNA prophylactic treatment on survival of virus-infected mice. Kaplan-Meier survival plots. Mice (n=7 mice/group) were intranasally administered a single dose of LNA9, Scrambled LNA, or Vehicle (mock-treated) followed by a lethal inoculum of wild-type PR8 virus (a) dosed with 20 µg LNA 3 days before infection (Day −3) or 1 day before infection (Day −1); (b) one week pretreatment with a single 30 µg dose of LNA9 or vehicle control. (c) Target sites of LNA9 and newly designed, LNA14, mapped to the PSL2 structure. (d) Electrophoretic profile of SHAPE analysis performed on non-treated, Scrambled LNA, LNA9, and LNA14 at 100 nM concentration in the presence of PR8 PB2 vRNA. Labeling with 1M7 SHAPE reagent shown. (e) Kaplan-Meier survival plot of mice (n=7 mice/group) intranasally pretreated with a single dose of 30 µg LNA14 or vehicle control one week (Day −7) before lethal PR8 infection. (f-h) A single dose of 40 µg LNA14 or vehicle was I.N. administered two weeks (Day −14) before PR8 virus infection. (f) Kaplan-Meier survival plot. (g) Percent day 0 weight of mice. (h) Clinical score. (i-l) Mice (n=7) were given a single 40 g intranasal dose of LNA14 one week prior to a primary lethal infection at 1 LD100 of PR8 virus (e). Sixty-five days post-initial infection, surviving mice from (e) along with age-matched naïve controls (n=7/group) were challenged a second time at 10 LD100. (i) Challenge study timeline. (j) Percent day 0 weight of mice. (k) Clinical score. (l) Kaplan-Meier survival curve. (m) Mice (n=10/group) were infected with a lethal dose of PR8 wild-type virus. Three days post-infection, mice were given a single dose of 40 µg of LNA14, LNA9, Scrambled LNA, or vehicle control by I.V. injection. Kaplan-Meier survival plot.

LNAs that inhibit respiratory viruses can be used as a just-in-time vaccine as shown in FIG. 23. (a-b) Effect of intranasal LNA prophylactic treatment on survival of virus-infected mice. Kaplan-Meier survival plots. Mice (n=7 mice/group) were intranasally administered a single dose of LNA9, Scrambled LNA, or Vehicle (mock-treated) followed by a lethal inoculum of wild-type PR8 virus (a) dosed with 20 μg LNA 3 days before infection (Day −3) or 1 day before infection (Day −1); (b) one week pretreatment with a single 30 μg dose of LNA9 or vehicle control. (c) Target sites of LNA9 and newly designed, LNA14, mapped to the PSL2 structure. (d) Electrophoretic profile of SHAPE analysis performed on non-treated, Scrambled LNA, LNA9, and LNA14 at 100 nM concentration in the presence of PR8 PB2 vRNA. Labeling with 1M7 SHAPE reagent shown. (e) Kaplan-Meier survival plot of mice (n=7 mice/group) intranasally pretreated with a single dose of 30 μg LNA14 or vehicle control one week (Day −7) before lethal PR8 infection. (f-h) A single dose of 40 μg LNA14 or vehicle was I.N. administered two weeks (Day −14) before PR8 virus infection. (f) Kaplan-Meier survival plot. (g) Percent day 0 weight of mice. (h) Clinical score. (i-l) Mice (n=7) were given a single 40 μg intranasal dose of LNA14 one week prior to a primary lethal infection at 1 LD100 of PR8 virus (e). Sixty-five days post-initial infection, surviving mice from (e) along with age-matched naïve controls (n=7/group) were challenged a second time at 10 LD100. (i) Challenge study timeline. (j) Percent day 0 weight of mice. (k) Clinical score. (l) Kaplan-Meier survival curve. (m) Mice (n=10/group) were infected with a lethal dose of PR8 wild-type virus. Three days post-infection, mice were given a single dose of 40 μg of LNA14, LNA9, Scrambled LNA, or vehicle control by I.V. injection. Kaplan-Meier survival plot.

REFERENCES

1. M. J. Memoli, R. J. Hrabal, A. Hassantoufighi, M. C. Eichelberger, J. K. Taubenberger, Rapid selection of oseltamivir- and peramivir-resistant pandemic H1N1 virus during therapy in 2 immunocompromised hosts. Clin Infect Dis 50, 1252-1255 (2010); published online Epub-May 1 (10.1086/651605).
2. R. Hai, M. Schmolke, V. H. Leyva-Grado, R. R. Thangavel, I. Margine, E. L. Jaffe, F. Krammer, A. Solorzano, A. Garcia-Sastre, P. Palese, N. M. Bouvier, Influenza A(H7N9) virus gains neuraminidase inhibitor resistance without loss of in vivo virulence or transmissibility. Nature communications 4, 2854 (2013)10.1038/ncomms3854).
3. F. G. Hayden, M. D. de Jong, Emerging influenza antiviral resistance threats. J Infect Dis 203, 6-10 (2011); published online EpubJan 1 (10.1093/infdis/jiq012).
4. X. Liu, T. Li, Y. Zheng, K. W. Wong, S. Lu, H. Lu, Poor responses to oseltamivir treatment in a patient with influenza A (H7N9) virus infection. Emerging microbes & infections 2, e27 (2013); published online EpubMay (10.1038/emi.2013.30).
5. J. Parsons, M. P. Castaldi, S. Dutta, S. M. Dibrov, D. L. Wyles, T. Hermann, Conformational inhibition of the hepatitis C virus internal ribosome entry site RNA. Nat Chem Biol 5, 823-825 (2009); published online EpubNov (10.1038/nchembio.217).
6. C. Romero-Lopez, A. Berzal-Herranz, Unmasking the information encoded as structural motifs of viral RNA genomes: a potential antiviral target. Rev Med Virol 23, 340-354 (2013); published online EpubNov (10.1002/rmv.1756).
7. P. S. Palese, M. L., Fields Virology. D. M. e. a. Knipe, Ed., Orthomyxoviridae (Lippincott Williams & Wilkins, ed. 5th, 2007).
8. R. W. Compans, J. Content, P. H. Duesberg, Structure of the ribonucleoprotein of influenza virus. J Virol 10, 795-800 (1972); published online EpubOct (
9. E. C. Hutchinson, J. C. von Kirchbach, J. R. Gog, P. Digard, Genome packaging in influenza A virus. J Gen Virol 91, 313-328 (2010); published online EpubFeb (10.1099/vir.0.017608-0).
10. T. Noda, Y. Kawaoka, Structure of influenza virus ribonucleoprotein complexes and their packaging into virions. Rev Med Virol 20, 380-391 (2010); published online EpubNov (10.1002/rmv.666).
11. Y. Muramoto, A. Takada, K. Fujii, T. Noda, K. Iwatsuki-Horimoto, S. Watanabe, T. Horimoto, H. Kida, Y. Kawaoka, Hierarchy among viral RNA (vRNA) segments in their role in vRNA incorporation into influenza A virions. J Virol 80, 2318-2325 (2006); published online EpubMar (10.1128/jvi.80.5.2318-2325.2006).
12. Q. Gao, Y. Y. Chou, S. Doganay, R. Vafabakhsh, T. Ha, P. Palese, The influenza A virus PB2, PA, NP, and M segments play a pivotal role during genome packaging. J Virol 86, 7043-7051 (2012); published online EpubJul (10.1128/jvi.00662-12).
13. G. A. Marsh, R. Rabadan, A. J. Levine, P. Palese, Highly conserved regions of influenza a virus polymerase gene segments are critical for efficient viral RNA packaging. J Virol 82, 2295-2304 (2008); published online EpubMar (10.1128/jvi.02267-07).
14. E. Fournier, V. Moules, B. Essere, J. C. Paillart, J. D. Sirbat, C. Isel, A. Cavalier, J. P. Rolland, D. Thomas, B. Lina, R. Marquet, A supramolecular assembly formed by influenza A virus genomic RNA segments. Nucleic Acids Res 40, 2197-2209 (2012); published online EpubMar (10.1093/nar/gkr985).
15. C. Gavazzi, C. Isel, E. Fournier, V. Moules, A. Cavalier, D. Thomas, B. Lina, R. Marquet, An in vitro network of intermolecular interactions between viral RNA segments of an avian H5N2 influenza A virus: comparison with a human H3N2 virus. Nucleic Acids Res 41, 1241-1254 (2013); published online EpubJan (10.1093/nar/gks1181).
16. J. R. Gog, S. Afonso Edos, R. M. Dalton, I. Leclercq, L. Tiley, D. Elton, J. C. von Kirchbach, N. Naffakh, N. Escriou, P. Digard, Codon conservation in the influenza A virus genome defines RNA packaging signals. Nucleic Acids Res 35, 1897-1907 (2007)10.1093/nar/gkm087).
17. W. N. Moss, S. F. Priore, D. H. Turner, Identification of potential conserved RNA secondary structure throughout influenza A coding regions. Rna 17, 991-1011 (2011); published online EpubJun (10.1261/rna.2619511).
18. Y. Liang, T. Huang, H. Ly, T. G. Parslow, Mutational analyses of packaging signals in influenza virus PA, PB1, and PB2 genomic RNA segments. J Virol 82, 229-236 (2008); published online EpubJan (10.1128/JVI.01541-07).
19. K. A. Wilkinson, E. J. Merino, K. M. Weeks, Selective 2'-hydroxyl acylation analyzed by primer extension (SHAPE): quantitative RNA structure analysis at single nucleotide resolution. Nature protocols 1, 1610-1616 (2006)10.1038/nprot.2006.249).
20. P. S. Pang, M. Elazar, E. A. Pham, J. S. Glenn, Simplified RNA secondary structure mapping by automation of SHAPE data analysis. Nucleic Acids Res 39, e151 (2011); published online EpubDec (10.1093/nar/gkr773).
21. S. F. Priore, W. N. Moss, D. H. Turner, Influenza A virus coding regions exhibit host-specific global ordered RNA structure. PLoS One 7, e35989 (2012)10.1371/journal-.pone.0035989).
22. W. Kladwang, R. Das, A mutate-and-map strategy for inferring base pairs in structured nucleic acids: proof of concept on a DNA/RNA helix. Biochemistry 49, 7414-7416 (2010); published online EpubSep 7 (10.1021/bi101123g).
23. S. Tian, P. Cordero, W. Kladwang, R. Das, High-throughput mutate-map-rescue evaluates SHAPE-directed RNA structure and uncovers excited states. Rna 20, 1815-1826 (2014); published online EpubNov (10.1261/rna.044321.114).
24. B. Vester, J. Wengel, LNA (locked nucleic acid): high-affinity targeting of complementary RNA and DNA. Biochemistry 43, 13233-13241 (2004); published online EpubOct 26 (10.1021/bi0485732).
25. K. Klumpp, R. W. Ruigrok, F. Baudin, Roles of the influenza virus polymerase and nucleoprotein in forming a functional RNP structure. Embo J 16, 1248-1257 (1997); published online EpubMar 17 (10.1093/emboj/16.6.1248).
26. R. Coloma, J. M. Valpuesta, R. Arranz, J. L. Carrascosa, J. Ortin, J. Martin-Benito, The structure of a biologically active influenza virus ribonucleoprotein complex. PLoS Pathog 5, e1000491 (2009); published online EpubJun (10.1371/journal.ppat.1000491).
27. F. Baudin, C. Bach, S. Cusack, R. W. Ruigrok, Structure of influenza virus RNP. I. Influenza virus nucleoprotein melts secondary structure in panhandle RNA and exposes the bases to the solvent. Embo J 13, 3158-3165 (1994); published online EpubJul 1 (
28. T. Coelho, D. Adams, A. Silva, P. Lozeron, P. N. Hawkins, T. Mant, J. Perez, J. Chiesa, S. Warrington, E. Tranter, M. Munisamy, R. Falzone, J. Harrop, J. Cehelsky, B. R. Bettencourt, M. Geissler, J. S. Butler, A. Sehgal, R. E. Meyers, Q. Chen, T. Borland, R. M. Hutabarat, V. A. Clausen, R. Alvarez, K. Fitzgerald, C. Gamba-Vitalo, S. V. Nochur, A. K. Vaishnaw, D. W. Sah, J. A. Gollob, O. B. Suhr, Safety and efficacy of RNAi therapy for transthyretin amyloidosis. N Engl J Med 369, 819-829 (2013); published online EpubAug 29 (10.1056/NEJMoa1208760).
29. K. Fitzgerald, M. Frank-Kamenetsky, S. Shulga-Morskaya, A. Liebow, B. R. Bettencourt, J. E. Sutherland, R. M. Hutabarat, V. A. Clausen, V. Karsten, J. Cehelsky, S. V. Nochur, V. Kotelianski, J. Horton, T. Mant, J. Chiesa, J. Ritter, M. Munisamy, A. K. Vaishnaw, J. A. Gollob, A. Simon, Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet 383, 60-68 (2014); published online EpubJan 4 (10.1016/S0140-6736(13) 61914-5).
30. J. Gottlieb, M. R. Zamora, T. Hodges, A. W. Musk, U. Sommerwerk, D. Dilling, S. Arcasoy, J. DeVincenzo, V. Karsten, S. Shah, B. R. Bettencourt, J. Cehelsky, S. Nochur, J. Gollob, A. Vaishnaw, A. R. Simon, A. R. Glanville, ALN-RSV01 for prevention of bronchiolitis obliterans syndrome after respiratory syncytial virus infection in lung transplant recipients. J Heart Lung Transplant 35, 213-221 (2016); published online EpubFeb (10.1016/j.healun.2015.08.012).
31. E. Hoffmann, G. Neumann, Y. Kawaoka, G. Hobom, R. G. Webster, A DNA transfection system for generation of influenza A virus from eight plasmids. Proc Natl Acad Sci USA 97, 6108-6113 (2000); published online EpubMay 23 (10.1073/pnas.100133697).
32. K. J. Szretter, A. L. Balish, J. M. Katz, Influenza: propagation, quantification, and storage. Current protocols in microbiology Chapter 15, Unit 15G 11 (2006); published online EpubDec (10.1002/0471729256.mc15g01s3).
33. G. A. Marsh, R. Hatami, P. Palese, Specific residues of the influenza A virus hemagglutinin viral RNA are important for efficient packaging into budding virions. J Virol 81, 9727-9736 (2007); published online EpubSep (10.1128/jvi.01144-07).
34. S. A. Mortimer, K. M. Weeks, Time-resolved RNA SHAPE chemistry: quantitative RNA structure analysis in one-second snapshots and at single-nucleotide resolution. Nature protocols 4, 1413-1421 (2009)10.1038/nprot.2009.126).
35. A. Akbari, G. Marthinsen, J. T. Lifjeld, F. Albregtsen, L. Wennerberg, N. C. Stenseth, K. S. Jakobsen, Improved DNA fragment length estimation in capillary electrophoresis. Electrophoresis 29, 1273-1285 (2008); published online EpubMar (10.1002/elps.200700523).
36. P. S. Pang, E. A. Pham, M. Elazar, S. G. Patel, M. R. Eckart, J. S. Glenn, Structural map of a microRNA-122: hepatitis C virus complex. J Virol 86, 1250-1254 (2012); published online EpubJan (10.1128/JVI.06367-11).
37. K. E. Deigan, T. W. Li, D. H. Mathews, K. M. Weeks, Accurate SHAPE-directed RNA structure determination. Proc Natl Acad Sci USA 106, 97-102 (2009); published online EpubJan 6 (10.1073/pnas.0806929106).
38. P. De Rijk, J. Wuyts, R. De Wachter, RnaViz 2: an improved representation of RNA secondary structure. Bioinformatics 19, 299-300 (2003); published online EpubJan 22.
39. W. Kladwang, C. C. VanLang, P. Cordero, R. Das, A two-dimensional mutate-and-map strategy for non-coding RNA structure. Nature chemistry 3, 954-962 (2011); published online EpubDec (10.1038/nchem.1176).
40. W. Kladwang, P. Cordero, R. Das, A mutate-and-map strategy accurately infers the base pairs of a 35-nucleotide model RNA. Rna 17, 522-534 (2011); published online EpubMar (10.1261/rna.2516311).
41. P. Cordero, W. Kladwang, C. C. VanLang, R. Das, in RNA Folding (Methods in Molecular Biology), C. Waldsich, Ed. (2013), pp. in press.
42. S. A. Mortimer, K. M. Weeks, A fast-acting reagent for accurate analysis of RNA secondary and tertiary structure by SHAPE chemistry. J Am Chem Soc 129, 4144-4145 (2007); published online EpubApr 11 (10.1021/ja0704028).

43. S. Yoon, J. Kim, J. Hum, H. Kim, S. Park, W. Kladwang, R. Das, HiTRACE: high-throughput robust analysis for capillary electrophoresis. Bioinformatics 27, 1798-1805 (2011); published online EpubJul 1 (10.1093/bioinformatics/btr277).

44. H. Kim, P. Cordero, R. Das, S. Yoon, HiTRACE-Web: an online tool for robust analysis of high-throughput capillary electrophoresis. Nucleic Acids Research 41, W492-W498 (2013); published online EpubJul. 1, 2013 (10.1093/nar/gkt501).

45. J. Kim, S. Yu, B. Shim, H. Kim, H. Min, E.-Y. Chung, R. Das, S. Yoon, A robust peak detection method for RNA structure inference by high-throughput contact mapping. Bioinformatics 25, 1137-1144 (2009); published online EpubMay 1, 2009 (10.1093/bioinformatics/btp110).

46. W. Kladwang, T. H. Mann, A. Becka, S. Tian, H. Kim, S. Yoon, R. Das, Standardization of RNA chemical mapping experiments. Biochemistry 53, 3063-3065 (2014); published online EpubMay 20 (10.1021/bi5003426).

47. D. H. Mathews, M. D. Disney, J. L. Childs, S. J. Schroeder, M. Zuker, D. H. Turner, Incorporating chemical modification constraints into a dynamic programming algorithm for prediction of RNA secondary structure. Proc Natl Acad Sci USA 101, 7287-7292 (2004); published online EpubMay 11 (10.1073/pnas.0401799101).

48. K. Darty, A. Denise, Y. Ponty, VARNA: Interactive drawing and editing of the RNA secondary structure. Bioinformatics 25, 1974-1975 (2009); published online EpubAug 1 (10.1093/bioinformatics/btp250).

49. P. Cordero, J. B. Lucks, R. Das, An RNA Mapping DataBase for curating RNA structure mapping experiments. Bioinformatics 28, 3006-3008 (2012); published online EpubNov 15 (10.1093/bioinformatics/bts554).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

Notwithstanding the appended claims, the disclosure set forth herein is also described by the following clauses:

Clause 1. An oligonucleotide compound, comprising an oligonucleotide sequence complementary to a PB2 vRNA region, wherein the region comprises nucleotides 34-87 in the (−)-sense notation of the 5' terminal coding region of the PB2 vRNA, or a salt thereof.

Clause 2. The compound of clause 1, comprising an oligonucleotide sequence comprising at least 8 nucleoside subunits complementary to the region of PB2 vRNA.

Clause 3. The compound of any one of clauses 1-2, wherein the oligonucleotide is complementary to a region of the Packaging Stem-Loop 2 (PSL2) motif of the region of PB2 vRNA.

Clause 4. The compound of any one of clauses 1-3, wherein the oligonucleotide comprises an internucleoside linkage selected from: phosphorothioate, phosphorodithioate, phosphoramidate and thiophosphoramidate linkages.

Clause 5. The compound of any one of clauses 1-4, wherein all of the internucleoside linkages of the oligonucleotide are selected from: phosphorothioate, phosphorodithioate, phosphoramidate, thiophosphoramidate and phosphodiester linkages.

Clause 6. The compound of any one of clause 4 or 5, wherein the oligonucleotide internucleoside linkage is chiral.

Clause 7. The compound on any one of clauses 1-5, wherein the oligonucleotide comprises a bridged nucleic acid (BNA) nucleotide.

Clause 8. The compound of any one of clauses 1-5, wherein the oligonucleotide comprises a locked nucleic acid (LNA) nucleotide.

Clause 9. The compound of any one of clauses 1-5, wherein the oligonucleotide comprises a ethylene-bridged nucleic acid (ENA) nucleotide.

Clause 10. The compound of any one of clauses 1-5, wherein the oligonucleotide comprises a constrained ethyl nucleic acid (cEt) nucleotide.

Clause 11. The compound of any one of clauses 1-5, wherein the oligonucleotide comprises a 2'-modified nucleotide.

Clause 12. The compound of any one of clauses 1-11, wherein the oligonucleotide comprises a sequence selected from:

(SEQ ID NO: 45)
5' ACCAAAAGAAT 3';

(SEQ ID NO: 46)
5' TGGCCATCAAT 3';

(SEQ ID NO: 47)
5' TAGCATACTTA 3';

(SEQ ID NO: 48)
5' CCAAAAGA 3';

(SEQ ID NO: 49)
5' CATACTTA 3';

(SEQ ID NO: 50)
5' CAGACACGACCAAAA 3';

(SEQ ID NO: 51)
5' TACTTACTGACAGCC 3';

(SEQ ID NO: 52)
5' AGACACGACCAAAAG 3';

(SEQ ID NO: 53)
5' ACCAAAAGAAT 3';

(SEQ ID NO: 54)
5' TGGCCATCAAT 3';

-continued (SEQ ID NO: 55)
5' TAGCATACTTA 3';

(SEQ ID NO: 56)
5' CGACCAAAAGAATTC 3';

(SEQ ID NO: 57)
5' CGACCAAAAGAATTC 3';

(SEQ ID NO: 58)
5' GATGGCCATCAATTA 3';

(SEQ ID NO: 59)
5' GATGGCCATCAATTA 3';

(SEQ ID NO: 60)
5' TCTAGCATACTTACT 3';

(SEQ ID NO: 61)
5' TCTAGCATACTTACT 3';

(SEQ ID NO: 62)
5' GAATTCGGATGGCCA 3';

(SEQ ID NO: 63)
5' GGCCATCAATTAGTG 3';

(SEQ ID NO: 64)
5' TTCGGATGGCCATCA 3';

(SEQ ID NO: 65)
5' AGCCAGACAGCGA 3';

(SEQ ID NO: 66)
5' GACAGCCAGACAGCA 3';

(SEQ ID NO: 98)
5'CGACCAAAAGAATT 3';

(SEQ ID NO: 99)
5'GACCAAAAGAATTCGG 3';

(SEQ ID NO: 100)
5' AGCATACTTACTGACA 3';

(SEQ ID NO: 101)
5' CATACTTACTGACA 3';

(SEQ ID NO: 102)
5' ATACTTACTGACAG 3';

(SEQ ID NO: 103)
5' CATACTTACTGACAGC 3';

(SEQ ID NO: 104)
5' AGACAGCGACCAAAAG 3';

(SEQ ID NO: 105)
5' ACAGCGACCAAAAG;

(SEQ ID NO: 106)
5'CAGCCAGACAGCGAC 3';

(SEQ ID NO: 107)
5'CAGCCAGACAGCGA 3';

(SEQ ID NO: 108)
5'ACAGCCAGACAGCGA 3';

(SEQ ID NO: 109)
5'GACAGCCAGACAGCG 3';

(SEQ ID NO: 110)
5' CATCAATTAGTGTCG 3';

(SEQ ID NO: 111)
5' CCATCAATTAGTGTCG 3';

(SEQ ID NO: 112)
5' GCCATCAATTAGTGTG 3';

-continued (SEQ ID NO: 113)
5' AAGAATTCGGATGGC 3';

(SEQ ID NO: 114)
5' CAGACAGCGACCAA 3';

(SEQ ID NO: 115)
5' TGACAGCCAGACAGC 3';

Clause 13. The compound of clause 12, wherein the oligonucleotide comprises a sequence selected from:

(SEQ ID NO: 62)
5' GAATTCGGATGGCCA 3';

(SEQ ID NO: 63)
5' GGCCATCAATTAGTG 3';

(SEQ ID NO: 98)
5'CGACCAAAAGAATT 3';

(SEQ ID NO: 99)
5'GACCAAAAGAATTCGG 3';

(SEQ ID NO: 100)
5' AGCATACTTACTGACA 3';

(SEQ ID NO: 101)
5' CATACTTACTGACA 3';

(SEQ ID NO: 102)
5' ATACTTACTGACAG 3';

(SEQ ID NO: 103)
5' CATACTTACTGACAGC 3';

(SEQ ID NO: 104)
5' AGACAGCGACCAAAAG 3';

(SEQ ID NO: 105)
5' ACAGCGACCAAAAG;

(SEQ ID NO: 106)
5'CAGCCAGACAGCGAC 3';

(SEQ ID NO: 107)
5'CAGCCAGACAGCGA 3';

(SEQ ID NO: 108)
5'ACAGCCAGACAGCGA 3';

(SEQ ID NO: 109)
5'GACAGCCAGACAGCG 3';

(SEQ ID NO: 110)
5' CATCAATTAGTGTCG 3';

(SEQ ID NO: 111)
5' CCATCAATTAGTGTCG 3';

(SEQ ID NO: 112)
5' GCCATCAATTAGTGTG 3';

(SEQ ID NO: 113)
5' AAGAATTCGGATGGC 3';

(SEQ ID NO: 114)
5' CAGACAGCGACCAA 3';

(SEQ ID NO: 115)
5' TGACAGCCAGACAGC 3'.

Clause 14. The compound of clause 12, comprising an oligonucleotide having at least 70% sequence identity with a sequence selected from (SEQ ID Nos 45-66), and (SEQ ID Nos 98-115).

Clause 15. The compound of clause 14, comprising an oligonucleotide having at least 80% sequence identity with a sequence selected from (SEQ ID Nos 45-66), and (SEQ ID Nos 98-115).

Clause 16. The compound of clause 15, comprising an oligonucleotide having at least 90% sequence identity with a sequence selected from (SEQ ID Nos 45-66), and (SEQ ID Nos 98-115).

Clause 17. The compound of clause 12, wherein one or more of the nucleotides of the oligonucleotide are modified nucleotides (e.g., as described herein).

Clause 18. The compound of clause 12, wherein one or more of the nucleotides of the oligonucleotide are bridged nucleic acid (BNA) nucleotides.

Clause 19. The compound of clause 12, wherein all the nucleotides of the oligonucleotide are locked nucleic acid (LNA) nucleotides.

Clause 20. The compound of clause 12, wherein one or more of the nucleotides of the oligonucleotide are ethylene-bridged nucleic acid (ENA) nucleotides.

Clause 21. The compound of clause 12, wherein one or more of the nucleotides of the oligonucleotide are constrained ethyl nucleic acid (cEt) nucleotides.

Clause 22. The compound clause 12, wherein one or more of the nucleotides of the oligonucleotide comprise 2'-modified nucleotides.

Clause 23. The compound of clause 12, wherein the oligonucleotide comprises a sequence selected from:

```
LNA 1:
                                (SEQ ID NO: 67)
5' AccAaaAGaaT 3'

LNA 2:
                                (SEQ ID NO: 68)
5' TggCcATcaaT 3'

LNA 3:
                                (SEQ ID NO: 69)
5' TagCAtActtA 3'

LNA 4:
                                (SEQ ID NO: 70)
5' CCAAAAGA 3'

LNA 5:
                                (SEQ ID NO: 71)
5' CATACTTA 3'

LNA 6:
                                (SEQ ID NO: 72)
5' CagaCaCGaCCaaAA 3'

LNA 7:
                                (SEQ ID NO: 73)
5' TAcTtaCTgaCagCC 3'

LNA 8:
                                (SEQ ID NO: 74)
5' AGACacgaccaAAAG  3'

LNA 9:
                                (SEQ ID NO: 75)
5' TACTtactgacaGCC 3'

LNA9.2:
                                (SEQ ID NO: 76)
5' TACttactgacAGCC 3'

LNA10:
                                (SEQ ID NO: 77)
5'ACCaaaagAAT 3'
```

-continued

```
LNA11:
                                (SEQ ID NO: 78)
5' TGGccatcAAT 3'

LNA12:
                                (SEQ ID NO: 79)
5'TAGcatacTTA 3'

LNA13:
                                (SEQ ID NO: 80)
5'CgacCAaaAGaattC 3'

LNA14:
                                (SEQ ID NO: 81)
5'CGACcaaaagaATTC 3'

LNA15:
                                (SEQ ID NO: 82)
5'GaTGgCcATcaAttA 3'

LNA16:
                                (SEQ ID NO: 83)
5'GATGgccatcaATTA 3'

LNA17:
                                (SEQ ID NO: 84)
5'TcTAgCaTActTacT 3'

LNA18:
                                (SEQ ID NO: 85)
5'TCTAgcatactTACT 3'

LNA19:
                                (SEQ ID NO: 86)
5'GAAttcggatgGCCA 3'

LNA20:
                                (SEQ ID NO: 87)
5'GGCCatcaattaGTG 3'

LNA21:
                                (SEQ ID NO: 88)
5'TTCGgatggccaTCA 3'

LNA22:
                                (SEQ ID NO: 89)
5'AGCCagacagCGA 3'

LNA23:
                                (SEQ ID NO: 90)
5'GACAgccagacaGCA 3'

LNA 9.G74C:
                                (SEQ ID NO: 91)
5'TACTtactgacaGTC 3'
and

LNA 9.T80C:
                                (SEQ ID NO: 92)
5'TACTtaccgacaGCC 3'
```

wherein capitalized letters denote LNA nucleotides and lowercase letters denote DNA nucleotides.

Clause 24. The compound of clause 12, wherein the oligonucleotide comprises a sequence selected from:

```
LNA19:
                                (SEQ ID NO: 86)
5'GAAttcggatgGCCA 3';

LNA22:
                                (SEQ ID NO: 89)
5'AGCCagacagCGA 3';

LNA22.2:
                               (SEQ ID NO: 116)
5'CAGCcagacagCGAC 3';
```

-continued

LNA22.3:
(SEQ ID NO: 117)
5'CAGccagacagCGAC 3';

LNA22.5:
(SEQ ID NO: 118)
5'CAGccagacaGCGA 3';

LNA22.6:
(SEQ ID NO: 119)
5'CAGccagacagCGA 3';

LNA22.7:
(SEQ ID NO: 120)
5'CAGCcagacagCGA 3';

LNA22.8:
(SEQ ID NO: 121)
5'ACAgccagacagCGA 3';

LNA22.9:
(SEQ ID NO: 122)
5'ACAGccagacaGCGA 3';

LNA22.10:
(SEQ ID NO: 123)
5'ACAgccagacaGCGA 3';

LNA22.11:
(SEQ ID NO: 124)
5'GACAgccagacaGCG 3';

LNA22.13:
(SEQ ID NO: 125)
5'GACagccagacaGCG 3';
and

LNA22.14:
(SEQ ID NO: 126)
5'GACAgccagacAGCG.

Clause 25. The compound of clause 12, wherein the oligonucleotide comprises a sequence selected from:

LNA24:
(SEQ ID NO: 127)
5'CATcaattagtgTCG 3';

LNA25:
(SEQ ID NO: 128)
5'CCAtcaattagtgTCG 3';

LNA26:
(SEQ ID NO: 129)
5'GCCatcaattagtGTG 3';

LNA27:
(SEQ ID NO: 130)
5'AAGAattcggaTGGC 3';

LNA28:
(SEQ ID NO: 131)
5' CAGacagcgacCAA 3';
and

LNA29:
(SEQ ID NO: 132)
5' TGAcagccagacAGC 3'.

Clause 26. The compound of clause 12, wherein the oligonucleotide comprises a sequence selected from:

LNA14:
(SEQ ID NO: 81)
5'CGACcaaaagaATTC 3';

-continued

LNA14.5:
(SEQ ID NO: 135)
5'CGACcaaaagaATT 3';

LNA14.8:
(SEQ ID NO: 137)
5'CGACcaaaagaaTTC 3';

LNA14.28:
(SEQ ID NO: 148)
5'GACcaaaagaatTCGG 3';

LNA14.30:
(SEQ ID NO: 149)
5'GACCaaaagaattCGG 3';

LNA 9:
(SEQ ID NO: 75)
5' TACTtactgacaGCC 3';

LNA9.1:
(SEQ ID NO: 159)
5' AGCAtacttactGACA 3';

LNA9.2a:
(SEQ ID NO: 160)
5' CATacttactgACA 3';

LNA9.8:
(SEQ ID NO: 164)
5' ATActtactgACAG;

LNA9.12:
(SEQ ID NO: 167)
5' CATActtactgacAGC;

LNA8a:
(SEQ ID NO: 188)
5' AGAcagcgaccaaAAG;

LNA8a.1:
(SEQ ID NO: 189)
5' AGACagcgaccaAAAG;
and

LNA8a.2:
(SEQ ID NO: 190)
5' ACAGcgaccaAAAG.

Clause 27. The compound of any one of clauses 23-26, comprising an oligonucleotide having at least 70% sequence identity with a sequence selected from (SEQ ID Nos 67-92), and (SEQ ID Nos: 116-191).

Clause 28. The compound of clause 27, comprising an oligonucleotide having at least 80% sequence identity with a sequence selected from (SEQ ID Nos 67-92), and (SEQ ID Nos: 116-191).

Clause 29. The compound of clause 28, comprising an oligonucleotide having at least 90% sequence identity with a sequence selected from (SEQ ID Nos 67-92), and (SEQ ID Nos: 116-191).

Clause 30. The compound of any one of clauses 1-29, wherein the oligonucleotide comprises at least 5 deoxyribonucleotide units and is capable of recruiting an RNase.

Clause 31. The compound of any one of clauses 1-30, wherein binding of the compound to the region of PB2 vRNA disrupts the overall secondary RNA structure of the PB2 vRNA.

Clause 32. The compound of any one of clauses 1-30, wherein binding of the compound to the region of PB2 vRNA inhibits the packaging ability of the PB2 vRNA.

Clause 33. The compound of any one of clauses 1-32, wherein the compound is an oligonucleotide conjugate having enhanced cellular uptake.

Clause 34. The compound of clause 33, wherein the compound is an oligonucleotide-lipid conjugate.

Clause 35. The compound of any one of clauses 1-33, wherein the compound is an oligonucleotide conjugate with a cell-specific protein.

Clause 36. A method of inhibiting influenza A virus in a cell, the method comprising: contacting a sample comprising viral RNA (vRNA) having a PSL2 motif with an effective amount of an agent that specifically binds the PSL2 motif to inhibit the influenza A virus.

Clause 37. The method of clause 36, wherein the agent is an oligonucleotide compound comprising at least 8 nucleoside subunits complementary to a PSL2 motif of the vRNA, or a salt thereof.

Clause 38. The method of clause 36 or 37, wherein the agent is an oligonucleotide compound according to one of clauses 1-35.

Clause 39. The method of any one of clauses 36-38, wherein the vRNA in the sample is a PB2 vRNA.

Clause 40. The method of any one of clauses 36-39, wherein contacting the sample with an agent results in at least 1 $\log_{10}$ titer deficits of the virus.

Clause 41. The method of any one of clauses 36-39, wherein contacting the sample with an agent results in at least 2 $\log_{10}$ titer deficits of the virus.

Clause 42. The method of any one of clauses 36-41, wherein the agent disrupts the overall structure of the PSL2 motif of the vRNA.

Clause 43. The method of any one of clauses 36-41, wherein the agent inhibits the packaging ability of the PSL2 motif of the vRNA.

Clause 44. The method of any one of clauses 36-41, wherein the vRNA is isolated from a virion or a cell.

Clause 45. The method of any one of clauses 36-41, wherein the vRNA is comprised in a virion or an infected cell.

Clause 46. The method of any one of clauses 36-45, wherein the sample is in vitro.

Clause 47. The method of any one of clauses 36-41 or 45, wherein the sample is in vivo.

Clause 48. A method of treating or preventing influenza A virus infection in a subject, the method comprising: administering to a subject in need thereof a pharmaceutical composition comprising an effective amount of an active agent that specifically binds to a PSL2 motif of a viral RNA (vRNA).

Clause 49. The method of clause 48, wherein the vRNA is a PB2 vRNA.

Clause 50. The method of any one of clauses 48-49, wherein the active agent is a compound comprising an oligonucleotide sequence comprising at least 8 nucleoside subunits complementary to the region of PB2 vRNA.

Clause 51. The method of any one of clauses 48-50, wherein the agent is an oligonucleotide compound according to one of clauses 1-35.

Clause 52. The method of any one of clauses 48-51, wherein the subject is at risk of influenza A virus infection and the administering of the oligonucleotide compound protects the subject against infection for 1 week or more (e.g., 2 weeks or more, 3 weeks or more, 1 month or more, 2 months or more, 3 months or more, etc).

Clause 53 The method of clause 52, wherein the administering comprises weekly, biweekly, or monthly administration of an effective dose of the oligonucleotide compound.

Clause 54. The method of any one of clauses 48-53, wherein the administering results in at least 1 $\log_{10}$ titer deficits of the virus in a sample of the subject.

Clause 55. The method of any one of clauses 48-53, wherein the administering results in at least 2 $\log_{10}$ titer deficits of the virus in a sample of the subject.

Clause 56. The method of any one of clauses 48-53, wherein the active agent is an oligonucleotide conjugate having enhanced cellular uptake.

Clause 57. The method of any one of clauses 48-55, wherein the active agent is an oligonucleotide conjugate with a cell-specific protein.

Clause 58. The method of any one of clauses 48-55, wherein the pharmaceutical composition comprises an enhancer of cellular uptake.

Clause 59. The method of any one of clauses 48-55, wherein the pharmaceutical composition further comprises an additional active agent selected from a second oligonucleotide active agent and an antiviral drug.

Clause 60. The method of any one of clauses 48-55, wherein the active agent is an siRNA, an shRNA, an antisense RNA, or an antisense DNA.

Clause 61. The method of any one of clauses 48-55, wherein the subject is at risk of influenza A virus infection, and the method prevents infection.

Clause 62. The method of any one of clauses 48-55, wherein the subject is diagnosed with or suspect of having an influenza A virus infection, and the method treats infection.

Clause 63. A method for screening a candidate agent for the ability to inhibit influenza A virus in a cell, the method comprising:

contacting a sample comprising viral RNA (vRNA) comprising a PSL2 motif with a candidate agent; and determining whether the candidate agent specifically binds to the PSL2 motif;

wherein an agent that specifically binds to the PSL2 motif will inhibit influenza A virus in a cell.

Clause 64. The method of clause 63, wherein the candidate agent is selected from: a small molecule, a nucleic acid and a polypeptide.

Clause 65. The method of clause 64, wherein the determining step comprises detecting a cellular parameter, wherein a change in the parameter in the cell as compared to in a cell not contacted with candidate agent indicates that the candidate agent specifically binds the PSL2 motif.

Clause 66. The method of any one of clauses 63-65, wherein an agent that specifically binds to the PSL2 motif will treat the subject having the influenza A virus infection.

Clause 67. A method of treating or preventing respiratory virus infection in a subject, the method comprising:

administering to a subject in need thereof a pharmaceutical composition comprising an effective amount of an active agent that specifically binds to a target motif of a viral RNA (vRNA) or a miRNA of the subject that associates with the target motif.

Clause 68. The method of clause 67, wherein the agent is an oligonucleotide compound according to comprising a sequence selected from the group consisting of SEQ ID NOS: 45 to 907.

Clause 69. The method of clause 68, wherein the method comprises administered two or more sequences selected from the group consisting of SEQ ID NOS: 45 to 907.

Clause 70. The method according to clause 69, wherein the two or more sequences are directed to different respiratory viruses.

Clause 71. The method of any one of clauses 67-70, wherein the subject is at risk of respiratory virus infection and the administering of the oligonucleotide compound protects the subject against infection for 1 week or more (e.g., 2 weeks or more, 3 weeks or more, 1 month or more, 2 months or more, 3 months or more, etc).

Clause 72 The method of clause 71, wherein the administering comprises weekly, biweekly, or monthly administration of an effective dose of the oligonucleotide compound.

Clause 73. The method of any one of clauses 67-72, wherein the administering results in at least 1 $\log_{10}$ titer deficits of the virus in a sample of the subject.

Clause 74. The method of any one of clauses 67-73, wherein the subject is at risk of respiratory virus infection, and the method prevents infection.

Clause 75. The method of any one of clauses 67-73, wherein the subject is diagnosed with or suspect of having respiratory virus infection, and the method treats infection.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. An antiviral oligonucleotide compound or salt thereof comprising an oligonucleotide sequence 5' ATGCT-GATCCCTGTC 3' (SEQ ID NO:508).

2. The antiviral oligonucleotide compound of claim 1, wherein the oligonucleotide comprises at least one internucleoside linkage selected from phosphorothioate, phosphorodithioate, phosphoramidate and thiophosphoramidate linkages.

3. The antiviral oligonucleotide compound of claim 2, wherein the oligonucleotide comprises at least one phosphorothioate linkage.

4. The antiviral oligonucleotide compound of claim 3, wherein all of the internucleoside linkages are phosphorothioate linkages.

5. The antiviral oligonucleotide compound of claim 1, wherein the oligonucleotide comprises one or more 2'-modified nucleotides.

6. The antiviral oligonucleotide compound of claim 5, wherein the oligonucleotide comprises at least one LNA nucleotide.

7. The antiviral oligonucleotide compound of claim 6, wherein the oligonucleotide comprises a plurality of LNA nucleotides.

8. The antiviral oligonucleotide compound of claim 7 comprising an oligonucleotide sequence 5' ATGCt-gatccctGTC 3' (SEQ ID NO:784), wherein capitalized letters denote LNA nucleotides and lowercase letters denote DNA nucleotides.

9. The antiviral oligonucleotide compound of claim 6, wherein the oligonucleotide comprises at least one phosphorothioate internucleoside linkage.

10. The antiviral oligonucleotide compound of claim 9, wherein all of the internucleoside linkages are phosphorothioate linkages.

11. A pharmaceutical composition comprising an antiviral oligonucleotide compound or salt thereof, comprising an oligonucleotide sequence of claim 1 and a pharmaceutically acceptable excipient.

12. The pharmaceutical composition of claim 11 comprising an oligonucleotide sequence 5' ATGCtgatccctGTC 3' (SEQ ID NO:784), wherein capitalized letters denote LNA nucleotides and lowercase letters denote DNA nucleotides.

13. The pharmaceutical composition of claim 11, wherein the oligonucleotide comprises at least one internucleoside linkage selected from phosphorothioate, phosphorodithioate, phosphoramidate and thiophosphoramidate linkages.

14. The pharmaceutical composition of claim 13, wherein the oligonucleotide comprises at least one phosphorothioate internucleoside linkage.

15. The pharmaceutical composition of claim 14, all of the internucleoside linkages are phosphorothioate linkages.

16. The antiviral oligonucleotide compound of claim 11, wherein the oligonucleotide comprises one or more 2'-modified nucleotides.

17. The antiviral oligonucleotide compound of claim 16, wherein the oligonucleotide comprises at least one LNA nucleotide.

18. The antiviral oligonucleotide compound of claim 17, wherein the oligonucleotide comprises a plurality of LNA nucleotides.

* * * * *

SEQUENCE LISTING

```
Sequence total quantity: 908
SEQ ID NO: 1            moltype = RNA  length = 196
FEATURE                 Location/Qualifiers
misc_feature            1..196
                        note = Synthetic polynucleotide
source                  1..196
                        mol_type = other RNA
                        organism = synthetic construct
SEQUENCE: 1
agtagaaaca aggtcgtttt taaactattc gacactaatt gatggccatc cgaattcttt  60
tggtcgctgt ctggctgtca gtaagtatgc tagagtcccg ttttcgtttc attaccaaca  120
ccacgtctcc ttgcccaatt agcacattag cctttttttat tctttccata ttgaatataa  180
ttgacctgct ttcgct                                                  196

SEQ ID NO: 2            moltype = RNA  length = 182
FEATURE                 Location/Qualifiers
misc_feature            1..182
                        note = Synthetic polynucleotide
source                  1..182
                        mol_type = other RNA
                        organism = synthetic construct
SEQUENCE: 2
agtagaaaca aggtcgtttt taaactattc gacactaatt gatcgccatc cgaattcttt  60
tggtcgctgt ctggctgtca gtaagtatgc tagagtcccg ttttcgtttc gcgagactgc  120
gacattagat ttcttagttc ttttattctt tccatattga atataattga cctgctttcg  180
ct                                                                 182

SEQ ID NO: 3            moltype = RNA  length = 198
FEATURE                 Location/Qualifiers
misc_feature            1..198
                        note = Synthetic polynucleotide
source                  1..198
                        mol_type = other RNA
                        organism = synthetic construct
SEQUENCE: 3
agtagaaaca aggtcgtttt taaactattc gacactaatt gatggccatc cgaattcttt  60
tggtcgctgt ctggctgtct gtaagtatgc tagagtcccg ttttcgtttc ggactctcaa  120
aaacgtgcga gactgcgaca ttagatttct tagttctttt attctttcca tattgaatat  180
aattgacctg ctttcgct                                                198

SEQ ID NO: 4            moltype = RNA  length = 155
FEATURE                 Location/Qualifiers
misc_feature            1..155
                        note = Synthetic polynucleotide
source                  1..155
                        mol_type = other RNA
                        organism = synthetic construct
SEQUENCE: 4
agtagaaaca aggtcgtttt taaactattc gacactaatt gatggccatc cgaattcttt  60
tggtcgctgt ctggctgtca gtaagtatgc tagagtcccg tttccgtttc attaccaaca  120
ccacgtctct tgaatataat tgacctgctt tcgct                             155

SEQ ID NO: 5            moltype = RNA  length = 178
FEATURE                 Location/Qualifiers
misc_feature            1..178
                        note = Synthetic polynucleotide
source                  1..178
                        mol_type = other RNA
                        organism = synthetic construct
SEQUENCE: 5
agtagaaaca aggtcgtttt taaataattc gacactaatt gatggccatc cgaattcttt  60
tggtcgctgt ctggctgtca gtaagtatgc tagagtcccg ttttcgtttc attaccaaca  120
ccacgtctcc ttgccctttt attctctcca tattgaatat atttgacctg ctttcgct    178

SEQ ID NO: 6            moltype = RNA  length = 290
FEATURE                 Location/Qualifiers
misc_feature            1..290
                        note = Synthetic polynucleotide
source                  1..290
                        mol_type = other RNA
                        organism = synthetic construct
```

```
SEQUENCE: 6
agtagaaaca aggtcgtttt taaactattc gacactaatt gatggccatc cgaattcttt  60
tggtcgctgt ctggctgtca gtaagtatgc tagagtcccg ttttcgtttc attaccaaca  120
ctacgtcccc ttgcccaatt agcacattag ccttctctcc ttttgcaaga ttgctcagtt  180
cattgatgct taatgctggg ccatatctct tgtcttcttt gcccaaaatg agaaatcctc  240
tcaggacagc atattctctc catattgaat ataattgacc tgctttcgct             290

SEQ ID NO: 7           moltype = RNA  length = 178
FEATURE                Location/Qualifiers
misc_feature           1..178
                       note = Synthetic polynucleotide
modified_base          104
                       mod_base = i
source                 1..178
                       mol_type = other RNA
                       organism = synthetic construct
SEQUENCE: 7
agtagaaaca aggtcgtttt taaactattc gacactaatt gatggccatc cgaattcttt  60
tggtcgctgt ctggctgtca gtaagtatgc tagagtcccg tttacgtttc attaccaaca  120
ccacgtctcc ttgccctttt attctttcca tattgaatat aattgacctg ctttcgct    178

SEQ ID NO: 8           moltype = RNA  length = 197
FEATURE                Location/Qualifiers
misc_feature           1..197
                       note = Synthetic polynucleotide
source                 1..197
                       mol_type = other RNA
                       organism = synthetic construct
SEQUENCE: 8
agtagaaaca aggtcgtttt taaactattc gacactaatt gatggccatc cgaattcttt  60
tggtcgctgt ctggctgtca gttaatatgc tagagtcccg ttttcgtttc attaccaaca  120
ccacgtctcc ttgcccaatt agcacgtcga taggtttttt attctttcca tattgaatat  180
aatgacctgc tttcgct                                                 197

SEQ ID NO: 9           moltype = RNA  length = 198
FEATURE                Location/Qualifiers
misc_feature           1..198
                       note = Synthetic polynucleotide
source                 1..198
                       mol_type = other RNA
                       organism = synthetic construct
SEQUENCE: 9
agtagaaaca aggtcgtttt taaactattc gacactaatt gatggccatc cgaattcttt  60
tggtcgctgt ctggctgtct gtaagtatgc tagagtcccg ttttcgtttc ggactctcaa  120
aaacgtgcga gactgcgaca ttagatttct tagttctttt attctttcca tattgaatat  180
aattgacctg ctttcgct                                                198

SEQ ID NO: 10          moltype = RNA  length = 178
FEATURE                Location/Qualifiers
misc_feature           1..178
                       note = Synthetic polynucleotide
source                 1..178
                       mol_type = other RNA
                       organism = synthetic construct
SEQUENCE: 10
agtagaaaca aggtcgtttt taaactattc gacatctaat tgatggccat ccgaattctt  60
ttggtcgctg tctggctgtc agtaagtatg ctagagtccc gttttcgttt gactgcgaca  120
ttagatttct tagttctttt attctttcca tattgaatat aattgacctg ctttcgct    178

SEQ ID NO: 11          moltype = RNA  length = 182
FEATURE                Location/Qualifiers
misc_feature           1..182
                       note = Synthetic polynucleotide
source                 1..182
                       mol_type = other RNA
                       organism = synthetic construct
SEQUENCE: 11
agtagaaaca aggtcgtttt taaactattc gacactaatt gatcgccatc cgaattcttt  60
tggtcgctgt ctggctgtca gtaagtatgc tagagtcccg ttttcgtttc gcgagactgc  120
gacattagat ttcttagttc ttttattctt tccatattga atataattga cctgctttcg  180
ct                                                                 182

SEQ ID NO: 12          moltype = RNA  length = 59
FEATURE                Location/Qualifiers
misc_feature           1..59
                       note = Synthetic polynucleotide
source                 1..59
                       mol_type = other RNA
                       organism = synthetic construct
```

```
SEQUENCE: 12
cgacactaat tgatggccat ccgaattctt ttggtcgctg tctggctgtc agtaagtat   59

SEQ ID NO: 13          moltype = RNA  length = 59
FEATURE                Location/Qualifiers
misc_feature           1..59
                       note = Synthetic polynucleotide
source                 1..59
                       mol_type = other RNA
                       organism = synthetic construct
SEQUENCE: 13
cgacactaat tgatggccat ccgaattctt ttggtcgctg tctggctgtc agtaagtat   59

SEQ ID NO: 14          moltype = DNA  length = 108
FEATURE                Location/Qualifiers
misc_feature           1..108
                       note = Synthetic polynucleotide
source                 1..108
                       mol_type = other DNA
                       organism = synthetic construct
SEQUENCE: 14
attgggcaag gagacgtggt gttggtaatg aaacggaaac ggaactctag catacttact  60
gacagccaga cagcgaccaa aagaattcgg atggccatca attagtgt               108

SEQ ID NO: 15          moltype = DNA  length = 108
FEATURE                Location/Qualifiers
misc_feature           1..108
                       note = Synthetic polynucleotide
source                 1..108
                       mol_type = other DNA
                       organism = synthetic construct
SEQUENCE: 15
attgggcaag gagacgtcgt gttggtaatg aaacggaaac ggaactctag catattaaca  60
gacagccaaa cagcgacgaa aagaattcgg atggcgatca attgatgt               108

SEQ ID NO: 16          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 16
tacttactga cagtcagaca gcg                                          23

SEQ ID NO: 17          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 17
cgctgtctga ctgtcagtaa gta                                          23

SEQ ID NO: 18          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 18
tacttactga ctcgcagaca gcg                                          23

SEQ ID NO: 19          moltype = DNA  length = 23
FEATURE                Location/Qualifiers
misc_feature           1..23
                       note = Synthetic polynucleotide
source                 1..23
                       mol_type = other DNA
                       organism = synthetic construct
SEQUENCE: 19
cgctgtctgc gagtcagtaa gta                                          23

SEQ ID NO: 20          moltype = DNA  length = 30
FEATURE                Location/Qualifiers
misc_feature           1..30
                       note = Synthetic polynucleotide
```

```
source                  1..30
                        mol_type = other DNA
                        organism = synthetic construct
SEQUENCE: 20
tgacagccag actgcgacca aaagaattcg                                 30

SEQ ID NO: 21           moltype = DNA  length = 30
FEATURE                 Location/Qualifiers
misc_feature            1..30
                        note = Synthetic polynucleotide
source                  1..30
                        mol_type = other DNA
                        organism = synthetic construct
SEQUENCE: 21
cgaattcttt tggtcgcagt ctggctgtca                                 30

SEQ ID NO: 22           moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 22
agcgaccaaa agcattcgga tggc                                       24

SEQ ID NO: 23           moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 23
gccatccgaa tgcttttggt cgct                                       24

SEQ ID NO: 24           moltype = RNA  length = 176
FEATURE                 Location/Qualifiers
misc_feature            1..176
                        note = Synthetic polynucleotide
source                  1..176
                        mol_type = other RNA
                        organism = synthetic construct
SEQUENCE: 24
agtagaaaca aggtcgtttt taaactattc gacactaatt gatggccatc cgaattcttt  60
tggtcgctgt ctggctgtca gtaagtatgc tagagtcccg ttttcgtttc attaccaaca  120
cgacgtctcc ttgcttttat tctttccata ttgaatataa ttgacctgct ttcgct      176

SEQ ID NO: 25           moltype = RNA  length = 151
FEATURE                 Location/Qualifiers
misc_feature            1..151
                        note = Synthetic polynucleotide
source                  1..151
                        mol_type = other RNA
                        organism = synthetic construct
SEQUENCE: 25
agtagaaaca aggtcgtttt taaactattc gacactaatt gatggccatc cgaattcttt  60
tcgtcgctgt ctggctgtca gtaagtatgc tagagtcccg ttttcgtttc tttattcttt  120
ccatattgaa tataattgac ctgctttcgc t                                 151

SEQ ID NO: 26           moltype = RNA  length = 149
FEATURE                 Location/Qualifiers
misc_feature            1..149
                        note = Synthetic polynucleotide
source                  1..149
                        mol_type = other RNA
                        organism = synthetic construct
SEQUENCE: 26
agtagaaaca aggtcgtttt taaactattc gacactaatt gatggccatc cgaattcttt  60
tggtcgctgt ttggctgtca gtaagtatgc tagagtcccg ttttagtttt tattctttcc  120
atattgaata taattgacct gctttcgct                                    149

SEQ ID NO: 27           moltype = RNA  length = 59
FEATURE                 Location/Qualifiers
misc_feature            1..59
                        note = Synthetic polynucleotide
source                  1..59
                        mol_type = other RNA
                        organism = synthetic construct
```

```
SEQUENCE: 27
cgacactaat tgatggccat ccgaattctt ttggtcgctg tctggctgtc agtaagtat   59

SEQ ID NO: 28           moltype = DNA  length = 29
FEATURE                 Location/Qualifiers
misc_feature            1..29
                        note = Synthetic polynucleotide
source                  1..29
                        mol_type = other DNA
                        organism = synthetic construct
SEQUENCE: 28
agaattcgga tgcccatcaa ttagtgtcg                                     29

SEQ ID NO: 29           moltype = DNA  length = 29
FEATURE                 Location/Qualifiers
misc_feature            1..29
                        note = Synthetic polynucleotide
source                  1..29
                        mol_type = other DNA
                        organism = synthetic construct
SEQUENCE: 29
cgacactaat tgatgggcat ccgaattct                                     29

SEQ ID NO: 30           moltype = DNA  length = 23
FEATURE                 Location/Qualifiers
misc_feature            1..23
                        note = Synthetic polynucleotide
source                  1..23
                        mol_type = other DNA
                        organism = synthetic construct
SEQUENCE: 30
tacttactga caggcagaca gcg                                           23

SEQ ID NO: 31           moltype = DNA  length = 23
FEATURE                 Location/Qualifiers
misc_feature            1..23
                        note = Synthetic polynucleotide
source                  1..23
                        mol_type = other DNA
                        organism = synthetic construct
SEQUENCE: 31
cgctgtctgc ctgtcagtaa gta                                           23

SEQ ID NO: 32           moltype = DNA  length = 25
FEATURE                 Location/Qualifiers
misc_feature            1..25
                        note = Synthetic polynucleotide
source                  1..25
                        mol_type = other DNA
                        organism = synthetic construct
SEQUENCE: 32
ttcggatggg catcaattag tgtcg                                         25

SEQ ID NO: 33           moltype = DNA  length = 25
FEATURE                 Location/Qualifiers
misc_feature            1..25
                        note = Synthetic polynucleotide
source                  1..25
                        mol_type = other DNA
                        organism = synthetic construct
SEQUENCE: 33
cgacactaat tgatgcccat ccgaa                                         25

SEQ ID NO: 34           moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 34
atacttactg acacccagac agcg                                          24

SEQ ID NO: 35           moltype = DNA  length = 24
FEATURE                 Location/Qualifiers
misc_feature            1..24
                        note = Synthetic polynucleotide
```

```
source                  1..24
                        mol_type = other DNA
                        organism = synthetic construct
SEQUENCE: 35
cgctgtctgg gtgtcagtaa gtat                                        24

SEQ ID NO: 36           moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 36
tcggatggcc atgaattagt gtcg                                        24

SEQ ID NO: 37           moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 37
cgacactaat tcatggccat ccga                                        24

SEQ ID NO: 38           moltype = DNA  length = 26
FEATURE                 Location/Qualifiers
misc_feature            1..26
                        note = Synthetic polynucleotide
source                  1..26
                        mol_type = other DNA
                        organism = synthetic construct
SEQUENCE: 38
agcatactta ctcacagcca gacagc                                      26

SEQ ID NO: 39           moltype = DNA  length = 26
FEATURE                 Location/Qualifiers
misc_feature            1..26
                        note = Synthetic polynucleotide
source                  1..26
                        mol_type = other DNA
                        organism = synthetic construct
SEQUENCE: 39
gctgtctggc tgtgagtaag tatgct                                      26

SEQ ID NO: 40           moltype = DNA  length = 34
FEATURE                 Location/Qualifiers
misc_feature            1..34
                        note = Synthetic polynucleotide
source                  1..34
                        mol_type = other DNA
                        organism = synthetic construct
SEQUENCE: 40
ccaaaagaat taggatggcc atcaattagt gtcg                             34

SEQ ID NO: 41           moltype = DNA  length = 34
FEATURE                 Location/Qualifiers
misc_feature            1..34
                        note = Synthetic polynucleotide
source                  1..34
                        mol_type = other DNA
                        organism = synthetic construct
SEQUENCE: 41
cgacactaat tgatggccat cctaattctt ttgg                             34

SEQ ID NO: 42           moltype = DNA  length = 29
FEATURE                 Location/Qualifiers
misc_feature            1..29
                        note = Synthetic polynucleotide
source                  1..29
                        mol_type = other DNA
                        organism = synthetic construct
SEQUENCE: 42
gacagccaga cagctaccaa aagaattcg                                   29

SEQ ID NO: 43           moltype = DNA  length = 29
FEATURE                 Location/Qualifiers
```

```
misc_feature           1..29
                       note = Synthetic polynucleotide
source                 1..29
                       mol_type = other DNA
                       organism = synthetic construct
SEQUENCE: 43
cgaattcttt tggtagctgt ctggctgtc                               29

SEQ ID NO: 44          moltype = RNA  length = 71
FEATURE                Location/Qualifiers
misc_feature           1..71
                       note = Synthetic polynucleotide
source                 1..71
                       mol_type = other RNA
                       organism = synthetic construct
SEQUENCE: 44
tcgacactaa ttgatggcca tccgaattct tttggtcgct gtctggctgt cagtaagtat  60
gctagccttg c                                                  71

SEQ ID NO: 45          moltype = DNA  length = 11
FEATURE                Location/Qualifiers
misc_feature           1..11
                       note = Synthetic polynucleotide
source                 1..11
                       mol_type = other DNA
                       organism = synthetic construct
SEQUENCE: 45
accaaaagaa t                                                  11

SEQ ID NO: 46          moltype = DNA  length = 11
FEATURE                Location/Qualifiers
misc_feature           1..11
                       note = Synthetic polynucleotide
source                 1..11
                       mol_type = other DNA
                       organism = synthetic construct
SEQUENCE: 46
tggccatcaa t                                                  11

SEQ ID NO: 47          moltype = DNA  length = 11
FEATURE                Location/Qualifiers
misc_feature           1..11
                       note = Synthetic polynucleotide
source                 1..11
                       mol_type = other DNA
                       organism = synthetic construct
SEQUENCE: 47
tagcatactt a                                                  11

SEQ ID NO: 48          moltype =   length =
SEQUENCE: 48
000

SEQ ID NO: 49          moltype =   length =
SEQUENCE: 49
000

SEQ ID NO: 50          moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 50
cagacacgac caaaa                                              15

SEQ ID NO: 51          moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 51
tacttactga cagcc                                              15

SEQ ID NO: 52          moltype = DNA  length = 15
FEATURE                Location/Qualifiers
```

```
misc_feature          1..15
                      note = Synthetic polynucleotide
source                1..15
                      mol_type = other DNA
                      organism = synthetic construct
SEQUENCE: 52
agacacgacc aaaag                                                  15

SEQ ID NO: 53         moltype = DNA  length = 11
FEATURE               Location/Qualifiers
misc_feature          1..11
                      note = Synthetic polynucleotide
source                1..11
                      mol_type = other DNA
                      organism = synthetic construct
SEQUENCE: 53
accaaaagaa t                                                      11

SEQ ID NO: 54         moltype = DNA  length = 11
FEATURE               Location/Qualifiers
misc_feature          1..11
                      note = Synthetic polynucleotide
source                1..11
                      mol_type = other DNA
                      organism = synthetic construct
SEQUENCE: 54
tggccatcaa t                                                      11

SEQ ID NO: 55         moltype = DNA  length = 11
FEATURE               Location/Qualifiers
misc_feature          1..11
                      note = Synthetic polynucleotide
source                1..11
                      mol_type = other DNA
                      organism = synthetic construct
SEQUENCE: 55
tagcatactt a                                                      11

SEQ ID NO: 56         moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 56
cgaccaaaag aattc                                                  15

SEQ ID NO: 57         moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 57
cgaccaaaag aattc                                                  15

SEQ ID NO: 58         moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 58
gatggccatc aatta                                                  15

SEQ ID NO: 59         moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 59
gatggccatc aatta                                                  15

SEQ ID NO: 60         moltype = DNA  length = 15
```

```
FEATURE                Location/Qualifiers
misc_feature           1..15
                       note = Synthetic polynucleotide
source                 1..15
                       mol_type = other DNA
                       organism = synthetic construct
SEQUENCE: 60
tctagcatac ttact                                                       15

SEQ ID NO: 61          moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 61
tctagcatac ttact                                                       15

SEQ ID NO: 62          moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 62
gaattcggat ggcca                                                       15

SEQ ID NO: 63          moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 63
ggccatcaat tagtg                                                       15

SEQ ID NO: 64          moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 64
ttcggatggc catca                                                       15

SEQ ID NO: 65          moltype = DNA  length = 13
FEATURE                Location/Qualifiers
misc_feature           1..13
                       note = Synthetic polynucleotide
source                 1..13
                       mol_type = other DNA
                       organism = synthetic construct
SEQUENCE: 65
agccagacag cga                                                         13

SEQ ID NO: 66          moltype = DNA  length = 15
FEATURE                Location/Qualifiers
misc_feature           1..15
                       note = Synthetic polynucleotide
source                 1..15
                       mol_type = other DNA
                       organism = synthetic construct
SEQUENCE: 66
gacagccaga cagca                                                       15

SEQ ID NO: 67          moltype = DNA  length = 11
FEATURE                Location/Qualifiers
misc_feature           1..11
                       note = Synthetic polynucleotide
misc_feature           1
                       note = LNA
misc_feature           4
                       note = LNA
misc_feature           7..8
                       note = LNA
```

```
misc_feature            11
                        note = LNA
source                  1..11
                        mol_type = other DNA
                        organism = synthetic construct
SEQUENCE: 67
accaaaagaa t                                                                  11

SEQ ID NO: 68           moltype = DNA  length = 11
FEATURE                 Location/Qualifiers
misc_feature            1..11
                        note = Synthetic polynucleotide
misc_feature            1
                        note = LNA
misc_feature            4
                        note = LNA
misc_feature            6..7
                        note = LNA
misc_feature            11
                        note = LNA
source                  1..11
                        mol_type = other DNA
                        organism = synthetic construct
SEQUENCE: 68
tggccatcaa t                                                                  11

SEQ ID NO: 69           moltype = DNA  length = 11
FEATURE                 Location/Qualifiers
misc_feature            1..11
                        note = Synthetic polynucleotide
misc_feature            1
                        note = LNA
misc_feature            4..5
                        note = LNA
misc_feature            7
                        note = LNA
misc_feature            11
                        note = LNA
source                  1..11
                        mol_type = other DNA
                        organism = synthetic construct
SEQUENCE: 69
tagcatactt a                                                                  11

SEQ ID NO: 70           moltype =   length =
SEQUENCE: 70
000

SEQ ID NO: 71           moltype =   length =
SEQUENCE: 71
000

SEQ ID NO: 72           moltype = DNA  length = 15
FEATURE                 Location/Qualifiers
misc_feature            1..15
                        note = Synthetic polynucleotide
misc_feature            1
                        note = LNA
misc_feature            5
                        note = LNA
misc_feature            7..8
                        note = LNA
misc_feature            10..11
                        note = LNA
misc_feature            14..15
                        note = LNA
source                  1..15
                        mol_type = other DNA
                        organism = synthetic construct
SEQUENCE: 72
cagacacgac caaaa                                                              15

SEQ ID NO: 73           moltype = DNA  length = 15
FEATURE                 Location/Qualifiers
misc_feature            1..15
                        note = Synthetic polynucleotide
misc_feature            1..2
                        note = LNA
```

```
misc_feature          4
                      note = LNA
misc_feature          7..8
                      note = LNA
misc_feature          11
                      note = LNA
misc_feature          14..15
                      note = LNA
source                1..15
                      mol_type = other DNA
                      organism = synthetic construct
SEQUENCE: 73
tacttactga cagcc                                                    15

SEQ ID NO: 74         moltype = DNA  length = 15
FEATURE               Location/Qualifiers
misc_feature          1..15
                      note = Synthetic polynucleotide
misc_feature          1..4
                      note = LNA
misc_feature          12..15
                      note = LNA
source                1..15
                      mol_type = other DNA
                      organism = synthetic construct
SEQUENCE: 74
agacacgacc aaaag                                                    15

SEQ ID NO: 75         moltype = DNA  length = 15
FEATURE               Location/Qualifiers
misc_feature          1..15
                      note = Synthetic polynucleotide
misc_feature          1..4
                      note = LNA
misc_feature          13..15
                      note = LNA
source                1..15
                      mol_type = other DNA
                      organism = synthetic construct
SEQUENCE: 75
tacttactga cagcc                                                    15

SEQ ID NO: 76         moltype = DNA  length = 15
FEATURE               Location/Qualifiers
misc_feature          1..15
                      note = Synthetic polynucleotide
misc_feature          1..3
                      note = LNA
misc_feature          12..15
                      note = LNA
source                1..15
                      mol_type = other DNA
                      organism = synthetic construct
SEQUENCE: 76
tacttactga cagcc                                                    15

SEQ ID NO: 77         moltype = DNA  length = 11
FEATURE               Location/Qualifiers
misc_feature          1..11
                      note = Synthetic polynucleotide
misc_feature          1..3
                      note = LNA
misc_feature          9..11
                      note = LNA
source                1..11
                      mol_type = other DNA
                      organism = synthetic construct
SEQUENCE: 77
accaaaagaa t                                                        11

SEQ ID NO: 78         moltype = DNA  length = 11
FEATURE               Location/Qualifiers
misc_feature          1..11
                      note = Synthetic polynucleotide
misc_feature          1..3
                      note = LNA
misc_feature          9..11
                      note = LNA
```

```
source                1..11
                      mol_type = other DNA
                      organism = synthetic construct
SEQUENCE: 78
tggccatcaa t                                                  11

SEQ ID NO: 79         moltype = DNA  length = 11
FEATURE               Location/Qualifiers
misc_feature          1..11
                      note = Synthetic polynucleotide
misc_feature          1..3
                      note = LNA
misc_feature          9..11
                      note = LNA
source                1..11
                      mol_type = other DNA
                      organism = synthetic construct
SEQUENCE: 79
tagcatactt a                                                  11

SEQ ID NO: 80         moltype = DNA  length = 15
FEATURE               Location/Qualifiers
misc_feature          1..15
                      note = Synthetic polynucleotide
misc_feature          1
                      note = LNA
misc_feature          5..6
                      note = LNA
misc_feature          9..10
                      note = LNA
misc_feature          15
                      note = LNA
source                1..15
                      mol_type = other DNA
                      organism = synthetic construct
SEQUENCE: 80
cgaccaaaag aattc                                              15

SEQ ID NO: 81         moltype = DNA  length = 15
FEATURE               Location/Qualifiers
misc_feature          1..15
                      note = Synthetic polynucleotide
misc_feature          1..4
                      note = LNA
misc_feature          12..15
                      note = LNA
source                1..15
                      mol_type = other DNA
                      organism = synthetic construct
SEQUENCE: 81
cgaccaaaag aattc                                              15

SEQ ID NO: 82         moltype = DNA  length = 15
FEATURE               Location/Qualifiers
misc_feature          1..15
                      note = Synthetic polynucleotide
misc_feature          1
                      note = LNA
misc_feature          3..4
                      note = LNA
misc_feature          6
                      note = LNA
misc_feature          8..9
                      note = LNA
misc_feature          12
                      note = LNA
misc_feature          15
                      note = LNA
source                1..15
                      mol_type = other DNA
                      organism = synthetic construct
SEQUENCE: 82
gatggccatc aatta                                              15

SEQ ID NO: 83         moltype = DNA  length = 15
FEATURE               Location/Qualifiers
misc_feature          1..15
                      note = Synthetic polynucleotide
```

```
misc_feature           1..4
                       note = LNA
misc_feature           12..15
                       note = LNA
source                 1..15
                       mol_type = other DNA
                       organism = synthetic construct
SEQUENCE: 83
gatggccatc aatta                                                            15

SEQ ID NO: 84          moltype = DNA  length = 15
FEATURE                Location/Qualifiers
misc_feature           1..15
                       note = Synthetic polynucleotide
misc_feature           1
                       note = LNA
misc_feature           3..4
                       note = LNA
misc_feature           6
                       note = LNA
misc_feature           8..9
                       note = LNA
misc_feature           12
                       note = LNA
misc_feature           15
                       note = LNA
source                 1..15
                       mol_type = other DNA
                       organism = synthetic construct
SEQUENCE: 84
tctagcatac ttact                                                            15

SEQ ID NO: 85          moltype = DNA  length = 15
FEATURE                Location/Qualifiers
misc_feature           1..15
                       note = Synthetic polynucleotide
misc_feature           1..4
                       note = LNA
misc_feature           12..15
                       note = LNA
source                 1..15
                       mol_type = other DNA
                       organism = synthetic construct
SEQUENCE: 85
tctagcatac ttact                                                            15

SEQ ID NO: 86          moltype = DNA  length = 15
FEATURE                Location/Qualifiers
misc_feature           1..15
                       note = Synthetic polynucleotide
misc_feature           1..3
                       note = LNA
misc_feature           12..15
                       note = LNA
source                 1..15
                       mol_type = other DNA
                       organism = synthetic construct
SEQUENCE: 86
gaattcggat ggcca                                                            15

SEQ ID NO: 87          moltype = DNA  length = 15
FEATURE                Location/Qualifiers
misc_feature           1..15
                       note = Synthetic polynucleotide
misc_feature           1..4
                       note = LNA
misc_feature           13..15
                       note = LNA
source                 1..15
                       mol_type = other DNA
                       organism = synthetic construct
SEQUENCE: 87
ggccatcaat tagtg                                                            15

SEQ ID NO: 88          moltype = DNA  length = 15
FEATURE                Location/Qualifiers
misc_feature           1..15
                       note = Synthetic polynucleotide
```

```
misc_feature          1..4
                      note = LNA
misc_feature          13..15
                      note = LNA
source                1..15
                      mol_type = other DNA
                      organism = synthetic construct
SEQUENCE: 88
ttcggatggc catca                                                    15

SEQ ID NO: 89         moltype = DNA  length = 13
FEATURE               Location/Qualifiers
misc_feature          1..13
                      note = Synthetic polynucleotide
misc_feature          1..4
                      note = LNA
misc_feature          11..13
                      note = LNA
source                1..13
                      mol_type = other DNA
                      organism = synthetic construct
SEQUENCE: 89
agccagacag cga                                                      13

SEQ ID NO: 90         moltype = DNA  length = 15
FEATURE               Location/Qualifiers
misc_feature          1..15
                      note = Synthetic polynucleotide
misc_feature          1..4
                      note = LNA
misc_feature          13..15
                      note = LNA
source                1..15
                      mol_type = other DNA
                      organism = synthetic construct
SEQUENCE: 90
gacagccaga cagca                                                    15

SEQ ID NO: 91         moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 91
tacttactga cagtc                                                    15

SEQ ID NO: 92         moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 92
tacttaccga cagcc                                                    15

SEQ ID NO: 93         moltype = DNA  length = 16
FEATURE               Location/Qualifiers
misc_feature          1..16
                      note = Synthetic polynucleotide
source                1..16
                      mol_type = other DNA
                      organism = synthetic construct
SEQUENCE: 93
ggatttcgga tggcca                                                   16

SEQ ID NO: 94         moltype = DNA  length = 15
FEATURE               Location/Qualifiers
misc_feature          1..15
                      note = Synthetic polynucleotide
misc_feature          1..4
                      note = LNA
misc_feature          13..15
                      note = LNA
source                1..15
                      mol_type = other DNA
                      organism = synthetic construct
```

```
SEQUENCE: 94
tacttactga cagtc                                                   15

SEQ ID NO: 95          moltype = DNA  length = 15
FEATURE                Location/Qualifiers
misc_feature           1..15
                       note = Synthetic polynucleotide
misc_feature           1..4
                       note = LNA
misc_feature           13..15
                       note = LNA
source                 1..15
                       mol_type = other DNA
                       organism = synthetic construct
SEQUENCE: 95
tacttaccga cagcc                                                   15

SEQ ID NO: 96          moltype = DNA  length = 16
FEATURE                Location/Qualifiers
misc_feature           1..16
                       note = Synthetic polynucleotide
misc_feature           1..4
                       note = LNA
misc_feature           14..16
                       note = LNA
source                 1..16
                       mol_type = other DNA
                       organism = synthetic construct
SEQUENCE: 96
ggatttcgga tggcca                                                  16

SEQ ID NO: 97          moltype = DNA  length = 26
FEATURE                Location/Qualifiers
misc_feature           1..26
                       note = Synthetic polynucleotide
source                 1..26
                       mol_type = other DNA
                       organism = synthetic construct
SEQUENCE: 97
agggctcttc ggccagcraa agcagg                                       26

SEQ ID NO: 98          moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 98
cgaccaaaag aatt                                                    14

SEQ ID NO: 99          moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 99
gaccaaaaga attcgg                                                  16

SEQ ID NO: 100         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 100
agcatactta ctgaca                                                  16

SEQ ID NO: 101         moltype = DNA  length = 14
FEATURE                Location/Qualifiers
misc_feature           1..14
                       note = synthetic sequence
source                 1..14
                       mol_type = other DNA
                       organism = synthetic construct
```

```
SEQUENCE: 101
catacttact gaca                                                     14

SEQ ID NO: 102          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 102
atacttactg acag                                                     14

SEQ ID NO: 103          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 103
catacttact gacagc                                                   16

SEQ ID NO: 104          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 104
agacagcgac caaaag                                                   16

SEQ ID NO: 105          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 105
acagcgacca aaag                                                     14

SEQ ID NO: 106          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 106
cagccagaca gcgac                                                    15

SEQ ID NO: 107          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 107
cagccagaca gcga                                                     14

SEQ ID NO: 108          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 108
acagccagac agcga                                                    15

SEQ ID NO: 109          moltype = DNA  length = 15
FEATURE                 Location/Qualifiers
misc_feature            1..15
                        note = synthetic sequence
```

```
source                  1..15
                        mol_type = other DNA
                        organism = synthetic construct
SEQUENCE: 109
gacagccaga cagcg                                                    15

SEQ ID NO: 110          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 110
catcaattag tgtcg                                                    15

SEQ ID NO: 111          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 111
ccatcaatta gtgtcg                                                   16

SEQ ID NO: 112          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 112
gccatcaatt agtgtg                                                   16

SEQ ID NO: 113          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 113
aagaattcgg atggc                                                    15

SEQ ID NO: 114          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 114
cagacagcga ccaa                                                     14

SEQ ID NO: 115          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 115
tgacagccag acagc                                                    15

SEQ ID NO: 116          moltype = DNA  length = 15
FEATURE                 Location/Qualifiers
misc_feature            1..15
                        note = synthetic sequence
misc_feature            1..4
                        note = LNA
misc_feature            12..15
                        note = LNA
source                  1..15
                        mol_type = other DNA
                        organism = synthetic construct
SEQUENCE: 116
cagccagaca gcgac                                                    15
```

```
SEQ ID NO: 117          moltype = DNA  length = 15
FEATURE                 Location/Qualifiers
misc_feature            1..15
                        note = synthetic sequence
misc_feature            1..3
                        note = LNA
misc_feature            12..15
                        note = LNA
source                  1..15
                        mol_type = other DNA
                        organism = synthetic construct
SEQUENCE: 117
cagccagaca gcgac                                                   15

SEQ ID NO: 118          moltype = DNA  length = 14
FEATURE                 Location/Qualifiers
misc_feature            1..14
                        note = synthetic sequence
misc_feature            1..3
                        note = LNA
misc_feature            11..14
                        note = LNA
source                  1..14
                        mol_type = other DNA
                        organism = synthetic construct
SEQUENCE: 118
cagccagaca gcga                                                    14

SEQ ID NO: 119          moltype = DNA  length = 14
FEATURE                 Location/Qualifiers
misc_feature            1..14
                        note = synthetic sequence
misc_feature            1..3
                        note = LNA
misc_feature            12..14
                        note = LNA
source                  1..14
                        mol_type = other DNA
                        organism = synthetic construct
SEQUENCE: 119
cagccagaca gcga                                                    14

SEQ ID NO: 120          moltype = DNA  length = 14
FEATURE                 Location/Qualifiers
misc_feature            1..14
                        note = synthetic sequence
misc_feature            1..4
                        note = LNA
misc_feature            12..14
                        note = LNA
source                  1..14
                        mol_type = other DNA
                        organism = synthetic construct
SEQUENCE: 120
cagccagaca gcga                                                    14

SEQ ID NO: 121          moltype = DNA  length = 15
FEATURE                 Location/Qualifiers
misc_feature            1..15
                        note = synthetic sequence
misc_feature            1..3
                        note = LNA
misc_feature            13..15
                        note = LNA
source                  1..15
                        mol_type = other DNA
                        organism = synthetic construct
SEQUENCE: 121
acagccagac agcga                                                   15

SEQ ID NO: 122          moltype = DNA  length = 15
FEATURE                 Location/Qualifiers
misc_feature            1..15
                        note = synthetic sequence
misc_feature            1..4
                        note = LNA
misc_feature            12..15
                        note = LNA
```

```
source                  1..15
                        mol_type = other DNA
                        organism = synthetic construct
SEQUENCE: 122
acagccagac agcga                                                          15

SEQ ID NO: 123          moltype = DNA  length = 15
FEATURE                 Location/Qualifiers
misc_feature            1..15
                        note = synthetic sequence
misc_feature            1..3
                        note = LNA
misc_feature            12..15
                        note = LNA
source                  1..15
                        mol_type = other DNA
                        organism = synthetic construct
SEQUENCE: 123
acagccagac agcga                                                          15

SEQ ID NO: 124          moltype = DNA  length = 15
FEATURE                 Location/Qualifiers
misc_feature            1..15
                        note = synthetic sequence
misc_feature            1..4
                        note = LNA
misc_feature            13..15
                        note = LNA
source                  1..15
                        mol_type = other DNA
                        organism = synthetic construct
SEQUENCE: 124
gacagccaga cagcg                                                          15

SEQ ID NO: 125          moltype = DNA  length = 15
FEATURE                 Location/Qualifiers
misc_feature            1..15
                        note = synthetic sequence
misc_feature            1..3
                        note = LNA
misc_feature            13..15
                        note = LNA
source                  1..15
                        mol_type = other DNA
                        organism = synthetic construct
SEQUENCE: 125
gacagccaga cagcg                                                          15

SEQ ID NO: 126          moltype = DNA  length = 15
FEATURE                 Location/Qualifiers
misc_feature            1..15
                        note = synthetic sequence
misc_feature            1..4
                        note = LNA
misc_feature            12..15
                        note = LNA
source                  1..15
                        mol_type = other DNA
                        organism = synthetic construct
SEQUENCE: 126
gacagccaga cagcg                                                          15

SEQ ID NO: 127          moltype = DNA  length = 15
FEATURE                 Location/Qualifiers
misc_feature            1..15
                        note = synthetic sequence
misc_feature            1..3
                        note = LNA
misc_feature            13..15
                        note = LNA
source                  1..15
                        mol_type = other DNA
                        organism = synthetic construct
SEQUENCE: 127
catcaattag tgtcg                                                          15

SEQ ID NO: 128          moltype = DNA  length = 16
FEATURE                 Location/Qualifiers
```

```
misc_feature         1..16
                     note = synthetic sequence
misc_feature         1..3
                     note = LNA
misc_feature         14..16
                     note = LNA
source               1..16
                     mol_type = other DNA
                     organism = synthetic construct
SEQUENCE: 128
ccatcaatta gtgtcg                                                  16

SEQ ID NO: 129       moltype = DNA  length = 16
FEATURE              Location/Qualifiers
misc_feature         1..16
                     note = synthetic sequence
misc_feature         1..3
                     note = LNA
misc_feature         14..16
                     note = LNA
source               1..16
                     mol_type = other DNA
                     organism = synthetic construct
SEQUENCE: 129
gccatcaatt agtgtg                                                  16

SEQ ID NO: 130       moltype = DNA  length = 15
FEATURE              Location/Qualifiers
misc_feature         1..15
                     note = synthetic sequence
misc_feature         1..4
                     note = LNA
misc_feature         12..15
                     note = LNA
source               1..15
                     mol_type = other DNA
                     organism = synthetic construct
SEQUENCE: 130
aagaattcgg atggc                                                   15

SEQ ID NO: 131       moltype = DNA  length = 14
FEATURE              Location/Qualifiers
misc_feature         1..14
                     note = synthetic sequence
misc_feature         1..3
                     note = LNA
misc_feature         12..14
                     note = LNA
source               1..14
                     mol_type = other DNA
                     organism = synthetic construct
SEQUENCE: 131
cagacagcga ccaa                                                    14

SEQ ID NO: 132       moltype = DNA  length = 15
FEATURE              Location/Qualifiers
misc_feature         1..15
                     note = synthetic sequence
misc_feature         1..3
                     note = LNA
misc_feature         13..15
                     note = LNA
source               1..15
                     mol_type = other DNA
                     organism = synthetic construct
SEQUENCE: 132
tgacagccag acagc                                                   15

SEQ ID NO: 133       moltype = DNA  length = 15
FEATURE              Location/Qualifiers
misc_feature         1..15
                     note = synthetic sequence
misc_feature         1..4
                     note = LNA
misc_feature         13..15
                     note = LNA
source               1..15
                     mol_type = other DNA
                     organism = synthetic construct
```

```
SEQUENCE: 133
gcgaccaaaa gaatt                                                        15

SEQ ID NO: 134          moltype = DNA  length = 15
FEATURE                 Location/Qualifiers
misc_feature            1..15
                        note = synthetic sequence
misc_feature            1..4
                        note = LNA
misc_feature            12..15
                        note = LNA
source                  1..15
                        mol_type = other DNA
                        organism = synthetic construct
SEQUENCE: 134
gcgaccaaaa gaatt                                                        15

SEQ ID NO: 135          moltype = DNA  length = 14
FEATURE                 Location/Qualifiers
misc_feature            1..14
                        note = synthetic sequence
misc_feature            1..4
                        note = LNA
misc_feature            12..14
                        note = LNA
source                  1..14
                        mol_type = other DNA
                        organism = synthetic construct
SEQUENCE: 135
cgaccaaaag aatt                                                         14

SEQ ID NO: 136          moltype = DNA  length = 15
FEATURE                 Location/Qualifiers
misc_feature            1..15
                        note = synthetic sequence
misc_feature            1..3
                        note = LNA
misc_feature            12..15
                        note = LNA
source                  1..15
                        mol_type = other DNA
                        organism = synthetic construct
SEQUENCE: 136
cgaccaaaag aattc                                                        15

SEQ ID NO: 137          moltype = DNA  length = 15
FEATURE                 Location/Qualifiers
misc_feature            1..15
                        note = synthetic sequence
misc_feature            1..4
                        note = LNA
misc_feature            13..15
                        note = LNA
source                  1..15
                        mol_type = other DNA
                        organism = synthetic construct
SEQUENCE: 137
cgaccaaaag aattc                                                        15

SEQ ID NO: 138          moltype = DNA  length = 15
FEATURE                 Location/Qualifiers
misc_feature            1..15
                        note = synthetic sequence
misc_feature            1..3
                        note = LNA
misc_feature            13..15
                        note = LNA
source                  1..15
                        mol_type = other DNA
                        organism = synthetic construct
SEQUENCE: 138
cgaccaaaag aattc                                                        15

SEQ ID NO: 139          moltype = DNA  length = 14
FEATURE                 Location/Qualifiers
misc_feature            1..14
                        note = synthetic sequence
misc_feature            1..3
                        note = LNA
```

```
misc_feature          12..14
                      note = LNA
source                1..14
                      mol_type = other DNA
                      organism = synthetic construct
SEQUENCE: 139
gaccaaaaga attc                                                   14

SEQ ID NO: 140        moltype = DNA  length = 16
FEATURE               Location/Qualifiers
misc_feature          1..16
                      note = synthetic sequence
misc_feature          1..4
                      note = LNA
misc_feature          13..16
                      note = LNA
source                1..16
                      mol_type = other DNA
                      organism = synthetic construct
SEQUENCE: 140
gcgaccaaaa gaattc                                                 16

SEQ ID NO: 141        moltype = DNA  length = 16
FEATURE               Location/Qualifiers
misc_feature          1..16
                      note = synthetic sequence
misc_feature          1..3
                      note = LNA
misc_feature          13..16
                      note = LNA
source                1..16
                      mol_type = other DNA
                      organism = synthetic construct
SEQUENCE: 141
gcgaccaaaa gaattc                                                 16

SEQ ID NO: 142        moltype = DNA  length = 16
FEATURE               Location/Qualifiers
misc_feature          1..16
                      note = synthetic sequence
misc_feature          1..3
                      note = LNA
misc_feature          14..16
                      note = LNA
source                1..16
                      mol_type = other DNA
                      organism = synthetic construct
SEQUENCE: 142
gcgaccaaaa gaattc                                                 16

SEQ ID NO: 143        moltype = DNA  length = 16
FEATURE               Location/Qualifiers
misc_feature          1..16
                      note = synthetic sequence
misc_feature          1..3
                      note = LNA
misc_feature          13..16
                      note = LNA
source                1..16
                      mol_type = other DNA
                      organism = synthetic construct
SEQUENCE: 143
cgaccaaaag aattcg                                                 16

SEQ ID NO: 144        moltype = DNA  length = 16
FEATURE               Location/Qualifiers
misc_feature          1..16
                      note = synthetic sequence
misc_feature          1..4
                      note = LNA
misc_feature          13..16
                      note = LNA
source                1..16
                      mol_type = other DNA
                      organism = synthetic construct
SEQUENCE: 144
cgaccaaaag aattcg                                                 16

SEQ ID NO: 145        moltype = DNA  length = 14
```

```
FEATURE                 Location/Qualifiers
misc_feature            1..14
                        note = synthetic sequence
misc_feature            1..3
                        note = LNA
misc_feature            12..14
                        note = LNA
source                  1..14
                        mol_type = other DNA
                        organism = synthetic construct
SEQUENCE: 145
gaccaaaaga attc                                                   14

SEQ ID NO: 146          moltype = DNA  length = 13
FEATURE                 Location/Qualifiers
misc_feature            1..13
                        note = synthetic sequence
misc_feature            1..4
                        note = LNA
misc_feature            11..13
                        note = LNA
source                  1..13
                        mol_type = other DNA
                        organism = synthetic construct
SEQUENCE: 146
accaaaagaa ttc                                                    13

SEQ ID NO: 147          moltype = DNA  length = 17
FEATURE                 Location/Qualifiers
misc_feature            1..17
                        note = synthetic sequence
misc_feature            1..3
                        note = LNA
misc_feature            14..17
                        note = LNA
source                  1..17
                        mol_type = other DNA
                        organism = synthetic construct
SEQUENCE: 147
cgaccaaaag aattcgg                                                17

SEQ ID NO: 148          moltype = DNA  length = 16
FEATURE                 Location/Qualifiers
misc_feature            1..16
                        note = synthetic sequence
misc_feature            1..3
                        note = LNA
misc_feature            13..16
                        note = LNA
source                  1..16
                        mol_type = other DNA
                        organism = synthetic construct
SEQUENCE: 148
gaccaaaaga attcgg                                                 16

SEQ ID NO: 149          moltype = DNA  length = 16
FEATURE                 Location/Qualifiers
misc_feature            1..16
                        note = synthetic sequence
misc_feature            1..4
                        note = LNA
misc_feature            14..16
                        note = LNA
source                  1..16
                        mol_type = other DNA
                        organism = synthetic construct
SEQUENCE: 149
gaccaaaaga attcgg                                                 16

SEQ ID NO: 150          moltype = DNA  length = 16
FEATURE                 Location/Qualifiers
misc_feature            1..16
                        note = synthetic sequence
misc_feature            1..3
                        note = LNA
misc_feature            14..16
                        note = LNA
```

```
source                  1..16
                        mol_type = other DNA
                        organism = synthetic construct
SEQUENCE: 150
gaccaaaaga attcgg                                                    16

SEQ ID NO: 151          moltype = DNA  length = 16
FEATURE                 Location/Qualifiers
misc_feature            1..16
                        note = synthetic sequence
misc_feature            1..4
                        note = LNA
misc_feature            13..16
                        note = LNA
source                  1..16
                        mol_type = other DNA
                        organism = synthetic construct
SEQUENCE: 151
accaaaagaa ttcgga                                                    16

SEQ ID NO: 152          moltype = DNA  length = 15
FEATURE                 Location/Qualifiers
misc_feature            1..15
                        note = synthetic sequence
misc_feature            1..4
                        note = LNA
misc_feature            12..15
                        note = LNA
source                  1..15
                        mol_type = other DNA
                        organism = synthetic construct
SEQUENCE: 152
ccaaaagaat tcgga                                                     15

SEQ ID NO: 153          moltype = DNA  length = 14
FEATURE                 Location/Qualifiers
misc_feature            1..14
                        note = synthetic sequence
misc_feature            1..4
                        note = LNA
misc_feature            12..14
                        note = LNA
source                  1..14
                        mol_type = other DNA
                        organism = synthetic construct
SEQUENCE: 153
caaaagaatt cgga                                                      14

SEQ ID NO: 154          moltype = DNA  length = 14
FEATURE                 Location/Qualifiers
misc_feature            1..14
                        note = synthetic sequence
misc_feature            1..3
                        note = LNA
misc_feature            12..14
                        note = LNA
source                  1..14
                        mol_type = other DNA
                        organism = synthetic construct
SEQUENCE: 154
caaaagaatt cgga                                                      14

SEQ ID NO: 155          moltype = DNA  length = 16
FEATURE                 Location/Qualifiers
misc_feature            1..16
                        note = synthetic sequence
misc_feature            1..3
                        note = LNA
misc_feature            14..16
                        note = LNA
source                  1..16
                        mol_type = other DNA
                        organism = synthetic construct
SEQUENCE: 155
ccaaaagaat tcggat                                                    16

SEQ ID NO: 156          moltype = DNA  length = 16
FEATURE                 Location/Qualifiers
```

```
misc_feature          1..16
                      note = synthetic sequence
misc_feature          1..4
                      note = LNA
misc_feature          14..16
                      note = LNA
source                1..16
                      mol_type = other DNA
                      organism = synthetic construct
SEQUENCE: 156
ccaaaagaat tcggat                                                   16

SEQ ID NO: 157        moltype = DNA  length = 15
FEATURE               Location/Qualifiers
misc_feature          1..15
                      note = synthetic sequence
misc_feature          1..4
                      note = LNA
misc_feature          12..15
                      note = LNA
source                1..15
                      mol_type = other DNA
                      organism = synthetic construct
SEQUENCE: 157
caaaagaatt cggat                                                    15

SEQ ID NO: 158        moltype = DNA  length = 15
FEATURE               Location/Qualifiers
misc_feature          1..15
                      note = synthetic sequence
misc_feature          1..3
                      note = LNA
misc_feature          12..15
                      note = LNA
source                1..15
                      mol_type = other DNA
                      organism = synthetic construct
SEQUENCE: 158
caaaagaatt cggat                                                    15

SEQ ID NO: 159        moltype = DNA  length = 16
FEATURE               Location/Qualifiers
misc_feature          1..16
                      note = synthetic sequence
misc_feature          1..4
                      note = LNA
misc_feature          13..16
                      note = LNA
source                1..16
                      mol_type = other DNA
                      organism = synthetic construct
SEQUENCE: 159
agcatactta ctgaca                                                   16

SEQ ID NO: 160        moltype = DNA  length = 14
FEATURE               Location/Qualifiers
misc_feature          1..14
                      note = synthetic sequence
misc_feature          1..3
                      note = LNA
misc_feature          12..14
                      note = LNA
source                1..14
                      mol_type = other DNA
                      organism = synthetic construct
SEQUENCE: 160
catacttact gaca                                                     14

SEQ ID NO: 161        moltype = DNA  length = 15
FEATURE               Location/Qualifiers
misc_feature          1..15
                      note = synthetic sequence
misc_feature          1..4
                      note = LNA
misc_feature          12..15
                      note = LNA
source                1..15
                      mol_type = other DNA
                      organism = synthetic construct
```

```
SEQUENCE: 161
catacttact gacag                                                   15

SEQ ID NO: 162          moltype = DNA  length = 14
FEATURE                 Location/Qualifiers
misc_feature            1..14
                        note = synthetic sequence
misc_feature            1..3
                        note = LNA
misc_feature            12..14
                        note = LNA
source                  1..14
                        mol_type = other DNA
                        organism = synthetic construct
SEQUENCE: 162
atacttactg acag                                                    14

SEQ ID NO: 163          moltype = DNA  length = 14
FEATURE                 Location/Qualifiers
misc_feature            1..14
                        note = synthetic sequence
misc_feature            1..4
                        note = LNA
misc_feature            11..14
                        note = LNA
source                  1..14
                        mol_type = other DNA
                        organism = synthetic construct
SEQUENCE: 163
atacttactg acag                                                    14

SEQ ID NO: 164          moltype = DNA  length = 14
FEATURE                 Location/Qualifiers
misc_feature            1..14
                        note = synthetic sequence
misc_feature            1..3
                        note = LNA
misc_feature            11..14
                        note = LNA
source                  1..14
                        mol_type = other DNA
                        organism = synthetic construct
SEQUENCE: 164
atacttactg acag                                                    14

SEQ ID NO: 165          moltype = DNA  length = 16
FEATURE                 Location/Qualifiers
misc_feature            1..16
                        note = synthetic sequence
misc_feature            1..4
                        note = LNA
misc_feature            13..16
                        note = LNA
source                  1..16
                        mol_type = other DNA
                        organism = synthetic construct
SEQUENCE: 165
catacttact gacagc                                                  16

SEQ ID NO: 166          moltype = DNA  length = 16
FEATURE                 Location/Qualifiers
misc_feature            1..16
                        note = synthetic sequence
misc_feature            1..3
                        note = LNA
misc_feature            13..16
                        note = LNA
source                  1..16
                        mol_type = other DNA
                        organism = synthetic construct
SEQUENCE: 166
catacttact gacagc                                                  16

SEQ ID NO: 167          moltype = DNA  length = 16
FEATURE                 Location/Qualifiers
misc_feature            1..16
                        note = synthetic sequence
misc_feature            1..4
                        note = LNA
```

```
misc_feature          14..16
                      note = LNA
source                1..16
                      mol_type = other DNA
                      organism = synthetic construct
SEQUENCE: 167
catacttact gacagc                                                   16

SEQ ID NO: 168        moltype = DNA  length = 15
FEATURE               Location/Qualifiers
misc_feature          1..15
                      note = synthetic sequence
misc_feature          1..3
                      note = LNA
misc_feature          13..15
                      note = LNA
source                1..15
                      mol_type = other DNA
                      organism = synthetic construct
SEQUENCE: 168
atacttactg acagc                                                    15

SEQ ID NO: 169        moltype = DNA  length = 15
FEATURE               Location/Qualifiers
misc_feature          1..15
                      note = synthetic sequence
misc_feature          1..4
                      note = LNA
misc_feature          12..15
                      note = LNA
source                1..15
                      mol_type = other DNA
                      organism = synthetic construct
SEQUENCE: 169
atacttactg acagc                                                    15

SEQ ID NO: 170        moltype = DNA  length = 15
FEATURE               Location/Qualifiers
misc_feature          1..15
                      note = synthetic sequence
misc_feature          1..4
                      note = LNA
misc_feature          13..15
                      note = LNA
source                1..15
                      mol_type = other DNA
                      organism = synthetic construct
SEQUENCE: 170
atacttactg acagc                                                    15

SEQ ID NO: 171        moltype = DNA  length = 15
FEATURE               Location/Qualifiers
misc_feature          1..15
                      note = synthetic sequence
misc_feature          1..3
                      note = LNA
misc_feature          12..15
                      note = LNA
source                1..15
                      mol_type = other DNA
                      organism = synthetic construct
SEQUENCE: 171
atacttactg acagc                                                    15

SEQ ID NO: 172        moltype = DNA  length = 14
FEATURE               Location/Qualifiers
misc_feature          1..14
                      note = synthetic sequence
misc_feature          1..3
                      note = LNA
misc_feature          12..14
                      note = LNA
source                1..14
                      mol_type = other DNA
                      organism = synthetic construct
SEQUENCE: 172
tacttactga cagc                                                     14

SEQ ID NO: 173        moltype = DNA  length = 14
```

```
FEATURE                  Location/Qualifiers
misc_feature             1..14
                         note = synthetic sequence
misc_feature             1..3
                         note = LNA
misc_feature             11..14
                         note = LNA
source                   1..14
                         mol_type = other DNA
                         organism = synthetic construct
SEQUENCE: 173
tacttactga cagc                                                  14

SEQ ID NO: 174           moltype = DNA  length = 14
FEATURE                  Location/Qualifiers
misc_feature             1..14
                         note = synthetic sequence
misc_feature             1..4
                         note = LNA
misc_feature             11..14
                         note = LNA
source                   1..14
                         mol_type = other DNA
                         organism = synthetic construct
SEQUENCE: 174
tacttactga cagc                                                  14

SEQ ID NO: 175           moltype = DNA  length = 16
FEATURE                  Location/Qualifiers
misc_feature             1..16
                         note = synthetic sequence
misc_feature             1..3
                         note = LNA
misc_feature             14..16
                         note = LNA
source                   1..16
                         mol_type = other DNA
                         organism = synthetic construct
SEQUENCE: 175
atacttactg acagcc                                                16

SEQ ID NO: 176           moltype = DNA  length = 16
FEATURE                  Location/Qualifiers
misc_feature             1..16
                         note = synthetic sequence
misc_feature             1..3
                         note = LNA
misc_feature             13..16
                         note = LNA
source                   1..16
                         mol_type = other DNA
                         organism = synthetic construct
SEQUENCE: 176
atacttactg acagcc                                                16

SEQ ID NO: 177           moltype = DNA  length = 15
FEATURE                  Location/Qualifiers
misc_feature             1..15
                         note = synthetic sequence
misc_feature             1..4
                         note = LNA
misc_feature             12..15
                         note = LNA
source                   1..15
                         mol_type = other DNA
                         organism = synthetic construct
SEQUENCE: 177
tacttactga cagcc                                                 15

SEQ ID NO: 178           moltype = DNA  length = 15
FEATURE                  Location/Qualifiers
misc_feature             1..15
                         note = synthetic sequence
misc_feature             1..3
                         note = LNA
misc_feature             13..15
                         note = LNA
```

```
source                  1..15
                        mol_type = other DNA
                        organism = synthetic construct
SEQUENCE: 178
tacttactga cagcc                                                              15

SEQ ID NO: 179          moltype = DNA  length = 16
FEATURE                 Location/Qualifiers
misc_feature            1..16
                        note = synthetic sequence
misc_feature            1..4
                        note = LNA
misc_feature            13..16
                        note = LNA
source                  1..16
                        mol_type = other DNA
                        organism = synthetic construct
SEQUENCE: 179
tacttactga cagcca                                                             16

SEQ ID NO: 180          moltype = DNA  length = 16
FEATURE                 Location/Qualifiers
misc_feature            1..16
                        note = synthetic sequence
misc_feature            1..3
                        note = LNA
misc_feature            13..16
                        note = LNA
source                  1..16
                        mol_type = other DNA
                        organism = synthetic construct
SEQUENCE: 180
tacttactga cagcca                                                             16

SEQ ID NO: 181          moltype = DNA  length = 16
FEATURE                 Location/Qualifiers
misc_feature            1..16
                        note = synthetic sequence
misc_feature            1..4
                        note = LNA
misc_feature            14..16
                        note = LNA
source                  1..16
                        mol_type = other DNA
                        organism = synthetic construct
SEQUENCE: 181
tacttactga cagcca                                                             16

SEQ ID NO: 182          moltype = DNA  length = 16
FEATURE                 Location/Qualifiers
misc_feature            1..16
                        note = synthetic sequence
misc_feature            1..3
                        note = LNA
misc_feature            14..16
                        note = LNA
source                  1..16
                        mol_type = other DNA
                        organism = synthetic construct
SEQUENCE: 182
tacttactga cagcca                                                             16

SEQ ID NO: 183          moltype = DNA  length = 15
FEATURE                 Location/Qualifiers
misc_feature            1..15
                        note = synthetic sequence
misc_feature            1..3
                        note = LNA
misc_feature            12..15
                        note = LNA
source                  1..15
                        mol_type = other DNA
                        organism = synthetic construct
SEQUENCE: 183
acttactgac agcca                                                              15

SEQ ID NO: 184          moltype = DNA  length = 15
FEATURE                 Location/Qualifiers
```

```
misc_feature            1..15
                        note = synthetic sequence
misc_feature            1..3
                        note = LNA
misc_feature            13..15
                        note = LNA
source                  1..15
                        mol_type = other DNA
                        organism = synthetic construct
SEQUENCE: 184
acttactgac agcca                                                   15

SEQ ID NO: 185          moltype = DNA  length = 15
FEATURE                 Location/Qualifiers
misc_feature            1..15
                        note = synthetic sequence
misc_feature            1..4
                        note = LNA
misc_feature            12..15
                        note = LNA
source                  1..15
                        mol_type = other DNA
                        organism = synthetic construct
SEQUENCE: 185
acttactgac agcca                                                   15

SEQ ID NO: 186          moltype = DNA  length = 15
FEATURE                 Location/Qualifiers
misc_feature            1..15
                        note = synthetic sequence
misc_feature            1..4
                        note = LNA
misc_feature            12..15
                        note = LNA
source                  1..15
                        mol_type = other DNA
                        organism = synthetic construct
SEQUENCE: 186
cttactgaca gccag                                                   15

SEQ ID NO: 187          moltype = DNA  length = 15
FEATURE                 Location/Qualifiers
misc_feature            1..15
                        note = synthetic sequence
misc_feature            1..3
                        note = LNA
misc_feature            13..15
                        note = LNA
source                  1..15
                        mol_type = other DNA
                        organism = synthetic construct
SEQUENCE: 187
ttactgacag ccaga                                                   15

SEQ ID NO: 188          moltype = DNA  length = 16
FEATURE                 Location/Qualifiers
misc_feature            1..16
                        note = synthetic sequence
misc_feature            1..3
                        note = LNA
misc_feature            14..16
                        note = LNA
source                  1..16
                        mol_type = other DNA
                        organism = synthetic construct
SEQUENCE: 188
agacagcgac caaaag                                                  16

SEQ ID NO: 189          moltype = DNA  length = 16
FEATURE                 Location/Qualifiers
misc_feature            1..16
                        note = synthetic sequence
misc_feature            1..4
                        note = LNA
misc_feature            13..16
                        note = LNA
source                  1..16
                        mol_type = other DNA
                        organism = synthetic construct
```

```
SEQUENCE: 189
agacagcgac caaaag                                                    16

SEQ ID NO: 190          moltype = DNA  length = 14
FEATURE                 Location/Qualifiers
misc_feature            1..14
                        note = synthetic sequence
misc_feature            1..4
                        note = LNA
misc_feature            11..14
                        note = LNA
source                  1..14
                        mol_type = other DNA
                        organism = synthetic construct
SEQUENCE: 190
acagcgacca aaag                                                      14

SEQ ID NO: 191          moltype = DNA  length = 14
FEATURE                 Location/Qualifiers
misc_feature            1..14
                        note = synthetic sequence
misc_feature            1..3
                        note = LNA
misc_feature            12..14
                        note = LNA
source                  1..14
                        mol_type = other DNA
                        organism = synthetic construct
SEQUENCE: 191
acagcgacca aaag                                                      14

SEQ ID NO: 192          moltype = DNA  length = 28
FEATURE                 Location/Qualifiers
source                  1..28
                        mol_type = other DNA
                        organism = SARS-CoV-2
SEQUENCE: 192
ggtgacatgg taccacatat atcacgtc                                       28

SEQ ID NO: 193          moltype = DNA  length = 28
FEATURE                 Location/Qualifiers
source                  1..28
                        mol_type = other DNA
                        organism = SARS-CoV-2
SEQUENCE: 193
gacgtgatat atgtggtacc atgtcacc                                       28

SEQ ID NO: 194          moltype = DNA  length = 16
FEATURE                 Location/Qualifiers
source                  1..16
                        mol_type = other DNA
                        organism = SARS-CoV-2
SEQUENCE: 194
gacgtgatat atgtgg                                                    16

SEQ ID NO: 195          moltype = DNA  length = 16
FEATURE                 Location/Qualifiers
source                  1..16
                        mol_type = other DNA
                        organism = SARS-CoV-2
SEQUENCE: 195
cgtgatatat gtggta                                                    16

SEQ ID NO: 196          moltype = DNA  length = 15
FEATURE                 Location/Qualifiers
source                  1..15
                        mol_type = other DNA
                        organism = SARS-CoV-2
SEQUENCE: 196
gatatgtggt accat                                                     15

SEQ ID NO: 197          moltype = DNA  length = 14
FEATURE                 Location/Qualifiers
source                  1..14
                        mol_type = other DNA
                        organism = SARS-CoV-2
SEQUENCE: 197
tggtaccatg tcac                                                      14
```

```
SEQ ID NO: 198          moltype = DNA  length = 25
FEATURE                 Location/Qualifiers
source                  1..25
                        mol_type = other DNA
                        organism = SARS-CoV-2
SEQUENCE: 198
gtcactaaga aatctgctgc tgagg                                          25

SEQ ID NO: 199          moltype = DNA  length = 25
FEATURE                 Location/Qualifiers
source                  1..25
                        mol_type = other DNA
                        organism = SARS-CoV-2
SEQUENCE: 199
cctcagcagc agatttctta gtgac                                          25

SEQ ID NO: 200          moltype = DNA  length = 16
FEATURE                 Location/Qualifiers
source                  1..16
                        mol_type = other DNA
                        organism = SARS-CoV-2
SEQUENCE: 200
cctcagcagc agattt                                                    16

SEQ ID NO: 201          moltype = DNA  length = 15
FEATURE                 Location/Qualifiers
source                  1..15
                        mol_type = other DNA
                        organism = SARS-CoV-2
SEQUENCE: 201
tcagcagcag atttc                                                     15

SEQ ID NO: 202          moltype = DNA  length = 14
FEATURE                 Location/Qualifiers
source                  1..14
                        mol_type = other DNA
                        organism = SARS-CoV-2
SEQUENCE: 202
cagcagcaga tttc                                                      14

SEQ ID NO: 203          moltype = DNA  length = 16
FEATURE                 Location/Qualifiers
source                  1..16
                        mol_type = other DNA
                        organism = SARS-CoV-2
SEQUENCE: 203
cagatttctt agtgac                                                    16

SEQ ID NO: 204          moltype = DNA  length = 25
FEATURE                 Location/Qualifiers
source                  1..25
                        mol_type = other DNA
                        organism = SARS-CoV-2
SEQUENCE: 204
tgcttacggt ttcgtccgtg ttgca                                          25

SEQ ID NO: 205          moltype = DNA  length = 25
FEATURE                 Location/Qualifiers
source                  1..25
                        mol_type = other DNA
                        organism = SARS-CoV-2
SEQUENCE: 205
tgcaacacgg acgaaaccgt aagca                                          25

SEQ ID NO: 206          moltype = DNA  length = 16
FEATURE                 Location/Qualifiers
source                  1..16
                        mol_type = other DNA
                        organism = SARS-CoV-2
SEQUENCE: 206
tgcaacacgg acgaaa                                                    16

SEQ ID NO: 207          moltype = DNA  length = 16
FEATURE                 Location/Qualifiers
source                  1..16
                        mol_type = other DNA
                        organism = SARS-CoV-2
SEQUENCE: 207
gcaacacgga cgaaac                                                    16
```

SEQ ID NO: 208 moltype = DNA length = 15
FEATURE Location/Qualifiers
source 1..15
mol_type = other DNA
organism = SARS-CoV-2
SEQUENCE: 208
acacggacga aaccg 15

SEQ ID NO: 209 moltype = DNA length = 15
FEATURE Location/Qualifiers
source 1..15
mol_type = other DNA
organism = SARS-CoV-2
SEQUENCE: 209
ggacgaaacc cgtaa 15

SEQ ID NO: 210 moltype = DNA length = 15
FEATURE Location/Qualifiers
source 1..15
mol_type = other DNA
organism = SARS-CoV-2
SEQUENCE: 210
acgaaaccgt aagca 15

SEQ ID NO: 211 moltype = DNA length = 15
FEATURE Location/Qualifiers
source 1..15
mol_type = other DNA
organism = SARS-CoV-2
SEQUENCE: 211
acgaaaccgt aagca 15

SEQ ID NO: 212 moltype = DNA length = 16
FEATURE Location/Qualifiers
source 1..16
mol_type = other DNA
organism = SARS-CoV-2
SEQUENCE: 212
gcaacacgga cgaaac 16

SEQ ID NO: 213 moltype = DNA length = 15
FEATURE Location/Qualifiers
source 1..15
mol_type = other DNA
organism = SARS-CoV-2
SEQUENCE: 213
gcaacacgga cgaaa 15

SEQ ID NO: 214 moltype = DNA length = 16
FEATURE Location/Qualifiers
source 1..16
mol_type = other DNA
organism = SARS-CoV-2
SEQUENCE: 214
gcaacacgga cgaaac 16

SEQ ID NO: 215 moltype = DNA length = 16
FEATURE Location/Qualifiers
source 1..16
mol_type = other DNA
organism = SARS-CoV-2
SEQUENCE: 215
gcaacacgga cgaaac 16

SEQ ID NO: 216 moltype = DNA length = 16
FEATURE Location/Qualifiers
source 1..16
mol_type = other DNA
organism = SARS-CoV-2
SEQUENCE: 216
gcaacacgga cgaaac 16

SEQ ID NO: 217 moltype = DNA length = 14
FEATURE Location/Qualifiers
source 1..14
mol_type = other DNA
organism = SARS-CoV-2

```
SEQUENCE: 217
gcaacacgga cgaa                                                   14

SEQ ID NO: 218          moltype = DNA  length = 15
FEATURE                 Location/Qualifiers
source                  1..15
                        mol_type = other DNA
                        organism = SARS-CoV-2
SEQUENCE: 218
acacggacga aaccg                                                  15

SEQ ID NO: 219          moltype = DNA  length = 15
FEATURE                 Location/Qualifiers
source                  1..15
                        mol_type = other DNA
                        organism = SARS-CoV-2
SEQUENCE: 219
acacggacga aaccg                                                  15

SEQ ID NO: 220          moltype = DNA  length = 16
FEATURE                 Location/Qualifiers
source                  1..16
                        mol_type = other DNA
                        organism = SARS-CoV-2
SEQUENCE: 220
aacacggacg aaaccg                                                 16

SEQ ID NO: 221          moltype = DNA  length = 16
FEATURE                 Location/Qualifiers
source                  1..16
                        mol_type = other DNA
                        organism = SARS-CoV-2
SEQUENCE: 221
aacacggacg aaaccg                                                 16

SEQ ID NO: 222          moltype = DNA  length = 15
FEATURE                 Location/Qualifiers
source                  1..15
                        mol_type = other DNA
                        organism = SARS-CoV-2
SEQUENCE: 222
acgaaaccgt aagca                                                  15

SEQ ID NO: 223          moltype = DNA  length = 15
FEATURE                 Location/Qualifiers
source                  1..15
                        mol_type = other DNA
                        organism = SARS-CoV-2
SEQUENCE: 223
acgaaaccgt aagca                                                  15

SEQ ID NO: 224          moltype = DNA  length = 19
FEATURE                 Location/Qualifiers
source                  1..19
                        mol_type = other DNA
                        organism = SARS-CoV-2
SEQUENCE: 224
ataggtccag acatgttcc                                              19

SEQ ID NO: 225          moltype = DNA  length = 19
FEATURE                 Location/Qualifiers
source                  1..19
                        mol_type = other DNA
                        organism = SARS-CoV-2
SEQUENCE: 225
ggaacatgtc tggacctat                                              19

SEQ ID NO: 226          moltype = DNA  length = 16
FEATURE                 Location/Qualifiers
source                  1..16
                        mol_type = other DNA
                        organism = SARS-CoV-2
SEQUENCE: 226
aacatgtctg gaccta                                                 16

SEQ ID NO: 227          moltype = DNA  length = 16
FEATURE                 Location/Qualifiers
```

```
source                  1..16
                        mol_type = other DNA
                        organism = SARS-CoV-2
SEQUENCE: 227
acatgtctgg acctat                                                 16

SEQ ID NO: 228          moltype = DNA  length = 19
FEATURE                 Location/Qualifiers
source                  1..19
                        mol_type = other DNA
                        organism = SARS-CoV-2
SEQUENCE: 228
tatgactatg tcatattca                                              19

SEQ ID NO: 229          moltype = DNA  length = 23
FEATURE                 Location/Qualifiers
source                  1..23
                        mol_type = other DNA
                        organism = SARS-CoV-2
SEQUENCE: 229
agtgaatatg acatagtcat att                                         23

SEQ ID NO: 230          moltype = DNA  length = 15
FEATURE                 Location/Qualifiers
source                  1..15
                        mol_type = other DNA
                        organism = SARS-CoV-2
SEQUENCE: 230
tgaatatgac atagt                                                  15

SEQ ID NO: 231          moltype = DNA  length = 14
FEATURE                 Location/Qualifiers
source                  1..14
                        mol_type = other DNA
                        organism = SARS-CoV-2
SEQUENCE: 231
aatatgacat agtc                                                   14

SEQ ID NO: 232          moltype = DNA  length = 44
FEATURE                 Location/Qualifiers
source                  1..44
                        mol_type = other DNA
                        organism = SARS-CoV-2
SEQUENCE: 232
gatctcttgt agatctgttc tctaaacgaa ctttaaaatc tgtg                  44

SEQ ID NO: 233          moltype = DNA  length = 44
FEATURE                 Location/Qualifiers
source                  1..44
                        mol_type = other DNA
                        organism = SARS-CoV-2
SEQUENCE: 233
cacagatttt aaagttcgtt tagagaacag atctacaaga gatc                  44

SEQ ID NO: 234          moltype = DNA  length = 16
FEATURE                 Location/Qualifiers
source                  1..16
                        mol_type = other DNA
                        organism = SARS-CoV-2
SEQUENCE: 234
cacagatttt aaagtt                                                 16

SEQ ID NO: 235          moltype = DNA  length = 16
FEATURE                 Location/Qualifiers
source                  1..16
                        mol_type = other DNA
                        organism = SARS-CoV-2
SEQUENCE: 235
cacagatttt aaagtt                                                 16

SEQ ID NO: 236          moltype = DNA  length = 16
FEATURE                 Location/Qualifiers
source                  1..16
                        mol_type = other DNA
                        organism = SARS-CoV-2
SEQUENCE: 236
cagattttaa agttcg                                                 16

SEQ ID NO: 237          moltype = DNA  length = 15
```

```
FEATURE                 Location/Qualifiers
source                  1..15
                        mol_type = other DNA
                        organism = SARS-CoV-2
SEQUENCE: 237
gattttaaag ttcgt                                                    15

SEQ ID NO: 238          moltype = DNA  length = 15
FEATURE                 Location/Qualifiers
source                  1..15
                        mol_type = other DNA
                        organism = SARS-CoV-2
SEQUENCE: 238
taaagttcgt ttaga                                                    15

SEQ ID NO: 239          moltype = DNA  length = 14
FEATURE                 Location/Qualifiers
source                  1..14
                        mol_type = other DNA
                        organism = SARS-CoV-2
SEQUENCE: 239
aaagttcgtt taga                                                     14

SEQ ID NO: 240          moltype = DNA  length = 17
FEATURE                 Location/Qualifiers
source                  1..17
                        mol_type = other DNA
                        organism = SARS-CoV-2
SEQUENCE: 240
tcgtttagag aacagat                                                  17

SEQ ID NO: 241          moltype = DNA  length = 16
FEATURE                 Location/Qualifiers
source                  1..16
                        mol_type = other DNA
                        organism = SARS-CoV-2
SEQUENCE: 241
agagaacaga tctaca                                                   16

SEQ ID NO: 242          moltype = DNA  length = 14
FEATURE                 Location/Qualifiers
source                  1..14
                        mol_type = other DNA
                        organism = SARS-CoV-2
SEQUENCE: 242
agatctacaa gaga                                                     14

SEQ ID NO: 243          moltype = DNA  length = 14
FEATURE                 Location/Qualifiers
source                  1..14
                        mol_type = other DNA
                        organism = SARS-CoV-2
SEQUENCE: 243
atctacaaga gatc                                                     14

SEQ ID NO: 244          moltype = DNA  length = 16
FEATURE                 Location/Qualifiers
source                  1..16
                        mol_type = other DNA
                        organism = SARS-CoV-2
SEQUENCE: 244
agattttaaa gttcgt                                                   16

SEQ ID NO: 245          moltype = DNA  length = 15
FEATURE                 Location/Qualifiers
source                  1..15
                        mol_type = other DNA
                        organism = SARS-CoV-2
SEQUENCE: 245
gattttaaag ttcgt                                                    15

SEQ ID NO: 246          moltype = DNA  length = 15
FEATURE                 Location/Qualifiers
source                  1..15
                        mol_type = other DNA
                        organism = SARS-CoV-2
SEQUENCE: 246
gattttaaag ttcgt                                                    15
```

-continued

```
SEQ ID NO: 247          moltype = DNA  length = 15
FEATURE                 Location/Qualifiers
source                  1..15
                        mol_type = other DNA
                        organism = SARS-CoV-2
SEQUENCE: 247
agattttaaa gttcg                                                  15

SEQ ID NO: 248          moltype = DNA  length = 17
FEATURE                 Location/Qualifiers
source                  1..17
                        mol_type = other DNA
                        organism = SARS-CoV-2
SEQUENCE: 248
tcgtttagag aacagat                                                17

SEQ ID NO: 249          moltype = DNA  length = 16
FEATURE                 Location/Qualifiers
source                  1..16
                        mol_type = other DNA
                        organism = SARS-CoV-2
SEQUENCE: 249
ttcgtttaga gaacag                                                 16

SEQ ID NO: 250          moltype = DNA  length = 16
FEATURE                 Location/Qualifiers
source                  1..16
                        mol_type = other DNA
                        organism = SARS-CoV-2
SEQUENCE: 250
ttcgtttaga gaacag                                                 16

SEQ ID NO: 251          moltype = DNA  length = 31
FEATURE                 Location/Qualifiers
source                  1..31
                        mol_type = other DNA
                        organism = SARS-CoV-2
SEQUENCE: 251
gagaaaacac acgtccaact cagtttgcct g                                31

SEQ ID NO: 252          moltype = DNA  length = 31
FEATURE                 Location/Qualifiers
source                  1..31
                        mol_type = other DNA
                        organism = SARS-CoV-2
SEQUENCE: 252
caggcaaact gagttggacg tgtgttttct c                                31

SEQ ID NO: 253          moltype = DNA  length = 16
FEATURE                 Location/Qualifiers
source                  1..16
                        mol_type = other DNA
                        organism = SARS-CoV-2
SEQUENCE: 253
caggcaaact gagttg                                                 16

SEQ ID NO: 254          moltype = DNA  length = 16
FEATURE                 Location/Qualifiers
source                  1..16
                        mol_type = other DNA
                        organism = SARS-CoV-2
SEQUENCE: 254
caggcaaact gagttg                                                 16

SEQ ID NO: 255          moltype = DNA  length = 14
FEATURE                 Location/Qualifiers
source                  1..14
                        mol_type = other DNA
                        organism = SARS-CoV-2
SEQUENCE: 255
caggcaaact gagt                                                   14

SEQ ID NO: 256          moltype = DNA  length = 16
FEATURE                 Location/Qualifiers
source                  1..16
                        mol_type = other DNA
                        organism = SARS-CoV-2
SEQUENCE: 256
caaactgagt tggacg                                                 16
```

```
SEQ ID NO: 257         moltype = DNA  length = 14
FEATURE                Location/Qualifiers
source                 1..14
                       mol_type = other DNA
                       organism = SARS-CoV-2
SEQUENCE: 257
aaactgagtt ggac                                                      14

SEQ ID NO: 258         moltype = DNA  length = 16
FEATURE                Location/Qualifiers
source                 1..16
                       mol_type = other DNA
                       organism = SARS-CoV-2
SEQUENCE: 258
aaactgagtt ggacgt                                                    16

SEQ ID NO: 259         moltype = DNA  length = 15
FEATURE                Location/Qualifiers
source                 1..15
                       mol_type = other DNA
                       organism = SARS-CoV-2
SEQUENCE: 259
gagttggacg tgtgt                                                     15

SEQ ID NO: 260         moltype = DNA  length = 16
FEATURE                Location/Qualifiers
source                 1..16
                       mol_type = other DNA
                       organism = SARS-CoV-2
SEQUENCE: 260
ttggacgtgt gttttc                                                    16

SEQ ID NO: 261         moltype = DNA  length = 16
FEATURE                Location/Qualifiers
source                 1..16
                       mol_type = other DNA
                       organism = SARS-CoV-2
SEQUENCE: 261
ggacgtgtgt tttctc                                                    16

SEQ ID NO: 262         moltype = DNA  length = 21
FEATURE                Location/Qualifiers
source                 1..21
                       mol_type = other DNA
                       organism = SARS-CoV-2
SEQUENCE: 262
ggtttcgtcc gggtgtgacc g                                              21

SEQ ID NO: 263         moltype = DNA  length = 29
FEATURE                Location/Qualifiers
source                 1..29
                       mol_type = other DNA
                       organism = SARS-CoV-2
SEQUENCE: 263
tttcggtcac acccggacga aacctagat                                      29

SEQ ID NO: 264         moltype = DNA  length = 16
FEATURE                Location/Qualifiers
source                 1..16
                       mol_type = other DNA
                       organism = SARS-CoV-2
SEQUENCE: 264
tttcggtcac acccgg                                                    16

SEQ ID NO: 265         moltype = DNA  length = 16
FEATURE                Location/Qualifiers
source                 1..16
                       mol_type = other DNA
                       organism = SARS-CoV-2
SEQUENCE: 265
cggtcacacc cggacg                                                    16

SEQ ID NO: 266         moltype = DNA  length = 16
FEATURE                Location/Qualifiers
source                 1..16
                       mol_type = other DNA
                       organism = SARS-CoV-2
```

```
SEQUENCE: 266
tcacacccgg acgaaa                                                    16

SEQ ID NO: 267         moltype = DNA  length = 14
FEATURE                Location/Qualifiers
source                 1..14
                       mol_type = other DNA
                       organism = SARS-CoV-2
SEQUENCE: 267
caccccggacg aaac                                                     14

SEQ ID NO: 268         moltype = DNA  length = 15
FEATURE                Location/Qualifiers
source                 1..15
                       mol_type = other DNA
                       organism = SARS-CoV-2
SEQUENCE: 268
cacccggacg aaacc                                                     15

SEQ ID NO: 269         moltype = DNA  length = 16
FEATURE                Location/Qualifiers
source                 1..16
                       mol_type = other DNA
                       organism = SARS-CoV-2
SEQUENCE: 269
cacccggacg aaacct                                                    16

SEQ ID NO: 270         moltype = DNA  length = 14
FEATURE                Location/Qualifiers
source                 1..14
                       mol_type = other DNA
                       organism = SARS-CoV-2
SEQUENCE: 270
ccggacgaaa ccta                                                      14

SEQ ID NO: 271         moltype = DNA  length = 17
FEATURE                Location/Qualifiers
source                 1..17
                       mol_type = other DNA
                       organism = SARS-CoV-2
SEQUENCE: 271
cggtcacacc cggacga                                                   17

SEQ ID NO: 272         moltype = DNA  length = 16
FEATURE                Location/Qualifiers
source                 1..16
                       mol_type = other DNA
                       organism = SARS-CoV-2
SEQUENCE: 272
cggtcacacc cggacg                                                    16

SEQ ID NO: 273         moltype = DNA  length = 16
FEATURE                Location/Qualifiers
source                 1..16
                       mol_type = other DNA
                       organism = SARS-CoV-2
SEQUENCE: 273
cggtcacacc cggacg                                                    16

SEQ ID NO: 274         moltype = DNA  length = 16
FEATURE                Location/Qualifiers
source                 1..16
                       mol_type = other DNA
                       organism = SARS-CoV-2
SEQUENCE: 274
cggtcacacc cggacg                                                    16

SEQ ID NO: 275         moltype = DNA  length = 14
FEATURE                Location/Qualifiers
source                 1..14
                       mol_type = other DNA
                       organism = SARS-CoV-2
SEQUENCE: 275
gtcacacccg gacg                                                      14

SEQ ID NO: 276         moltype = DNA  length = 14
FEATURE                Location/Qualifiers
```

```
source                  1..14
                        mol_type = other DNA
                        organism = SARS-CoV-2
SEQUENCE: 276
gtcacacccg gacg                                                      14

SEQ ID NO: 277          moltype = DNA  length = 15
FEATURE                 Location/Qualifiers
source                  1..15
                        mol_type = other DNA
                        organism = SARS-CoV-2
SEQUENCE: 277
cacccggacg aaacc                                                     15

SEQ ID NO: 278          moltype = DNA  length = 15
FEATURE                 Location/Qualifiers
source                  1..15
                        mol_type = other DNA
                        organism = SARS-CoV-2
SEQUENCE: 278
cacccggacg aaacc                                                     15

SEQ ID NO: 279          moltype = DNA  length = 14
FEATURE                 Location/Qualifiers
source                  1..14
                        mol_type = other DNA
                        organism = SARS-CoV-2
SEQUENCE: 279
cacccggacg aaac                                                      14

SEQ ID NO: 280          moltype = DNA  length = 16
FEATURE                 Location/Qualifiers
source                  1..16
                        mol_type = other DNA
                        organism = SARS-CoV-2
SEQUENCE: 280
cacacccgga cgaaac                                                    16

SEQ ID NO: 281          moltype = DNA  length = 15
FEATURE                 Location/Qualifiers
source                  1..15
                        mol_type = other DNA
                        organism = SARS-CoV-2
SEQUENCE: 281
cacacccgga cgaaa                                                     15

SEQ ID NO: 282          moltype = DNA  length = 14
FEATURE                 Location/Qualifiers
source                  1..14
                        mol_type = other DNA
                        organism = SARS-CoV-2
SEQUENCE: 282
cacacccgga cgaa                                                      14

SEQ ID NO: 283          moltype = DNA  length = 24
FEATURE                 Location/Qualifiers
source                  1..24
                        mol_type = other DNA
                        organism = SARS-CoV-2
SEQUENCE: 283
cgaggccacg cggagtacga tcga                                           24

SEQ ID NO: 284          moltype = DNA  length = 31
FEATURE                 Location/Qualifiers
source                  1..31
                        mol_type = other DNA
                        organism = SARS-CoV-2
SEQUENCE: 284
actcgatcgt actccgcgtg gcctcggtga a                                   31

SEQ ID NO: 285          moltype = DNA  length = 15
FEATURE                 Location/Qualifiers
source                  1..15
                        mol_type = other DNA
                        organism = SARS-CoV-2
SEQUENCE: 285
tcgatcgtac tccgc                                                     15

SEQ ID NO: 286          moltype = DNA  length = 14
```

```
FEATURE                Location/Qualifiers
source                 1..14
                       mol_type = other DNA
                       organism = SARS-CoV-2
SEQUENCE: 286
tcgatcgtac tccg                                                   14

SEQ ID NO: 287         moltype = DNA  length = 15
FEATURE                Location/Qualifiers
source                 1..15
                       mol_type = other DNA
                       organism = SARS-CoV-2
SEQUENCE: 287
atcgtactcc gcgtg                                                  15

SEQ ID NO: 288         moltype = DNA  length = 14
FEATURE                Location/Qualifiers
source                 1..14
                       mol_type = other DNA
                       organism = SARS-CoV-2
SEQUENCE: 288
actcgatcgt actc                                                   14

SEQ ID NO: 289         moltype = DNA  length = 15
FEATURE                Location/Qualifiers
source                 1..15
                       mol_type = other DNA
                       organism = SARS-CoV-2
SEQUENCE: 289
cgtggcctcg gtgaa                                                  15

SEQ ID NO: 290         moltype = DNA  length = 14
FEATURE                Location/Qualifiers
source                 1..14
                       mol_type = other DNA
                       organism = SARS-CoV-2
SEQUENCE: 290
gtggcctcgg tgaa                                                   14

SEQ ID NO: 291         moltype = DNA  length = 35
FEATURE                Location/Qualifiers
source                 1..35
                       mol_type = other DNA
                       organism = SARS-CoV-2
SEQUENCE: 291
tagttaactt taatctcaca tagcaatctt taatc                            35

SEQ ID NO: 292         moltype = DNA  length = 35
FEATURE                Location/Qualifiers
source                 1..35
                       mol_type = other DNA
                       organism = SARS-CoV-2
SEQUENCE: 292
gattaaagat tgctatgtga gattaaagtt aacta                            35

SEQ ID NO: 293         moltype = DNA  length = 16
FEATURE                Location/Qualifiers
source                 1..16
                       mol_type = other DNA
                       organism = SARS-CoV-2
SEQUENCE: 293
gattaaagat tgctat                                                 16

SEQ ID NO: 294         moltype = DNA  length = 16
FEATURE                Location/Qualifiers
source                 1..16
                       mol_type = other DNA
                       organism = SARS-CoV-2
SEQUENCE: 294
taaagattgc tatgtg                                                 16

SEQ ID NO: 295         moltype = DNA  length = 16
FEATURE                Location/Qualifiers
source                 1..16
                       mol_type = other DNA
                       organism = SARS-CoV-2
SEQUENCE: 295
aagattgcta tgtgag                                                 16
```

```
SEQ ID NO: 296          moltype = DNA  length = 16
FEATURE                 Location/Qualifiers
source                  1..16
                        mol_type = other DNA
                        organism = SARS-CoV-2
SEQUENCE: 296
gctatgtgag ttaaag                                                   16

SEQ ID NO: 297          moltype = DNA  length = 16
FEATURE                 Location/Qualifiers
source                  1..16
                        mol_type = other DNA
                        organism = SARS-CoV-2
SEQUENCE: 297
tatgtgagtt aaagtt                                                   16

SEQ ID NO: 298          moltype = DNA  length = 16
FEATURE                 Location/Qualifiers
source                  1..16
                        mol_type = other DNA
                        organism = SARS-CoV-2
SEQUENCE: 298
tgtgagttaa agttaa                                                   16

SEQ ID NO: 299          moltype = DNA  length = 50
FEATURE                 Location/Qualifiers
source                  1..50
                        mol_type = other DNA
                        organism = SARS-CoV-2
SEQUENCE: 299
cgtgctacaa cttcctcaag gaacaacatt gccaaaaggc ttctacgcag              50

SEQ ID NO: 300          moltype = DNA  length = 50
FEATURE                 Location/Qualifiers
source                  1..50
                        mol_type = other DNA
                        organism = SARS-CoV-2
SEQUENCE: 300
ctgcgtagaa gccttttggc aatgttgttc cttgaggaag ttgtagcacg              50

SEQ ID NO: 301          moltype = DNA  length = 16
FEATURE                 Location/Qualifiers
source                  1..16
                        mol_type = other DNA
                        organism = SARS-CoV-2
SEQUENCE: 301
tcgtagaagc cttttg                                                   16

SEQ ID NO: 302          moltype = DNA  length = 17
FEATURE                 Location/Qualifiers
source                  1..17
                        mol_type = other DNA
                        organism = SARS-CoV-2
SEQUENCE: 302
cgtagaagcc ttttggc                                                  17

SEQ ID NO: 303          moltype = DNA  length = 16
FEATURE                 Location/Qualifiers
source                  1..16
                        mol_type = other DNA
                        organism = SARS-CoV-2
SEQUENCE: 303
tagaagcctt ttggca                                                   16

SEQ ID NO: 304          moltype = DNA  length = 16
FEATURE                 Location/Qualifiers
source                  1..16
                        mol_type = other DNA
                        organism = SARS-CoV-2
SEQUENCE: 304
aagccttttg gcaatg                                                   16

SEQ ID NO: 305          moltype = DNA  length = 16
FEATURE                 Location/Qualifiers
source                  1..16
                        mol_type = other DNA
                        organism = SARS-CoV-2
SEQUENCE: 305
ttggcaatgt tgttcc                                                   16
```

```
SEQ ID NO: 306          moltype = DNA  length = 14
FEATURE                 Location/Qualifiers
source                  1..14
                        mol_type = other DNA
                        organism = SARS-CoV-2
SEQUENCE: 306
gcaatgttgt tcct                                                    14

SEQ ID NO: 307          moltype = DNA  length = 14
FEATURE                 Location/Qualifiers
source                  1..14
                        mol_type = other DNA
                        organism = SARS-CoV-2
SEQUENCE: 307
cttgaggaag ttgt                                                    14

SEQ ID NO: 308          moltype = DNA  length = 16
FEATURE                 Location/Qualifiers
source                  1..16
                        mol_type = other DNA
                        organism = SARS-CoV-2
SEQUENCE: 308
aggaagttgt agcacg                                                  16

SEQ ID NO: 309          moltype = DNA  length = 43
FEATURE                 Location/Qualifiers
source                  1..43
                        mol_type = other DNA
                        organism = SARS-CoV-2
SEQUENCE: 309
gcctatatgg aagagcccta atgtgtaaaa ttaattttag tag                    43

SEQ ID NO: 310          moltype = DNA  length = 43
FEATURE                 Location/Qualifiers
source                  1..43
                        mol_type = other DNA
                        organism = SARS-CoV-2
SEQUENCE: 310
ctactaaaat taattttaca cattagggct cttccatata ggc                    43

SEQ ID NO: 311          moltype = DNA  length = 15
FEATURE                 Location/Qualifiers
source                  1..15
                        mol_type = other DNA
                        organism = SARS-CoV-2
SEQUENCE: 311
ctactaaaat taatt                                                   15

SEQ ID NO: 312          moltype = DNA  length = 15
FEATURE                 Location/Qualifiers
source                  1..15
                        mol_type = other DNA
                        organism = SARS-CoV-2
SEQUENCE: 312
tactaaaatt aattt                                                   15

SEQ ID NO: 313          moltype = DNA  length = 14
FEATURE                 Location/Qualifiers
source                  1..14
                        mol_type = other DNA
                        organism = SARS-CoV-2
SEQUENCE: 313
actaaaatta attt                                                    14

SEQ ID NO: 314          moltype = DNA  length = 16
FEATURE                 Location/Qualifiers
source                  1..16
                        mol_type = other DNA
                        organism = SARS-CoV-2
SEQUENCE: 314
aattaatttt acacat                                                  16

SEQ ID NO: 315          moltype = DNA  length = 16
FEATURE                 Location/Qualifiers
source                  1..16
                        mol_type = other DNA
                        organism = SARS-CoV-2
```

```
SEQUENCE: 315
attttacaca ttaggg                                                    16

SEQ ID NO: 316          moltype = DNA  length = 15
FEATURE                 Location/Qualifiers
source                  1..15
                        mol_type = other DNA
                        organism = SARS-CoV-2
SEQUENCE: 316
tacacattag ggctc                                                     15

SEQ ID NO: 317          moltype = DNA  length = 15
FEATURE                 Location/Qualifiers
source                  1..15
                        mol_type = other DNA
                        organism = SARS-CoV-2
SEQUENCE: 317
acattagggc tcttc                                                     15

SEQ ID NO: 318          moltype = DNA  length = 15
FEATURE                 Location/Qualifiers
source                  1..15
                        mol_type = other DNA
                        organism = SARS-CoV-2
SEQUENCE: 318
tagggctctt ccata                                                     15

SEQ ID NO: 319          moltype = DNA  length = 15
FEATURE                 Location/Qualifiers
source                  1..15
                        mol_type = other DNA
                        organism = SARS-CoV-2
SEQUENCE: 319
gctcttccat atagg                                                     15

SEQ ID NO: 320          moltype = DNA  length = 19
FEATURE                 Location/Qualifiers
source                  1..19
                        mol_type = other DNA
                        organism = SARS-CoV-2
SEQUENCE: 320
aggtaagatg gagagcctt                                                 19

SEQ ID NO: 321          moltype = DNA  length = 24
FEATURE                 Location/Qualifiers
source                  1..24
                        mol_type = other DNA
                        organism = SARS-CoV-2
SEQUENCE: 321
aaggctctcc atcttacctt tcgg                                           24

SEQ ID NO: 322          moltype = DNA  length = 16
FEATURE                 Location/Qualifiers
source                  1..16
                        mol_type = other DNA
                        organism = SARS-CoV-2
SEQUENCE: 322
aaggctctcc atctta                                                    16

SEQ ID NO: 323          moltype = DNA  length = 14
FEATURE                 Location/Qualifiers
source                  1..14
                        mol_type = other DNA
                        organism = SARS-CoV-2
SEQUENCE: 323
aaggctctcc atct                                                      14

SEQ ID NO: 324          moltype = DNA  length = 16
FEATURE                 Location/Qualifiers
source                  1..16
                        mol_type = other DNA
                        organism = SARS-CoV-2
SEQUENCE: 324
gctctccatc ttacct                                                    16

SEQ ID NO: 325          moltype = DNA  length = 16
FEATURE                 Location/Qualifiers
```

```
source                1..16
                      mol_type = other DNA
                      organism = SARS-CoV-2
SEQUENCE: 325
tccatcttac ctttcg                                                  16

SEQ ID NO: 326        moltype = DNA  length = 18
FEATURE               Location/Qualifiers
source                1..18
                      mol_type = other DNA
                      organism = SARS-CoV-2
SEQUENCE: 326
tgtgtaacat tagggagg                                                18

SEQ ID NO: 327        moltype = DNA  length = 18
FEATURE               Location/Qualifiers
source                1..18
                      mol_type = other DNA
                      organism = SARS-CoV-2
SEQUENCE: 327
cctccctaat gttacaca                                                18

SEQ ID NO: 328        moltype = DNA  length = 16
FEATURE               Location/Qualifiers
source                1..16
                      mol_type = other DNA
                      organism = SARS-CoV-2
SEQUENCE: 328
cctccctaat gttaca                                                  16

SEQ ID NO: 329        moltype = DNA  length = 16
FEATURE               Location/Qualifiers
source                1..16
                      mol_type = other DNA
                      organism = SARS-CoV-2
SEQUENCE: 329
ctccctaatg ttacag                                                  16

SEQ ID NO: 330        moltype = DNA  length = 16
FEATURE               Location/Qualifiers
source                1..16
                      mol_type = other DNA
                      organism = SARS-CoV-2
SEQUENCE: 330
ctccctaatg ttacag                                                  16

SEQ ID NO: 331        moltype = DNA  length = 22
FEATURE               Location/Qualifiers
source                1..22
                      mol_type = other DNA
                      organism = SARS-CoV-2
SEQUENCE: 331
tcatgtggta gtgttggttt ta                                           22

SEQ ID NO: 332        moltype = DNA  length = 22
FEATURE               Location/Qualifiers
source                1..22
                      mol_type = other DNA
                      organism = SARS-CoV-2
SEQUENCE: 332
taaaaccaac actaccacat ga                                           22

SEQ ID NO: 333        moltype = DNA  length = 16
FEATURE               Location/Qualifiers
source                1..16
                      mol_type = other DNA
                      organism = SARS-CoV-2
SEQUENCE: 333
taaaaccaac actacc                                                  16

SEQ ID NO: 334        moltype = DNA  length = 16
FEATURE               Location/Qualifiers
source                1..16
                      mol_type = other DNA
                      organism = SARS-CoV-2
SEQUENCE: 334
aaaccaacac taccac                                                  16

SEQ ID NO: 335        moltype = DNA  length = 16
```

```
FEATURE                 Location/Qualifiers
source                  1..16
                        mol_type = other DNA
                        organism = SARS-CoV-2
SEQUENCE: 335
aaaccaacac taccac                                                     16

SEQ ID NO: 336          moltype = DNA  length = 16
FEATURE                 Location/Qualifiers
source                  1..16
                        mol_type = other DNA
                        organism = SARS-CoV-2
SEQUENCE: 336
accaacacta ccacat                                                     16

SEQ ID NO: 337          moltype = DNA  length = 14
FEATURE                 Location/Qualifiers
source                  1..14
                        mol_type = other DNA
                        organism = influenza A virus
SEQUENCE: 337
tgtcagtaag tatg                                                       14

SEQ ID NO: 338          moltype = DNA  length = 16
FEATURE                 Location/Qualifiers
source                  1..16
                        mol_type = other DNA
                        organism = influenza A virus
SEQUENCE: 338
ctggctgtca gtaagt                                                     16

SEQ ID NO: 339          moltype = DNA  length = 15
FEATURE                 Location/Qualifiers
source                  1..15
                        mol_type = other DNA
                        organism = influenza A virus
SEQUENCE: 339
tcgctgtctg gctgt                                                      15

SEQ ID NO: 340          moltype = DNA  length = 16
FEATURE                 Location/Qualifiers
source                  1..16
                        mol_type = other DNA
                        organism = influenza A virus
SEQUENCE: 340
cttttggtcg ctgtct                                                     16

SEQ ID NO: 341          moltype = DNA  length = 14
FEATURE                 Location/Qualifiers
source                  1..14
                        mol_type = other DNA
                        organism = influenza A virus
SEQUENCE: 341
cttttggtcg ctgt                                                       14

SEQ ID NO: 342          moltype = DNA  length = 16
FEATURE                 Location/Qualifiers
source                  1..16
                        mol_type = other DNA
                        organism = influenza A virus
SEQUENCE: 342
ttggtcgctg tctggc                                                     16

SEQ ID NO: 343          moltype = DNA  length = 14
FEATURE                 Location/Qualifiers
source                  1..14
                        mol_type = other DNA
                        organism = influenza A virus
SEQUENCE: 343
ttggtcgctg tctg                                                       14

SEQ ID NO: 344          moltype = DNA  length = 16
FEATURE                 Location/Qualifiers
source                  1..16
                        mol_type = other DNA
                        organism = influenza A virus
SEQUENCE: 344
gaattctttt ggtcgc                                                     16
```

```
SEQ ID NO: 345          moltype = DNA  length = 15
FEATURE                 Location/Qualifiers
source                  1..15
                        mol_type = other DNA
                        organism = influenza A virus
SEQUENCE: 345
gaattctttt ggtcg                                                    15

SEQ ID NO: 346          moltype = DNA  length = 15
FEATURE                 Location/Qualifiers
source                  1..15
                        mol_type = other DNA
                        organism = influenza A virus
SEQUENCE: 346
aattcttttg gtcgc                                                    15

SEQ ID NO: 347          moltype = DNA  length = 16
FEATURE                 Location/Qualifiers
source                  1..16
                        mol_type = other DNA
                        organism = influenza A virus
SEQUENCE: 347
cgaattcttt tggtcg                                                   16

SEQ ID NO: 348          moltype = DNA  length = 15
FEATURE                 Location/Qualifiers
source                  1..15
                        mol_type = other DNA
                        organism = influenza A virus
SEQUENCE: 348
acactaattg atggc                                                    15

SEQ ID NO: 349          moltype = DNA  length = 13
FEATURE                 Location/Qualifiers
source                  1..13
                        mol_type = other DNA
                        organism = influenza A virus
SEQUENCE: 349
aattgatggc cat                                                      13

SEQ ID NO: 350          moltype = DNA  length = 16
FEATURE                 Location/Qualifiers
source                  1..16
                        mol_type = other DNA
                        organism = influenza B virus
SEQUENCE: 350
ccacaaaatg aaggca                                                   16

SEQ ID NO: 351          moltype = DNA  length = 15
FEATURE                 Location/Qualifiers
source                  1..15
                        mol_type = other DNA
                        organism = influenza B virus
SEQUENCE: 351
cacaaaatga aggca                                                    15

SEQ ID NO: 352          moltype = DNA  length = 14
FEATURE                 Location/Qualifiers
source                  1..14
                        mol_type = other DNA
                        organism = influenza B virus
SEQUENCE: 352
cacaaaatga aggc                                                     14

SEQ ID NO: 353          moltype = DNA  length = 14
FEATURE                 Location/Qualifiers
source                  1..14
                        mol_type = other DNA
                        organism = influenza B virus
SEQUENCE: 353
caataattgt acta                                                     14

SEQ ID NO: 354          moltype = DNA  length = 14
FEATURE                 Location/Qualifiers
source                  1..14
                        mol_type = other DNA
                        organism = influenza B virus
SEQUENCE: 354
caataattgt acta                                                     14
```

```
SEQ ID NO: 355          moltype = DNA  length = 14
FEATURE                 Location/Qualifiers
source                  1..14
                        mol_type = other DNA
                        organism = influenza B virus
SEQUENCE: 355
caataattgt acta                                                          14

SEQ ID NO: 356          moltype = DNA  length = 15
FEATURE                 Location/Qualifiers
source                  1..15
                        mol_type = other DNA
                        organism = influenza B virus
SEQUENCE: 356
caataattgt actac                                                         15

SEQ ID NO: 357          moltype = DNA  length = 15
FEATURE                 Location/Qualifiers
source                  1..15
                        mol_type = other DNA
                        organism = influenza B virus
SEQUENCE: 357
caataattgt actac                                                         15

SEQ ID NO: 358          moltype = DNA  length = 16
FEATURE                 Location/Qualifiers
source                  1..16
                        mol_type = other DNA
                        organism = influenza B virus
SEQUENCE: 358
tgtactactc atggta                                                        16

SEQ ID NO: 359          moltype = DNA  length = 16
FEATURE                 Location/Qualifiers
source                  1..16
                        mol_type = other DNA
                        organism = influenza B virus
SEQUENCE: 359
tgtactactc atggta                                                        16

SEQ ID NO: 360          moltype = DNA  length = 16
FEATURE                 Location/Qualifiers
source                  1..16
                        mol_type = other DNA
                        organism = influenza B virus
SEQUENCE: 360
tgtactactc atggta                                                        16

SEQ ID NO: 361          moltype = DNA  length = 14
FEATURE                 Location/Qualifiers
source                  1..14
                        mol_type = other DNA
                        organism = influenza B virus
SEQUENCE: 361
gtactactca tggt                                                          14

SEQ ID NO: 362          moltype = DNA  length = 15
FEATURE                 Location/Qualifiers
source                  1..15
                        mol_type = other DNA
                        organism = influenza B virus
SEQUENCE: 362
ttgtactact catgg                                                         15

SEQ ID NO: 363          moltype = DNA  length = 15
FEATURE                 Location/Qualifiers
source                  1..15
                        mol_type = other DNA
                        organism = influenza B virus
SEQUENCE: 363
catggtagta acatc                                                         15

SEQ ID NO: 364          moltype = DNA  length = 17
FEATURE                 Location/Qualifiers
source                  1..17
                        mol_type = other DNA
                        organism = influenza B virus
```

```
SEQUENCE: 364
ctcatggtag taacatc                                               17

SEQ ID NO: 365          moltype = DNA  length = 16
FEATURE                 Location/Qualifiers
source                  1..16
                        mol_type = other DNA
                        organism = influenza B virus
SEQUENCE: 365
ctcatggtag taacat                                                16

SEQ ID NO: 366          moltype = DNA  length = 16
FEATURE                 Location/Qualifiers
source                  1..16
                        mol_type = other DNA
                        organism = influenza B virus
SEQUENCE: 366
ctcatggtag taacat                                                16

SEQ ID NO: 367          moltype = DNA  length = 16
FEATURE                 Location/Qualifiers
source                  1..16
                        mol_type = other DNA
                        organism = influenza B virus
SEQUENCE: 367
actcatggta gtaaca                                                16

SEQ ID NO: 368          moltype = DNA  length = 16
FEATURE                 Location/Qualifiers
source                  1..16
                        mol_type = other DNA
                        organism = influenza B virus
SEQUENCE: 368
actcatggta gtaaca                                                16

SEQ ID NO: 369          moltype = DNA  length = 15
FEATURE                 Location/Qualifiers
source                  1..15
                        mol_type = other DNA
                        organism = influenza B virus
SEQUENCE: 369
actcatggta gtaac                                                 15

SEQ ID NO: 370          moltype = DNA  length = 14
FEATURE                 Location/Qualifiers
source                  1..14
                        mol_type = other DNA
                        organism = influenza B virus
SEQUENCE: 370
actcatggta gtaa                                                  14

SEQ ID NO: 371          moltype = DNA  length = 15
FEATURE                 Location/Qualifiers
source                  1..15
                        mol_type = other DNA
                        organism = influenza B virus
SEQUENCE: 371
caatgcagat cgaat                                                 15

SEQ ID NO: 372          moltype = DNA  length = 15
FEATURE                 Location/Qualifiers
source                  1..15
                        mol_type = other DNA
                        organism = influenza B virus
SEQUENCE: 372
caatgcagat cgaat                                                 15

SEQ ID NO: 373          moltype = DNA  length = 16
FEATURE                 Location/Qualifiers
source                  1..16
                        mol_type = other DNA
                        organism = influenza B virus
SEQUENCE: 373
gattgccttc acgaaa                                                16

SEQ ID NO: 374          moltype = DNA  length = 16
FEATURE                 Location/Qualifiers
```

source 1..16
mol_type = other DNA
organism = influenza B virus
SEQUENCE: 374
gattgccttc acgaaa 16

SEQ ID NO: 375 moltype = DNA length = 14
FEATURE Location/Qualifiers
source 1..14
mol_type = other DNA
organism = influenza B virus
SEQUENCE: 375
gccttcattt tgtg 14

SEQ ID NO: 376 moltype = DNA length = 16
FEATURE Location/Qualifiers
source 1..16
mol_type = other DNA
organism = influenza B virus
SEQUENCE: 376
attgccttca ttttgt 16

SEQ ID NO: 377 moltype = DNA length = 16
FEATURE Location/Qualifiers
source 1..16
mol_type = other DNA
organism = influenza B virus
SEQUENCE: 377
attgccttca ttttgt 16

SEQ ID NO: 378 moltype = DNA length = 16
FEATURE Location/Qualifiers
source 1..16
mol_type = other DNA
organism = influenza B virus
SEQUENCE: 378
tagtacaatt attgcc 16

SEQ ID NO: 379 moltype = DNA length = 15
FEATURE Location/Qualifiers
source 1..15
mol_type = other DNA
organism = influenza B virus
SEQUENCE: 379
agtacaatta ttgcc 15

SEQ ID NO: 380 moltype = DNA length = 16
FEATURE Location/Qualifiers
source 1..16
mol_type = other DNA
organism = influenza B virus
SEQUENCE: 380
gtacaattat tgcctt 16

SEQ ID NO: 381 moltype = DNA length = 15
FEATURE Location/Qualifiers
source 1..15
mol_type = other DNA
organism = influenza B virus
SEQUENCE: 381
accatgagta gtaca 15

SEQ ID NO: 382 moltype = DNA length = 15
FEATURE Location/Qualifiers
source 1..15
mol_type = other DNA
organism = influenza B virus
SEQUENCE: 382
catgagtagt acaat 15

SEQ ID NO: 383 moltype = DNA length = 17
FEATURE Location/Qualifiers
source 1..17
mol_type = other DNA
organism = influenza B virus
SEQUENCE: 383
gatgttacta ccatgag 17

SEQ ID NO: 384 moltype = DNA length = 16

```
FEATURE                Location/Qualifiers
source                 1..16
                       mol_type = other DNA
                       organism = influenza B virus
SEQUENCE: 384
atgttactac catgag                                                    16

SEQ ID NO: 385         moltype = DNA  length = 16
FEATURE                Location/Qualifiers
source                 1..16
                       mol_type = other DNA
                       organism = influenza B virus
SEQUENCE: 385
cattggatgt tactac                                                    16

SEQ ID NO: 386         moltype = DNA  length = 16
FEATURE                Location/Qualifiers
source                 1..16
                       mol_type = other DNA
                       organism = influenza B virus
SEQUENCE: 386
attggatgtt actacc                                                    16

SEQ ID NO: 387         moltype = DNA  length = 15
FEATURE                Location/Qualifiers
source                 1..15
                       mol_type = other DNA
                       organism = influenza B virus
SEQUENCE: 387
attggatgtt actac                                                     15

SEQ ID NO: 388         moltype = DNA  length = 16
FEATURE                Location/Qualifiers
source                 1..16
                       mol_type = other DNA
                       organism = influenza B virus
SEQUENCE: 388
tttcgtgaag gcaatc                                                    16

SEQ ID NO: 389         moltype = DNA  length = 14
FEATURE                Location/Qualifiers
source                 1..14
                       mol_type = other DNA
                       organism = influenza B virus
SEQUENCE: 389
tcgtgaaggc aatc                                                      14

SEQ ID NO: 390         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 390
ggtttcgtcc gtgtt                                                     15

SEQ ID NO: 391         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 391
gtttcgtccg tgtt                                                      14

SEQ ID NO: 392         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 392
gctgtcgccc gtgtc                                                     15

SEQ ID NO: 393         moltype = DNA  length = 15
FEATURE                Location/Qualifiers
```

```
misc_feature          1..15
                      note = synthetic sequence
source                1..15
                      mol_type = other DNA
                      organism = synthetic construct
SEQUENCE: 393
gctgtcgccc gtgtc                                                    15

SEQ ID NO: 394        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 394
gctgtcgccc gtgtc                                                    15

SEQ ID NO: 395        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 395
gctgtcgccc gtgt                                                     14

SEQ ID NO: 396        moltype = DNA  length = 10
FEATURE               Location/Qualifiers
misc_feature          1..10
                      note = synthetic sequence
source                1..10
                      mol_type = other DNA
                      organism = synthetic construct
SEQUENCE: 396
ttcgtccgtg                                                          10

SEQ ID NO: 397        moltype = DNA  length = 10
FEATURE               Location/Qualifiers
misc_feature          1..10
                      note = synthetic sequence
source                1..10
                      mol_type = other DNA
                      organism = synthetic construct
SEQUENCE: 397
ttcgtccgtg                                                          10

SEQ ID NO: 398        moltype = DNA  length = 10
FEATURE               Location/Qualifiers
misc_feature          1..10
                      note = synthetic sequence
source                1..10
                      mol_type = other DNA
                      organism = synthetic construct
SEQUENCE: 398
ttcgtccgtg                                                          10

SEQ ID NO: 399        moltype =   length =
SEQUENCE: 399
000

SEQ ID NO: 400        moltype =   length =
SEQUENCE: 400
000

SEQ ID NO: 401        moltype =   length =
SEQUENCE: 401
000

SEQ ID NO: 402        moltype = DNA  length = 10
FEATURE               Location/Qualifiers
misc_feature          1..10
                      note = synthetic sequence
source                1..10
                      mol_type = other DNA
                      organism = synthetic construct
SEQUENCE: 402
tttcgtccgt                                                          10
```

```
SEQ ID NO: 403          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 403
tttcgtccgt                                                         10

SEQ ID NO: 404          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 404
tttcgtccgt                                                         10

SEQ ID NO: 405          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 405
ccccacccac                                                         10

SEQ ID NO: 406          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 406
ccccacccac                                                         10

SEQ ID NO: 407          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 407
ccccacccac                                                         10

SEQ ID NO: 408          moltype = DNA  length = 12
FEATURE                 Location/Qualifiers
misc_feature            1..12
                        note = synthetic sequence
source                  1..12
                        mol_type = other DNA
                        organism = synthetic construct
SEQUENCE: 408
tttcgtccgt gt                                                      12

SEQ ID NO: 409          moltype = DNA  length = 12
FEATURE                 Location/Qualifiers
misc_feature            1..12
                        note = synthetic sequence
source                  1..12
                        mol_type = other DNA
                        organism = synthetic construct
SEQUENCE: 409
tttcgtccgt gt                                                      12

SEQ ID NO: 410          moltype = DNA  length = 12
FEATURE                 Location/Qualifiers
misc_feature            1..12
                        note = synthetic sequence
source                  1..12
                        mol_type = other DNA
                        organism = synthetic construct
```

```
SEQUENCE: 410
tttcgtccgt gt                                                   12

SEQ ID NO: 411          moltype = DNA  length = 12
FEATURE                 Location/Qualifiers
misc_feature            1..12
                        note = synthetic sequence
source                  1..12
                        mol_type = other DNA
                        organism = synthetic construct
SEQUENCE: 411
ttccatccat gt                                                   12

SEQ ID NO: 412          moltype = DNA  length = 12
FEATURE                 Location/Qualifiers
misc_feature            1..12
                        note = synthetic sequence
source                  1..12
                        mol_type = other DNA
                        organism = synthetic construct
SEQUENCE: 412
ttccatccat gt                                                   12

SEQ ID NO: 413          moltype = DNA  length = 12
FEATURE                 Location/Qualifiers
misc_feature            1..12
                        note = synthetic sequence
source                  1..12
                        mol_type = other DNA
                        organism = synthetic construct
SEQUENCE: 413
ttccatccat gt                                                   12

SEQ ID NO: 414          moltype = DNA  length = 12
FEATURE                 Location/Qualifiers
misc_feature            1..12
                        note = synthetic sequence
source                  1..12
                        mol_type = other DNA
                        organism = synthetic construct
SEQUENCE: 414
ttccatccat gt                                                   12

SEQ ID NO: 415          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 415
gtttcgtccg tgtt                                                 14

SEQ ID NO: 416          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 416
gtttcgtccg tgtt                                                 14

SEQ ID NO: 417          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 417
gtttcgtccg tgtt                                                 14

SEQ ID NO: 418          moltype = DNA  length = 14
FEATURE                 Location/Qualifiers
misc_feature            1..14
                        note = synthetic sequence
```

```
source                  1..14
                        mol_type = other DNA
                        organism = synthetic construct
SEQUENCE: 418
gtttcggcca tgtg                                                          14

SEQ ID NO: 419          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 419
cgtccgtgtt                                                               10

SEQ ID NO: 420          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 420
cgtccgtgtt                                                               10

SEQ ID NO: 421          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 421
cgtccgtgtt                                                               10

SEQ ID NO: 422          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 422
cgtccgtgtt                                                               10

SEQ ID NO: 423          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 423
cctccgtgtc                                                               10

SEQ ID NO: 424          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 424
cctccgtgtc                                                               10

SEQ ID NO: 425          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 425
cctccgtgtc                                                               10

SEQ ID NO: 426          moltype = DNA  length = 10
FEATURE                 Location/Qualifiers
```

```
misc_feature            1..10
                        note = synthetic sequence
source                  1..10
                        mol_type = other DNA
                        organism = synthetic construct
SEQUENCE: 426
tccgtgttgc                                                          10

SEQ ID NO: 427          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 427
tccgtgttgc                                                          10

SEQ ID NO: 428          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 428
tccgtgttgc                                                          10

SEQ ID NO: 429          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 429
tccgtcttgc                                                          10

SEQ ID NO: 430          moltype = DNA  length = 13
FEATURE                 Location/Qualifiers
misc_feature            1..13
                        note = synthetic sequence
misc_feature            13
                        note = n is a, c, g, or t
source                  1..13
                        mol_type = other DNA
                        organism = synthetic construct
SEQUENCE: 430
tccgtcttgc sdn                                                      13

SEQ ID NO: 431          moltype =   length =
SEQUENCE: 431
000

SEQ ID NO: 432          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 432
tttcgtccgt gtt                                                      13

SEQ ID NO: 433          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 433
tttcgtccgt gtt                                                      13

SEQ ID NO: 434          moltype = DNA  length = 13
FEATURE                 Location/Qualifiers
misc_feature            1..13
                        note = synthetic sequence
```

```
source                  1..13
                        mol_type = other DNA
                        organism = synthetic construct
SEQUENCE: 434
tttcctctat gtt                                                      13

SEQ ID NO: 435          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 435
tttcctctat gtt                                                      13

SEQ ID NO: 436          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 436
gtttcgtccg tgt                                                      13

SEQ ID NO: 437          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 437
ggtttcgtcc gtgtt                                                    15

SEQ ID NO: 438          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 438
ggtttcgtcc gtgtt                                                    15

SEQ ID NO: 439          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 439
aagtacgtcc tactt                                                    15

SEQ ID NO: 440          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 440
ggtttcgtcc                                                          10

SEQ ID NO: 441          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 441
ggtttcgtcc                                                          10

SEQ ID NO: 442          moltype = DNA  length = 15
FEATURE                 Location/Qualifiers
```

```
misc_feature            1..15
                        note = synthetic sequence
source                  1..15
                        mol_type = other DNA
                        organism = synthetic construct
SEQUENCE: 442
tgggtttcgt ccgtt                                                            15

SEQ ID NO: 443          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 443
ttttgggatt ccgt                                                             14

SEQ ID NO: 444          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 444
gcttttggga ttccgt                                                           16

SEQ ID NO: 445          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 445
gcttttggga ttccgt                                                           16

SEQ ID NO: 446          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 446
agctgctttt gggatt                                                           16

SEQ ID NO: 447          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 447
gagctgcttt tgggat                                                           16

SEQ ID NO: 448          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 448
ctgcttttgg gattcc                                                           16

SEQ ID NO: 449          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 449
tgcttttggg attc                                                             14

SEQ ID NO: 450          moltype = DNA  length = 16
```

```
FEATURE                 Location/Qualifiers
misc_feature            1..16
                        note = synthetic sequence
source                  1..16
                        mol_type = other DNA
                        organism = synthetic construct
SEQUENCE: 450
agctgctttt gggatt                                                 16

SEQ ID NO: 451          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 451
agctgctttt ggga                                                   14

SEQ ID NO: 452          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 452
cagctgcttt tgggat                                                 16

SEQ ID NO: 453          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 453
agctgctttt gggatt                                                 16

SEQ ID NO: 454          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 454
agctgctttt ggga                                                   14

SEQ ID NO: 455          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 455
agctgctttt ggga                                                   14

SEQ ID NO: 456          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 456
agctgctttt gggatt                                                 16

SEQ ID NO: 457          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 457
tgcttttggg attc                                                   14
```

```
SEQ ID NO: 458          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 458
gcggcgcccc gcct                                                    14

SEQ ID NO: 459          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 459
gcggcgcccc gcct                                                    14

SEQ ID NO: 460          moltype = DNA  length = 21
FEATURE                 Location/Qualifiers
misc_feature            1..21
                        note = synthetic sequence
source                  1..21
                        mol_type = other DNA
                        organism = synthetic construct
SEQUENCE: 460
cggtcccgcg gcgccccgcc t                                            21

SEQ ID NO: 461          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 461
tttgggcttc ctcgct                                                  16

SEQ ID NO: 462          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 462
tttgggcttc ctcg                                                    14

SEQ ID NO: 463          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 463
tttgggcttc ctcg                                                    14

SEQ ID NO: 464          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 464
tgggcttcct cgct                                                    14

SEQ ID NO: 465          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 465
atatactttg ggcttc                                                  16
```

```
SEQ ID NO: 466          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 466
atatactttg ggcttc                                                     16

SEQ ID NO: 467          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 467
atatactttg ggct                                                       14

SEQ ID NO: 468          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 468
atatactttg ggctt                                                      15

SEQ ID NO: 469          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 469
tagccctagc cccgca                                                     16

SEQ ID NO: 470          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 470
tagccctagc cccgca                                                     16

SEQ ID NO: 471          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 471
tagccctagc cccg                                                       14

SEQ ID NO: 472          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 472
tgctgttagc ccta                                                       14

SEQ ID NO: 473          moltype = DNA  length = 14
FEATURE                 Location/Qualifiers
misc_feature            1..14
                        note = synthetic sequence
source                  1..14
                        mol_type = other DNA
                        organism = synthetic construct
```

```
SEQUENCE: 473
tgctgttagc ccta                                                   14

SEQ ID NO: 474          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 474
gtgttagccc tagcc                                                  15

SEQ ID NO: 475          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 475
gcgcccagcc ccgc                                                   14

SEQ ID NO: 476          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 476
gcgcccagcc ccgc                                                   14

SEQ ID NO: 477          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 477
cgcgcgccca gccc                                                   14

SEQ ID NO: 478          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 478
cgcgcgccca gccccgc                                                17

SEQ ID NO: 479          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 479
tggcatggaa tggg                                                   14

SEQ ID NO: 480          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 480
atggaatggg ctccgc                                                 16

SEQ ID NO: 481          moltype = DNA  length = 14
FEATURE                 Location/Qualifiers
misc_feature            1..14
                        note = synthetic sequence
```

```
source                  1..14
                        mol_type = other DNA
                        organism = synthetic construct
SEQUENCE: 481
atggaatggg ctcc                                                             14

SEQ ID NO: 482          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 482
aatgggctcc gccag                                                            15

SEQ ID NO: 483          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 483
aatgggctcc gccag                                                            15

SEQ ID NO: 484          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 484
aatgggctcc gcca                                                             14

SEQ ID NO: 485          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 485
aatgggctcc gcca                                                             14

SEQ ID NO: 486          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 486
cttacccgag gcggtc                                                           16

SEQ ID NO: 487          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 487
ttacccgagg cggt                                                             14

SEQ ID NO: 488          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 488
accgtacctt acccga                                                           16

SEQ ID NO: 489          moltype = DNA  length = 14
FEATURE                 Location/Qualifiers
```

```
misc_feature            1..14
                        note = synthetic sequence
source                  1..14
                        mol_type = other DNA
                        organism = synthetic construct
SEQUENCE: 489
cgtaccttac ccga                                                    14

SEQ ID NO: 490          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 490
ctccgagccc cgcc                                                    14

SEQ ID NO: 491          moltype = DNA  length = 19
FEATURE                 Location/Qualifiers
misc_feature            1..19
                        note = synthetic sequence
source                  1..19
                        mol_type = other DNA
                        organism = synthetic construct
SEQUENCE: 491
cccggctccg agccccgcc                                               19

SEQ ID NO: 492          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 492
tggcctgtcc ccgca                                                   15

SEQ ID NO: 493          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 493
tggcctgtcc ccgca                                                   15

SEQ ID NO: 494          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 494
gatgccctgg cctg                                                    14

SEQ ID NO: 495          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 495
gatgccctgg cctg                                                    14

SEQ ID NO: 496          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 496
gcagccagct ctac                                                    14

SEQ ID NO: 497          moltype = DNA  length = 14
```

```
FEATURE                 Location/Qualifiers
misc_feature            1..14
                        note = synthetic sequence
source                  1..14
                        mol_type = other DNA
                        organism = synthetic construct
SEQUENCE: 497
gcagccagct ctac                                                            14

SEQ ID NO: 498          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 498
agccagctct accc                                                            14

SEQ ID NO: 499          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 499
agctctaccc ccgcca                                                          16

SEQ ID NO: 500          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 500
agctctaccc ccgcca                                                          16

SEQ ID NO: 501          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 501
aaagcagcgc ccactt                                                          16

SEQ ID NO: 502          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 502
acttcctccc cgct                                                            14

SEQ ID NO: 503          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 503
ctacagaagc cccata                                                          16

SEQ ID NO: 504          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 504
ctacagaagc cccata                                                          16
```

```
SEQ ID NO: 505          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 505
gaaatctcta cagaag                                                  16

SEQ ID NO: 506          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 506
gaaatctcta cagaag                                                  16

SEQ ID NO: 507          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 507
tgatccctgt ccccat                                                  16

SEQ ID NO: 508          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 508
atgctgatcc ctgtc                                                   15

SEQ ID NO: 509          moltype = DNA  length = 23
FEATURE                 Location/Qualifiers
misc_feature            1..23
                        note = synthetic sequence
source                  1..23
                        mol_type = other DNA
                        organism = synthetic construct
SEQUENCE: 509
gccatgctga tccctgtccc cat                                          23

SEQ ID NO: 510          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 510
ccatctcacc ccat                                                    14

SEQ ID NO: 511          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 511
gctgctcctc cccat                                                   15

SEQ ID NO: 512          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 512
tctccaaccc cacaa                                                   15
```

```
SEQ ID NO: 513          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 513
ctccaacccc acaa                                                    14

SEQ ID NO: 514          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 514
cagccagctc tccaa                                                   15

SEQ ID NO: 515          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 515
agccagctct ccaa                                                    14

SEQ ID NO: 516          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 516
atctgttctc taaacga                                                 17

SEQ ID NO: 517          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 517
atctgttctc taaacg                                                  16

SEQ ID NO: 518          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 518
agatctgttc tctaaa                                                  16

SEQ ID NO: 519          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 519
tctctaaacg aacttt                                                  16

SEQ ID NO: 520          moltype = DNA  length = 16
FEATURE                 Location/Qualifiers
misc_feature            1..16
                        note = synthetic sequence
source                  1..16
                        mol_type = other DNA
                        organism = synthetic construct
```

```
SEQUENCE: 520
tctctaaacg aacttt                                                   16

SEQ ID NO: 521         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 521
ctctaaacga acttta                                                   16

SEQ ID NO: 522         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 522
actttaaaat ctgt                                                     14

SEQ ID NO: 523         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 523
ggtttcgtcc gtgtt                                                    15

SEQ ID NO: 524         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 524
ggtttcgtcc gtgtt                                                    15

SEQ ID NO: 525         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 525
ggtttcgtcc gtgtt                                                    15

SEQ ID NO: 526         moltype = DNA  length = 17
FEATURE                Location/Qualifiers
misc_feature           1..17
                       note = synthetic sequence
source                 1..17
                       mol_type = other DNA
                       organism = synthetic construct
SEQUENCE: 526
tgcttacggt ttcgtcc                                                  17

SEQ ID NO: 527         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 527
gtttcgtccg tgttgc                                                   16

SEQ ID NO: 528         moltype = DNA  length = 14
FEATURE                Location/Qualifiers
misc_feature           1..14
                       note = synthetic sequence
```

```
source                  1..14
                        mol_type = other DNA
                        organism = synthetic construct
SEQUENCE: 528
taggtttcgt ccgg                                                     14

SEQ ID NO: 529          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 529
tcgtccgggt gtga                                                     14

SEQ ID NO: 530          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 530
ttcgtccggg tgtga                                                    15

SEQ ID NO: 531          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 531
tttcgtccgg gtgtga                                                   16

SEQ ID NO: 532          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 532
aggtttcgtc cgggt                                                    15

SEQ ID NO: 533          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 533
aggtttcgtc cggg                                                     14

SEQ ID NO: 534          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 534
aggtttcgtc cgggt                                                    15

SEQ ID NO: 535          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 535
tttcgtccgg gtgtg                                                    15

SEQ ID NO: 536          moltype = DNA  length = 15
FEATURE                 Location/Qualifiers
```

```
misc_feature          1..15
                      note = synthetic sequence
source                1..15
                      mol_type = other DNA
                      organism = synthetic construct
SEQUENCE: 536
aggccacgcg gagta                                                    15

SEQ ID NO: 537        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 537
cacgcggagt acgatc                                                   16

SEQ ID NO: 538        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 538
tgtcagtaag tatg                                                     14

SEQ ID NO: 539        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 539
ctggctgtca gtaagt                                                   16

SEQ ID NO: 540        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 540
tcgctgtctg gctgt                                                    15

SEQ ID NO: 541        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 541
cttttggtcg ctgtct                                                   16

SEQ ID NO: 542        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 542
cttttggtcg ctgt                                                     14

SEQ ID NO: 543        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 543
ttggtcgctg tctggc                                                   16

SEQ ID NO: 544        moltype = DNA  length = 14
```

```
FEATURE                 Location/Qualifiers
misc_feature            1..14
                        note = synthetic sequence
source                  1..14
                        mol_type = other DNA
                        organism = synthetic construct
SEQUENCE: 544
ttggtcgctg tctg                                                 14

SEQ ID NO: 545          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 545
gaattctttt ggtcgc                                               16

SEQ ID NO: 546          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 546
gaattctttt ggtcg                                                15

SEQ ID NO: 547          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 547
aattcttttg gtcgc                                                15

SEQ ID NO: 548          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 548
cgaattcttt tggtcg                                               16

SEQ ID NO: 549          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 549
acactaattg atggc                                                15

SEQ ID NO: 550          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 550
aattgatggc cat                                                  13

SEQ ID NO: 551          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 551
ccacaaaatg aaggca                                               16
```

```
SEQ ID NO: 552          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 552
cacaaaatga aggca                                                    15

SEQ ID NO: 553          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 553
cacaaaatga aggca                                                    15

SEQ ID NO: 554          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 554
cacaaaatga aggc                                                     14

SEQ ID NO: 555          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 555
caataattgt acta                                                     14

SEQ ID NO: 556          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 556
caataattgt acta                                                     14

SEQ ID NO: 557          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 557
caataattgt acta                                                     14

SEQ ID NO: 558          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 558
caataattgt actac                                                    15

SEQ ID NO: 559          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 559
caataattgt actac                                                    15
```

```
SEQ ID NO: 560          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 560
tgtactactc atggta                                                   16

SEQ ID NO: 561          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 561
tgtactactc atggta                                                   16

SEQ ID NO: 562          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 562
tgtactactc atggta                                                   16

SEQ ID NO: 563          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 563
gtactactca tggt                                                     14

SEQ ID NO: 564          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 564
gtactactca tggt                                                     14

SEQ ID NO: 565          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 565
ttgtactact catgg                                                    15

SEQ ID NO: 566          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 566
catggtagta acatc                                                    15

SEQ ID NO: 567          moltype = DNA  length = 17
FEATURE                 Location/Qualifiers
misc_feature            1..17
                        note = synthetic sequence
source                  1..17
                        mol_type = other DNA
                        organism = synthetic construct
```

```
SEQUENCE: 567
ctcatggtag taacatc                                                17

SEQ ID NO: 568         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 568
ctcatggtag taacat                                                 16

SEQ ID NO: 569         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 569
ctcatggtag taacat                                                 16

SEQ ID NO: 570         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 570
actcatggta gtaaca                                                 16

SEQ ID NO: 571         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 571
actcatggta gtaaca                                                 16

SEQ ID NO: 572         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 572
actcatggta gtaac                                                  15

SEQ ID NO: 573         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 573
actcatggta gtaa                                                   14

SEQ ID NO: 574         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 574
caatgcagat cgaat                                                  15

SEQ ID NO: 575         moltype = DNA  length = 15
FEATURE                Location/Qualifiers
misc_feature           1..15
                       note = synthetic sequence
```

```
source                  1..15
                        mol_type = other DNA
                        organism = synthetic construct
SEQUENCE: 575
caatgcagat cgaat                                                          15

SEQ ID NO: 576          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 576
gattgccttc acgaaa                                                         16

SEQ ID NO: 577          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 577
gattgccttc acgaaa                                                         16

SEQ ID NO: 578          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 578
gccttcattt tgtg                                                           14

SEQ ID NO: 579          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 579
attgccttca ttttgt                                                         16

SEQ ID NO: 580          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 580
attgccttca ttttgt                                                         16

SEQ ID NO: 581          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 581
tagtacaatt attgcc                                                         16

SEQ ID NO: 582          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 582
agtacaatta ttgcc                                                          15

SEQ ID NO: 583          moltype = DNA  length = 16
FEATURE                 Location/Qualifiers
```

```
misc_feature          1..16
                      note = synthetic sequence
source                1..16
                      mol_type = other DNA
                      organism = synthetic construct
SEQUENCE: 583
gtacaattat tgcctt                                                   16

SEQ ID NO: 584        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 584
accatgagta gtaca                                                    15

SEQ ID NO: 585        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 585
catgagtagt acaat                                                    15

SEQ ID NO: 586        moltype = DNA  length = 17
FEATURE               Location/Qualifiers
misc_feature          1..17
                      note = synthetic sequence
source                1..17
                      mol_type = other DNA
                      organism = synthetic construct
SEQUENCE: 586
gatgttacta ccatgag                                                  17

SEQ ID NO: 587        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 587
atgttactac catgag                                                   16

SEQ ID NO: 588        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 588
cattggatgt tactac                                                   16

SEQ ID NO: 589        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 589
attggatgtt actacc                                                   16

SEQ ID NO: 590        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 590
attggatgtt actac                                                    15

SEQ ID NO: 591        moltype = DNA  length = 16
```

```
FEATURE                 Location/Qualifiers
misc_feature            1..16
                        note = synthetic sequence
source                  1..16
                        mol_type = other DNA
                        organism = synthetic construct
SEQUENCE: 591
tttcgtgaag gcaatc                                                   16

SEQ ID NO: 592          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 592
tcgtgaaggc aatc                                                     14

SEQ ID NO: 593          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 593
atctgttctc taaacga                                                  17

SEQ ID NO: 594          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 594
atctgttctc taaacg                                                   16

SEQ ID NO: 595          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 595
agatctgttc tctaaa                                                   16

SEQ ID NO: 596          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 596
tctctaaacg aacttt                                                   16

SEQ ID NO: 597          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 597
tctctaaacg aacttt                                                   16

SEQ ID NO: 598          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 598
ctctaaacga acttta                                                   16
```

```
SEQ ID NO: 599          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 599
actttaaaat ctgt                                                      14

SEQ ID NO: 600          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 600
ggtttcgtcc gtgtt                                                     15

SEQ ID NO: 601          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 601
ggtttcgtcc gtgtt                                                     15

SEQ ID NO: 602          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 602
ggtttcgtcc gtgtt                                                     15

SEQ ID NO: 603          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 603
tgcttacggt ttcgtcc                                                   17

SEQ ID NO: 604          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 604
gtttcgtccg tgttgc                                                    16

SEQ ID NO: 605          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 605
taggtttcgt ccgg                                                      14

SEQ ID NO: 606          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 606
tcgtccgggt gtga                                                      14
```

```
SEQ ID NO: 607          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 607
ttcgtccggg tgtga                                                    15

SEQ ID NO: 608          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 608
tttcgtccgg gtgtga                                                   16

SEQ ID NO: 609          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 609
aggtttcgtc cgggt                                                    15

SEQ ID NO: 610          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 610
aggtttcgtc cggg                                                     14

SEQ ID NO: 611          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 611
aggtttcgtc cgggt                                                    15

SEQ ID NO: 612          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 612
tttcgtccgg gtgtg                                                    15

SEQ ID NO: 613          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 613
aggccacgcg gagta                                                    15

SEQ ID NO: 614          moltype = DNA  length = 16
FEATURE                 Location/Qualifiers
misc_feature            1..16
                        note = synthetic sequence
source                  1..16
                        mol_type = other DNA
                        organism = synthetic construct
```

```
SEQUENCE: 614
cacgcggagt acgatc                                            16

SEQ ID NO: 615          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 615
gcggagtacg atcga                                             15

SEQ ID NO: 616          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 616
gcggagtacg atcgag                                            16

SEQ ID NO: 617          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 617
gcggagtacg atcgag                                            16

SEQ ID NO: 618          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 618
aggccacgcg gagt                                              14

SEQ ID NO: 619          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 619
taactttaat ctcaca                                            16

SEQ ID NO: 620          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 620
atctcacata gcaatc                                            16

SEQ ID NO: 621          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 621
cacatagcaa tcttta                                            16

SEQ ID NO: 622          moltype = DNA  length = 16
FEATURE                 Location/Qualifiers
misc_feature            1..16
                        note = synthetic sequence
```

```
source                  1..16
                        mol_type = other DNA
                        organism = synthetic construct
SEQUENCE: 622
atagcaatct ttaatc                                                    16

SEQ ID NO: 623          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 623
gtagttaact ttaatct                                                   17

SEQ ID NO: 624          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 624
taactttaat ctcaca                                                    16

SEQ ID NO: 625          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 625
taactttaat ctcaca                                                    16

SEQ ID NO: 626          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 626
ctttaatctc acatagc                                                   17

SEQ ID NO: 627          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 627
cacatagcaa tctt                                                      14

SEQ ID NO: 628          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 628
ctcacatagc aatctt                                                    16

SEQ ID NO: 629          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 629
cgtgctacaa cttcct                                                    16

SEQ ID NO: 630          moltype = DNA  length = 15
FEATURE                 Location/Qualifiers
```

```
misc_feature          1..15
                      note = synthetic sequence
source                1..15
                      mol_type = other DNA
                      organism = synthetic construct
SEQUENCE: 630
tgctacaact tcctc                                                    15

SEQ ID NO: 631        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 631
ctcaaggaac aacatt                                                   16

SEQ ID NO: 632        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 632
aaggcttcta cgcag                                                    15

SEQ ID NO: 633        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 633
tgctacaact tcctc                                                    15

SEQ ID NO: 634        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 634
tgctacaact tcct                                                     14

SEQ ID NO: 635        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 635
tcgtgctaca acttc                                                    15

SEQ ID NO: 636        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 636
cgtgctacaa cttc                                                     14

SEQ ID NO: 637        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 637
cctatatgga agagc                                                    15

SEQ ID NO: 638        moltype = DNA  length = 16
```

```
FEATURE                Location/Qualifiers
misc_feature           1..16
                       note = synthetic sequence
source                 1..16
                       mol_type = other DNA
                       organism = synthetic construct
SEQUENCE: 638
tgcctatatg gaagag                                                    16

SEQ ID NO: 639         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 639
gcctatatgg aagag                                                     15

SEQ ID NO: 640         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 640
tatatggaag agcc                                                      14

SEQ ID NO: 641         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 641
agagccctaa tgtgta                                                    16

SEQ ID NO: 642         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 642
gaagagccct aatgtg                                                    16

SEQ ID NO: 643         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 643
tgtgtaacat taggga                                                    16

SEQ ID NO: 644         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 644
gtaacattag ggagga                                                    16

SEQ ID NO: 645         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 645
gtagtgttgg tttta                                                     15
```

```
SEQ ID NO: 646          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 646
gtagtgttgg tttt                                                   14

SEQ ID NO: 647          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 647
tcatgtggta gtgttg                                                 16

SEQ ID NO: 648          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 648
tcatgtggta gtgtt                                                  15

SEQ ID NO: 649          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 649
atgtggtagt gttggt                                                 16

SEQ ID NO: 650          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 650
atgtggtagt gttgg                                                  15

SEQ ID NO: 651          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 651
tgtggtagtg ttggt                                                  15

SEQ ID NO: 652          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 652
gtggtagtgt tggt                                                   14

SEQ ID NO: 653          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 653
gtggtagtgt tggttt                                                 16
```

```
SEQ ID NO: 654          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 654
tggtagtgtt ggttt                                                    15

SEQ ID NO: 655          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 655
ggtttcgtcc gtgtt                                                    15

SEQ ID NO: 656          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 656
gtttcgtccg tgtt                                                     14

SEQ ID NO: 657          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 657
gctgtcgccc gtgtc                                                    15

SEQ ID NO: 658          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 658
gctgtcgccc gtgtc                                                    15

SEQ ID NO: 659          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 659
gctgtcgccc gtgtc                                                    15

SEQ ID NO: 660          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 660
gctgtcgccc gtgt                                                     14

SEQ ID NO: 661          moltype = DNA  length = 10
FEATURE                 Location/Qualifiers
misc_feature            1..10
                        note = synthetic sequence
source                  1..10
                        mol_type = other DNA
                        organism = synthetic construct
```

```
SEQUENCE: 661
ttcgtccgtg                                                            10

SEQ ID NO: 662          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 662
ttcgtccgtg                                                            10

SEQ ID NO: 663          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 663
ttcgtccgtg                                                            10

SEQ ID NO: 664          moltype =   length =
SEQUENCE: 664
000

SEQ ID NO: 665          moltype =   length =
SEQUENCE: 665
000

SEQ ID NO: 666          moltype =   length =
SEQUENCE: 666
000

SEQ ID NO: 667          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 667
tttcgtccgt                                                            10

SEQ ID NO: 668          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 668
tttcgtccgt                                                            10

SEQ ID NO: 669          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 669
tttcgtccgt                                                            10

SEQ ID NO: 670          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 670
ccccacccac                                                            10

SEQ ID NO: 671          moltype = DNA  length = 10
FEATURE                 Location/Qualifiers
```

```
misc_feature          1..10
                      note = synthetic sequence
source                1..10
                      mol_type = other DNA
                      organism = synthetic construct
SEQUENCE: 671
ccccacccac                                                            10

SEQ ID NO: 672        moltype = DNA  length = 10
FEATURE               Location/Qualifiers
misc_feature          1..10
                      note = synthetic sequence
source                1..10
                      mol_type = other DNA
                      organism = synthetic construct
SEQUENCE: 672
ccccacccac                                                            10

SEQ ID NO: 673        moltype = DNA  length = 12
FEATURE               Location/Qualifiers
misc_feature          1..12
                      note = synthetic sequence
source                1..12
                      mol_type = other DNA
                      organism = synthetic construct
SEQUENCE: 673
tttcgtccgt gt                                                         12

SEQ ID NO: 674        moltype = DNA  length = 12
FEATURE               Location/Qualifiers
misc_feature          1..12
                      note = synthetic sequence
source                1..12
                      mol_type = other DNA
                      organism = synthetic construct
SEQUENCE: 674
tttcgtccgt gt                                                         12

SEQ ID NO: 675        moltype = DNA  length = 12
FEATURE               Location/Qualifiers
misc_feature          1..12
                      note = synthetic sequence
source                1..12
                      mol_type = other DNA
                      organism = synthetic construct
SEQUENCE: 675
tttcgtccgt gt                                                         12

SEQ ID NO: 676        moltype = DNA  length = 12
FEATURE               Location/Qualifiers
misc_feature          1..12
                      note = synthetic sequence
source                1..12
                      mol_type = other DNA
                      organism = synthetic construct
SEQUENCE: 676
ttccatccat gt                                                         12

SEQ ID NO: 677        moltype = DNA  length = 12
FEATURE               Location/Qualifiers
misc_feature          1..12
                      note = synthetic sequence
source                1..12
                      mol_type = other DNA
                      organism = synthetic construct
SEQUENCE: 677
ttccatccat gt                                                         12

SEQ ID NO: 678        moltype = DNA  length = 12
FEATURE               Location/Qualifiers
misc_feature          1..12
                      note = synthetic sequence
source                1..12
                      mol_type = other DNA
                      organism = synthetic construct
SEQUENCE: 678
ttccatccat gt                                                         12

SEQ ID NO: 679        moltype = DNA  length = 12
```

```
FEATURE                Location/Qualifiers
misc_feature           1..12
                       note = synthetic sequence
source                 1..12
                       mol_type = other DNA
                       organism = synthetic construct
SEQUENCE: 679
ttccatccat gt                                                                12

SEQ ID NO: 680         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 680
gtttcgtccg tgtt                                                              14

SEQ ID NO: 681         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 681
gtttcgtccg tgtt                                                              14

SEQ ID NO: 682         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 682
gtttcgtccg tgtt                                                              14

SEQ ID NO: 683         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 683
gtttcggcca tgtg                                                              14

SEQ ID NO: 684         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 684
gtttcggcca tgtg                                                              14

SEQ ID NO: 685         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 685
gtttcggcca tgtg                                                              14

SEQ ID NO: 686         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 686
gtttcggcca tgtg                                                              14
```

```
SEQ ID NO: 687          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 687
cgtccgtgtt                                                             10

SEQ ID NO: 688          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 688
cgtccgtgtt                                                             10

SEQ ID NO: 689          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 689
cgtccgtgtt                                                             10

SEQ ID NO: 690          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 690
cgtccgtgtt                                                             10

SEQ ID NO: 691          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 691
cctccgtgtc                                                             10

SEQ ID NO: 692          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 692
cctccgtgtc                                                             10

SEQ ID NO: 693          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 693
cctccgtgtc                                                             10

SEQ ID NO: 694          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 694
tccgtgttgc                                                             10
```

```
SEQ ID NO: 695          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 695
tccgtgttgc                                                             10

SEQ ID NO: 696          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 696
tccgtgttgc                                                             10

SEQ ID NO: 697          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 697
tccgtcttgc                                                             10

SEQ ID NO: 698          moltype = DNA  length = 10
FEATURE                 Location/Qualifiers
misc_feature            1..10
                        note = synthetic sequence
source                  1..10
                        mol_type = other DNA
                        organism = synthetic construct
SEQUENCE: 698
tccgtcttgc                                                             10

SEQ ID NO: 699          moltype =   length =
SEQUENCE: 699
000

SEQ ID NO: 700          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 700
tttcgtccgt gtt                                                         13

SEQ ID NO: 701          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 701
tttcgtccgt gtt                                                         13

SEQ ID NO: 702          moltype = DNA  length = 13
FEATURE                 Location/Qualifiers
misc_feature            1..13
                        note = synthetic sequence
source                  1..13
                        mol_type = other DNA
                        organism = synthetic construct
SEQUENCE: 702
tttcctctat gtt                                                         13

SEQ ID NO: 703          moltype = DNA  length = 13
FEATURE                 Location/Qualifiers
```

```
misc_feature          1..13
                      note = synthetic sequence
source                1..13
                      mol_type = other DNA
                      organism = synthetic construct
SEQUENCE: 703
tttcctctat gtt                                                            13

SEQ ID NO: 704        moltype = DNA  length = 13
FEATURE               Location/Qualifiers
misc_feature          1..13
                      note = synthetic sequence
source                1..13
                      mol_type = other DNA
                      organism = synthetic construct
SEQUENCE: 704
gtttcgtccg tgt                                                            13

SEQ ID NO: 705        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 705
ggtttcgtcc gtgtt                                                          15

SEQ ID NO: 706        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 706
ggtttcgtcc gtgtt                                                          15

SEQ ID NO: 707        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 707
ggtttcgtcc gtgtt                                                          15

SEQ ID NO: 708        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 708
aagtacgtcc tactt                                                          15

SEQ ID NO: 709        moltype = DNA  length = 10
FEATURE               Location/Qualifiers
misc_feature          1..10
                      note = synthetic sequence
source                1..10
                      mol_type = other DNA
                      organism = synthetic construct
SEQUENCE: 709
ggtttcgtcc                                                                10

SEQ ID NO: 710        moltype = DNA  length = 10
FEATURE               Location/Qualifiers
misc_feature          1..10
                      note = synthetic sequence
source                1..10
                      mol_type = other DNA
                      organism = synthetic construct
SEQUENCE: 710
ggtttcgtcc                                                                10

SEQ ID NO: 711        moltype = DNA  length = 15
```

```
FEATURE               Location/Qualifiers
misc_feature          1..15
                      note = synthetic sequence
source                1..15
                      mol_type = other DNA
                      organism = synthetic construct
SEQUENCE: 711
tgggtttcgt ccgtt                                                   15

SEQ ID NO: 712        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 712
ttttgggatt ccgt                                                    14

SEQ ID NO: 713        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 713
gcttttggga ttccgt                                                  16

SEQ ID NO: 714        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 714
gcttttggga ttccgt                                                  16

SEQ ID NO: 715        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 715
agctgctttt gggatt                                                  16

SEQ ID NO: 716        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 716
gagctgcttt tgggat                                                  16

SEQ ID NO: 717        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 717
ctgcttttgg gattcc                                                  16

SEQ ID NO: 718        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 718
tgcttttggg attc                                                    14
```

```
SEQ ID NO: 719          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 719
tgcttttggg attc                                                    14

SEQ ID NO: 720          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 720
agctgctttt gggatt                                                  16

SEQ ID NO: 721          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 721
agctgctttt ggga                                                    14

SEQ ID NO: 722          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 722
cagctgcttt tgggat                                                  16

SEQ ID NO: 723          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 723
agctgctttt gggatt                                                  16

SEQ ID NO: 724          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 724
agctgctttt ggga                                                    14

SEQ ID NO: 725          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 725
agctgctttt ggga                                                    14

SEQ ID NO: 726          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 726
agctgctttt gggatt                                                  16
```

```
SEQ ID NO: 727          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 727
tgcttttggg attc                                                    14

SEQ ID NO: 728          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 728
gcggcgcccc gcct                                                    14

SEQ ID NO: 729          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 729
gcggcgcccc gcct                                                    14

SEQ ID NO: 730          moltype = DNA  length = 21
FEATURE                 Location/Qualifiers
misc_feature            1..21
                        note = synthetic sequence
source                  1..21
                        mol_type = other DNA
                        organism = synthetic construct
SEQUENCE: 730
cggtcccgcg gcgccccgcc t                                            21

SEQ ID NO: 731          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 731
tttgggcttc ctcgct                                                  16

SEQ ID NO: 732          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 732
tttgggcttc ctcgct                                                  16

SEQ ID NO: 733          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 733
tttgggcttc ctcg                                                    14

SEQ ID NO: 734          moltype = DNA  length = 14
FEATURE                 Location/Qualifiers
misc_feature            1..14
                        note = synthetic sequence
source                  1..14
                        mol_type = other DNA
                        organism = synthetic construct
```

```
SEQUENCE: 734
tttgggcttc ctcg                                                   14

SEQ ID NO: 735          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 735
tgggcttcct cgct                                                   14

SEQ ID NO: 736          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 736
atatactttg ggcttc                                                 16

SEQ ID NO: 737          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 737
atatactttg ggcttc                                                 16

SEQ ID NO: 738          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 738
atatactttg ggct                                                   14

SEQ ID NO: 739          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 739
atatactttg ggctt                                                  15

SEQ ID NO: 740          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 740
tagccctagc cccgca                                                 16

SEQ ID NO: 741          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 741
tagccctagc cccgca                                                 16

SEQ ID NO: 742          moltype = DNA  length = 14
FEATURE                 Location/Qualifiers
misc_feature            1..14
                        note = synthetic sequence
```

source 1..14
mol_type = other DNA
organism = synthetic construct
SEQUENCE: 742
tagccctagc cccg 14

SEQ ID NO: 743 moltype = DNA length = 14
FEATURE Location/Qualifiers
misc_feature 1..14
note = synthetic sequence
source 1..14
mol_type = other DNA
organism = synthetic construct
SEQUENCE: 743
tgctgttagc ccta 14

SEQ ID NO: 744 moltype = DNA length = 14
FEATURE Location/Qualifiers
misc_feature 1..14
note = synthetic sequence
source 1..14
mol_type = other DNA
organism = synthetic construct
SEQUENCE: 744
tgctgttagc ccta 14

SEQ ID NO: 745 moltype = DNA length = 14
FEATURE Location/Qualifiers
misc_feature 1..14
note = synthetic sequence
source 1..14
mol_type = other DNA
organism = synthetic construct
SEQUENCE: 745
tgctgttagc ccta 14

SEQ ID NO: 746 moltype = DNA length = 15
FEATURE Location/Qualifiers
misc_feature 1..15
note = synthetic sequence
source 1..15
mol_type = other DNA
organism = synthetic construct
SEQUENCE: 746
gtgttagccc tagcc 15

SEQ ID NO: 747 moltype = DNA length = 14
FEATURE Location/Qualifiers
misc_feature 1..14
note = synthetic sequence
source 1..14
mol_type = other DNA
organism = synthetic construct
SEQUENCE: 747
gcgcccagcc ccgc 14

SEQ ID NO: 748 moltype = DNA length = 14
FEATURE Location/Qualifiers
misc_feature 1..14
note = synthetic sequence
source 1..14
mol_type = other DNA
organism = synthetic construct
SEQUENCE: 748
gcgcccagcc ccgc 14

SEQ ID NO: 749 moltype = DNA length = 14
FEATURE Location/Qualifiers
misc_feature 1..14
note = synthetic sequence
source 1..14
mol_type = other DNA
organism = synthetic construct
SEQUENCE: 749
cgcgcgccca gccc 14

SEQ ID NO: 750 moltype = DNA length = 17
FEATURE Location/Qualifiers

```
misc_feature            1..17
                        note = synthetic sequence
source                  1..17
                        mol_type = other DNA
                        organism = synthetic construct
SEQUENCE: 750
cgcgcgccca gccccgc                                                  17

SEQ ID NO: 751          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 751
tggcatggaa tgggct                                                   16

SEQ ID NO: 752          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 752
tggcatggaa tggg                                                     14

SEQ ID NO: 753          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 753
atggaatggg ctccgc                                                   16

SEQ ID NO: 754          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 754
atggaatggg ctcc                                                     14

SEQ ID NO: 755          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 755
aatgggctcc gccag                                                    15

SEQ ID NO: 756          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 756
aatgggctcc gccag                                                    15

SEQ ID NO: 757          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 757
aatgggctcc gcca                                                     14

SEQ ID NO: 758          moltype = DNA  length = 14
```

```
FEATURE                Location/Qualifiers
misc_feature           1..14
                       note = synthetic sequence
source                 1..14
                       mol_type = other DNA
                       organism = synthetic construct
SEQUENCE: 758
aatgggctcc gcca                                                      14

SEQ ID NO: 759         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 759
cttacccgag gcggtc                                                    16

SEQ ID NO: 760         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 760
ttacccgagg cggt                                                      14

SEQ ID NO: 761         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 761
accgtacctt acccga                                                    16

SEQ ID NO: 762         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 762
cgtaccttac ccga                                                      14

SEQ ID NO: 763         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 763
cgtaccttac ccga                                                      14

SEQ ID NO: 764         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 764
ctccgagccc cgcc                                                      14

SEQ ID NO: 765         moltype = DNA  length = 19
FEATURE                Location/Qualifiers
misc_feature           1..19
                       note = synthetic sequence
source                 1..19
                       mol_type = other DNA
                       organism = synthetic construct
SEQUENCE: 765
cccggctccg agccccgcc                                                 19
```

```
SEQ ID NO: 766          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 766
tggcctgtcc ccgca                                                    15

SEQ ID NO: 767          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 767
tggcctgtcc ccgca                                                    15

SEQ ID NO: 768          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 768
gatgccctgg cctg                                                     14

SEQ ID NO: 769          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 769
gatgccctgg cctg                                                     14

SEQ ID NO: 770          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 770
gcagccagct ctac                                                     14

SEQ ID NO: 771          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 771
gcagccagct ctac                                                     14

SEQ ID NO: 772          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 772
agccagctct accc                                                     14

SEQ ID NO: 773          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 773
agctctaccc ccgcca                                                   16
```

```
SEQ ID NO: 774          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 774
agctctaccc ccgcca                                                    16

SEQ ID NO: 775          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 775
aaagcagcgc ccactt                                                    16

SEQ ID NO: 776          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 776
aaagcagcgc ccact                                                     15

SEQ ID NO: 777          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 777
aaagcagcgc ccac                                                      14

SEQ ID NO: 778          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 778
acttcctccc cgct                                                      14

SEQ ID NO: 779          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 779
ctacagaagc cccata                                                    16

SEQ ID NO: 780          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 780
ctacagaagc cccata                                                    16

SEQ ID NO: 781          moltype = DNA  length = 16
FEATURE                 Location/Qualifiers
misc_feature            1..16
                        note = synthetic sequence
source                  1..16
                        mol_type = other DNA
                        organism = synthetic construct
```

```
SEQUENCE: 781
gaaatctcta cagaag                                                   16

SEQ ID NO: 782          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 782
gaaatctcta cagaag                                                   16

SEQ ID NO: 783          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 783
tgatccctgt ccccat                                                   16

SEQ ID NO: 784          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 784
atgctgatcc ctgtc                                                    15

SEQ ID NO: 785          moltype = DNA  length = 23
FEATURE                 Location/Qualifiers
misc_feature            1..23
                        note = synthetic sequence
source                  1..23
                        mol_type = other DNA
                        organism = synthetic construct
SEQUENCE: 785
gccatgctga tccctgtccc cat                                           23

SEQ ID NO: 786          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 786
ccatctcacc ccat                                                     14

SEQ ID NO: 787          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 787
gctgctcctc cccat                                                    15

SEQ ID NO: 788          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 788
tctccaaccc cacaa                                                    15

SEQ ID NO: 789          moltype = DNA  length = 14
FEATURE                 Location/Qualifiers
misc_feature            1..14
                        note = synthetic sequence
```

```
source                  1..14
                        mol_type = other DNA
                        organism = synthetic construct
SEQUENCE: 789
ctccaacccc acaa                                                    14

SEQ ID NO: 790          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 790
cagccagctc tccaa                                                   15

SEQ ID NO: 791          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 791
agccagctct ccaa                                                    14

SEQ ID NO: 792          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 792
gacgtgatat atgtgg                                                  16

SEQ ID NO: 793          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 793
cgtgatatat gtggta                                                  16

SEQ ID NO: 794          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 794
gatatgtggt accat                                                   15

SEQ ID NO: 795          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 795
tggtaccatg tcac                                                    14

SEQ ID NO: 796          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 796
cctcagcagc agattt                                                  16

SEQ ID NO: 797          moltype = DNA  length = 15
FEATURE                 Location/Qualifiers
```

```
misc_feature          1..15
                      note = synthetic sequence
source                1..15
                      mol_type = other DNA
                      organism = synthetic construct
SEQUENCE: 797
tcagcagcag atttc                                                   15

SEQ ID NO: 798        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 798
cagcagcaga tttc                                                    14

SEQ ID NO: 799        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 799
cagatttctt agtgac                                                  16

SEQ ID NO: 800        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 800
tgcaacacgg acgaaa                                                  16

SEQ ID NO: 801        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 801
gcaacacgga cgaaac                                                  16

SEQ ID NO: 802        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 802
acacggacga aaccg                                                   15

SEQ ID NO: 803        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 803
ggacgaaacc cgtaa                                                   15

SEQ ID NO: 804        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 804
acgaaaccgt aagca                                                   15

SEQ ID NO: 805        moltype = DNA  length = 15
```

```
FEATURE                Location/Qualifiers
misc_feature           1..15
                       note = synthetic sequence
source                 1..15
                       mol_type = other DNA
                       organism = synthetic construct
SEQUENCE: 805
acgaaaccgt aagca                                                    15

SEQ ID NO: 806         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 806
gcaacacgga cgaaac                                                   16

SEQ ID NO: 807         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 807
gcaacacgga cgaaa                                                    15

SEQ ID NO: 808         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 808
gcaacacgga cgaaac                                                   16

SEQ ID NO: 809         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 809
gcaacacgga cgaaac                                                   16

SEQ ID NO: 810         moltype = DNA  length = 16
FEATURE                Location/Qualifiers
misc_feature           1..16
                       note = synthetic sequence
source                 1..16
                       mol_type = other DNA
                       organism = synthetic construct
SEQUENCE: 810
gcaacacgga cgaaac                                                   16

SEQ ID NO: 811         moltype = DNA  length = 14
FEATURE                Location/Qualifiers
misc_feature           1..14
                       note = synthetic sequence
source                 1..14
                       mol_type = other DNA
                       organism = synthetic construct
SEQUENCE: 811
gcaacacgga cgaa                                                     14

SEQ ID NO: 812         moltype = DNA  length = 15
FEATURE                Location/Qualifiers
misc_feature           1..15
                       note = synthetic sequence
source                 1..15
                       mol_type = other DNA
                       organism = synthetic construct
SEQUENCE: 812
acacggacga aaccg                                                    15
```

```
SEQ ID NO: 813          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 813
acacggacga aaccg                                                    15

SEQ ID NO: 814          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 814
aacacggacg aaaccg                                                   16

SEQ ID NO: 815          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 815
aacacggacg aaaccg                                                   16

SEQ ID NO: 816          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 816
acgaaaccgt aagca                                                    15

SEQ ID NO: 817          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 817
acgaaaccgt aagca                                                    15

SEQ ID NO: 818          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 818
aacatgtctg gaccta                                                   16

SEQ ID NO: 819          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 819
acatgtctgg acctat                                                   16

SEQ ID NO: 820          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 820
tgaatatgac atagt                                                    15
```

```
SEQ ID NO: 821          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 821
aatatgacat agtc                                                      14

SEQ ID NO: 822          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 822
cacagatttt aaagtt                                                    16

SEQ ID NO: 823          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 823
cacagatttt aaagtt                                                    16

SEQ ID NO: 824          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 824
cagattttaa agttcg                                                    16

SEQ ID NO: 825          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 825
gattttaaag ttcgt                                                     15

SEQ ID NO: 826          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 826
taaagttcgt ttaga                                                     15

SEQ ID NO: 827          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 827
aaagttcgtt taga                                                      14

SEQ ID NO: 828          moltype = DNA  length = 17
FEATURE                 Location/Qualifiers
misc_feature            1..17
                        note = synthetic sequence
source                  1..17
                        mol_type = other DNA
                        organism = synthetic construct
```

```
SEQUENCE: 828
tcgtttagag aacagat                                                17

SEQ ID NO: 829          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 829
agagaacaga tctaca                                                 16

SEQ ID NO: 830          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 830
agatctacaa gaga                                                   14

SEQ ID NO: 831          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 831
atctacaaga gatc                                                   14

SEQ ID NO: 832          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 832
agattttaaa gttcgt                                                 16

SEQ ID NO: 833          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 833
gattttaaag ttcgt                                                  15

SEQ ID NO: 834          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 834
gattttaaag ttcgt                                                  15

SEQ ID NO: 835          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 835
agattttaaa gttcg                                                  15

SEQ ID NO: 836          moltype = DNA  length = 17
FEATURE                 Location/Qualifiers
misc_feature            1..17
                        note = synthetic sequence
```

```
source                  1..17
                        mol_type = other DNA
                        organism = synthetic construct
SEQUENCE: 836
tcgtttagag aacagat                                                        17

SEQ ID NO: 837          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 837
ttcgtttaga gaacag                                                         16

SEQ ID NO: 838          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 838
ttcgtttaga gaacag                                                         16

SEQ ID NO: 839          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 839
caggcaaact gagttg                                                         16

SEQ ID NO: 840          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 840
caggcaaact gagttg                                                         16

SEQ ID NO: 841          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 841
caggcaaact gagt                                                           14

SEQ ID NO: 842          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 842
caaactgagt tggacg                                                         16

SEQ ID NO: 843          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 843
aaactgagtt ggac                                                           14

SEQ ID NO: 844          moltype = DNA  length = 16
FEATURE                 Location/Qualifiers
```

```
misc_feature          1..16
                      note = synthetic sequence
source                1..16
                      mol_type = other DNA
                      organism = synthetic construct
SEQUENCE: 844
aaactgagtt ggacgt                                                   16

SEQ ID NO: 845        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 845
gagttggacg tgtgt                                                    15

SEQ ID NO: 846        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 846
ttggacgtgt gttttc                                                   16

SEQ ID NO: 847        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 847
ggacgtgtgt tttctc                                                   16

SEQ ID NO: 848        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 848
tttcggtcac acccgg                                                   16

SEQ ID NO: 849        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 849
cggtcacacc cggacg                                                   16

SEQ ID NO: 850        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 850
tcacacccgg acgaaa                                                   16

SEQ ID NO: 851        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 851
cacccggacg aaac                                                     14

SEQ ID NO: 852        moltype = DNA  length = 15
```

```
FEATURE                 Location/Qualifiers
misc_feature            1..15
                        note = synthetic sequence
source                  1..15
                        mol_type = other DNA
                        organism = synthetic construct
SEQUENCE: 852
cacccggacg aaacc                                                    15

SEQ ID NO: 853          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 853
cacccggacg aaacct                                                   16

SEQ ID NO: 854          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 854
ccggacgaaa ccta                                                     14

SEQ ID NO: 855          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 855
cggtcacacc cggacga                                                  17

SEQ ID NO: 856          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 856
cggtcacacc cggacg                                                   16

SEQ ID NO: 857          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 857
cggtcacacc cggacg                                                   16

SEQ ID NO: 858          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 858
cggtcacacc cggacg                                                   16

SEQ ID NO: 859          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 859
gtcacacccg gacg                                                     14
```

SEQ ID NO: 860 moltype = DNA length = 14
FEATURE Location/Qualifiers
misc_feature 1..14
note = synthetic sequence
source 1..14
mol_type = other DNA
organism = synthetic construct
SEQUENCE: 860
gtcacacccg gacg 14

SEQ ID NO: 861 moltype = DNA length = 15
FEATURE Location/Qualifiers
misc_feature 1..15
note = synthetic sequence
source 1..15
mol_type = other DNA
organism = synthetic construct
SEQUENCE: 861
cacccggacg aaacc 15

SEQ ID NO: 862 moltype = DNA length = 15
FEATURE Location/Qualifiers
misc_feature 1..15
note = synthetic sequence
source 1..15
mol_type = other DNA
organism = synthetic construct
SEQUENCE: 862
cacccggacg aaacc 15

SEQ ID NO: 863 moltype = DNA length = 14
FEATURE Location/Qualifiers
misc_feature 1..14
note = synthetic sequence
source 1..14
mol_type = other DNA
organism = synthetic construct
SEQUENCE: 863
cacccggacg aaac 14

SEQ ID NO: 864 moltype = DNA length = 16
FEATURE Location/Qualifiers
misc_feature 1..16
note = synthetic sequence
source 1..16
mol_type = other DNA
organism = synthetic construct
SEQUENCE: 864
cacacccgga cgaaac 16

SEQ ID NO: 865 moltype = DNA length = 15
FEATURE Location/Qualifiers
misc_feature 1..15
note = synthetic sequence
source 1..15
mol_type = other DNA
organism = synthetic construct
SEQUENCE: 865
cacacccgga cgaaa 15

SEQ ID NO: 866 moltype = DNA length = 14
FEATURE Location/Qualifiers
misc_feature 1..14
note = synthetic sequence
source 1..14
mol_type = other DNA
organism = synthetic construct
SEQUENCE: 866
cacacccgga cgaa 14

SEQ ID NO: 867 moltype = DNA length = 15
FEATURE Location/Qualifiers
misc_feature 1..15
note = synthetic sequence
source 1..15
mol_type = other DNA
organism = synthetic construct
SEQUENCE: 867
tcgatcgtac tccgc 15

```
SEQ ID NO: 868          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 868
tcgatcgtac tccg                                                14

SEQ ID NO: 869          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 869
atcgtactcc gcgtg                                               15

SEQ ID NO: 870          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 870
actcgatcgt actc                                                14

SEQ ID NO: 871          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 871
cgtggcctcg gtgaa                                               15

SEQ ID NO: 872          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 872
gtggcctcgg tgaa                                                14

SEQ ID NO: 873          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 873
gattaaagat tgctat                                              16

SEQ ID NO: 874          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 874
taaagattgc tatgtg                                              16

SEQ ID NO: 875          moltype = DNA  length = 16
FEATURE                 Location/Qualifiers
misc_feature            1..16
                        note = synthetic sequence
source                  1..16
                        mol_type = other DNA
                        organism = synthetic construct
```

```
SEQUENCE: 875
aagattgcta tgtgag                                                   16

SEQ ID NO: 876          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 876
gctatgtgag ttaaag                                                   16

SEQ ID NO: 877          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 877
tatgtgagtt aaagtt                                                   16

SEQ ID NO: 878          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 878
tgtgagttaa agttaa                                                   16

SEQ ID NO: 879          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 879
tcgtagaagc cttttg                                                   16

SEQ ID NO: 880          moltype = DNA  length = 17
FEATURE                 Location/Qualifiers
misc_feature            1..17
                        note = synthetic sequence
source                  1..17
                        mol_type = other DNA
                        organism = synthetic construct
SEQUENCE: 880
cgtagaagcc ttttggc                                                  17

SEQ ID NO: 881          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 881
tagaagcctt ttggca                                                   16

SEQ ID NO: 882          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 882
aagccttttg gcaatg                                                   16

SEQ ID NO: 883          moltype = DNA  length = 16
FEATURE                 Location/Qualifiers
misc_feature            1..16
                        note = synthetic sequence
```

```
source                  1..16
                        mol_type = other DNA
                        organism = synthetic construct
SEQUENCE: 883
ttggcaatgt tgttcc                                                    16

SEQ ID NO: 884          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 884
gcaatgttgt tcct                                                      14

SEQ ID NO: 885          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 885
cttgaggaag ttgt                                                      14

SEQ ID NO: 886          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 886
aggaagttgt agcacg                                                    16

SEQ ID NO: 887          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 887
ctactaaaat taatt                                                     15

SEQ ID NO: 888          moltype = DNA  length = 15
FEATURE                 Location/Qualifiers
misc_feature            1..15
                        note = synthetic sequence
source                  1..15
                        mol_type = other DNA
                        organism = synthetic construct
SEQUENCE: 888
tactaaaatt aattt                                                     15

SEQ ID NO: 889          moltype = DNA  length = 14
FEATURE                 Location/Qualifiers
misc_feature            1..14
                        note = synthetic sequence
source                  1..14
                        mol_type = other DNA
                        organism = synthetic construct
SEQUENCE: 889
actaaaatta attt                                                      14

SEQ ID NO: 890          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 890
aattaatttt acacat                                                    16

SEQ ID NO: 891          moltype = DNA  length = 16
FEATURE                 Location/Qualifiers
```

```
misc_feature          1..16
                      note = synthetic sequence
source                1..16
                      mol_type = other DNA
                      organism = synthetic construct
SEQUENCE: 891
attttacaca ttaggg                                                     16

SEQ ID NO: 892        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 892
tacacattag ggctc                                                      15

SEQ ID NO: 893        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 893
acattagggc tcttc                                                      15

SEQ ID NO: 894        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 894
tagggctctt ccata                                                      15

SEQ ID NO: 895        moltype = DNA  length = 15
FEATURE               Location/Qualifiers
misc_feature          1..15
                      note = synthetic sequence
source                1..15
                      mol_type = other DNA
                      organism = synthetic construct
SEQUENCE: 895
gctcttccat atagg                                                      15

SEQ ID NO: 896        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 896
aaggctctcc atctta                                                     16

SEQ ID NO: 897        moltype = DNA  length = 14
FEATURE               Location/Qualifiers
misc_feature          1..14
                      note = synthetic sequence
source                1..14
                      mol_type = other DNA
                      organism = synthetic construct
SEQUENCE: 897
aaggctctcc atct                                                       14

SEQ ID NO: 898        moltype = DNA  length = 16
FEATURE               Location/Qualifiers
misc_feature          1..16
                      note = synthetic sequence
source                1..16
                      mol_type = other DNA
                      organism = synthetic construct
SEQUENCE: 898
gctctccatc ttacct                                                     16

SEQ ID NO: 899        moltype = DNA  length = 16
```

```
FEATURE                 Location/Qualifiers
misc_feature            1..16
                        note = synthetic sequence
source                  1..16
                        mol_type = other DNA
                        organism = synthetic construct
SEQUENCE: 899
tccatcttac ctttcg                                                            16

SEQ ID NO: 900          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 900
cctccctaat gttaca                                                            16

SEQ ID NO: 901          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 901
ctccctaatg ttacag                                                            16

SEQ ID NO: 902          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 902
ctccctaatg ttacag                                                            16

SEQ ID NO: 903          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 903
taaaaccaac actacc                                                            16

SEQ ID NO: 904          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 904
aaaccaacac taccac                                                            16

SEQ ID NO: 905          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 905
aaaccaacac taccac                                                            16

SEQ ID NO: 906          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 906
accaacacta ccacat                                                            16
```

-continued

```
SEQ ID NO: 907          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 907
caacactacc acatga                                                   16

SEQ ID NO: 908          moltype = DNA  length = 16
FEATURE                 Location/Qualifiers
misc_feature            1..16
                        note = synthetic sequence
source                  1..16
                        mol_type = other DNA
                        organism = synthetic construct
SEQUENCE: 908
caacactacc acatga                                                   16
```